(12) United States Patent
Boyd

(10) Patent No.: US 8,418,895 B2
(45) Date of Patent: Apr. 16, 2013

(54) HOLDING DEVICES, PIECES AND SYSTEMS

(76) Inventor: Carol Boyd, Devon, PA (US)

( * ) Notice: Subject to any disclaimer, the term of this patent is extended or adjusted under 35 U.S.C. 154(b) by 153 days.

(21) Appl. No.: 13/041,403

(22) Filed: Mar. 6, 2011

(65) Prior Publication Data

US 2011/0215167 A1     Sep. 8, 2011

Related U.S. Application Data

(63) Continuation-in-part of application No. 12/012,159, filed on Jan. 30, 2008, now abandoned.

(51) Int. Cl.
*A41D 27/22* (2006.01)
*A41D 27/00* (2006.01)

(52) U.S. Cl.
USPC .......................................................... 223/86

(58) Field of Classification Search ............... 223/85–98
See application file for complete search history.

(56) References Cited

U.S. PATENT DOCUMENTS

| | | | | |
|---|---|---|---|---|
| 1,168,741 A | * | 1/1916 | Potter | 223/86 |
| 1,615,748 A | * | 1/1927 | Fischer | 223/86 |
| 1,981,072 A | * | 11/1934 | Roman et al. | 223/86 |
| 2,137,268 A | * | 11/1938 | Clairon | 223/86 |
| 2,187,691 A | * | 1/1940 | Newhouse | 223/86 |
| 2,529,294 A | * | 11/1950 | Hammond, Jr | 223/86 |
| 2,543,810 A | * | 3/1951 | Sklaar | 223/86 |
| 2,681,754 A | * | 6/1954 | Lefton et al. | 223/86 |
| 3,733,016 A | * | 5/1973 | Rood | 223/86 |
| 3,790,044 A | * | 2/1974 | Verdile | 223/86 |
| D367,768 S | * | 3/1996 | Wagner | D6/319 |
| 7,927,542 B2 | * | 4/2011 | Di Bono et al. | 422/5 |

* cited by examiner

*Primary Examiner* — Ismael Izaguirre
(74) *Attorney, Agent, or Firm* — Patricia A. Wenger

(57) ABSTRACT

Scented holding device systems, attacher systems, including attachment piece systems and attachment piece part systems, and devices used in the systems, including hangers. Scented hangers with widened shoulder areas, top oval area and center bar, and side hooks.

3 Claims, 116 Drawing Sheets

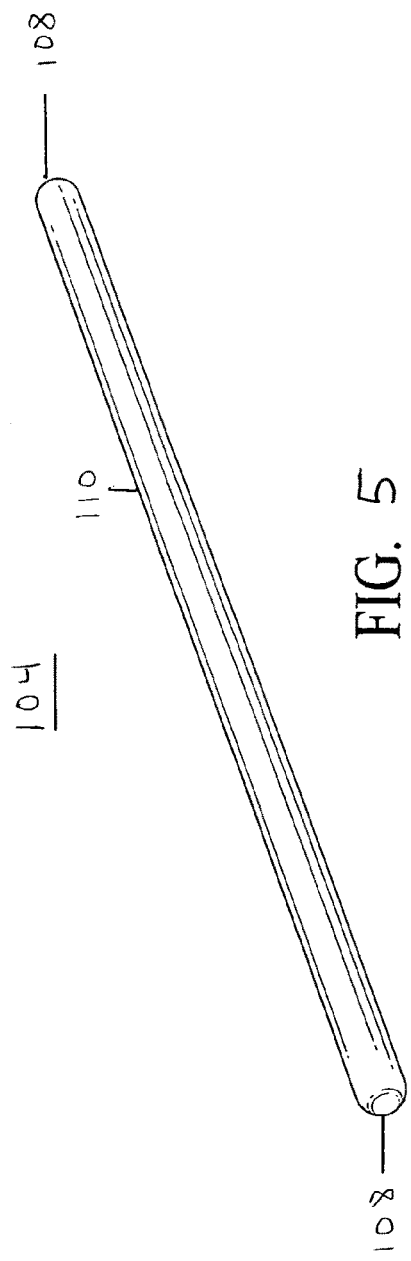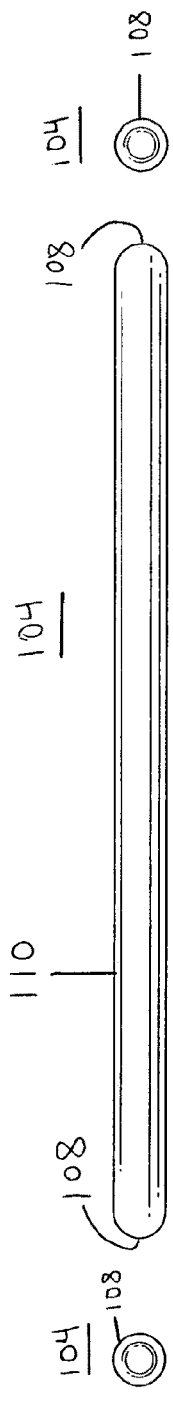

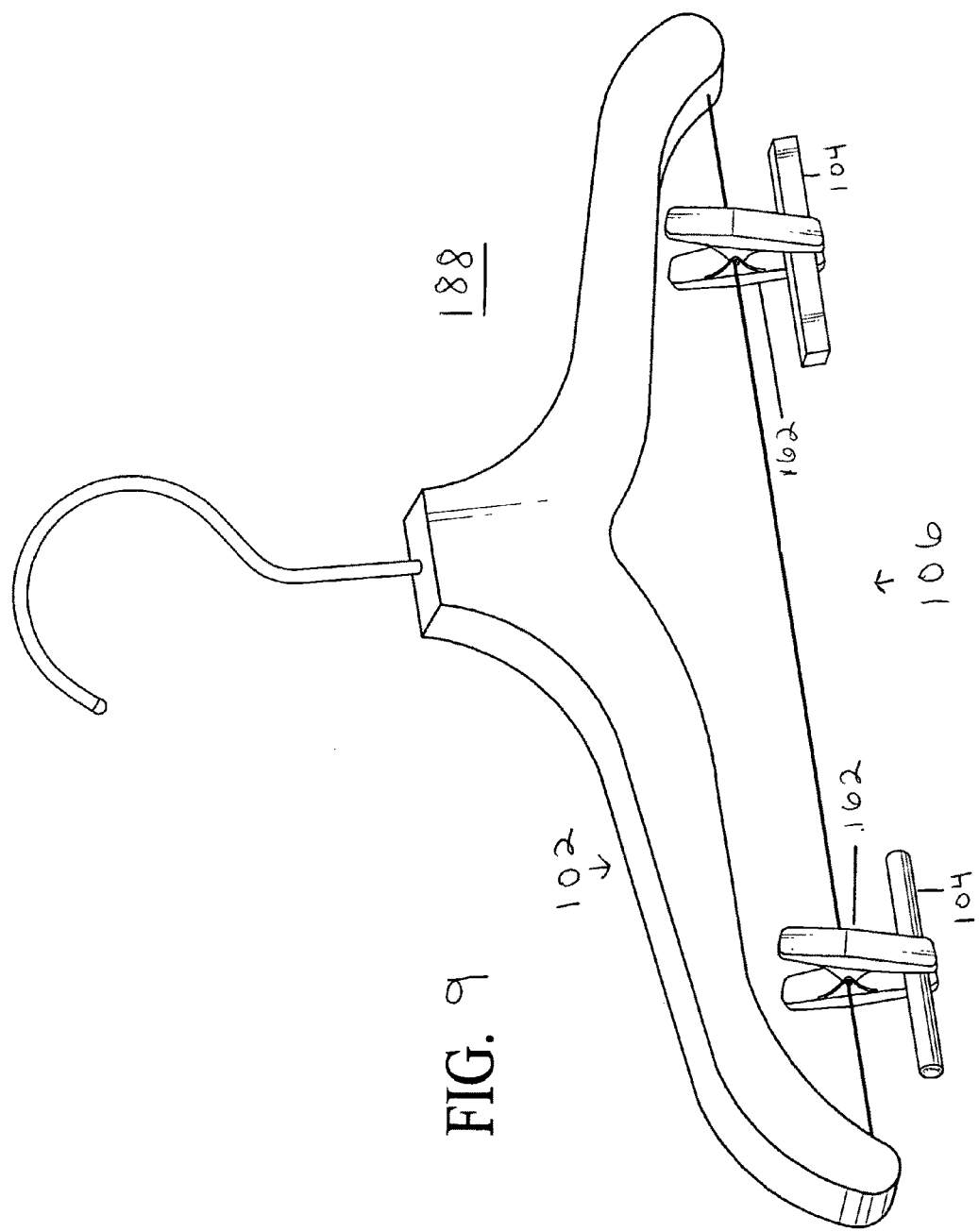

FIG. 17
FIG. 17a
FIG. 17b
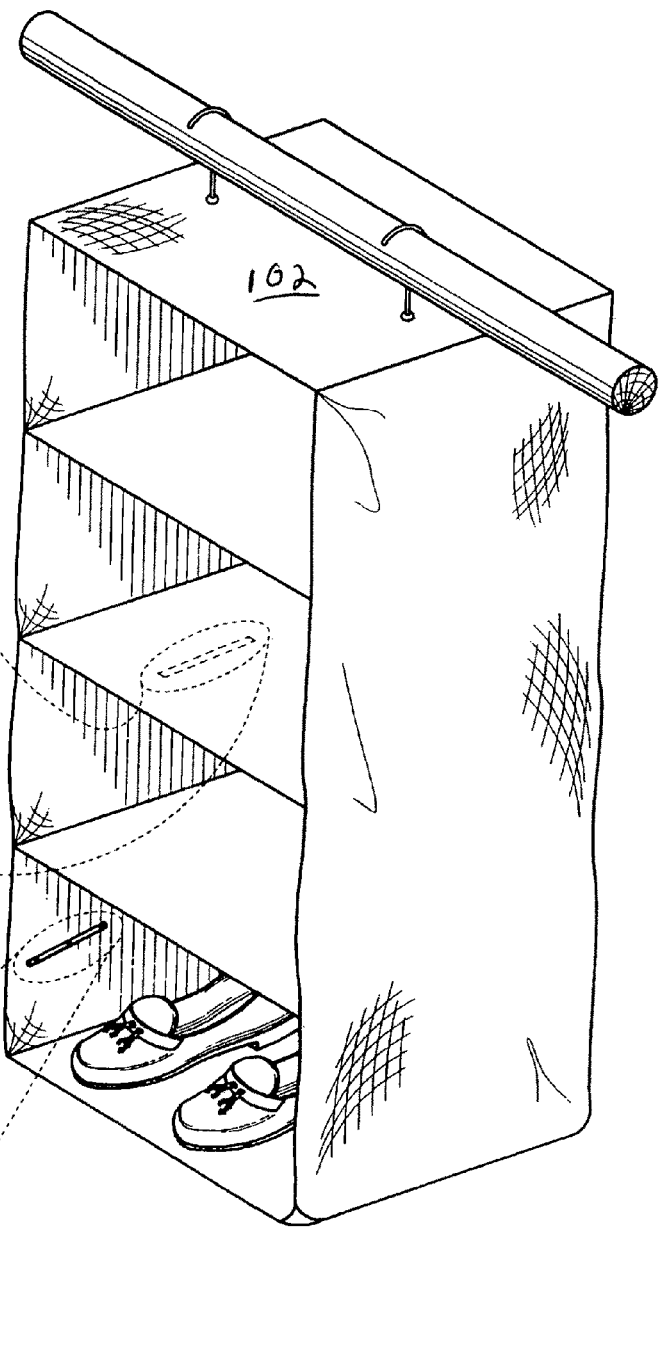
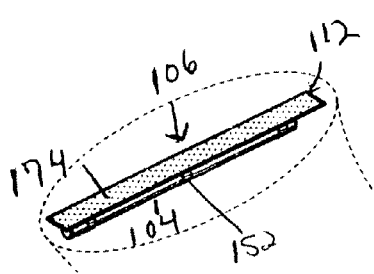
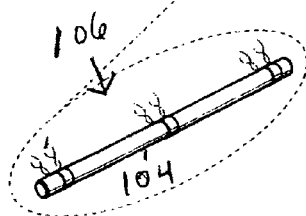

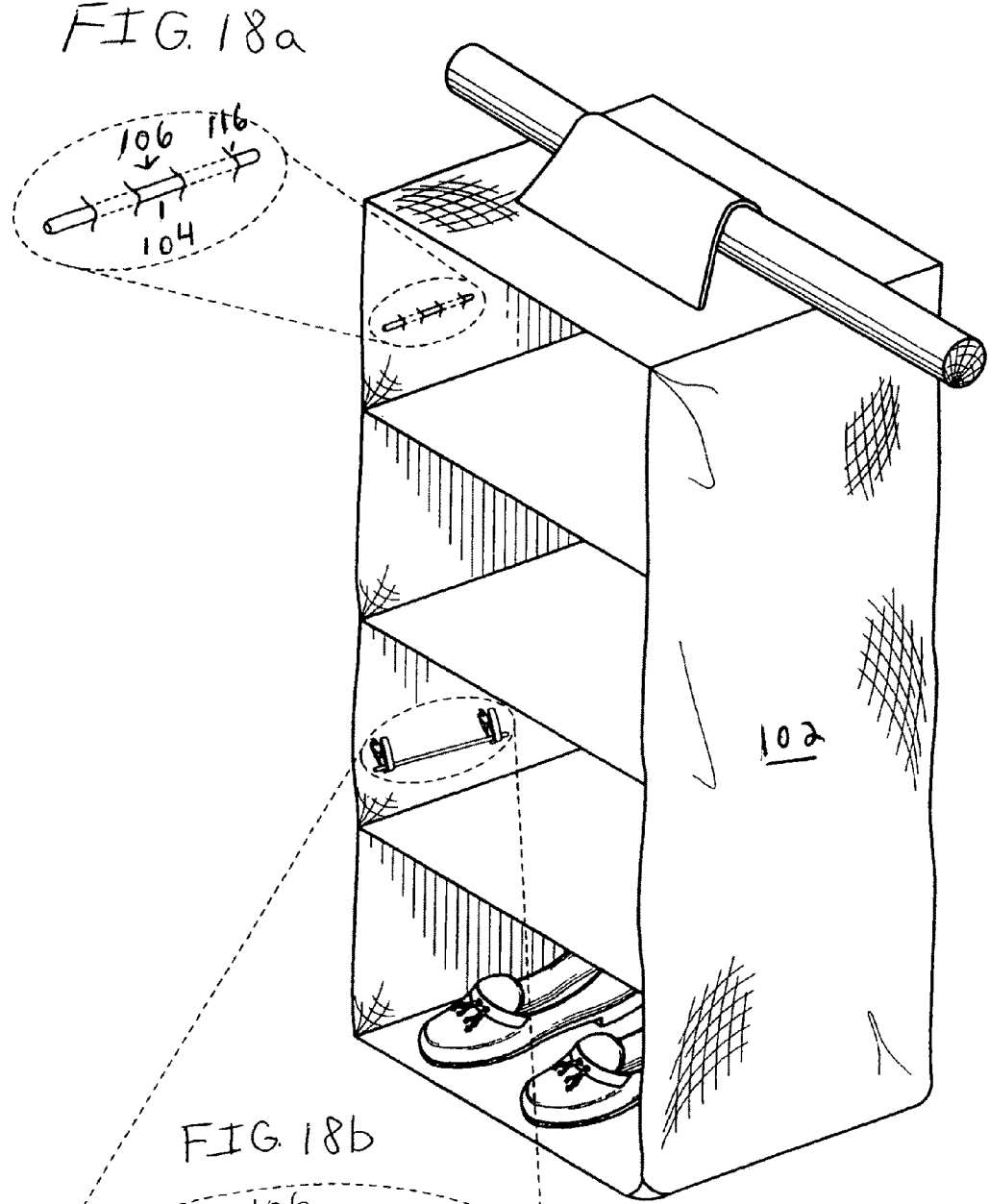
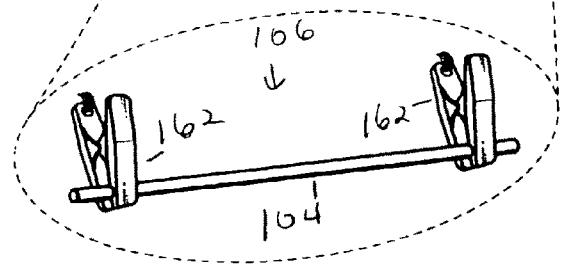
FIG. 18

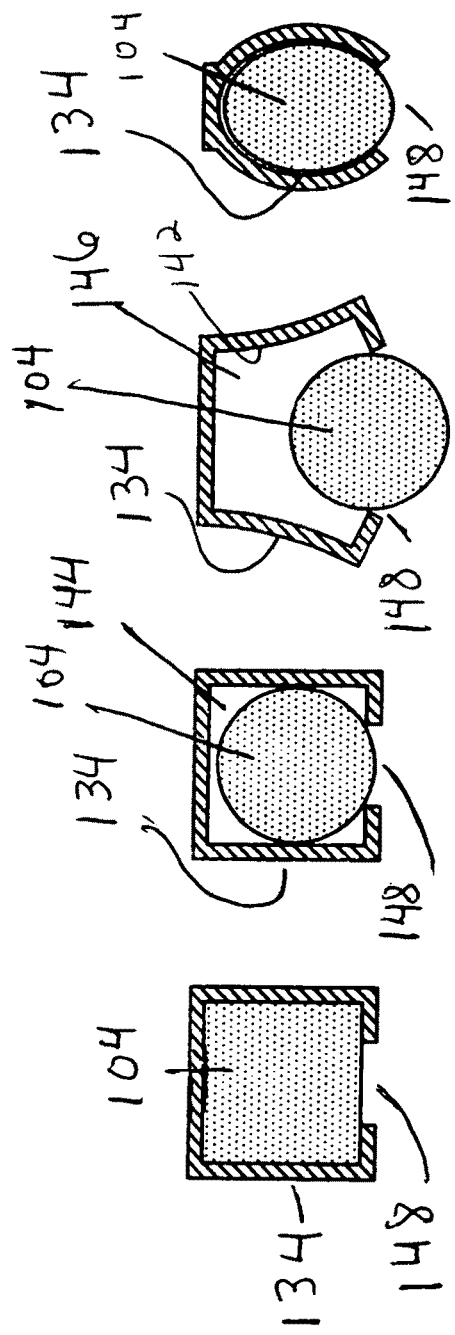

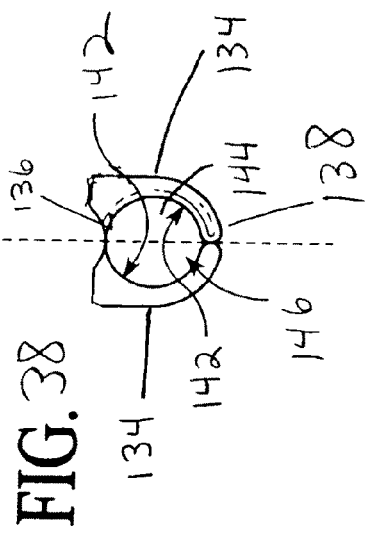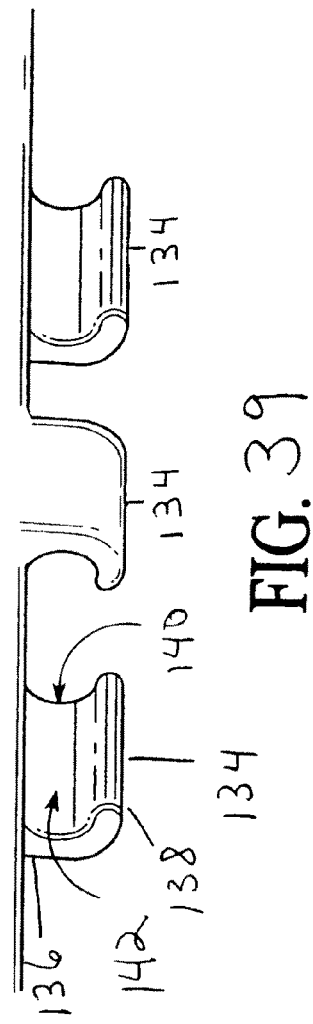

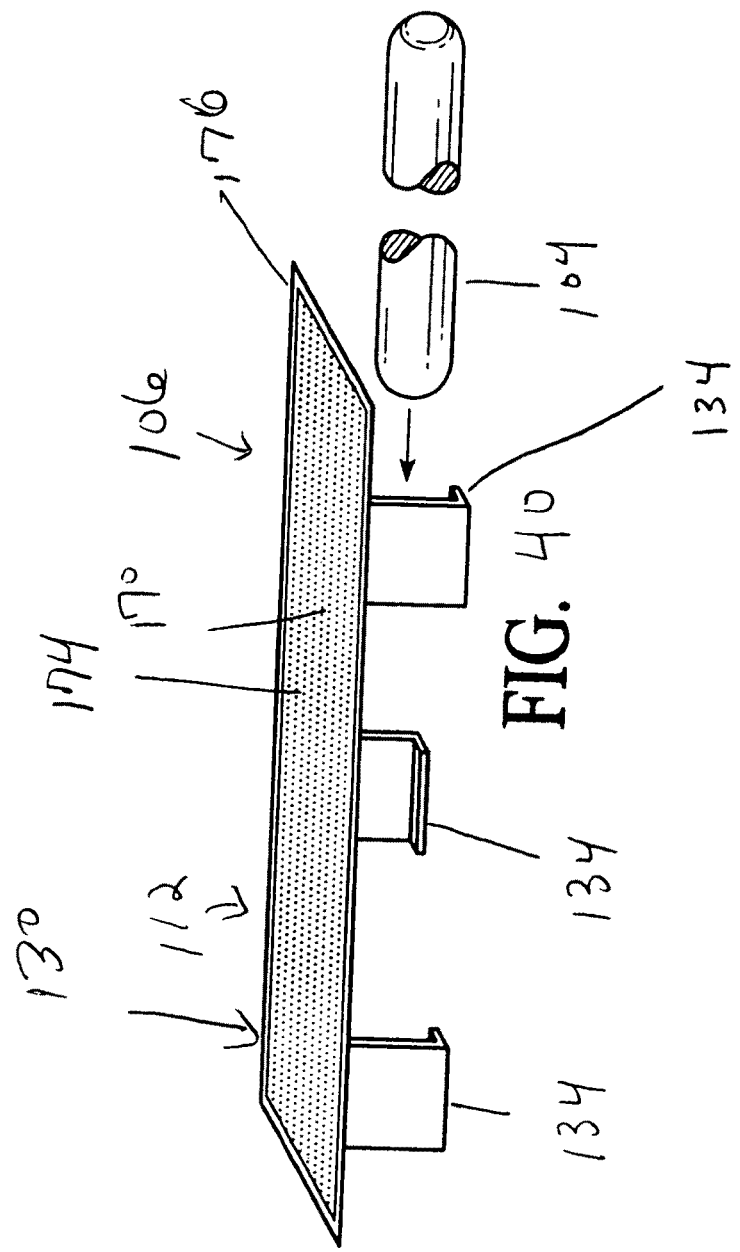

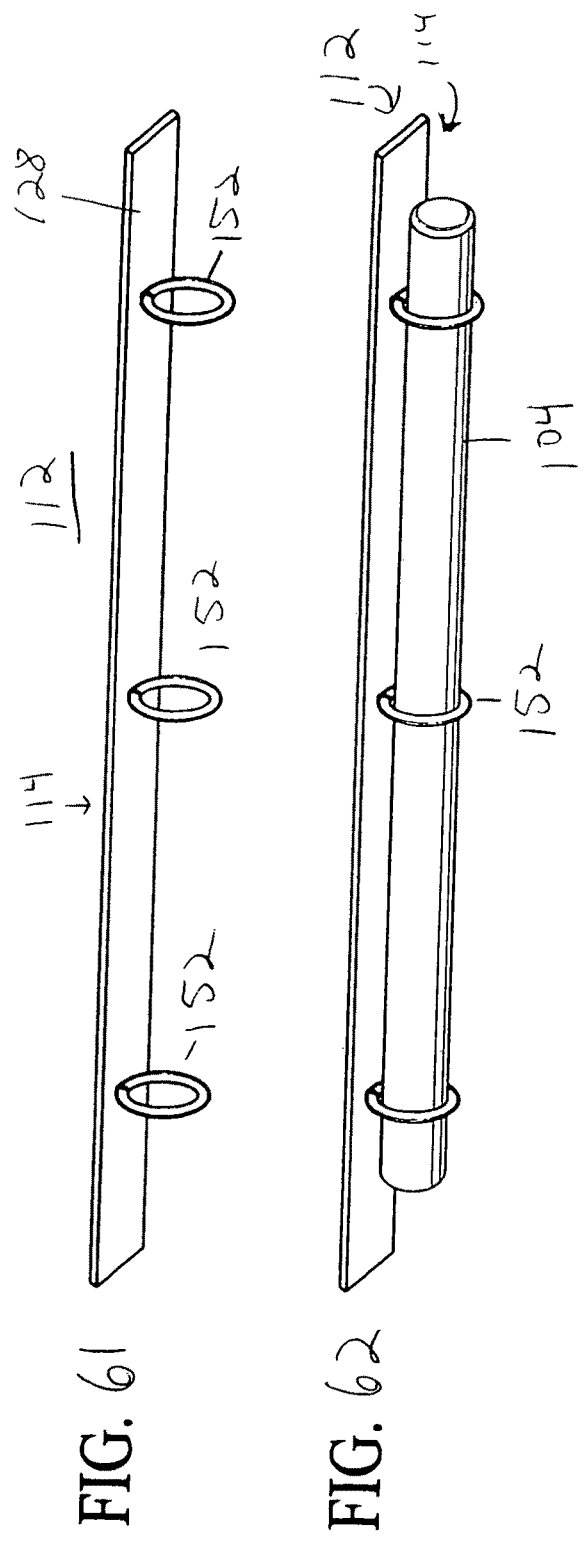

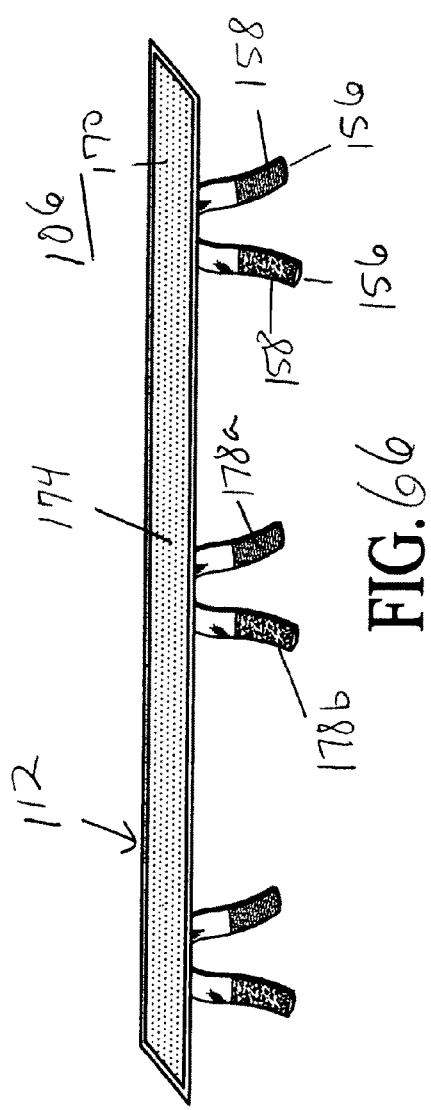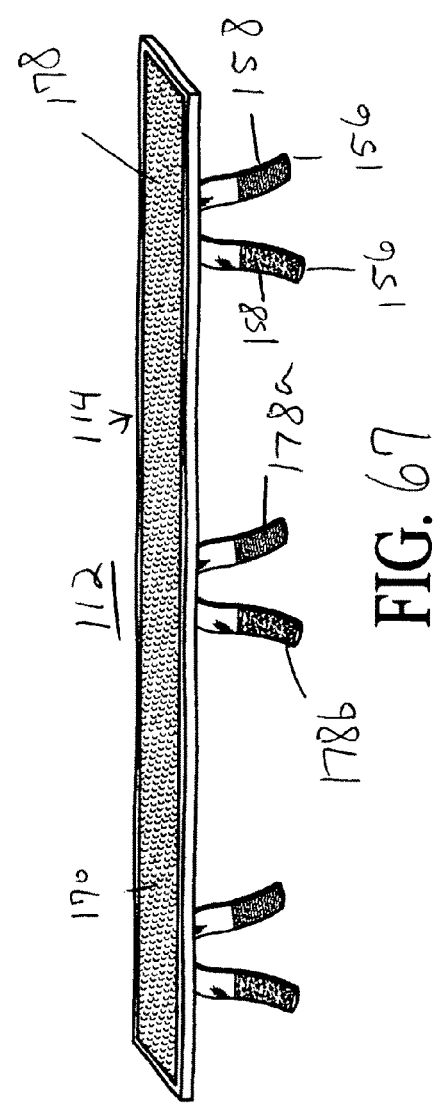

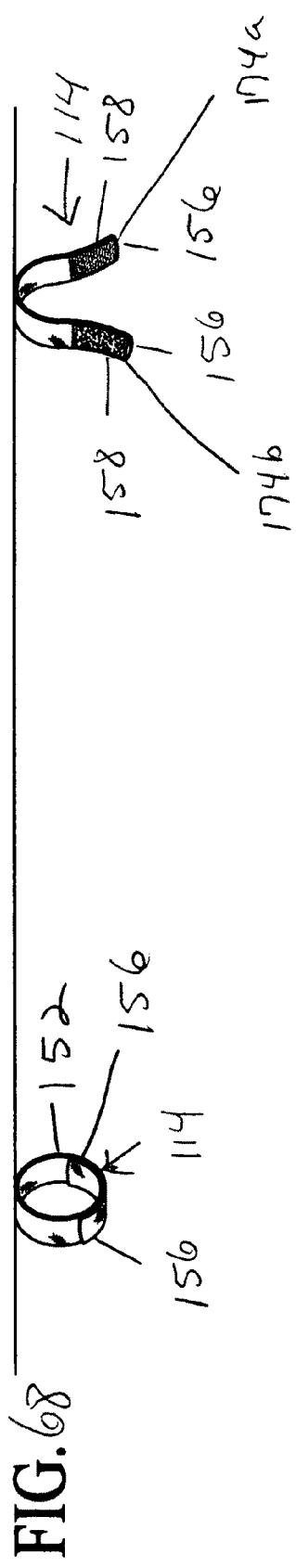

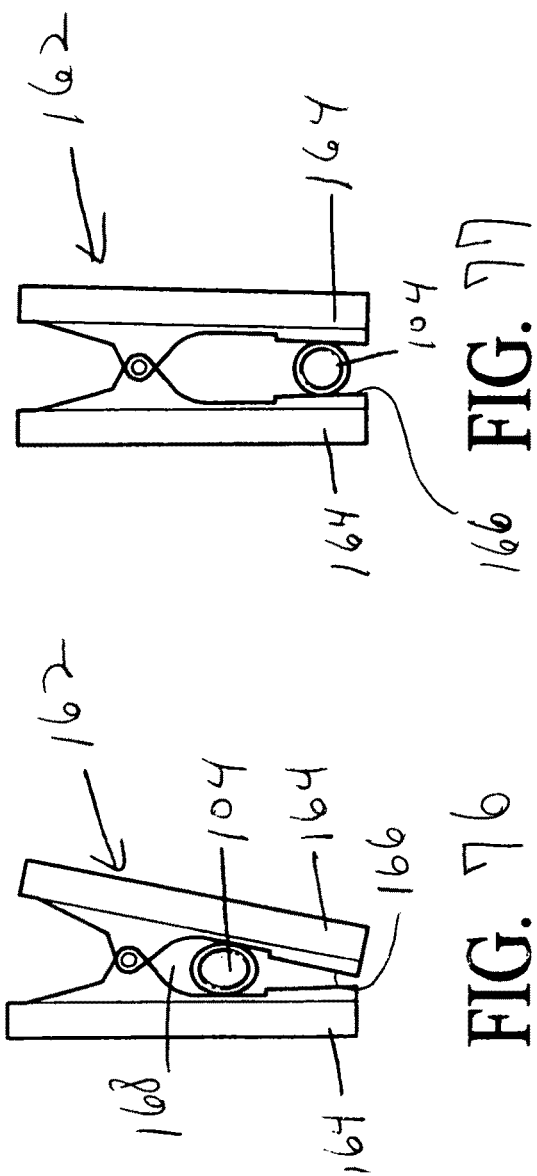

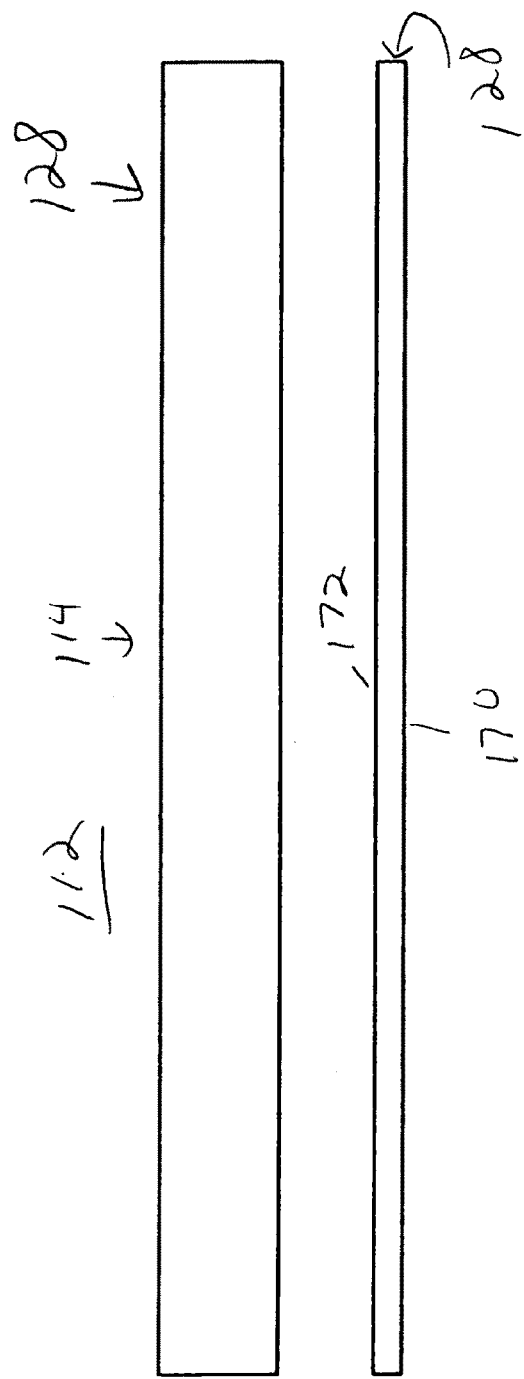

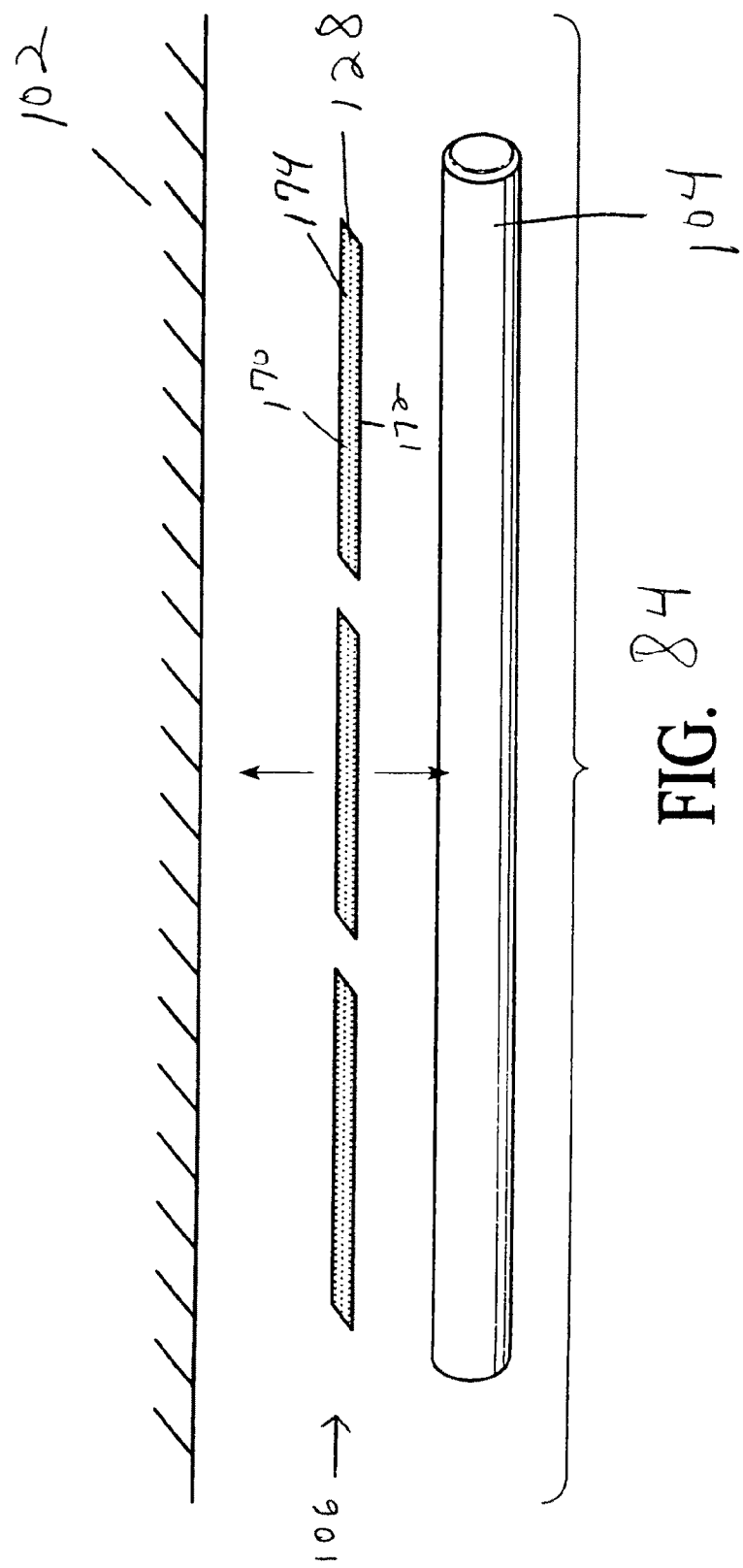

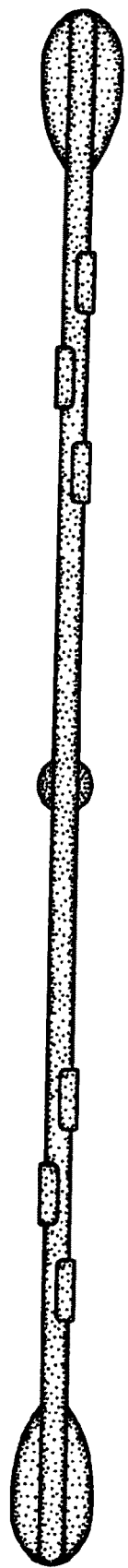
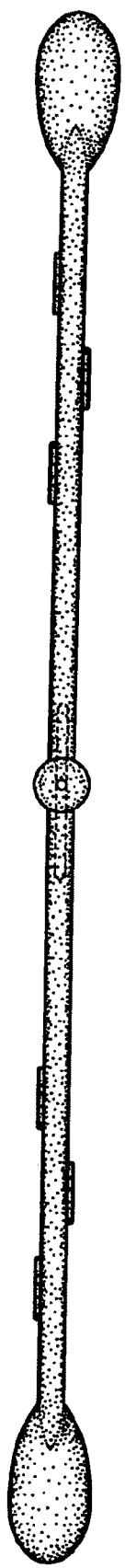
FIG. 104
FIG. 105

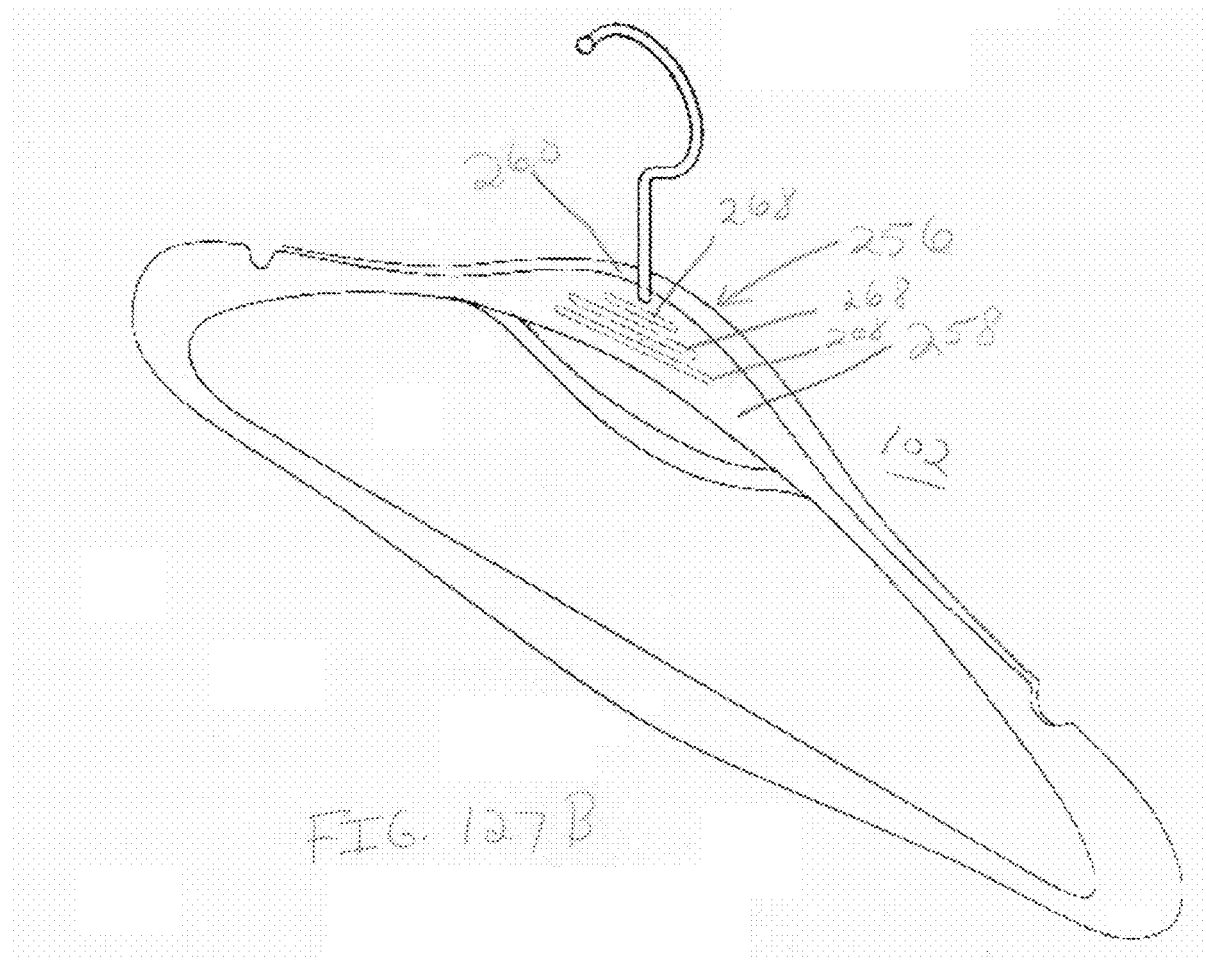

HOLDING DEVICES, PIECES AND SYSTEMS

CROSS REFERENCE TO RELATED APPLICATIONS AND INCORPORATION BY REFERENCE

This application is a continuation-in-part of non-provisional application of Carol Boyd, Ser. No. 12/012,159, now abandoned, filed on Jan. 30, 2008, entitled: Holding Devices, Pieces And Systems. The entire disclosure of parent patent application of Carol Boyd, Ser. No. 12/012,159, filed on Jan. 30, 2008, entitled: Holding Devices, Pieces And Systems, is incorporated herein by reference.

This application is related to, claims priority under and claims the benefit of the earliest available effective filing dates from the following listed applications: non-provisional application of Carol Boyd, Ser. No. 12/012,159, filed on Jan. 30, 2008, entitled: Holding Devices, Pieces And Systems.

FIELD OF THE INVENTION

The invention includes but is not limited to scented holding device systems, attacher systems, including attachment piece systems and attachment piece part systems, devices that are used in the systems, and hangers.

SUMMARY OF THE INVENTION

Embodiments of the invention include, but are not limited to the following:

A scented holding device system that includes at least one fragrance piece. The holding device has at least one attacher, whereby the at least one fragrance piece is removably attachable with the holding device by the attacher. In addition, the at least one fragrance piece can be removably attachable with the attacher without requiring the attacher to be removed from the holding device.

An attacher system that includes at least one fragrance piece. The attacher is attached with, integral with or attachable with a holding device, whereby the at least one fragrance piece is removably attachable with the holding device by the attacher. In addition, the at least one fragrance member can be removably attachable with the attacher without requiring the attacher to be removed from the holding device.

A system for attaching at least one fragrance piece with at least one holding device, the system includes: providing at least one fragrance piece; providing at least one holding device, providing at least one attacher, whereby the fragrance piece is removably attachable with the holding device by the attacher.

A scented holding device, which includes at least one fragrance piece. The at least one fragrance piece is removably attachable with the device.

An attachment device for a fragrance piece, whereby the attachment device includes at least one prong.

An attachment device for a fragrance piece, whereby the attachment device includes adhesive.

A holding device including at least one attacher, the attacher configured such that it can removably hold a fragrance piece that can be longer than it is wide to the device.

An attachment device for a fragrance piece, the attachment device includes at least one piece of a material. The at least one piece of a material can further include at least one attachment piece part.

An attachment device for a fragrance piece, whereby the attachment device includes at least one loop.

An attachment device for a fragrance piece, whereby the attachment device includes at least one clip.

An attachment device for a fragrance piece, whereby the attachment device includes at least one cavity.

A hanger that has at least one prong, whereby the at least one prong is configured such that it can removably hold a fragrance piece that can be longer than it is wide to the hanger.

A hanger including at least one attacher that is configured such that it can removably hold a fragrance piece that can be longer than it is wide to the hanger.

A hanger including two widened shoulder areas, whereby each of the shoulder areas is tapered.

A hanger including an oval portion that includes a partial crossbar.

A hanger including two side hook areas, whereby each of the side hook areas has a hook.

A scented hanger system that includes at least one attacher and at least one fragrance piece, whereby the at least one fragrance piece is removably attachable with the at least one attacher.

BRIEF DESCRIPTION OF THE DRAWINGS

The accompanying drawings, which are incorporated in and form a part of the specification, illustrate the embodiments of the present invention and, together with the description, serve to explain the principles of the invention.

FIGS. 5-6 are side views of a cylindrical fragrance piece;

FIGS. 7-8 are two opposing end views of the fragrance piece exemplarily illustrated in FIGS. 5-6;

FIG. 9 is a view of hanger with a cylindrical and a rectangular fragrance piece attached with clips;

FIG. 17 is a view of shoe bag with a fragrance piece attached with a set of sewn-in loop attachers, and a fragrance piece attached with a loop and strip attacher with adhesive;

FIG. 18 is view of a shoe bag with a fragrance piece attached with a set of sewn-in clip attachers, and a fragrance piece attached with a slot attacher;

FIG. 24 A is a view of square-shaped fragrance piece in prongs with a square inner surface shape;

FIG. 24 B is a view of a circular fragrance piece in prongs with a square inner surface shape;

FIG. 24 C is a view of a the circular fragrance piece in the accessible prong gap of the flexible prongs with a square inner surface shape that are exemplarily illustrated in FIG. 24 B;

FIG. 24 D is a view of an oval-shaped fragrance piece in prongs with an oval inner surface shape;

FIG. 34 A is a cross sectional view of point A-A exemplarily illustrated in FIG. 34;

FIG. 38 is a side view of a set of prongs;

FIG. 39 is a front view of the set of prongs exemplarily illustrated in FIG. 38;

FIG. 40 is a view of a plastic prong attachment piece and/or attachment piece part with adhesive on the holding device side, and a fragrance piece;

FIG. 61 is a view of a series of three sewn-on loop attachers, attachment pieces and/or attachment piece parts;

FIG. 62 is the view of FIG. 61 with an attached fragrance piece;

FIG. 66 is a view of a loops and piece of a material with the loop ends having hook and loop connectors and the holding device side of the piece of material having adhesive;

FIG. 67 is a view of a loops and a piece of material with the loops having hook and loop connectors and the holding device side of the piece of material having hook and loop material;

FIG. 68 is a view of two loops with the loop ends having hook and loop connectors;

FIG. 76 is a side view of FIG. 10;

FIG. 77 is a side view of a circular fragrance piece attached with a clip;

FIG. 80 is a front view of a piece of a material;

FIG. 81 is a side view of the piece of a material exemplarily illustrated in FIG. 80;

FIG. 84 is an exploded view of a holding device, three adhesive strips, and a fragrance piece;

FIG. 104 is an isometric bottom view thereof;

FIG. 105 is an isometric top view thereof;

FIG. 127B is a side view of a hanger.

FIG. 131 is a side view of an embodiment the top end of a hanger along with some other hanger sections illustrated in FIG. 128, and the fragrance piece illustrated in FIG. 126, with the fragrance piece inserted into the cavity of the top end of the hanger.

FIG. 132 is a view of an embodiment the top end of a hanger along with some other hanger sections illustrated in FIG. 128, and the fragrance piece illustrated in FIG. 126.

FIG. 133 is an embodiment the top end of a hanger along with some other hanger sections illustrated in FIG. 128, and a fragrance piece that has a heightened area.

FIG. 134 is the embodiment the top end of a hanger along with some other hanger sections illustrated in FIG. 133 and the fragrance piece that has a heightened area illustrated in FIG. 133 where the fragrance piece has been inserted in the cavity of the top end of the hanger.

FIG. 135 is a side drawing of an embodiment of an inside of a cavity where the risers of the fragrance piece are pressing against the center-facing walls of two hanger columns.

FIG. 136 is a side drawing of an embodiment of an inside of a cavity where the risers of the fragrance piece having an arch are pressing against the center-facing walls of two hanger columns with both a horizontal and vertical component.

FIG. 137 is a side view of an embodiment of a fragrance piece.

FIG. 138 is another side view of an embodiment of a fragrance piece.

FIG. 139 is a side view of an embodiment the top end of a hanger along with some other hanger sections illustrated, and the fragrance piece illustrated in FIG. 137.

FIG. 140 is a bottom view looking into a cavity in the top end of the hanger illustrated in FIG. 139.

FIG. 141 is a side view of an embodiment the top end of a hanger along with some other hanger sections illustrated in FIG. 139, and the fragrance piece illustrated in FIG. 137, with the fragrance piece inserted into the cavity of the top end of the hanger.

FIG. 142 is another view of an embodiment the top end of a hanger along with some other hanger sections illustrated in FIG. 139, and the fragrance piece illustrated in FIG. 137, with the fragrance piece inserted into the cavity of the top end of the hanger.

Figure 143:
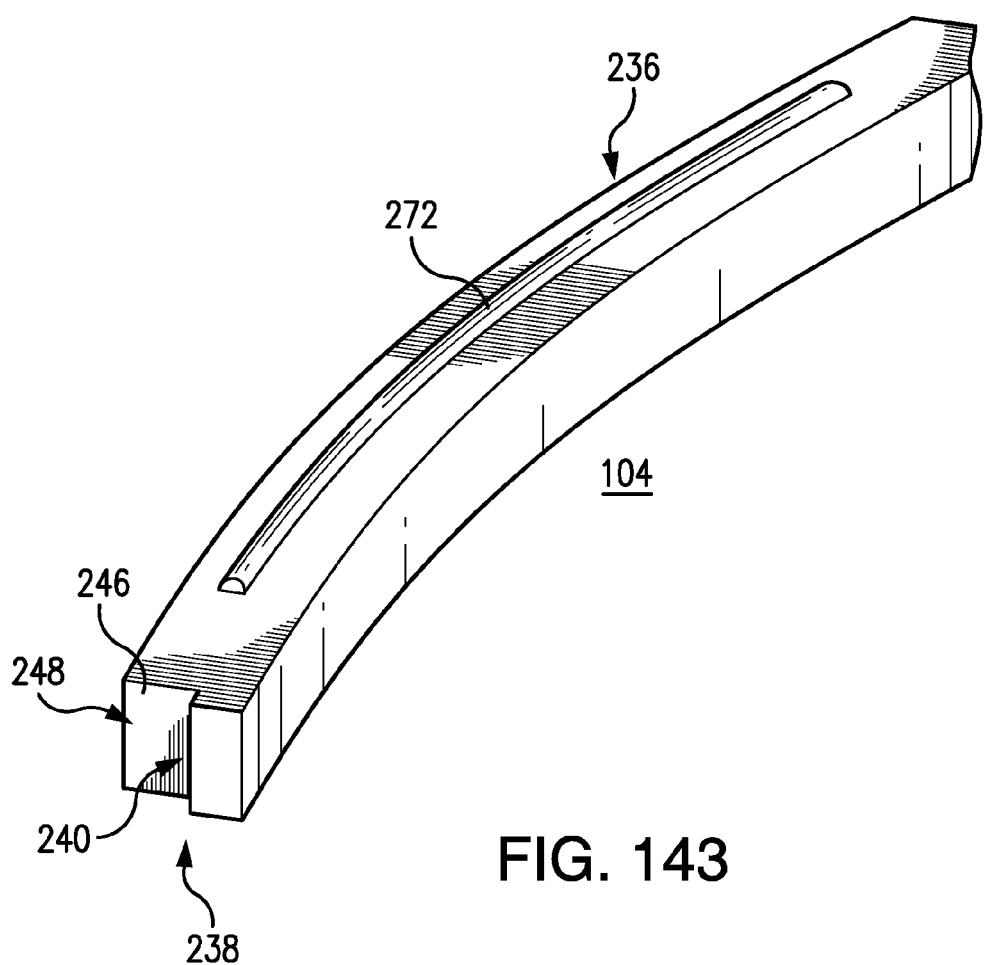

FIG. 143 is a view of an embodiment of a fragrance piece.

Figure 144:
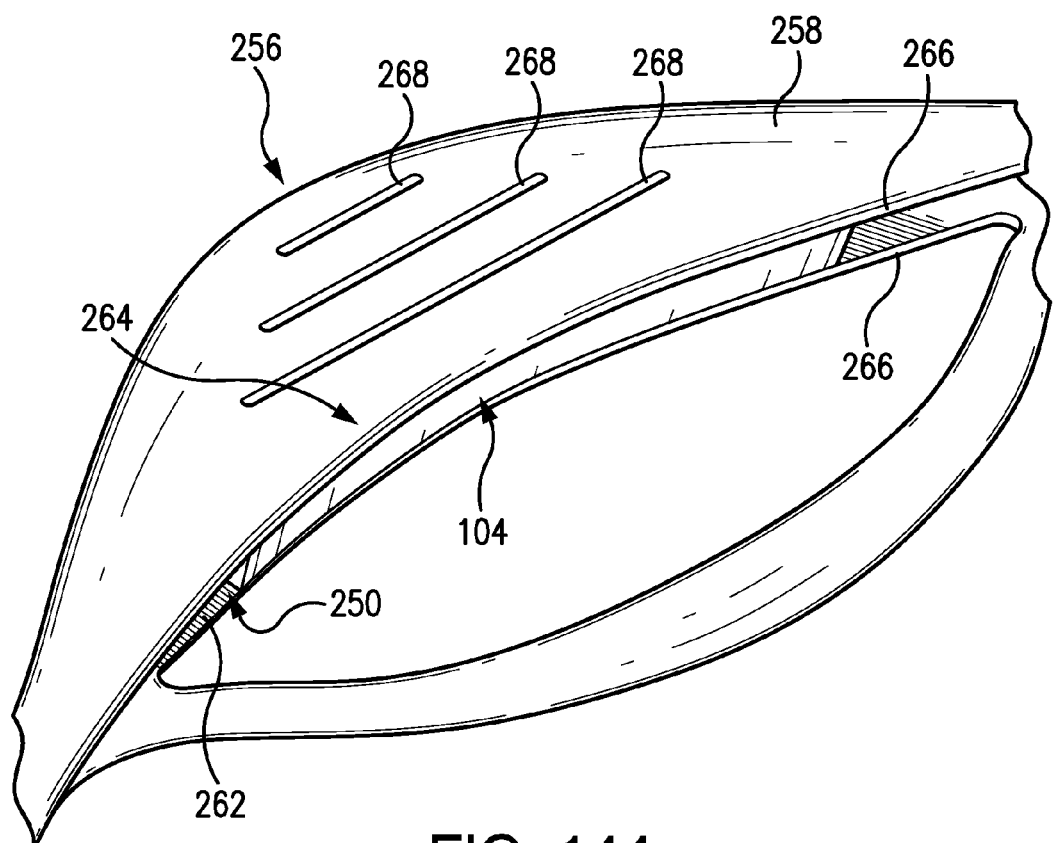

FIG. 144 is a view of the fragrance piece illustrated in FIG. 143 inserted in the cavity of a top end of a hanger.

Figure 145:
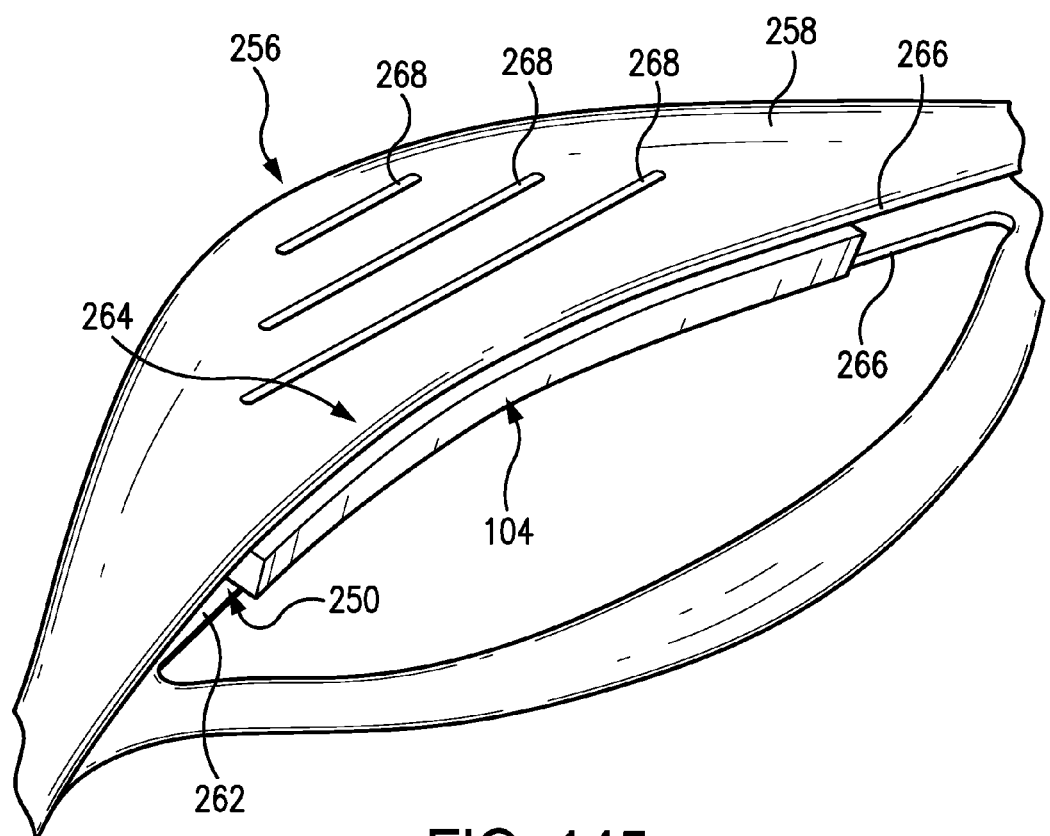

FIG. 145 is a view of the fragrance piece inserted in the cavity of a top end of a hanger where a portion of the length of the fragrance piece protrudes below the opening of the cavity.

DETAILED DESCRIPTION

Figure 1A:
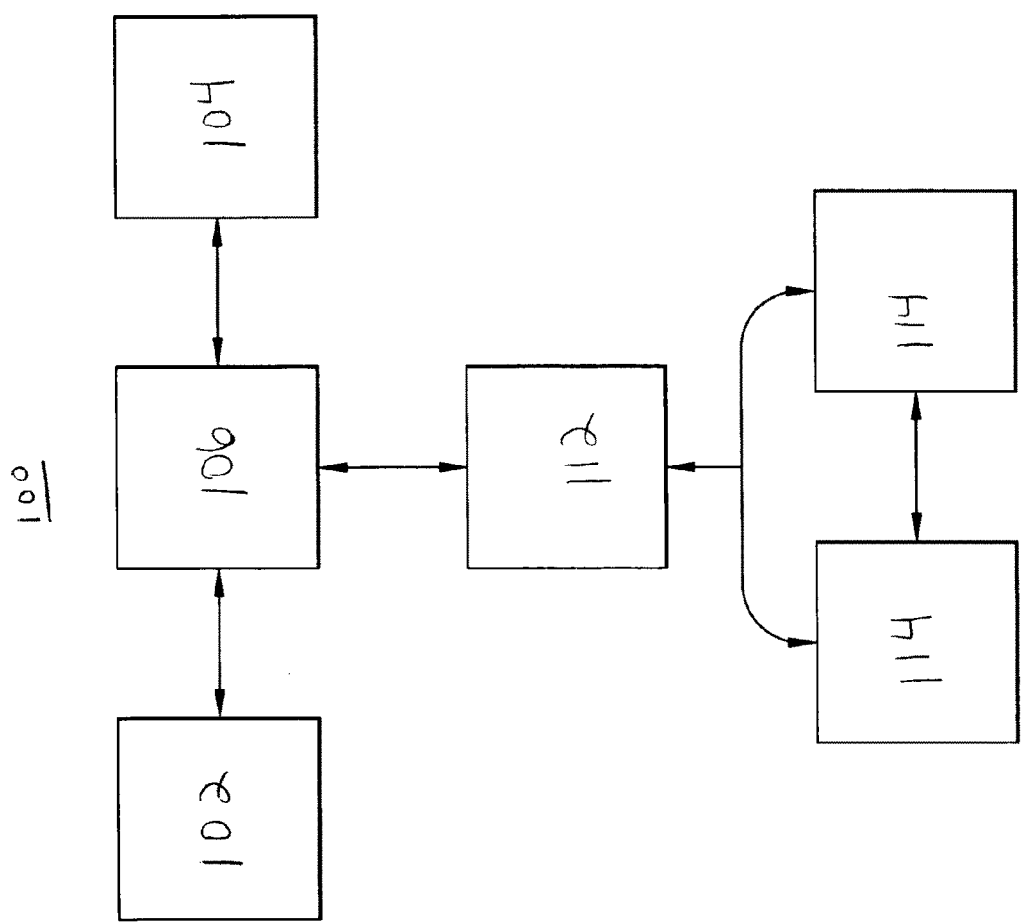
FIGS. 1A-V are illustrations of embodiments of scented holding device systems and attacher systems, including attachment piece systems and attachment piece part systems.
Figure 1B:
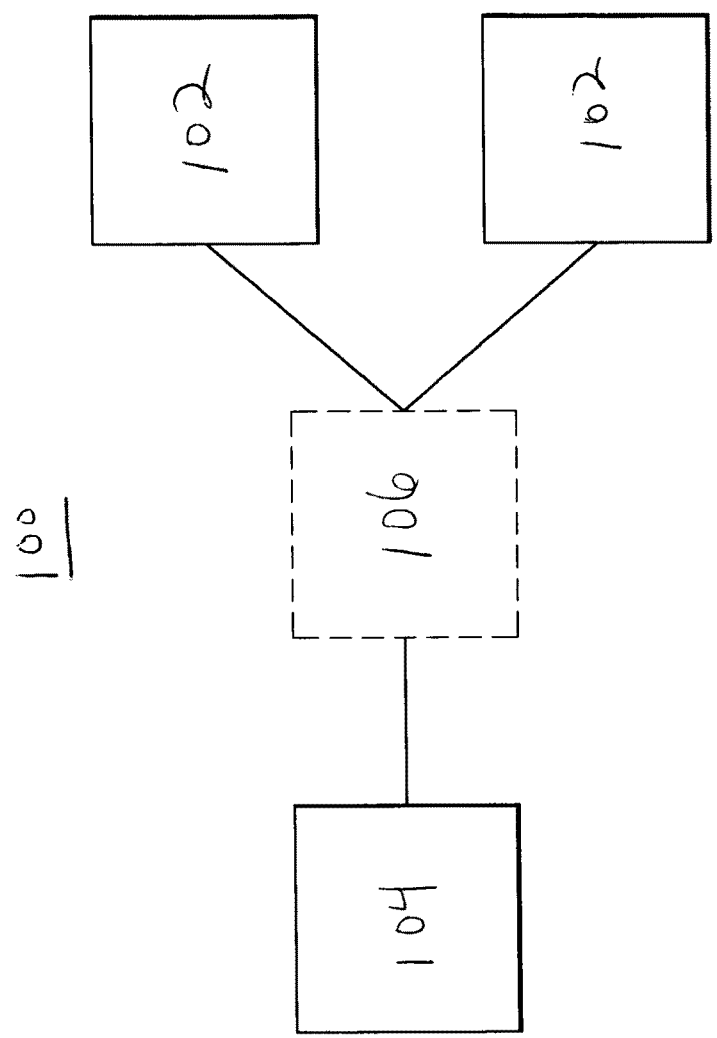
Figure 1C:
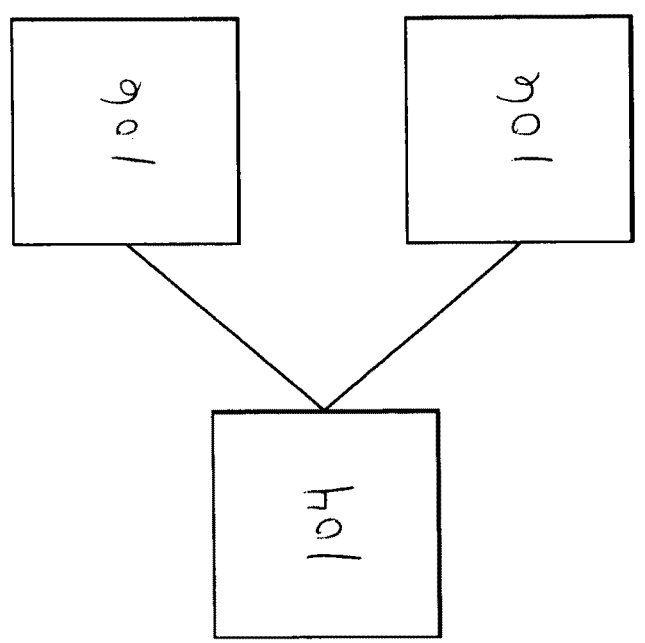
Figure 1D:
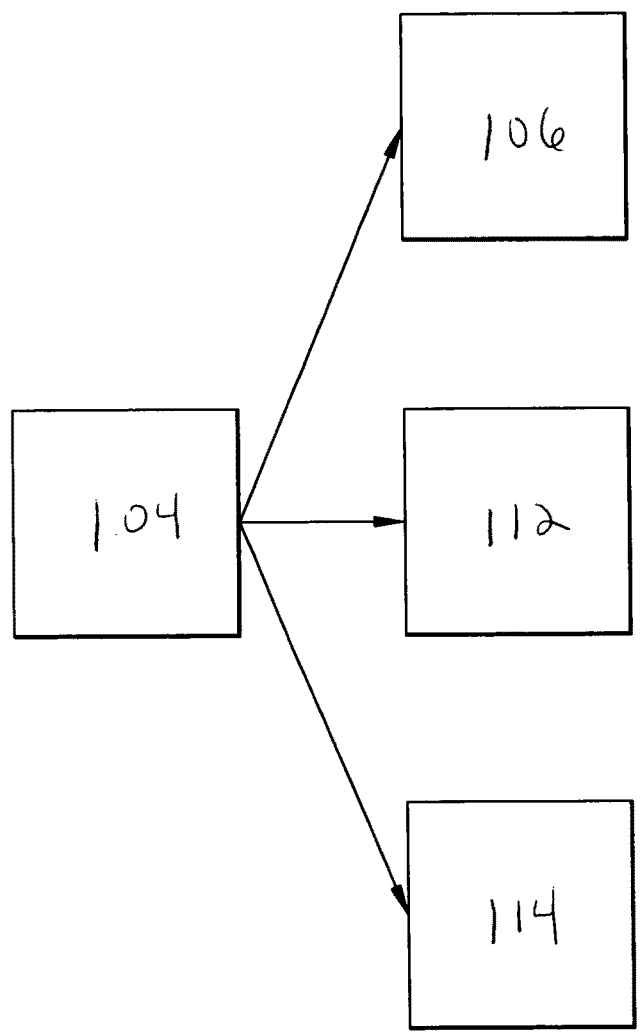
Figure 1E:
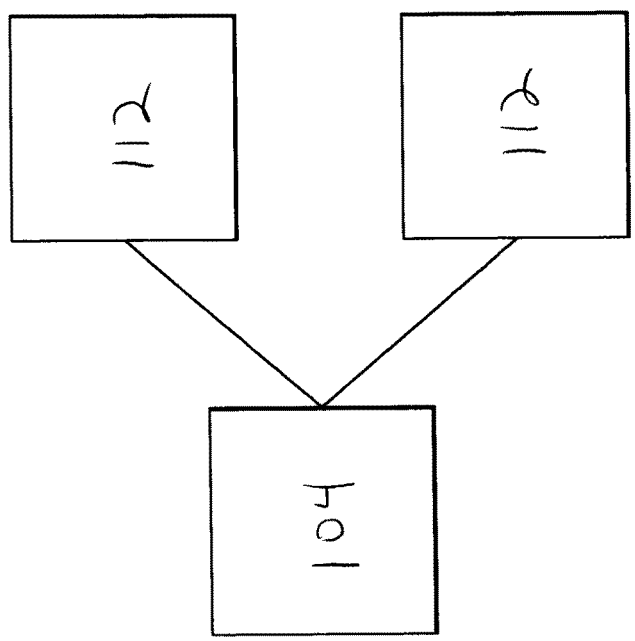
Figure 1F:
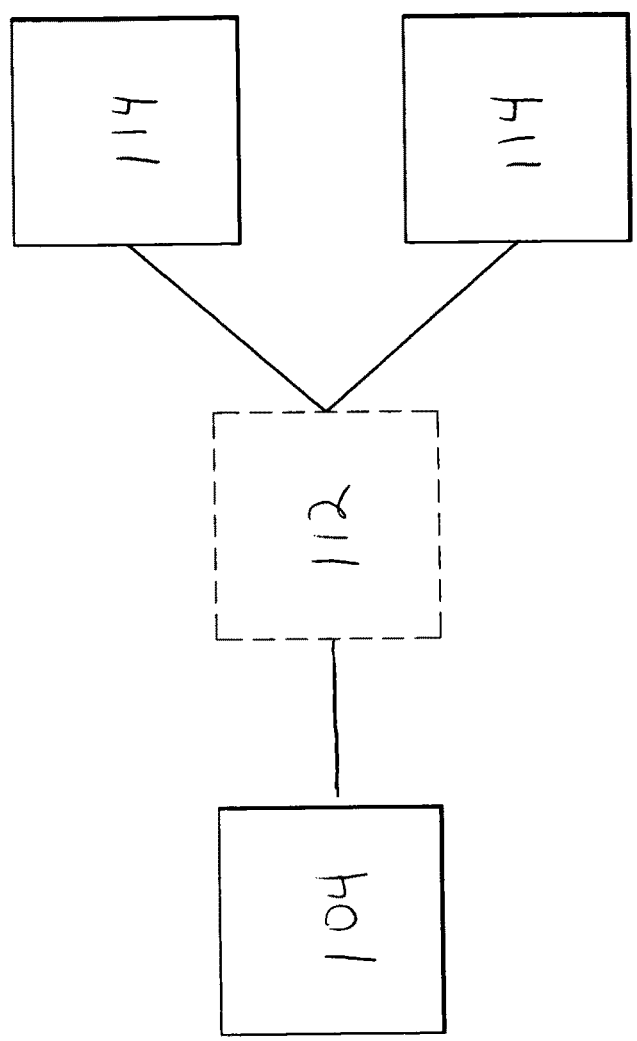
Figure 1G:
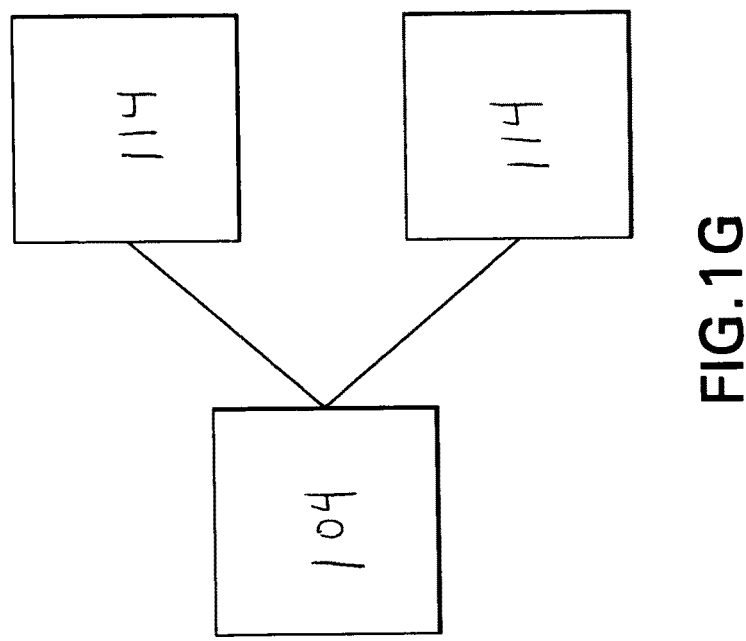
Figure 100:
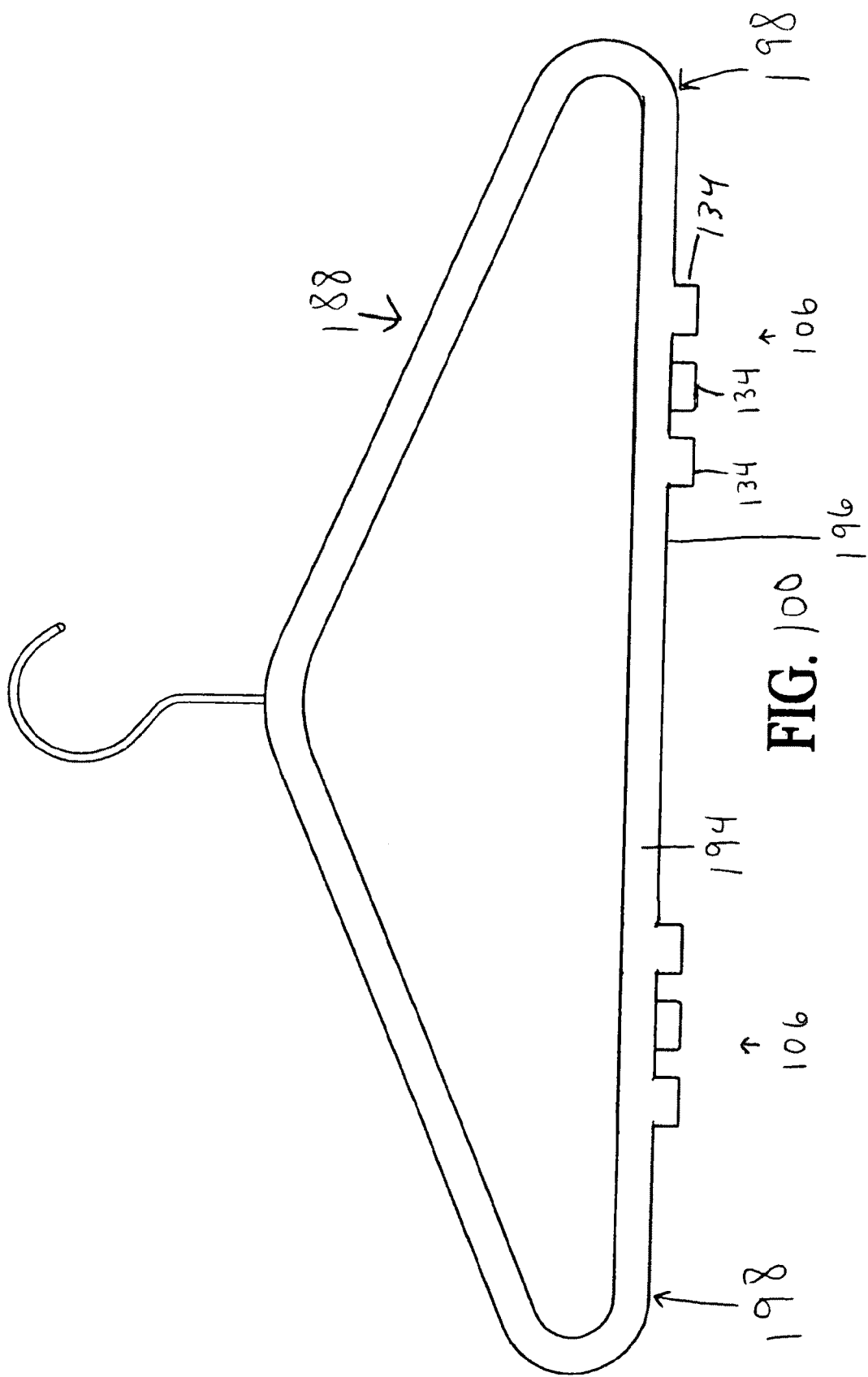
FIG. 100 is a view of prong embodiments on a hanger;
Design Drawings.

Referring now to FIGS. 1A-100, embodiments of scented holding device systems 100, and attacher systems 100*a* that include attachment piece systems and attachment piece part systems, devices that are used in the systems and hangers are exemplarily illustrated. Although the invention has been exemplarily illustrated by reference to specific embodiments, it will be apparent to those of ordinary skill in the art that various changes and modifications may be made which clearly fall within the scope of the invention. The invention is intended to be protected broadly within the spirit and scope of the appended claims.

It is to be understood that the term "readily" as used herein is intended to mean within between zero seconds and sixty seconds, preferable between zero seconds and five seconds, and more preferably between zero seconds and one second. It is to be further understood that between zero seconds and one second is further to be defined as being immediately.

As exemplarily illustrated in FIGS. including but not limited to FIGS. 9, 10, 16-22, 27, 47-51, 79, 92, 93A and 100, the holding device 102 may be any device that functions to hold at least one other item and that is large enough to which a user can attach at least one fragrance piece 104 to it without requiring the use of one or more tools. A number of different holding devices 102 are exemplarily illustrated in these FIGS., however it is to be understood that any device currently known or to be discovered in the art that holds at least one other item and that is large enough for the attachment and removal of at least one fragrance piece 104 without requiring the aid of one or more tools can be used, including, but not limited to, the following: clothes hangers 188, cabinets, drawers, storage bags, storage boxes or containers, jewelry boxes, garbage receptacles, garbage cans, waste basket, garbage bags, hampers, tote bags, back packs, luggage, luggage bags, boxes, car organizer bags, shoe racks, garment bags, shoe bags, hanging shoe bags, sweater bags, hanging sweater or shirt bags, sports bags, automobiles, automobile organizer bags, sectional or compartmental bag, hanging sectional or compartmental bag, automobile transport bags, including automobile transport bags in the shape of a box with or without a lid, which are often used for the transport of sports equipment. These items could be made of materials currently known or to be discovered, including but not limited to, plastic, metal, wood, fabric, fiberglass, vinyl, polyester, nylon, rubber, natural fibers such as cotton, and/or other fibers.

Without intending to be limiting, commonly known hanging bags can hang from one or more hook, or a one or two piece fabric and/or Velcro® band that can loop around a horizontal pole, the fabric can be attached to the bag via a metal screw or nail and cardboard, and can be attached around the pole with the use of the Velcro® or snaps.

Referring now to exemplary FIGS. including but not limited to FIGS. 2-8, the scented holding device system 100 includes at least one fragrance piece 104 that can be of a variety of sizes and shapes. In some embodiments, the fragrance piece 104 is elongated such that it is longer than it is wide, or vice versa, and, as exemplarily illustrated in FIGS. 2 and 5-8, in some of those embodiments, preferably the fragrance piece 104 will be generally cylindrical, as there will be no edges to snag on items being held in the holding device 102, and little or no wear and tear on the attacher 106 will be caused by fragrance piece 104 edges when it is attached with and removed from the holding device 102. Also, a generally cylindrically-shaped fragrance piece 104 may be easier than some other shaped pieces to attach with and remove from the attacher 106 on the holding device 102. The ends 108 of the fragrance piece 104 may be of any shape, such as but not limited to, rounded, pointed or squared-off, however, rounded, such as but not limited to those exemplarily illustrated in FIGS. 2 and 5-8 is preferable to ends 108 with sharp edges, as there will be less chance of the end 108 snagging items being held by the holding device 102.

Referring now to FIGS. 125, 126, 129, 132,133, 135, 136, 137, 138,139, and 143, in some embodiments, a fragrance piece 104 can be elongated with a middle portion 236 and two end portions 238. The end portions 238 can be in a variety of shapes. As seen in FIGS. 125, 126, 129, 133, 135, 136, 137, 138, 139, and 143, in some embodiments, at least one end portion 238 of the fragrance piece 104 can have a cut-out portion 240 where the height of the of the end portion of the fragrance piece is not as high as the middle portion section of the fragrance piece. (The term "height" refers to the dimension from top to bottom of the fragrance piece measured in the orientation that the fragrance piece would be found if the fragrance piece were attached to the holding device in normal use. By way of example, and without intending to be limiting, the height would be the top to bottom measurement of the fragrance piece inserted in a clothes hanger when the hanger is held in the orientation in which it would be found if hanging in a closet.) In addition in some embodiments at least one notch 242 can be cut out of the end portion. In some embodiments, at least one tab 244 can be included at the end portion. In some embodiments, at least one taller portion 254 included at the end portion It is to be understood that the addition of at least one cut-out portion 240, at least one tab 244, at least one taller portion 254 and/or at least one notch 242 on at least one end portion 238 can be configured in a variety of ways.

In some embodiments, the transition area 248 from the middle portion to the cut-out portion creates a step down 246, which herein will be called a "riser" 246 in the fragrance piece. In some embodiments, the riser 246 will be generally perpendicular or generally diagonal to the length of the fragrance piece 104.

Figure 126:
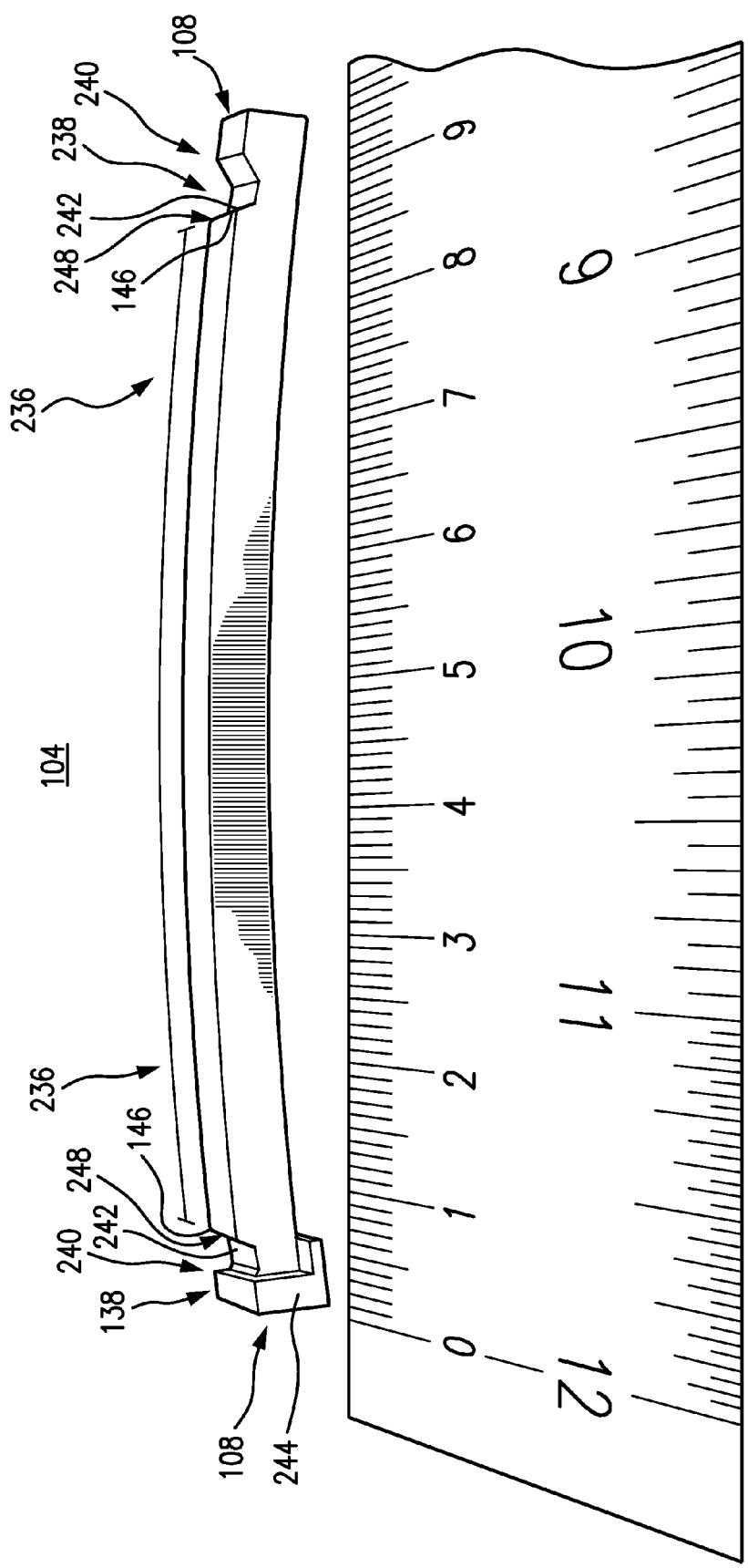
FIG. 126 is a view of an embodiment of a fragrance piece showing its length.
Figure 127A:
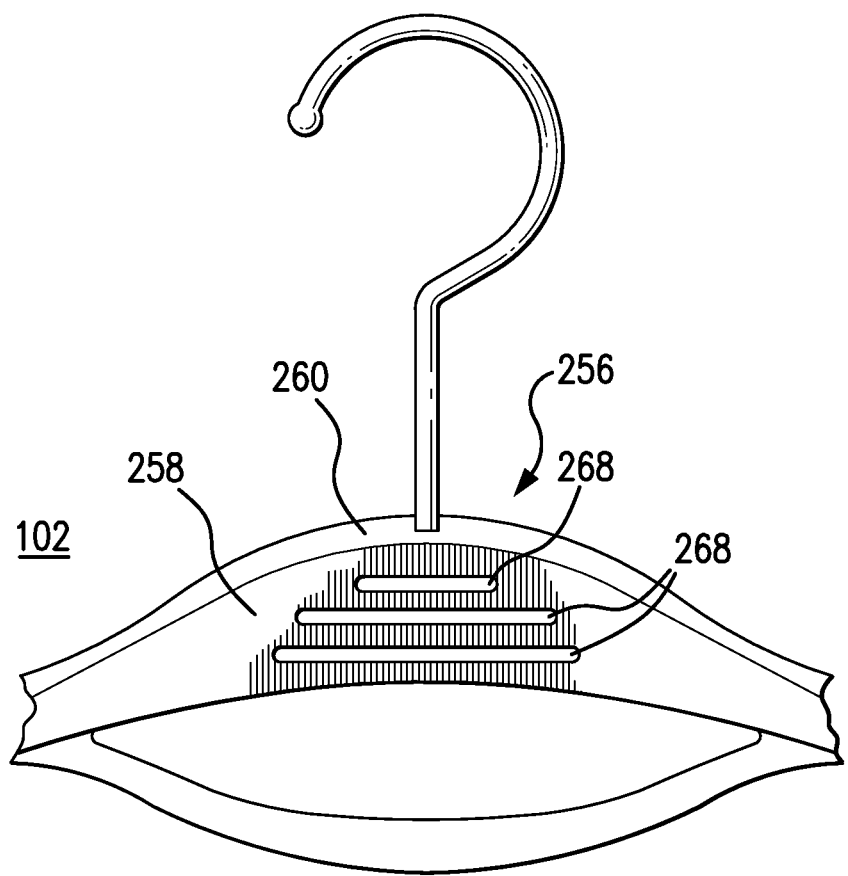
FIG. 127A is a partial view of a hanger.
Figure 128:
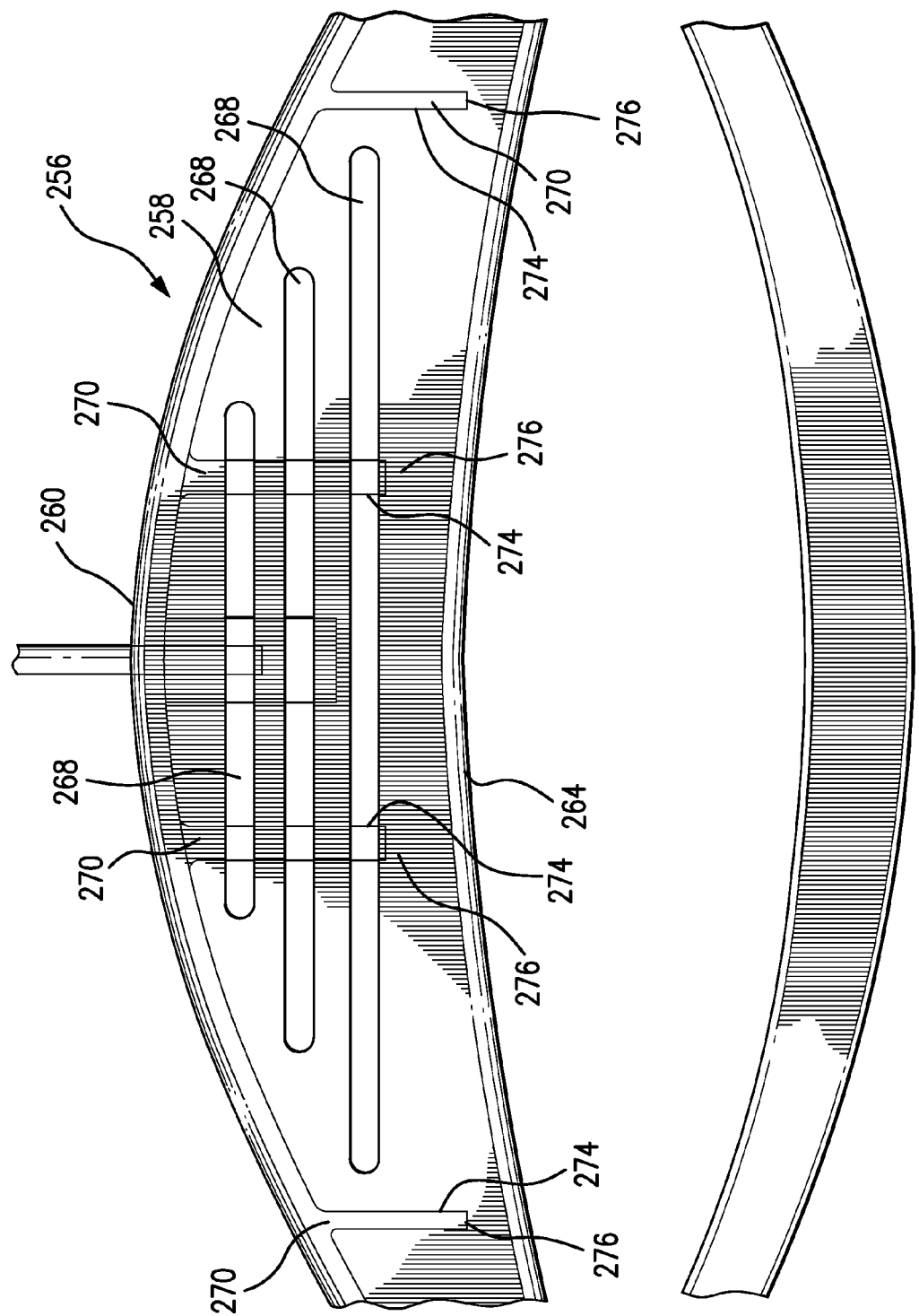
FIG. 128 is a view of a top end of a hanger along with some other hanger sections
Figure 129:
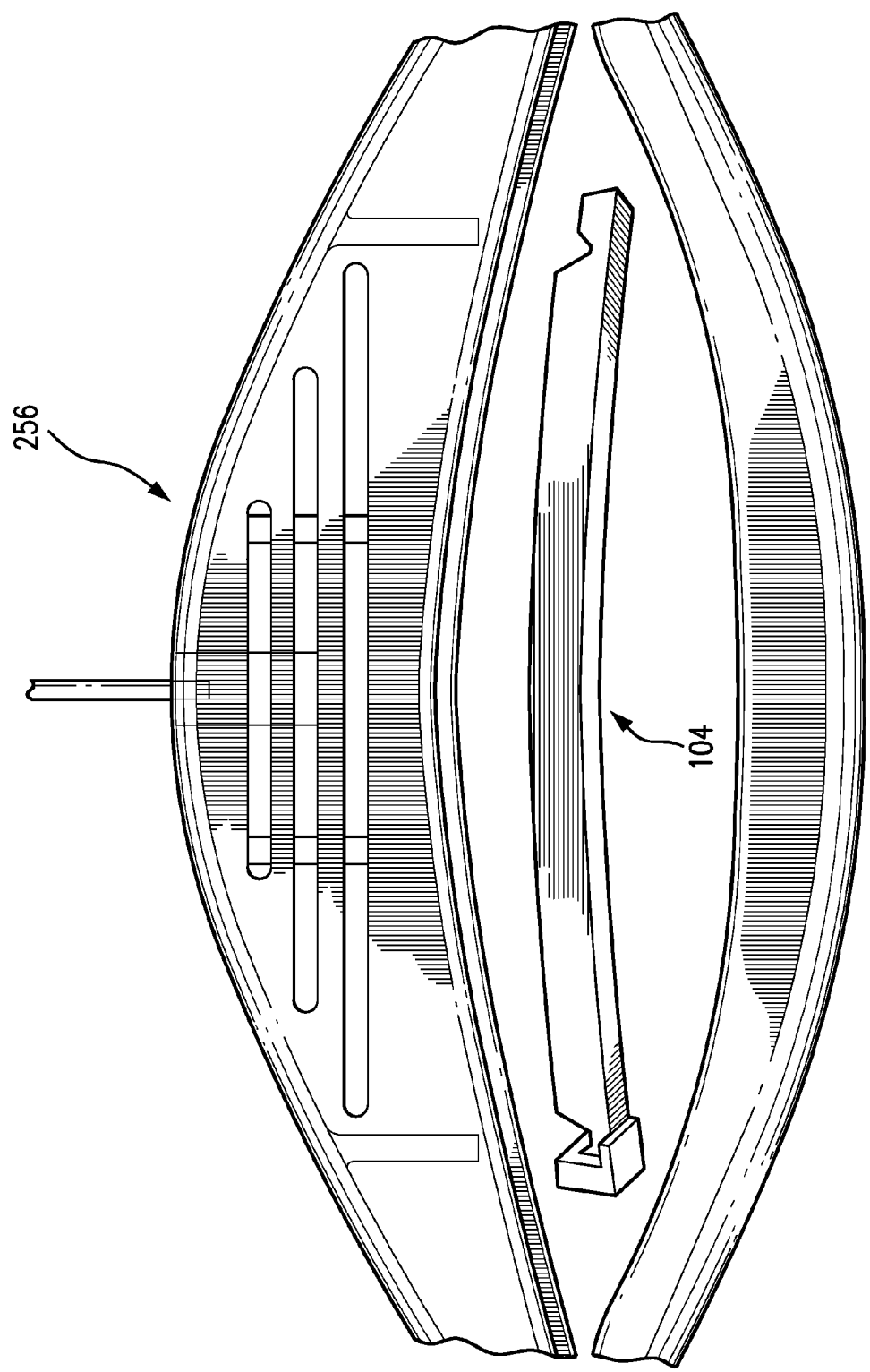
FIG. 129 is a view of an embodiment the top end of a hanger along with some other hanger sections illustrated in FIG. 128, and the fragrance piece illustrated in FIG. 126.
Figure 130:
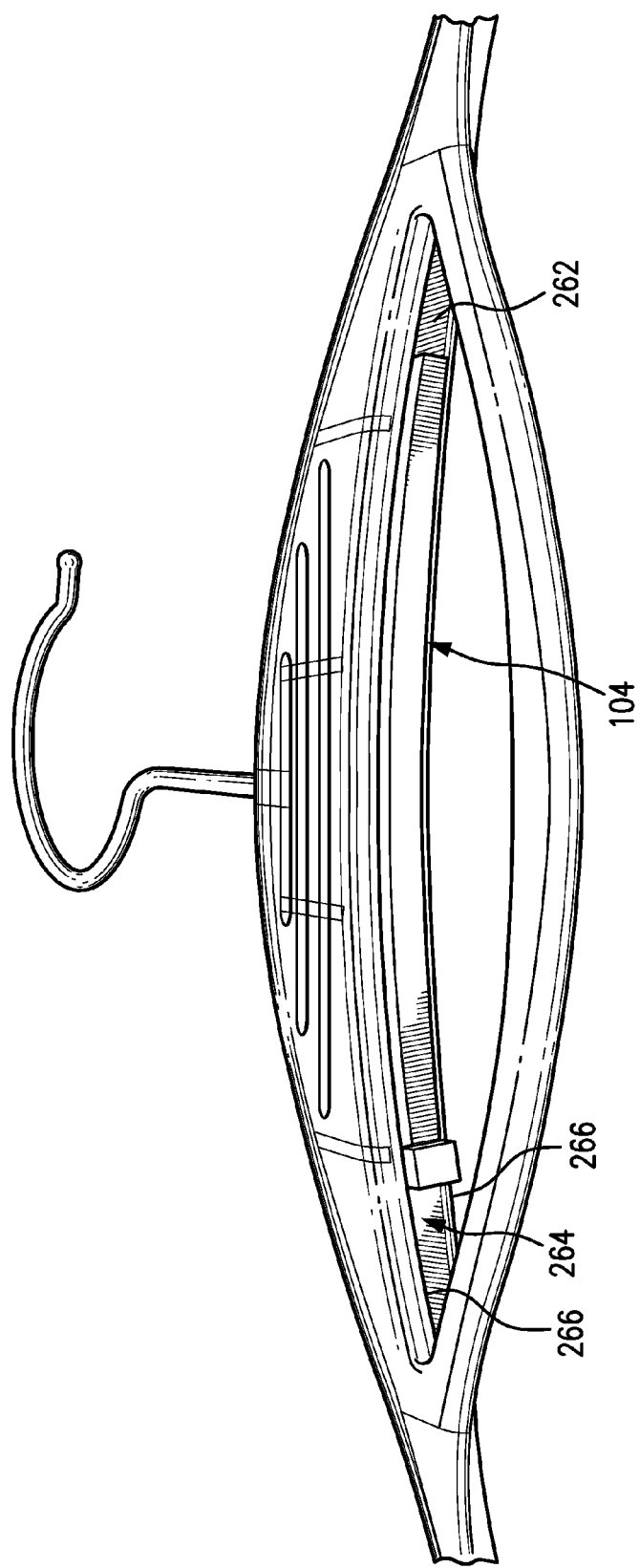
FIG. 130 is a view of an embodiment the top end of a hanger along with some other hanger sections illustrated in FIG. 128, and the fragrance piece illustrated in FIG. 126, with the fragrance piece inserted into the cavity of the top end of the hanger.
Figure 131:
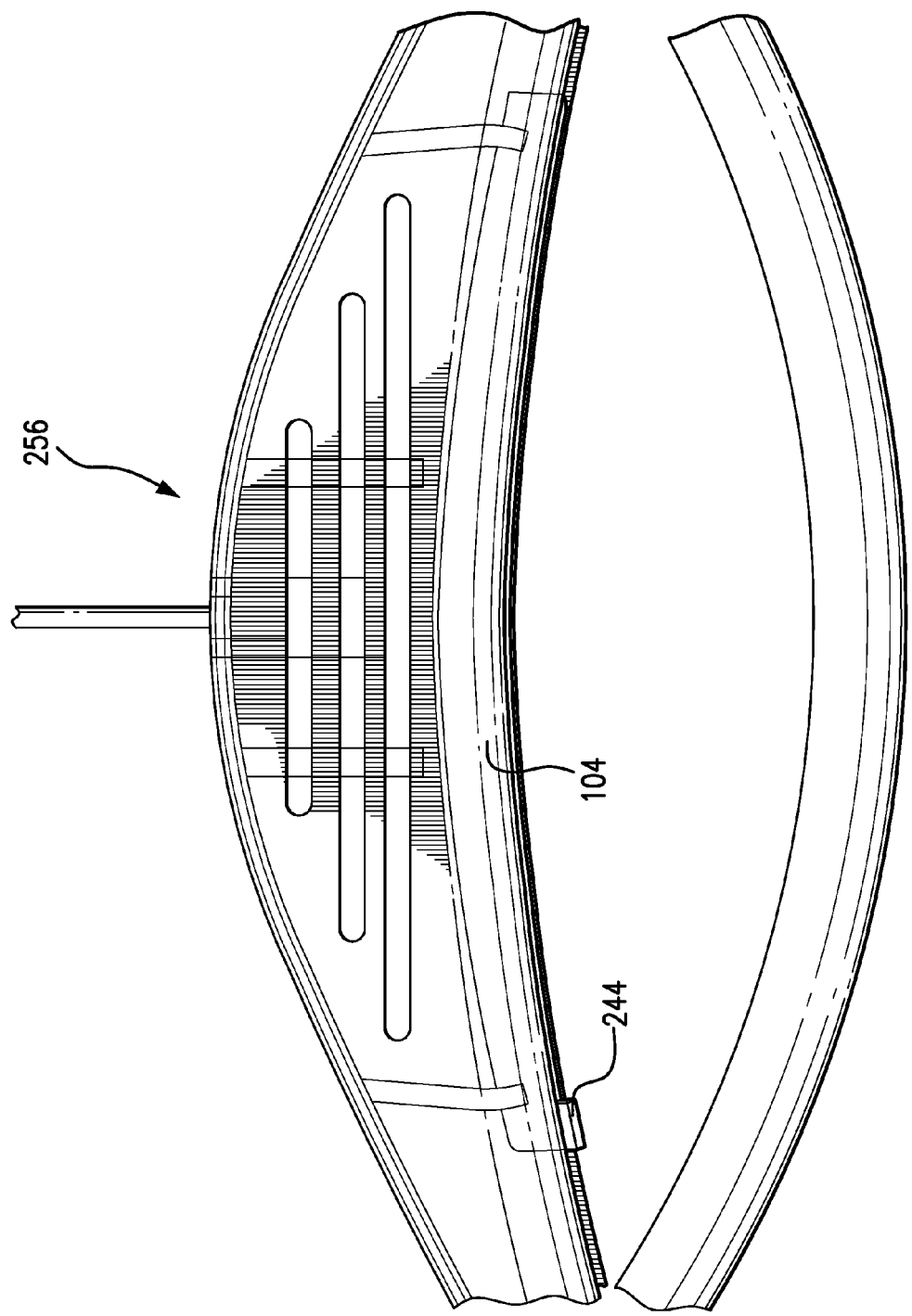
Figure 132:
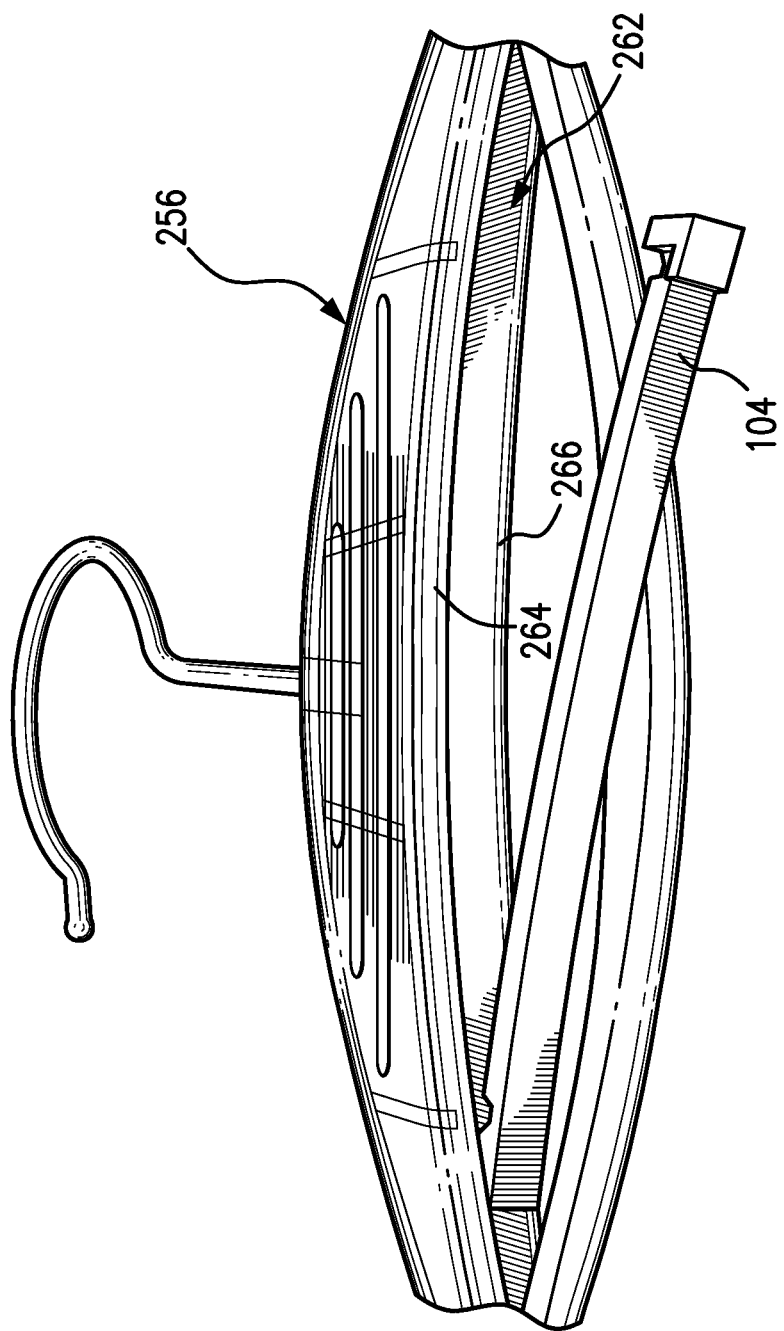

Specific reference is now made to FIGS. 126, 129, and 132. In this embodiment, one end portion 238 has a cut-out portion 240 and a notch 242 and the other end portion 238 has a cut-out portion 240, a notch 242 and a tab 244. Both transition areas in this embodiment include risers 246 that are generally diagonal to the length of the fragrance piece. In some further embodiments of this type of embodiment of fragrance piece the length of the fragrance piece is about 9.2 mm long.

Figure 125:
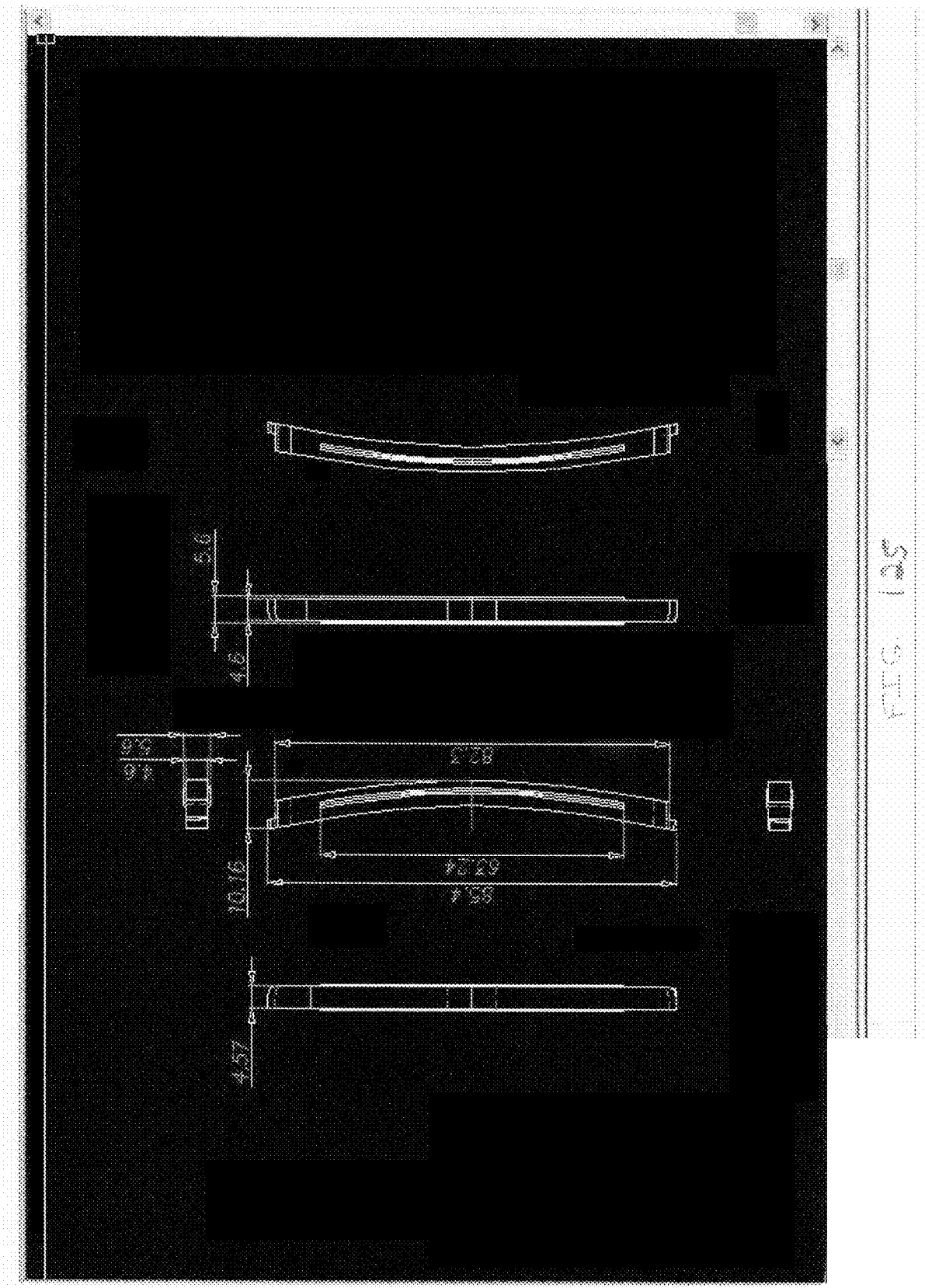
FIG. 125 is a variety of views of an embodiment of a fragrance piece. The left view is a view from the bottom of the fragrance piece; the second view from the left is a side view of the fragrance piece; the third view from the left is a view of the top of the fragrance piece; and the view to the right is a side view of the fragrance piece.

Specific reference is now made to FIG. 125. In this embodiment, one end portion has a cut-out portion 240 and the other end portion has a cut-out portion and a tab. Both transition areas in this embodiment include risers 246 that are generally perpendicular to the length of the fragrance piece 104. Referring specifically to FIG. 125, some further embodiments of this type of embodiment of a fragrance piece, have the following dimensions: 4.57 mm a the width of the fragrance piece 104 as measured from the bottom; 85.4 mm is the total length of the fragrance piece; 63.24 mm is the length of a projecting ridge 272 along the side of the fragrance piece; 82.3 mm is the top length of the middle portion 236 of the fragrance piece; 10.16 mm is the measurement of the top center part of an arched fragrance piece to the lowest point of depth from top to bottom; 4.6 mm is the width of the fragrance piece without the projecting ridges 272 measured; 5.6 mm is the width of the fragrance piece including the projecting ridges 272.

Figure 133:
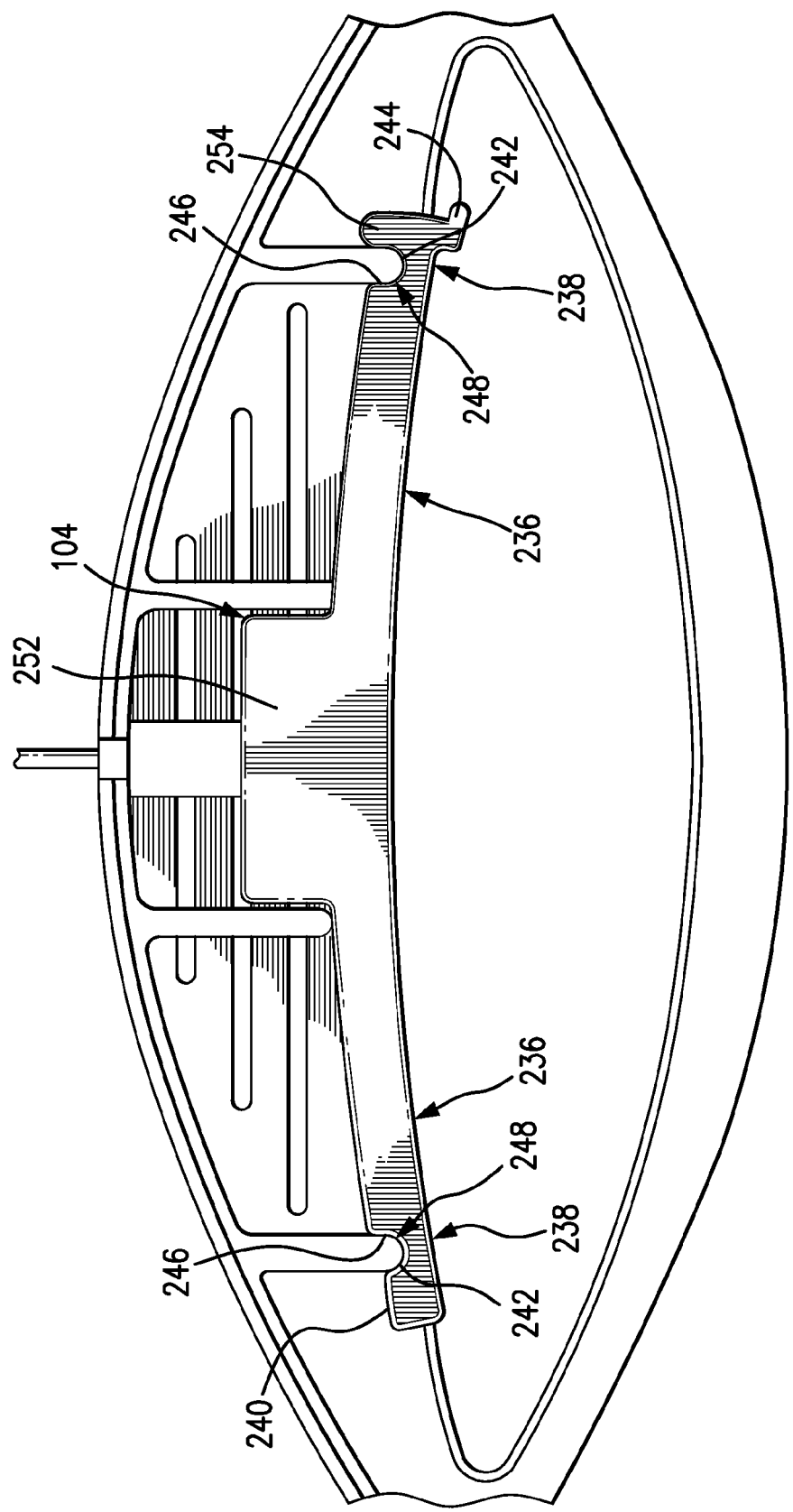

Reference is now made to FIG. 133, which exemplarily illustrates another embodiment of a fragrance piece. In this embodiment, a portion of the middle portion 236 of the fragrance piece can have a heightened area 252. The heightened area 252 can be of various sizes and shapes. The heightened area 252 exemplarily illustrated in FIG. has a generally rectangular shape. In addition, in this embodiment, one end portion 238 has a slight cut-out portion 240 and a notch 242 and the other end portion 238 has a notch 242 and a tab 244, and a taller portion 254 above the tab 244. Both transition areas in this embodiment that lead to the notches 242 include risers 246 that are generally diagonal to the length of the fragrance piece. It is to be understood, however, that a variety of end portions 238, cut-out portions 240, notches, 242, tabs 244, risers 246 transition areas 248 and/or taller portions 254 could be used with a fragrance piece 104 having a heightened area 252.

The fragrance piece can be made of any shape. Each fragrance piece 104 has an outer surface 110, which is the surface that can interact with the attacher 106 when the fragrance piece 104 is attached. At least a part of the outer surface 110 of the fragrance piece 104 will be made of any material currently known or to be discovered in the art that may be attached with a fragrance piece, or formed into a fragrance piece, and that either emits a fragrance and/or neutralizes the odors in the surrounding area.

It is to be understood that the terms "fragrance", "odor" or "scent" as used herein can include, but are not limited to, natural, synthetic, or a combination of natural and synthetic aroma chemicals. Further, the terms "fragrance", "odor" and "scent" as used herein, are intended to include a mixture of aroma chemicals. The term "natural aroma derivatives" is intended to include essential oils.

Some embodiments of the scented holding device system and fragrance piece in the current invention use natural aroma derivatives including but not limiting to cedar, lavender, rose, and synthetic aromas.

It is intended that at least a part of the outer surface 110 of the fragrance piece 104, and in some embodiments, the entire fragrance piece 104, will be made of materials known in the art or to be discovered that emit a fragrance and/or neutralize the fragrances and/or odors in the surrounding area, including but not limited to, general plastics, polymers, polyolefins, thermal plastic polymers and copolymers, under polyolefins, including but not limited to polypropylene (PP), LDPE, LLDPE, HDPE, under thermal plastic polymers, including but not limited to polycarbonate (PC), PVC, thermal plastic elastomers (TPE), under TPE including but not limited to TPS, under copolymers, including but not limited to Elvaloy and EVA (ethyl vinyl acetate) and green resins. In addition, polystyrene could be used particularly if its fragrance holding and/or emitting properties are enhanced.

The preferred fragrance load of an embodied fragrance piece is 1% or higher using the above-mentioned materials, including but not limited to general plastics, polymers, polyolefins, including but not limited to PP, LDPE, LLDPE, HDPE, thermal plastic polymers, including but not limited to PC, PVC, TPE, TPS, copolymers including but not limited to EVA and Elvaloy.

Any fragrance may be emitted by the fragrance piece 104. It is to be understood that the number of possible fragrances currently known or to be discovered is vast. Without intending to be limiting, scents among the vast varieties of possible fragrances that may be used include, but are not limited to, the following: lavender, rose, cedar, fresh linen, fresh cotton, vanilla and citrus. In addition, fragrances of perfumes currently known or to be discovered can be included.

Fragrances may be used for a variety or reasons, including, but not limited to the following: emitting a pleasant scent, emitting a scent that will compete with or replace a surrounding scent or odor, emitting a scent that will refresh the surrounding area, and/or emitting a scent that will neutralize the surrounding area. It is to be understood therefore that it is intended that fragrances included in the current invention may be of any odor that is generally considered by the user to be very pleasant, very unpleasant or anywhere in between.

Reference is now made to exemplarily illustrated FIGS. including but not limited to FIGS. 1A, 9-13, 15-22, 28, 29, 40, 47-51, 60, 66, 69, 78, 79, 84, 92 and 100. The at least one fragrance piece 104 is removably attachable with a holding device 102 by at least one attacher 106. The requirement that the at least one fragrance piece 104 is removably attachable with a holding device 102 by at least one attacher 106 is identified herein as the "required attachment parameter". The attacher 106 may be integral with the holding device 102 or it may be at least one separate piece that is fixedly or removably attached with the holding device 102.

In some embodiments, the fragrance piece 104 is removably attachable with the holding device 102 by at least one attacher 106 in a manner that in some embodiments can provide convenience, and will be identified as the "removal attachment parameters,"

defined as follows: when the attacher 106 is attached with the holding device 102, the fragrance piece 104 may be attached with and removed from the attacher 106 without requiring the removal of any part of the attacher 106 from the holding device 102. It is to be understood however, that when the attacher 106 is attached with the holding device 102 the parameter that the fragrance piece 104 may be attached with and removed from the attacher 106 without requiring the removal of any part of the attacher 106 from the holding device 102, does not mean that the attacher 106, or any part thereof, cannot be removed or may not be removed from the holding device 102 to attach or remove the fragrance piece 104, rather the requirement means that removal of any part of the attacher 106 from the holding device 102 is not required for the attachment or removal of the fragrance piece 104.

In some preferred embodiments, the fragrance piece 104 is removably attachable with the holding device 102 by at least one attacher 106 in a manner that will be identified as the "preferred attachment parameters," defined as follows: the fragrance piece 104 is removably attachable with the holding device 102 by at least one attacher 106 in a manner whereby when the fragrance piece 104 is attached with the holding device, 102 it is sufficiently snug that the fragrance piece 104 will remain attached and will not readily become unattached due to gravity if the holding device 102 is turned in any direction, however at the same time it is not so snuggly attached that one or more tools must be used to attach the fragrance piece 104 with or remove the fragrance piece 104 from the attacher 106.

In some more preferred embodiments, the fragrance piece 104 is removably attachable with the holding device 102 by at least one attacher 106 in a manner that will be identified as the "more preferred attachment parameters," defined as follows: the fragrance piece 104 is removably attachable with the holding device 102 by at least one attacher 106 in a manner whereby when the fragrance piece 104 is attached with the holding device, 102 it is sufficiently snug that the fragrance piece 104 will remain attached and will not readily become unattached due to gravity if the holding device 102 is turned in any direction, however at the same time it is not so snuggly attached that one or more tools or more than a moderate amount of force from an ordinary user must be used to attach the fragrance piece 104 with or remove the fragrance piece 104 from the attacher 106.

In some embodiments, the fragrance piece 104 is removably attachable with the holding device 102 by at least one attacher 106 in a manner that will be identified as the "removal and fit attachment parameters," defined as follows: the fragrance piece 104 is removably attachable with the holding device 102 by at least one attacher 106 in a manner in which: 1) when the attacher 106 is attached with the holding device 102, the fragrance piece 104 may be attached and removed from the attacher 106 without requiring the removal of any part of the attacher 106 from the holding device 102; and 2) the fragrance piece 104 is removably attachable with the holding device 102 in a manner whereby when the fragrance piece 104 is attached it is sufficiently snug that the fragrance piece 104 will remain attached and will not readily become unattached due to gravity if the holding device 102 is turned in any direction, however at the same time it is not so snuggly attached that one or more tools must be used to attach the fragrance piece 104 with or remove the fragrance piece 104 from the attacher 106. It is to be understood however, that within this definition, when the attacher 106 is attached with the holding device 102 the parameter that the fragrance piece 104 may be attached with and removed from the attacher 106 without requiring the removal of any part of the attacher 106 from the holding device 102, does not mean that the attacher 106, or any part thereof, cannot be removed or may not be removed from the holding device 102 to attach or remove that fragrance piece 104, rather the requirement means that removal of any part of the attacher 106 from the holding device 102 is not required for the attachment or removal of the fragrance piece 104.

In some embodiments, the fragrance piece 104 is removably attachable with the holding device 102 by at least one attacher 106 in a manner that will be identified as the "preferred removal and fit attachment parameters," defined as follows: the fragrance piece 104 is removably attachable with the holding device 102 by at least one attacher 106 in a manner in which: 1) when the attacher 106 is attached with the holding device 102, the fragrance piece 104 may be attached and removed from the attacher 106 without requiring the removal of any part of the attacher 106 from the holding device 102; and 2) the fragrance piece 104 is removably attachable with the holding device 102 in a manner whereby when the fragrance piece 104 is attached it is sufficiently snug that the fragrance piece 104 will remain attached and will not readily become unattached due to gravity if the holding device 102 is turned in any direction, however at the same time it is not so snuggly attached that one or more tools or more than a moderate amount of force from an ordinary user must be used to attach the fragrance piece 104 with or remove the fragrance piece 104 from the attacher 106. It is to be understood however, that within this definition, when the attacher 106 is attached with the holding device 102 the parameter that the fragrance piece 104 may be attached with and removed from the attacher 106 without requiring the removal of any part of the attacher 106 from the holding device 102, does not mean that the attacher 106, or any part thereof, cannot be removed or may not be removed from the holding device 102 to attach or remove that fragrance piece 104, rather the requirement means that removal of any part of the attacher 106 from the holding device 102 is not required for the attachment or removal of the fragrance piece 104.

In some embodiments, as exemplarily illustrated in FIGS. including but not limited to FIGS. 1A, 14, 15-17, 25-27, 30, 40, 42-45, 47-51, 59-70, 85-91, each attacher 106 may include one or more attachment pieces 112 that is or are integrally integrated with, and/or fixedly or removably attached or attachable with the holding device 102. Referring now to exemplary FIGS. 14 and 15, each attachment piece 112 may made up of more than one part, referred to as "attachment piece parts 114," that are compatible with and interact with each other, and that are attached, or are fixedly or removably attached or attachable with at least one other attachment piece part 114. Thereby, the at least one fragrance piece 104 may be removably attachable with a holding device 102 within the required attachment parameters, and in some embodiments also within the removal attachment parameters, the preferred attachment parameters, the more preferred attachment parameters, the removal and fit attachment parameters and/or the preferred removal and fit attachment parameters, with an attacher 106 that includes the attachment of the at least two attachment piece parts 114 with each other. It is to be understood that any number of attachment piece parts 114 may be attached or attachable with each other as long as at least one fragrance piece 104 is attachable with the holding device 102 within the required attachment parameters, and in some embodiments also within the removal attachment parameters, the preferred attachment parameters, the more preferred attachment parameters, the removal and fit parameters and/or the preferred removal and fit attachment parameters.

It is to be understood that in some embodiments, a single attachment piece 112 can in some embodiments be an attacher 106 without the requirement of the use of one or more attachment piece parts 114, and in some embodiments if the attachment piece 112 requires the addition of one or more attachment piece parts 114 to attach the at least one fragrance piece 104 with the holding device 102, the attachment piece 112 also can be an attachment piece part 114. For example, and without intending to be limiting, a loop 152 made of two-sided hook and loop material 178 such as the loop exemplarily illustrated in FIG. 70, could be attached directly with a holding device that is at least partially made of hook and loop material. In another embodiment, to attached the same loop 152 made of two-sided hook and loop material 178 that is exemplarily illustrated in FIG. 70 to a holding device that is not at least partially made of hook and loop material, an attachment piece part 114, such as the piece of hook and loop material 178 that is exemplarily illustrated in FIG. 86 or in FIG. 27, also would have to be attached with the holding device 102.

In some embodiments, the at least one fragrance piece 104 is removably attachable within the required attachment parameters with the holding device 102 with an integral attacher 106 and/or with an attacher that includes at least one attachment piece 112 or attachment piece part 114.

In some embodiments, the at least one fragrance piece 104 is removably attachable within the removal attachment parameters with the holding device 102 with an integral attacher 106 and/or with an attacher that includes at least one attachment piece 112 or attachment piece part 114.

In some embodiments, the at least one fragrance piece 104 is removably attachable within the preferred attachment parameters with the holding device 102 with an integral attacher 106 and/or with an attacher that includes at least one attachment piece 112 or attachment piece part 114.

In some embodiments, the at least one fragrance piece 104 is removably attachable within the more preferred attachment parameters with the holding device 102 with an integral attacher 106 and/or with an attacher that includes at least one attachment piece 112 or attachment piece part 114.

In some embodiments, the at least one fragrance piece 104 is removably attachable within the removal and fit attachment parameters with the holding device 102 with an integral attacher 106 and/or with an attacher that includes at least one attachment piece 112 or attachment piece part 114.

In some embodiments, the at least one fragrance piece 104 is removably attachable within the preferred removal and fit attachment parameters with the holding device 102 with an integral attacher 106 and/or with an attacher that includes at least one attachment piece 112 or attachment piece part 114.

As may be seen and/or understood in the illustrations and/or descriptions herein, in some embodiments, the at least one fragrance piece 104 is removably attachable by friction fit with the holding device 102 with an integral attacher 106 and/or with an attacher that includes at least one attachment piece 112 or attachment piece part 114.

Referring now to exemplary FIGS. including, but not limited to, FIGS. 1A-V, and 14-17, it is to be understood that in addition to being part of an embodiment of the fragrant holding device system 100, or attacher system 100a, including attachment piece systems and/or attachment piece part systems, each attachment piece 112 and/or attachment piece part 114 can be an attachment piece device. In addition, more than one attachment piece part 114 can be joined with at least one other attachment piece part 114 to comprise an attachment piece device and/or a part of an attacher system 100a, including an attachment piece system and/or attachment piece part system. By way of example, and without intending to be limiting, an attachment piece device may be at least one prong 134, loop 152, clip 162, adhesive 174, cavity 250 and/or piece of a material 128. Further, by way of example, and without intending to be limiting, a combination of at least one piece of a material 128 and at least one slot 116, prong 134, loop 152, clip 162, cavity 250 and/or adhesive 174, or a combination of at least one adhesive 174 and at least one slot 116, prong 134, loop 152, clip 162, cavity 250 and/or strip of a material 128 can create embodiments of attachment piece devices and/or systems.

Reference is now made to exemplary FIGS. including, but not limited to FIGS. 1A-27, which in addition to being viewed individually, may be viewed in conjunction with one another, that illustrate some exemplary embodiments of the fragrant holding devices, holding device systems 100, and embodiments of related attachers, attachment pieces, attachment piece parts, and attacher systems 100a, including attachment piece systems and/or attachment piece part systems; however, it is to be understood that the FIGS. exemplarily illustrated are intended to show some examples of embodiments of the devices and systems, and specifically are not intended to limit the interaction of the elements that may comprise a fragrant holding device, holding device system 100 or embodiments of a related attacher, attachment piece, attachment piece part, or attacher system 100a, including an attachment piece system and/or attachment piece part system. The descriptions and FIGS. described herein include embodiments for fragrant holding devices, holding device systems 100 and embodiments for related attachers, attachment pieces, attachment piece parts, and attacher systems 100a, including an attachment piece systems and/or attachment piece part systems, wherein the described fragrance pieces 104, attachers 106, attachment pieces 112 and/or attachment piece parts 114 are intended to be able to be used interchangeably.

Figures 2, 3, 4:
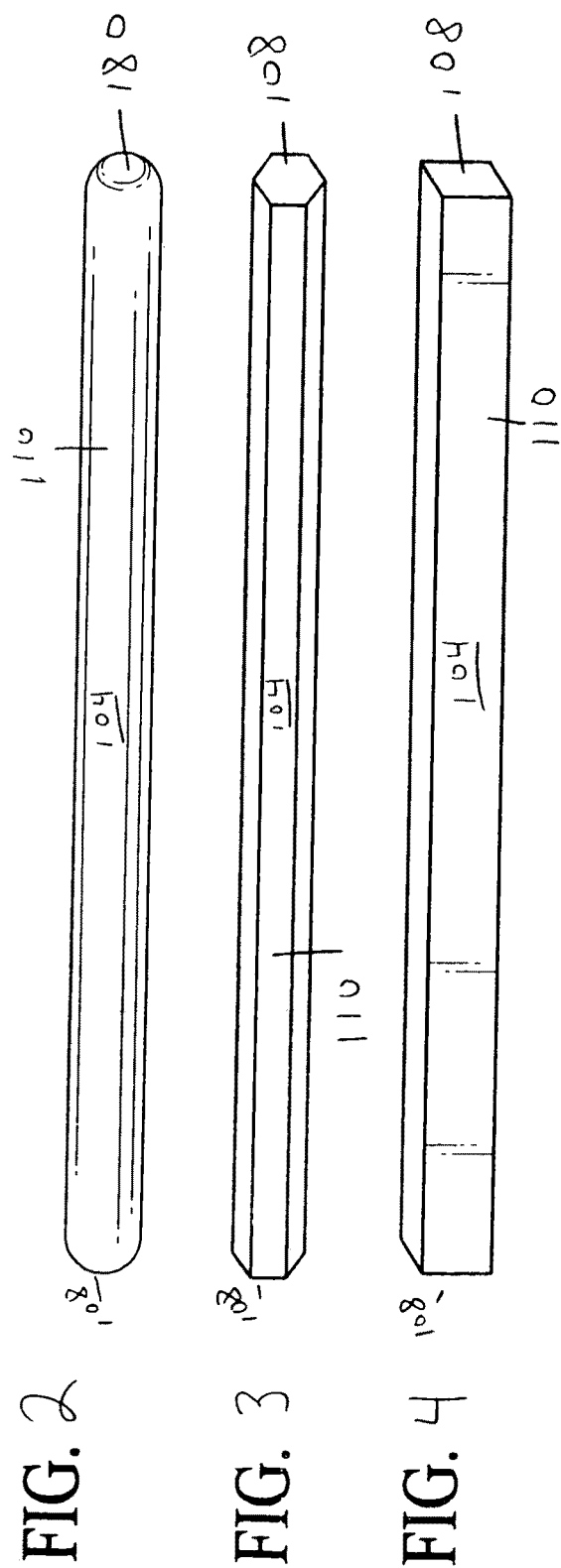
FIG. 2 is a view of a cylindrical fragrance piece with a rounded end.
FIG. 3 is a view of a six-sided fragrance piece with a hexagonal end.
FIG. 4 is a view of a rectangular fragrance piece with a square end.
Figure 10:
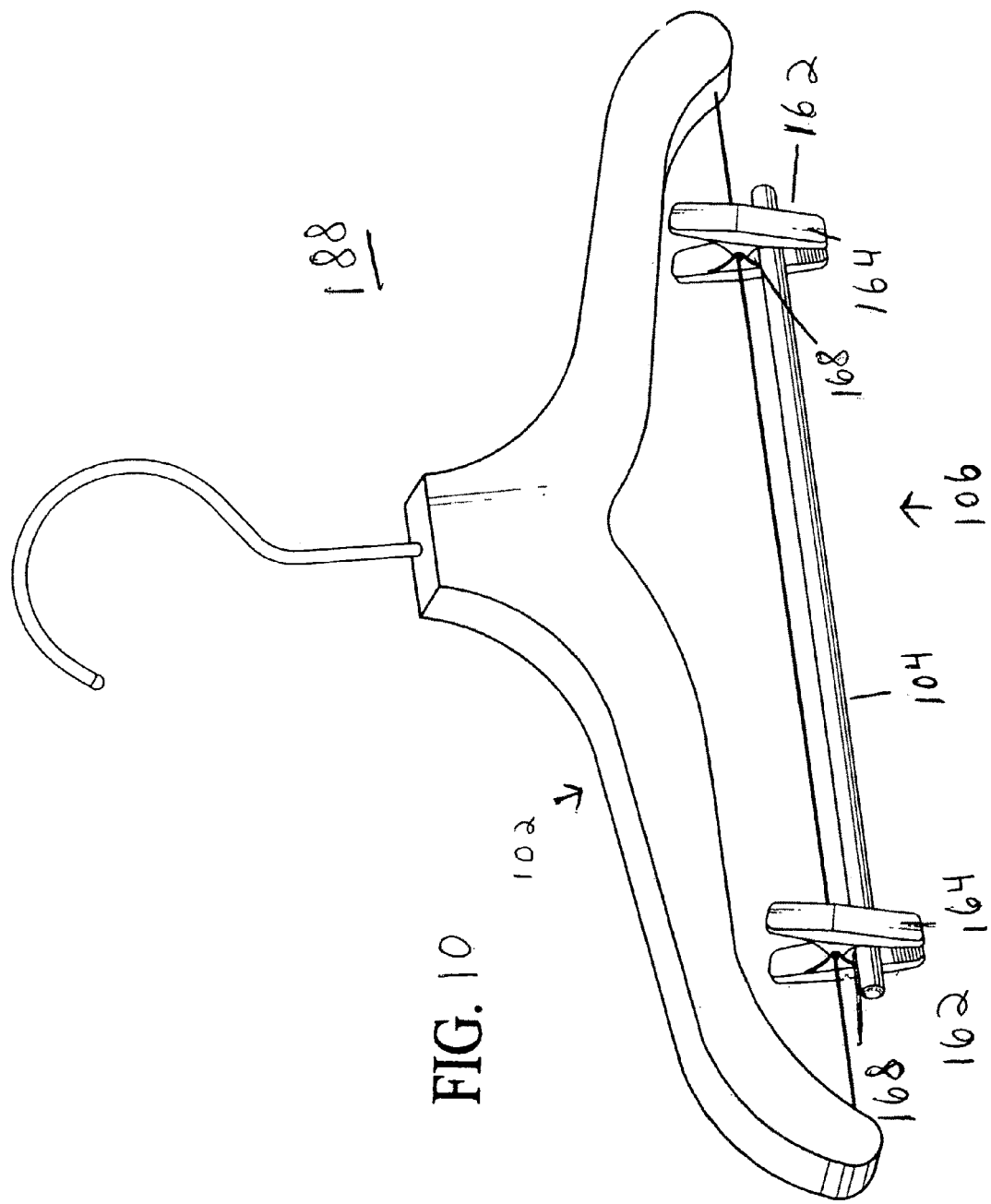
Figure 11:
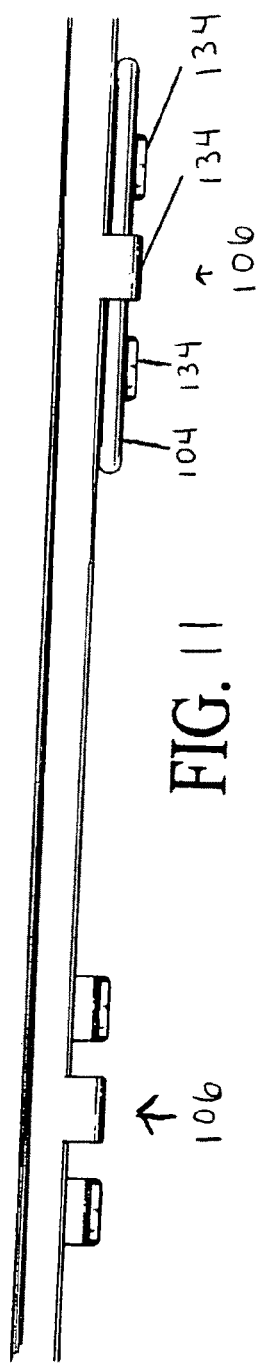
FIG. 11 is view of a fragrance piece attached with one set of prongs.
Figure 12:
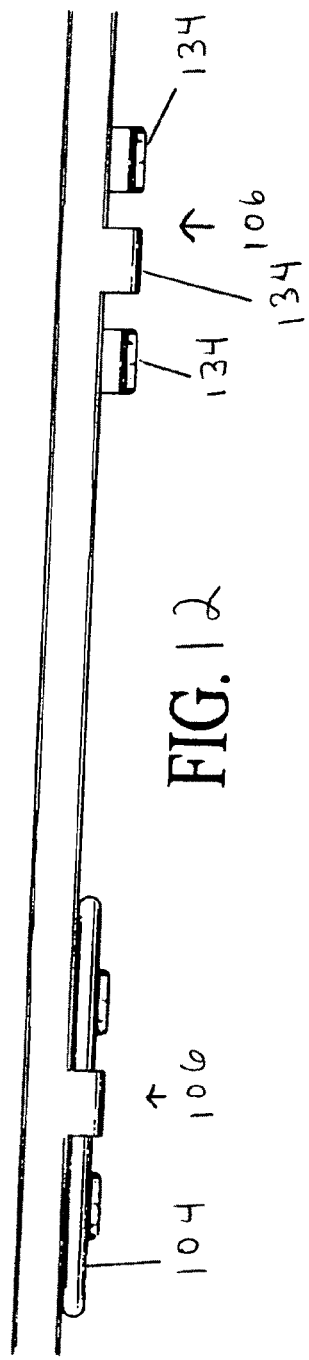
FIG. 12 is a view of a fragrance piece attached with one set of prongs.
Figure 13:
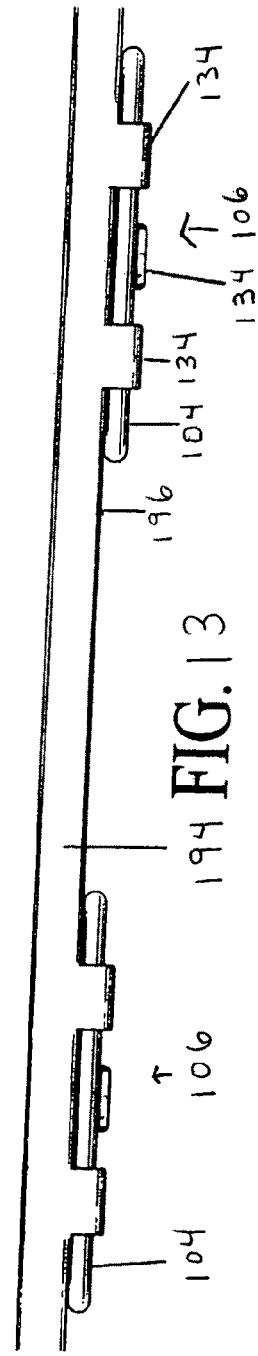
FIG. 13 is a view of two fragrance pieces, each attached with one set of prongs.
Figure 20:
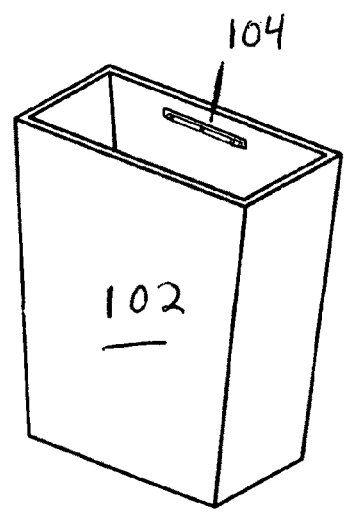
FIG. 20 is a view of waste basket with a fragrance piece attached with a loop and strip attacher with adhesive.
Figure 21:
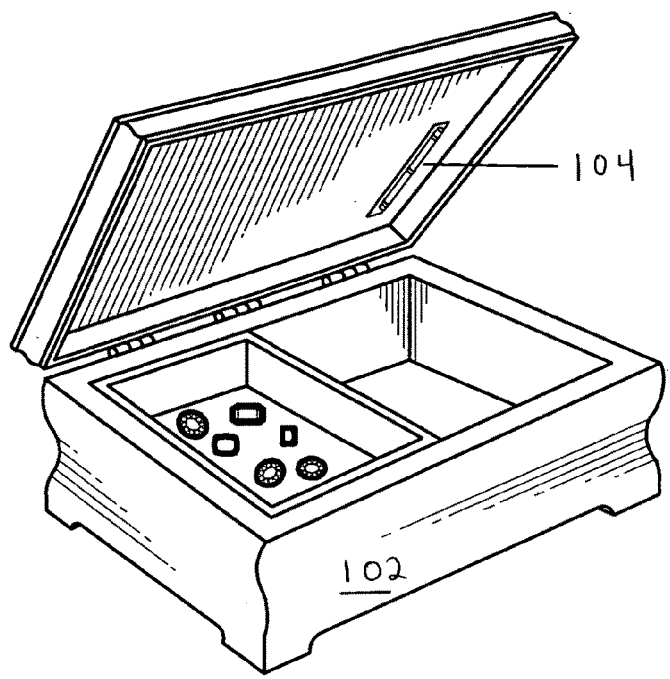
FIG. 21 is a view of jewelry box with a fragrance piece attached with a loop and strip attacher with adhesive.
Figure 22:
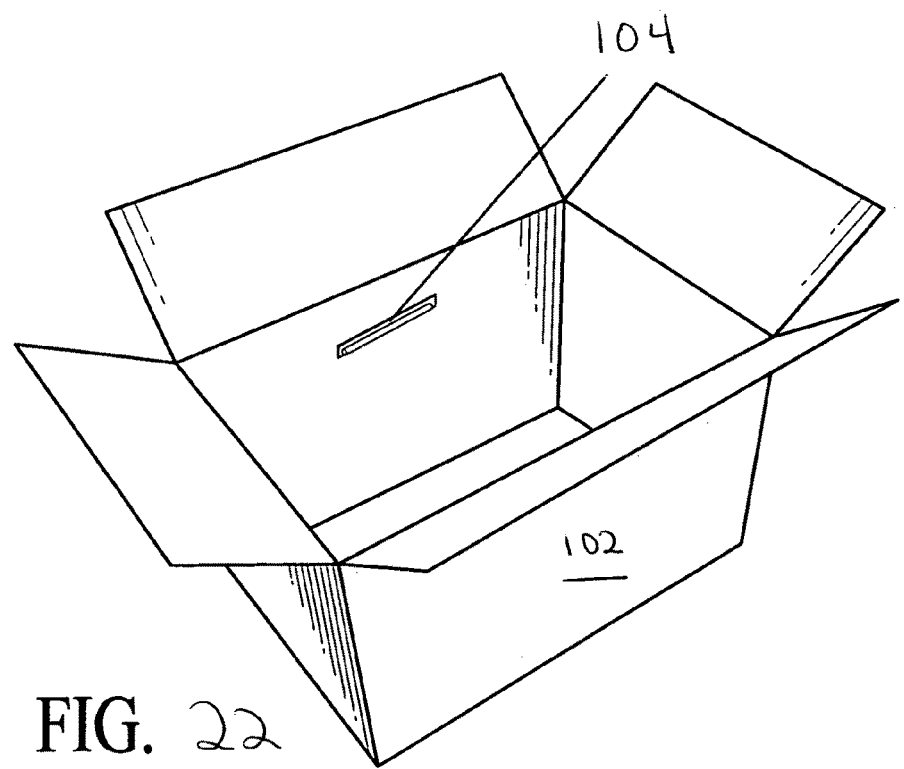
FIG. 22 is a view of box with a fragrance piece attached with an adhesive attacher.

Referring now to exemplary FIGS. including, but not limited to, FIGS. 1A, 1C-G, 2, 9, 11-13, 16-22, and 24 it is anticipated that in some embodiments a single fragrance piece 104, such as, but not limited to, the cylindrical fragrance piece 104 as exemplarily illustrated in FIG. 2, will be able to be used with a variety of attachers 106, attachment pieces 112, and/or attachment piece parts 114, such as, but not limited to, prongs 134 as exemplarily illustrated in FIGS. 11-13, 24, 40, 42-45, 47-51, 87, 88, 92, and 97A, clips 162 as exemplarily illustrated in FIGS. 9 and 18, loops 162 as exemplarily illustrated in FIGS. 16, 17, and 19-21, adhesive 174 as exemplarily illustrated in FIG. 22, cavities 250, and slots 116 as exemplarily illustrated in FIG. 18.

Figure 16:
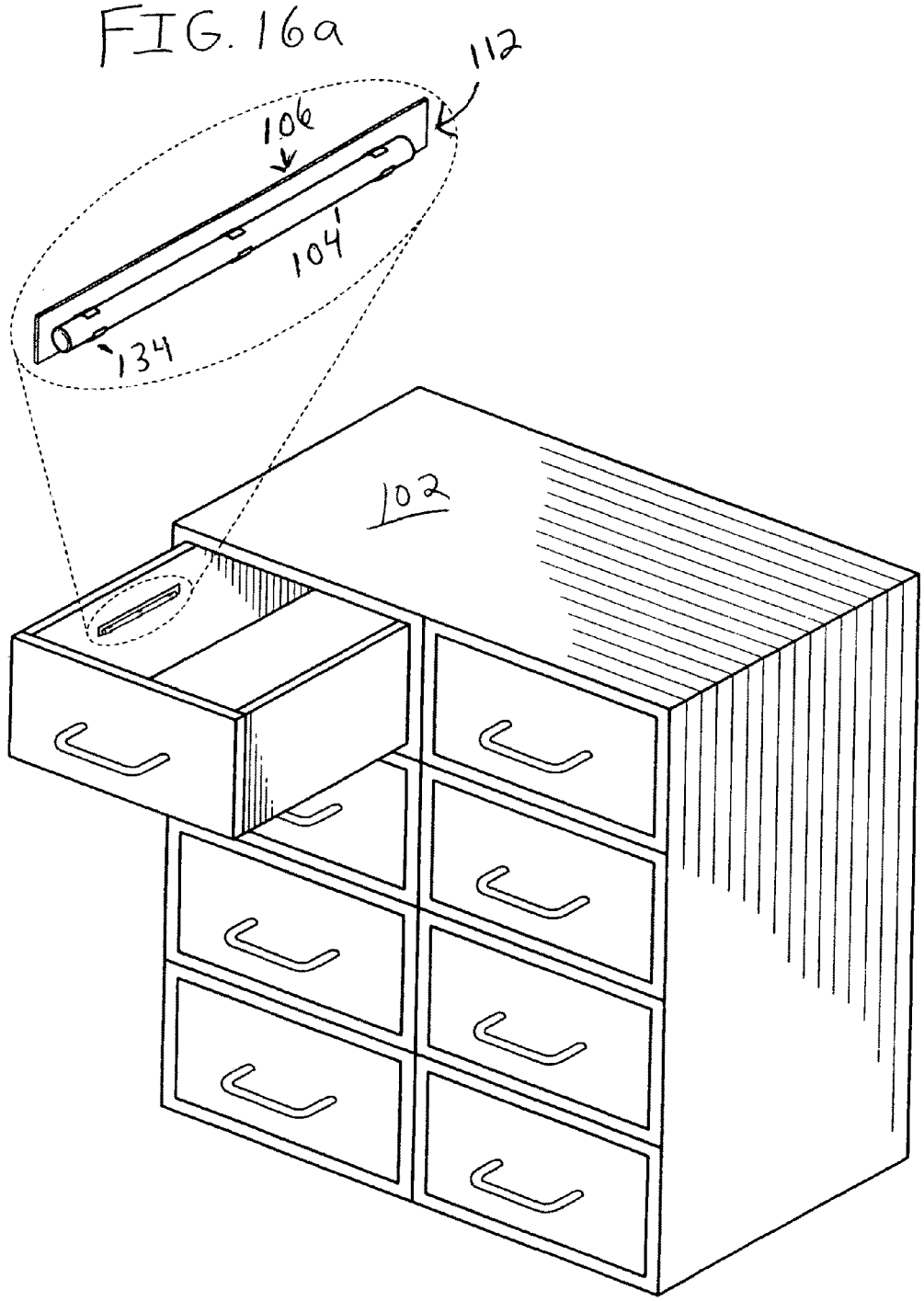
FIG. 16 is a view of a chest of drawers with a fragrance piece attached with a strip and prong attacher.
Figure 19:
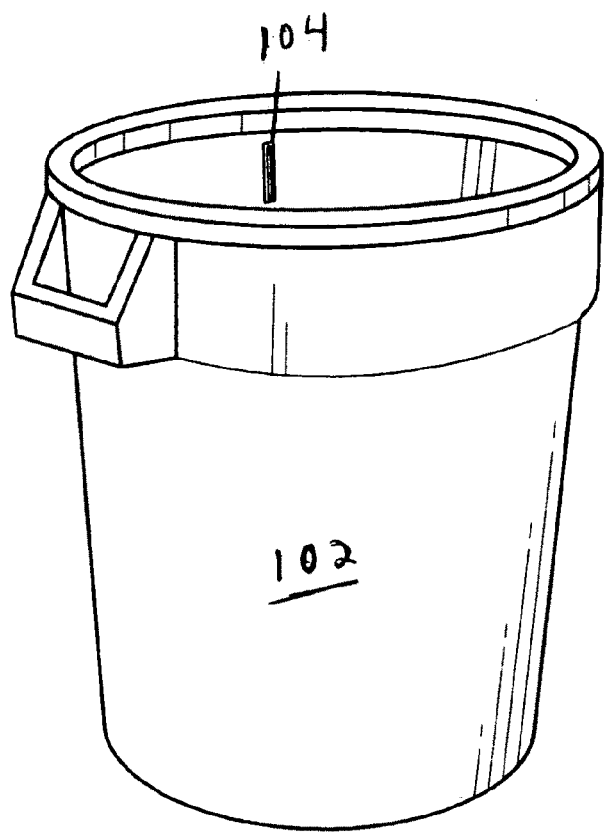
FIG. 19 is a view of garbage can with a fragrance piece attached with a loop and strip attacher with adhesive.

Referring now to exemplary FIGS. including, but not limited to, FIGS. 1B, 2, 9, 11-13, 16-22, and 24 it is anticipated that in some embodiments a single fragrance piece 104, such as, but not limited to, the cylindrical fragrance piece 104 as exemplarily illustrated in FIG. 2, will be able to be used with a variety of holding devices 102, such as, but not limited to, a hanger 188, as exemplarily illustrated in FIG. 1, a chest of drawers as exemplarily illustrated in FIG. 16, a shoe bag as exemplarily illustrated in FIGS. 17 and 18, a garbage can as exemplarily illustrated in FIG. 19, a waste basket, as exemplarily illustrated in FIG. 20, a jewelry box, as exemplarily illustrated in FIG. 21, and a box, as exemplarily illustrated in FIG. 22.

Figure 1H:
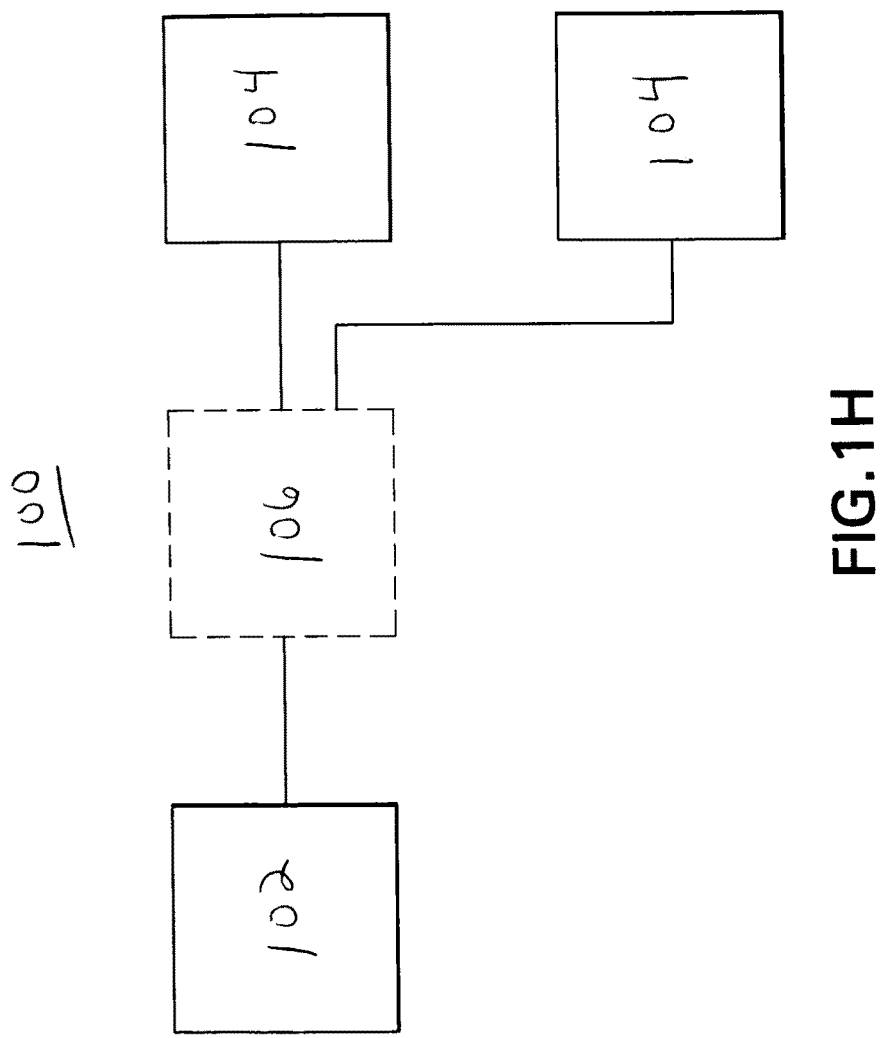
Figure 1I:
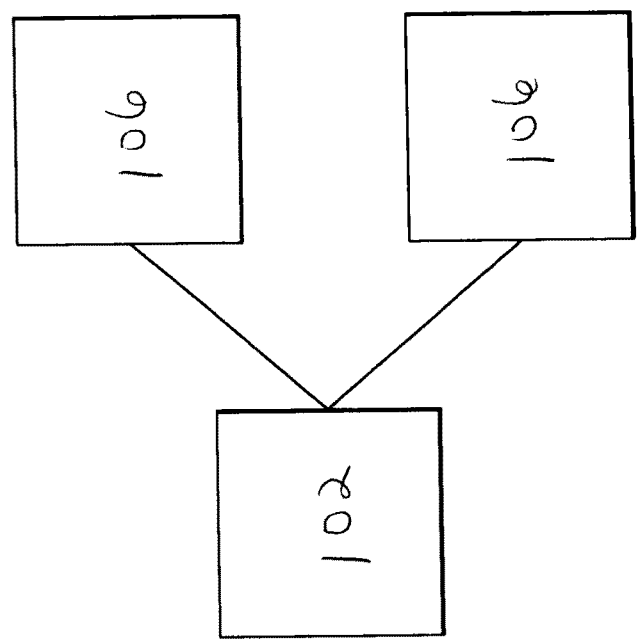
Figure 1J:
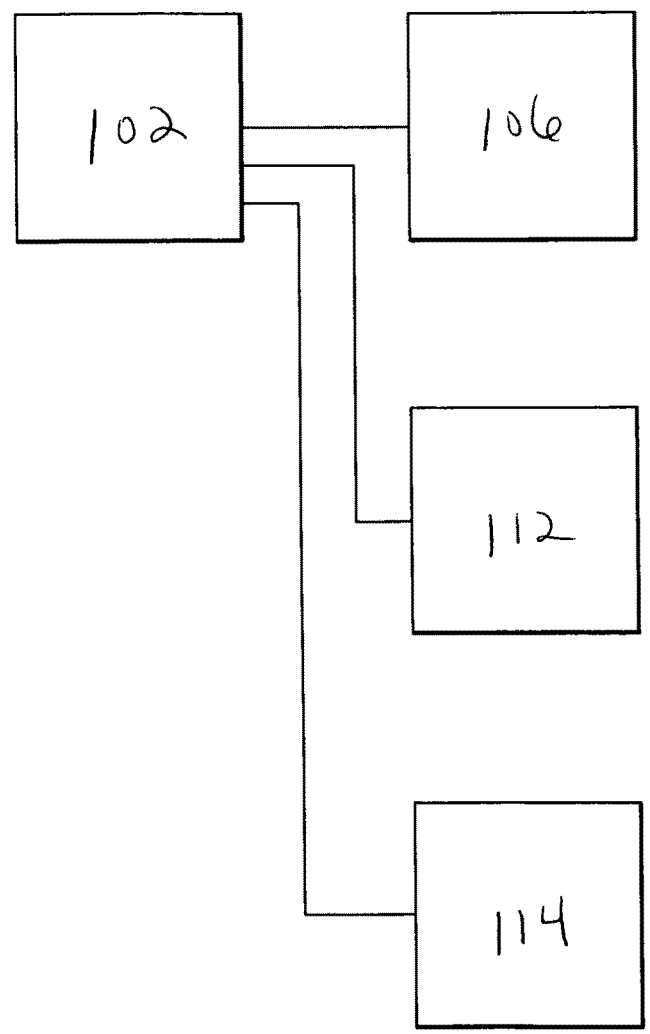
Figure 1K:
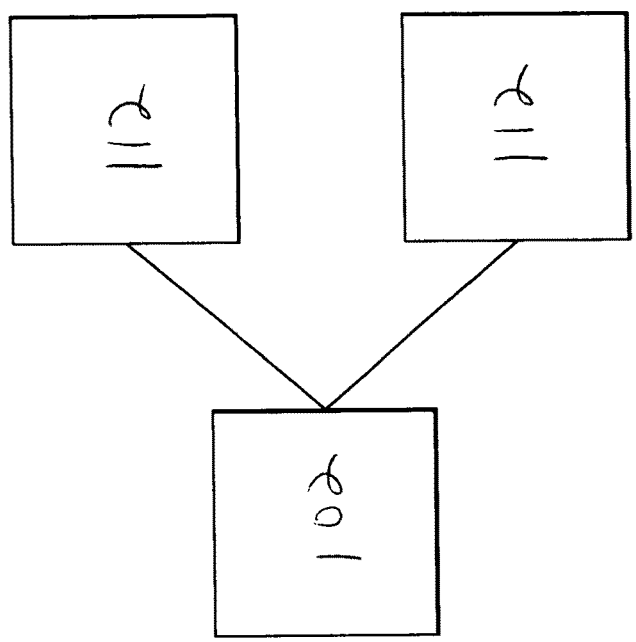
Figure 1L:
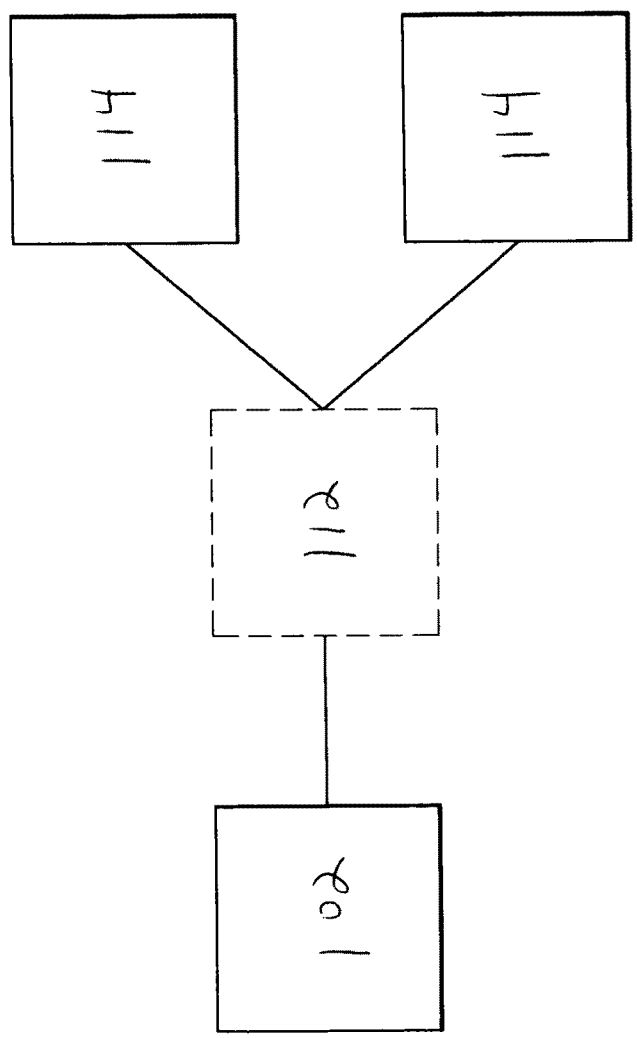
Figure 1M:
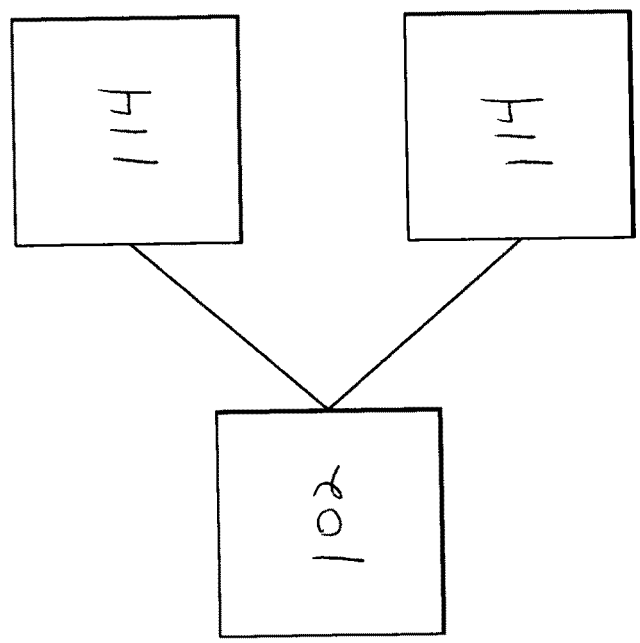
Figure 10:
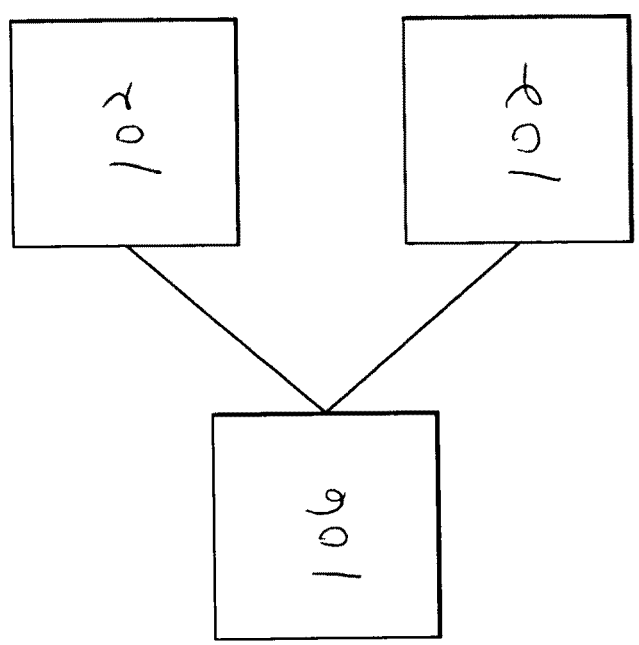
FIG. 10 is a view of a hanger with a cylindrical fragrance piece attached in the space above the clips.

In addition, referring now to exemplary FIGS. including, but not limited to, FIGS. 1H, 9 and 10 it is anticipated that in some embodiments a single holding device 102 will be able to be used with a variety of fragrance pieces 104. As exemplarily illustrated in FIGS. 9 and 10, and without intending to be limiting, a hanger with clips 162 may have attached with it, a long cylindrical fragrance piece 104 attached with two clips 162, as exemplarily illustrated in FIG. 10, a short cylindrical fragrance piece 104 attached with one clip 162, as exemplarily illustrated in FIG. 9, and/or a short rectangular fragrance piece 104 attached with one clip 162, as exemplarily illustrated in FIG. 9.

Further, referring to exemplary FIGS. including, but not limited to, FIGS. 1A, 1I-M, it is anticipated that in some embodiments a single holding device 102 will be able to use a variety of attachers 106, attachment pieces 112 and/or attachment piece parts 114. As exemplarily illustrated in exemplary FIGS. 16, 17 and 18, and without intending to be limiting, a shoe bag may have a slot 116 attacher cut into the sidewall, or have attached with it, a piece of a material 128 with loops 152, sewn-in loops 152, clips 162 and/or prongs 134.

Figure 1N:
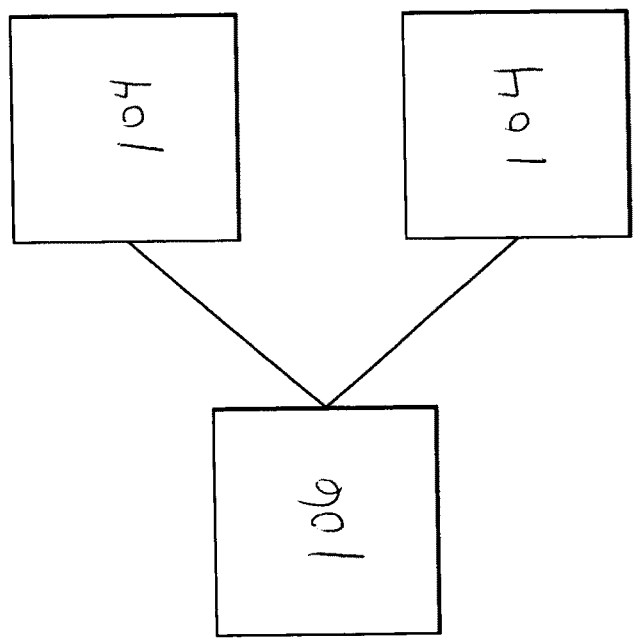
Figure 1P:
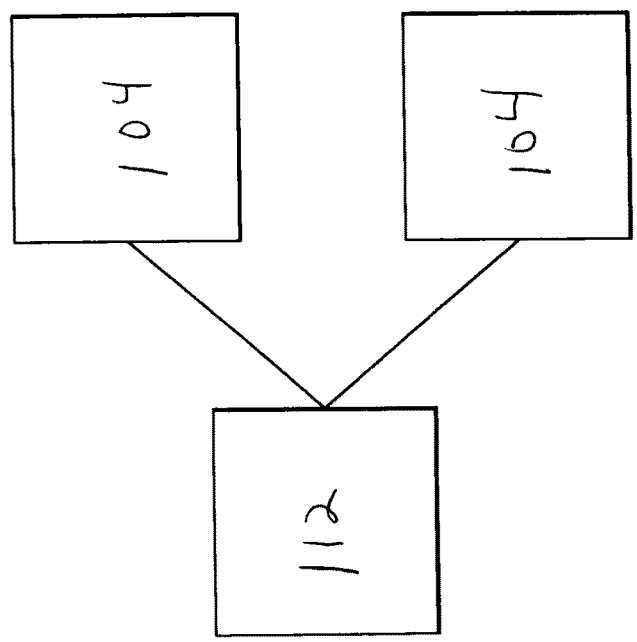
Figure 1Q:
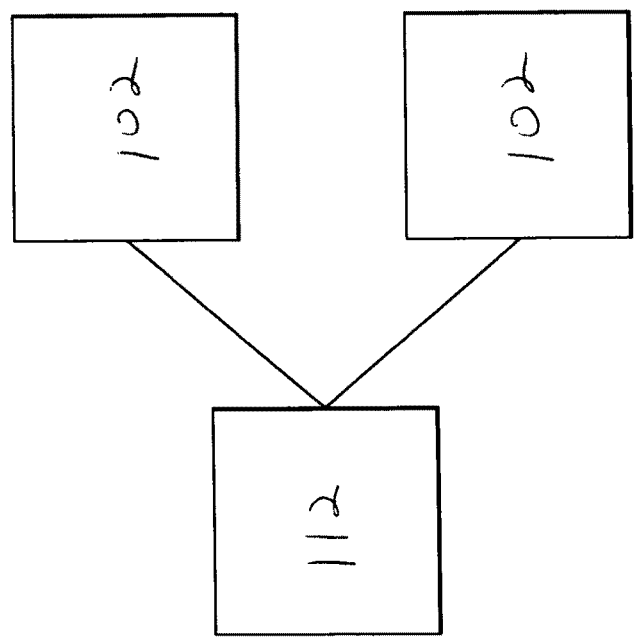
Figure 1R:
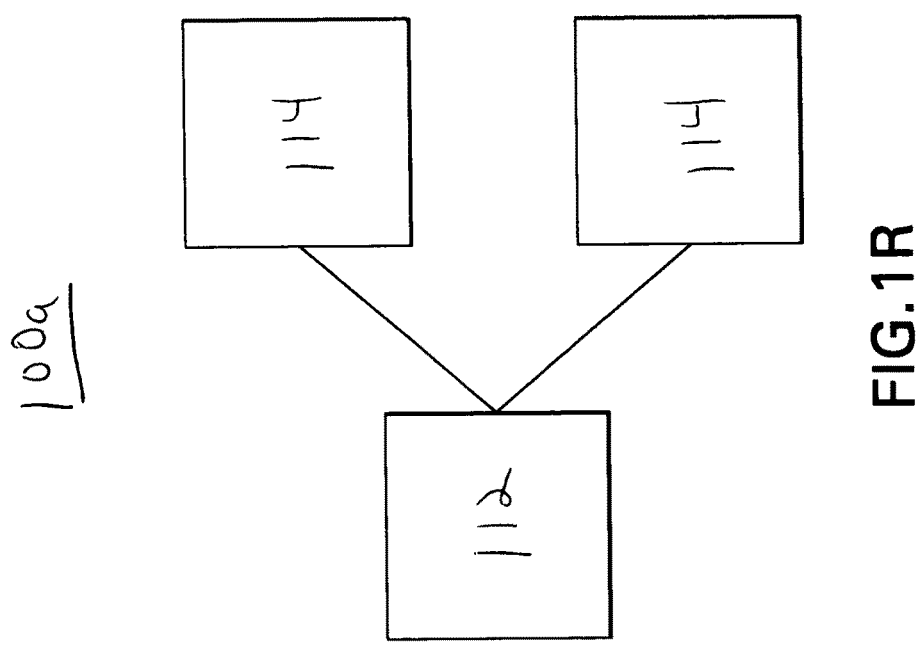
Figure 1S:
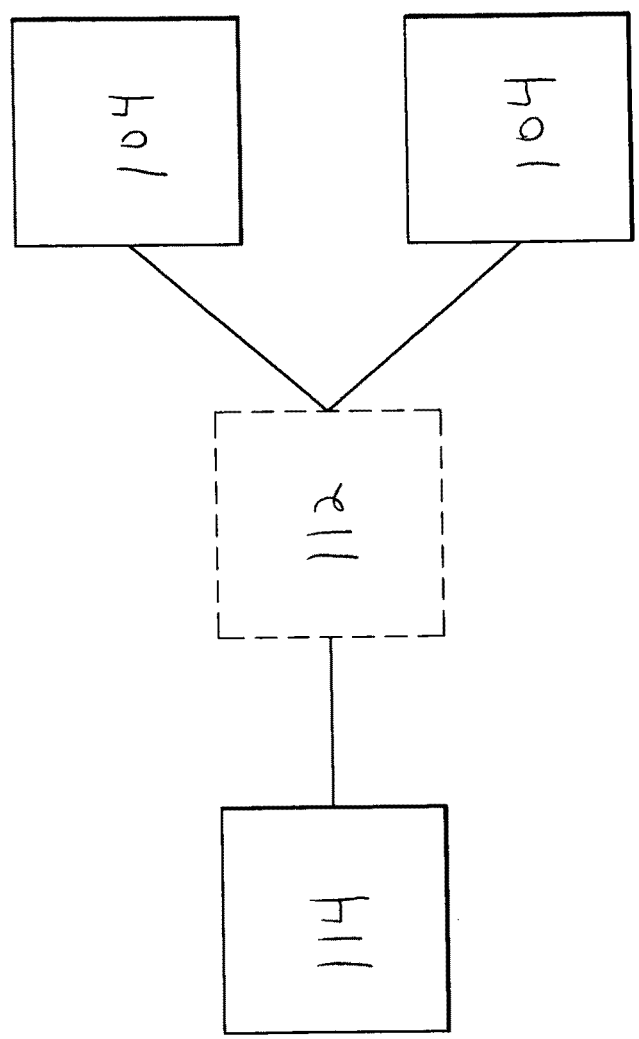

Further, referring to exemplary FIGS. including, but not limited to, FIGS. 1N, 1P and 1S, it is anticipated that in some embodiments a single attacher 106, attachment piece 112, and/or attachment piece part 114 will be able to be used with a variety of fragrance pieces 104. As exemplarily illustrated in FIGS. 24a and 24b, and without intending to be limiting, a set of prongs 134 can be used with a squared fragrance piece 104 or a cylindrical fragrance piece 104.

Figure 1T:
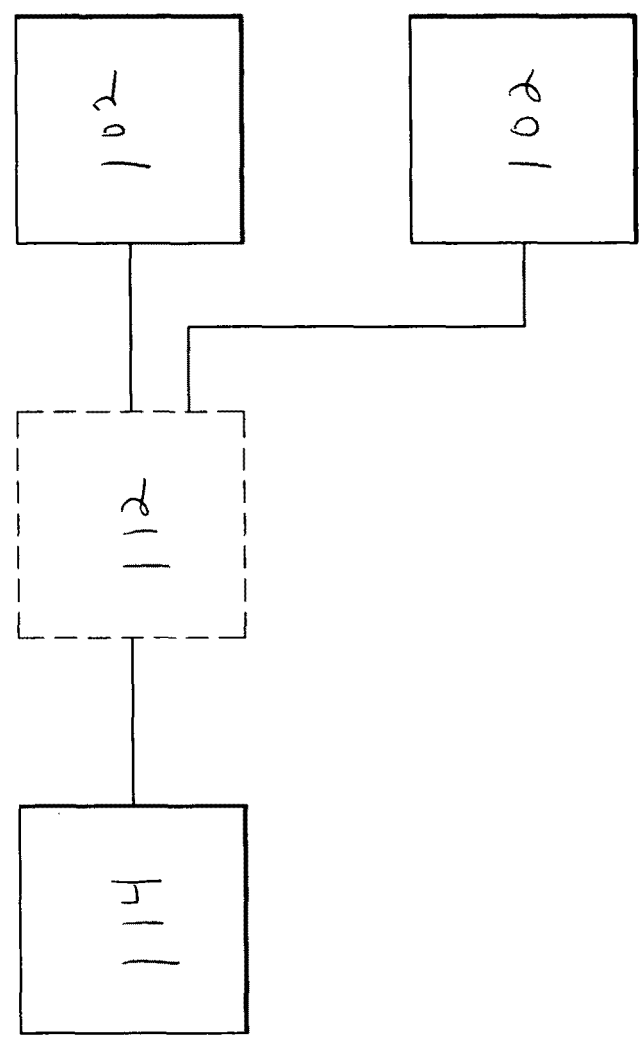

Referring to exemplary FIGS. including, but not limited to, FIGS. 10, 1Q and 1T, it is also anticipated that in some embodiments, a single attacher 106, attachment piece 112, and/or attachment piece part 114 will be able to be used with a variety of holding devices 102. As exemplarily illustrated in FIGS. 16, 17 and 19-21, and without intending to be limiting, a piece of a material 128 with loops 152 and/or prongs 134 on the fragrance piece side 172 (to be described in more detail later) and adhesive 174 on the holding device side 170 (to be described in more detail later) may be attached with a drawer, shoe bag, garbage can, waste basket, and/or jewelry box.

Figure 1U:
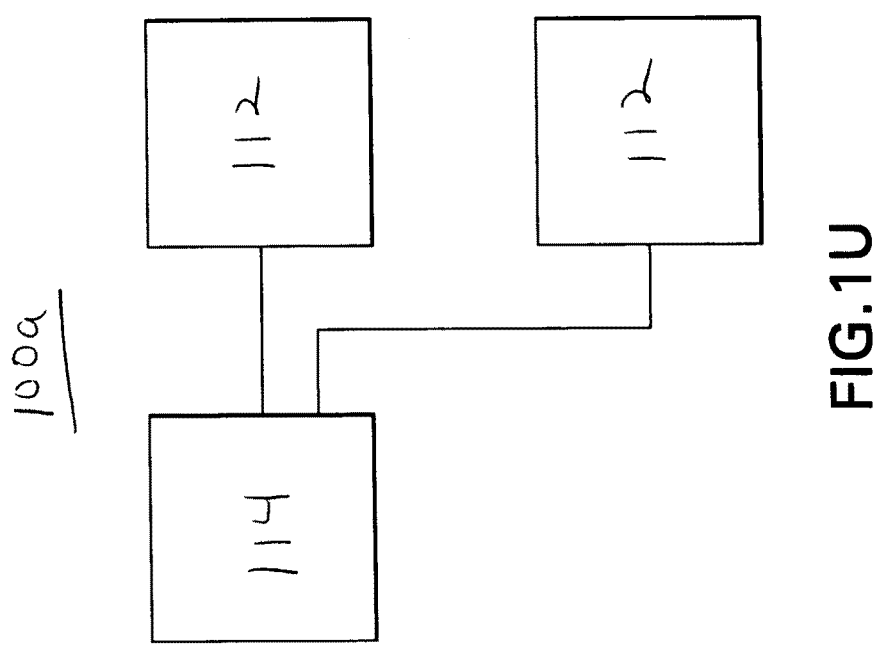
Figure 1V:
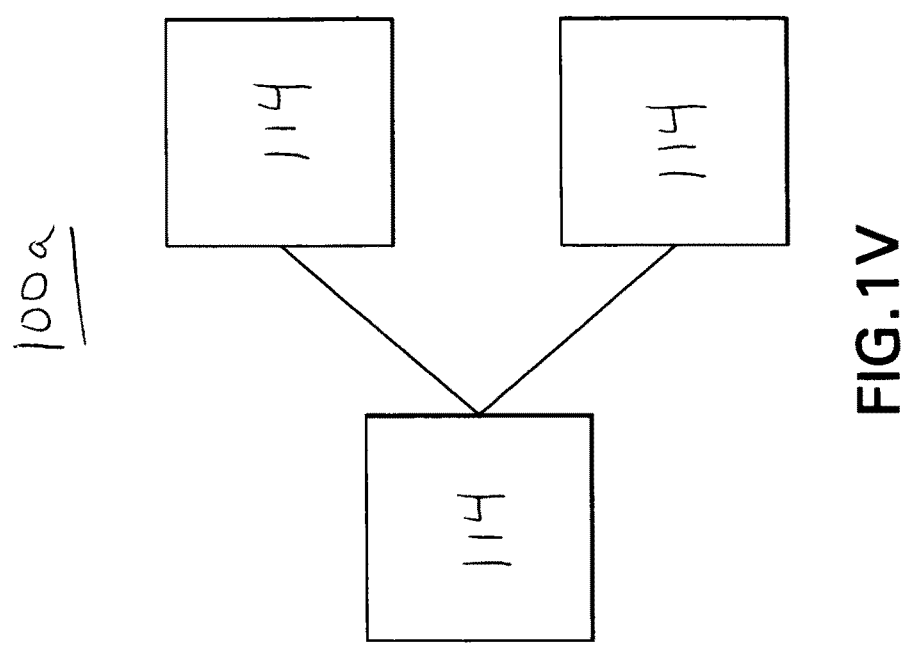

Referring to exemplary FIGS. including, but not limited to, FIGS. 1R and 1U, it is also anticipated that in some embodiments a single attachment piece part 114 will be able to be used with a variety of other attachment piece parts 114, and vice versa. As exemplarily illustrated in exemplary FIGS. 14 and 15, and without intending to be limiting, at least one prong 134, loop 152 and/or clip 162 can be attached with a piece of non-hook and loop fabric material 180. As exemplarily illustrated in FIGS. 25-27, at least one prong 134, loop 152, and/or supplemental piece 182 with loops 152 can be attached with a piece of hook and loop material 178.

Referring now to FIGS. including, but not limited to, FIGS. 18, and 28-34a, embodiments of the system 100 are exemplarily illustrated wherein the attacher 106 includes at least one slot 116. The at least one slot 116 may be located on any accessible portion of the holding device 102. By way of example, and not intending to be exhaustive, the at least one slot 116 may be located on a portion on the outer structure of the holding device 102, as exemplarily illustrated in FIG. 18, or an interior portion of a holding device 102 such as, but limited to a lining, inner compartment, or other interior portion. By way of example, and not intending to be limiting, the at least one slot 116 can be cut into the lining of a holding device 102, including but not limited to, luggage, sports bags garment bags, shoe bags and sweater bags. In addition, as exemplarily illustrated in FIG. 30, at least one slot 116 can be cut into a piece of a material 128, which can be integrally integrated with, and/or fixedly or removably attached and/or attachable with a holding device 102 in a variety of ways. The attachment piece of a material 128 is discussed in more detail in subsequent paragraphs and FIGS.

Figure 28:
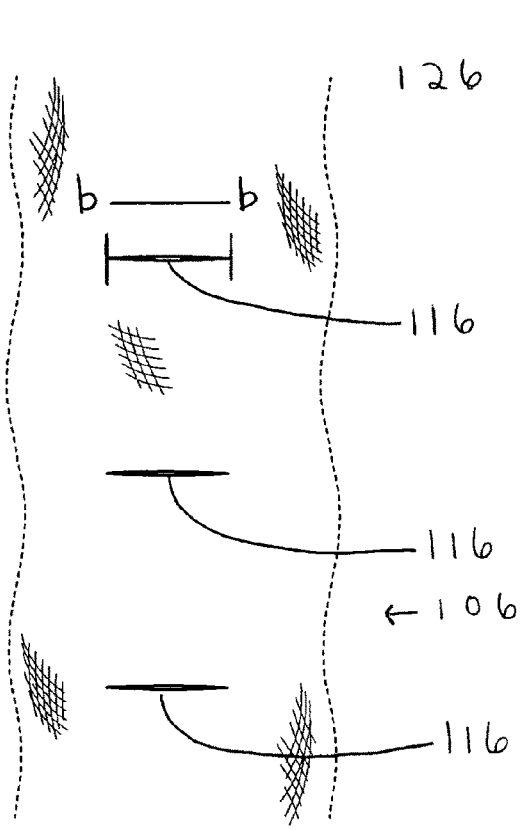
FIG. 28 is a front view of a series of slots.
Figure 29:
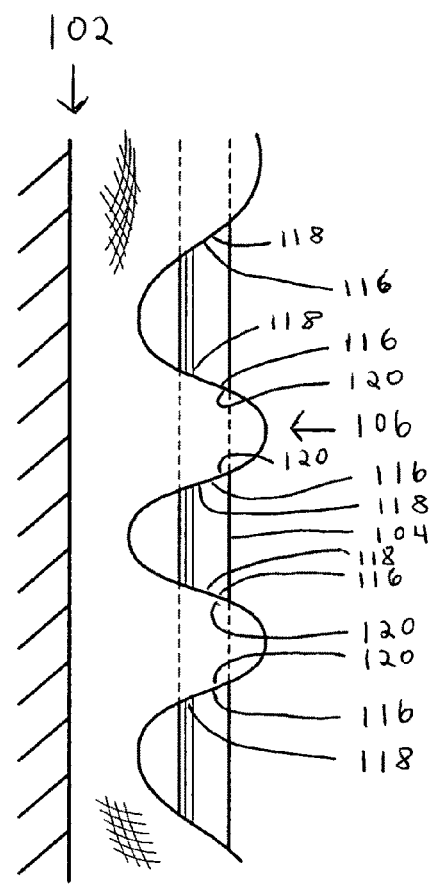
FIG. 29 is a cross-sectional view of a series of slots.

Specifically referring now to exemplary FIGS. 28 and 29, the portion of the holding device 102 or piece of a material 128 attachment piece having a slot 116 has a first side 118 and a second side 120. Each slot 116 is a cut in a portion of the holding device 102 or piece of a material 128 through which a fragrance piece 104 may be inserted from the first side 118 through the slot 116 to the second side 120, or vice versa from the second side 120 through the slot 116 to the first side 118. When attached with the holding device 102 by at least one slot 116, a portion of the fragrance piece 104 will be on the first side 118 and a portion of the fragrance piece 104 will be on the second side 120. The at least one slot 116 can be located anywhere on the holding device 102, including but not limited to, in the top, sides, or bottom of the holding device 102. The at least one fragrance piece 104 will be attachable with the at least one slot 116 within at least the required attachment parameters. Preferably, the interaction of the at least one fragrance piece 104 and the at least one slot 116 will be within the preferred attachment parameters, and more preferably at least within the more preferred attachment parameters. It is to be understood, however, that the type of materials and/or combination of materials, and/or the number of slots 116 that will accomplish the preferred attachment parameters and/or the more preferred attachment parameters between the fragrance piece 104 and the at least one slot 116 can vary. In addition, in some embodiments, the interaction of the at least one fragrance piece 104 and the at least one slot 116 will be within the removal attachment parameters, the removal and fit attachment parameters and/or the preferred removal and fit attachment parameters.

Slots 116 can vary in width and length, size, number, and placement in the holding device 102. When more than one slot 116 is included, they are generally aligned to enable a generally straight fragrance piece to be attached with and removed from the holding device 102 by weaving the fragrance piece 104 in and out of the slots 116. FIGS. 28 and 29 illustrate an exemplary embodiment wherein the attacher 106 includes more than one slot 116, and the slots 116 are aligned generally in a line, so that the generally straight fragrance piece 104 may easily be woven from one slot 116 to the next.

Referring now to exemplary FIGS. 28 and 31-34a, in some embodiments, the relationship of the size of the fragrance piece 104 and the length the at least one slot 116 is calculated by drawing an imaginary circle 122 around the outside general circumference of a fragrance piece and measuring the diameter "a-a" of the imaginary circle 122 (called "calculated diameter 124"). As exemplarily illustrated in FIGS. 34 and 34A, if the width of the fragrance piece 104 is not consistent, the calculated diameter 124 may be calculated from the widest part of the fragrance piece 104 that can engage the attacher 106 when the fragrance piece 104 is attached with the holding device 102. In these embodiments, the calculated diameter 124 is equal to or less than one half of the length "b-b" 126 of the slot 116 and equal to or greater than one fourth of the length "b-b" 126 of the slot 116. By way of example, and not intending to be limiting, if the length of the of a slot 116 is 1 inch, the calculated diameter 124 of the fragrance piece 104 will be equal to or less than ½ inch and equal to or greater than ¼ inch.

Figure 35:
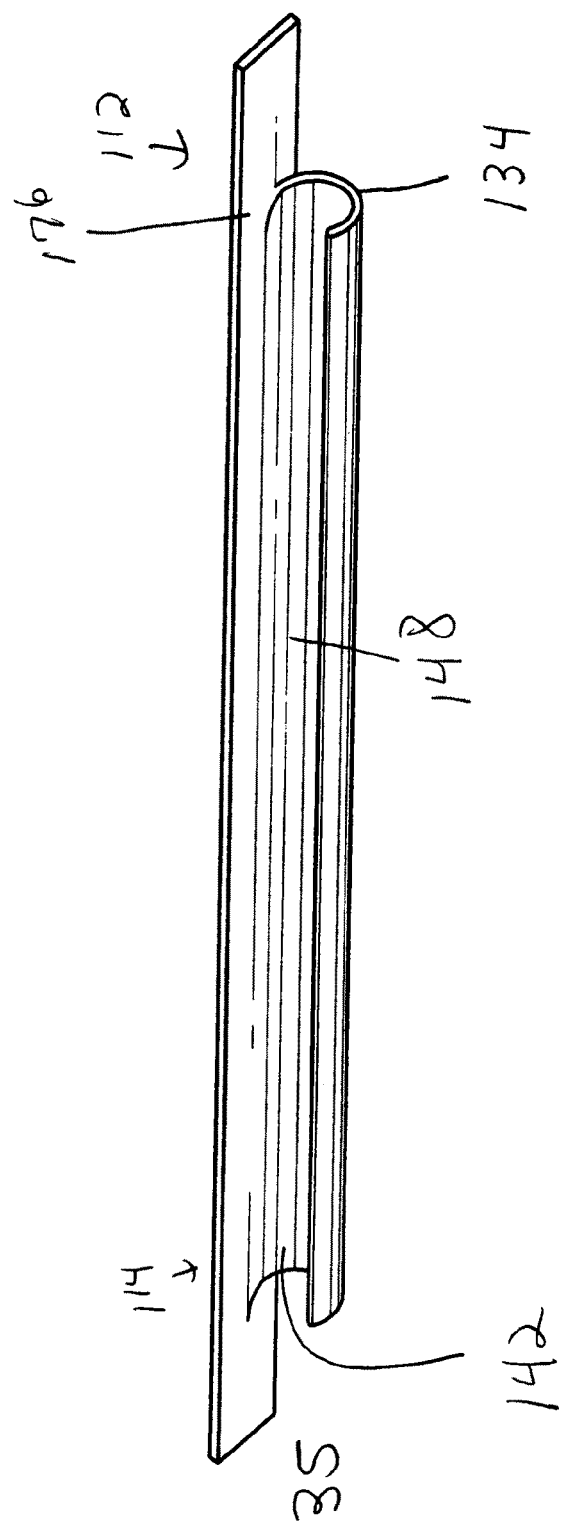
FIG. 35 is a view of a prong integrally molded on a piece of a material.

Other embodiments of the scented holding device system 100, attacher systems, 100a, including attachment piece systems, attachment piece part systems, and/or devices are exemplarily illustrated in FIGS. including but not limited to FIGS. 11-13, 15, 16, 23-25, 35-58, 87, 88, 92, 93-95 and 100, wherein the attachment piece 112 includes at least one prong 134. The at least one prong 134 may be directly fixedly or removably attached or attachable with the holding device 102 by ways currently known in the art or to be discovered, including but not limited to, tacking, stapling, bonding, taping, heat sealing, welding, molding, magnetic attraction, weaving, sewing, hook and loop material, such as but not limited to Velcro®, and/or mechanical interaction, such as but not limited to tongue and groove interaction, or may be directly fixedly or removably attached or attachable with a compatible attachment piece 112 or attachment piece part 114 by ways currently known or to be discovered in the art, including but not limited to tacking, stapling, bonding, taping, heat sealing, welding, molding, magnetic attraction, weaving, sewing, hook and loop material, such as but not limited to Velcro®, and/or mechanical interaction, such as but not limited to tongue and groove interaction. The at least one prong 134 can be integrally integrated with and/or attached or attachable with the holding device 102, as exemplarily illustrated in FIG. 92, or to an attachment piece 112 or attachment piece part 114, as exemplarily illustrated in FIG. 35 in a manner whereby each prong 134 is an integral part of the holding device 102 or attachment piece 112 or attachment piece part 114 by ways currently know in the art, such as, but not limited to by molding, weaving, and ways to be discovered in the art. The attachment piece part 114 can be a piece of a material 128, which is described in more detail in subsequent paragraphs and FIGS. If the at least one prong 134 is attached with at least one attachment piece 112 or attachment piece part 114, the at least one attachment piece 112 or at least one of the attachment piece parts 114 is integrally integrated with, and/or fixedly or removably attached or attachable with the holding device 102. When the at least one prong 134 is attached with the holding device 102 either directly or with the assistance of at least one attachment piece 112 or attachment piece part 114, the fragrance piece 104 will be removably attachable with the at least one prong 134 within the preferred attachment parameters and/or the more preferred attachment parameters, and in some embodiments also within the removal and fit attachment parameters and/or the preferred removal and fit parameters.

Figure 36:
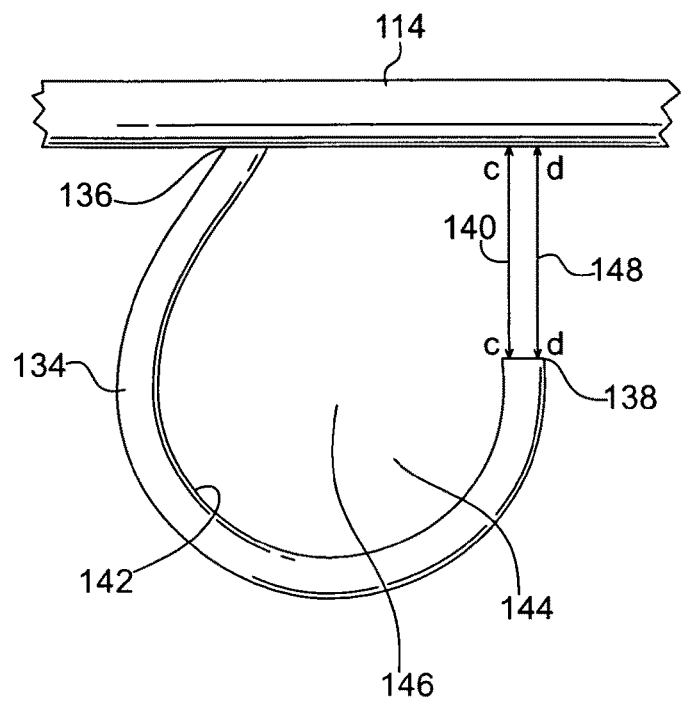
FIG. 36 is a side view of a prong gap c-c, and accessible prong gap d-d.
Figure 37:
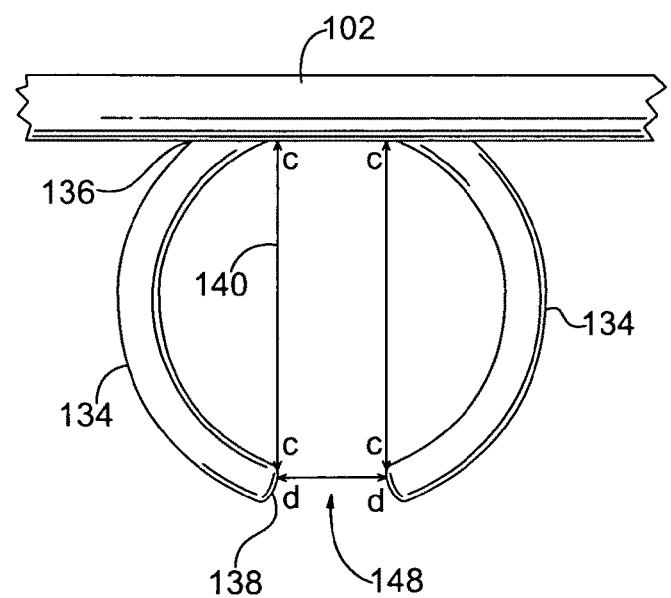
FIG. 37 is a side view of a prong gap c-c, and accessible prong gap d-d.
Figure 41:
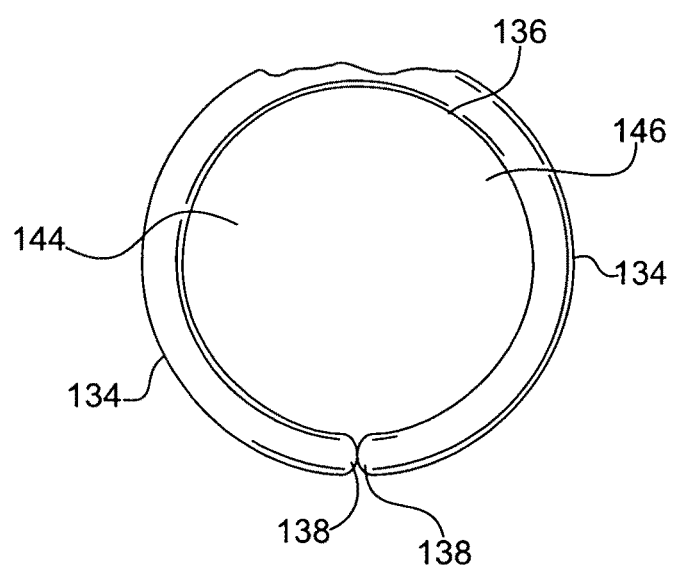
FIG. 41 is a view of a set of prongs and a fragrance piece space.
Figures 42, 43, 44:
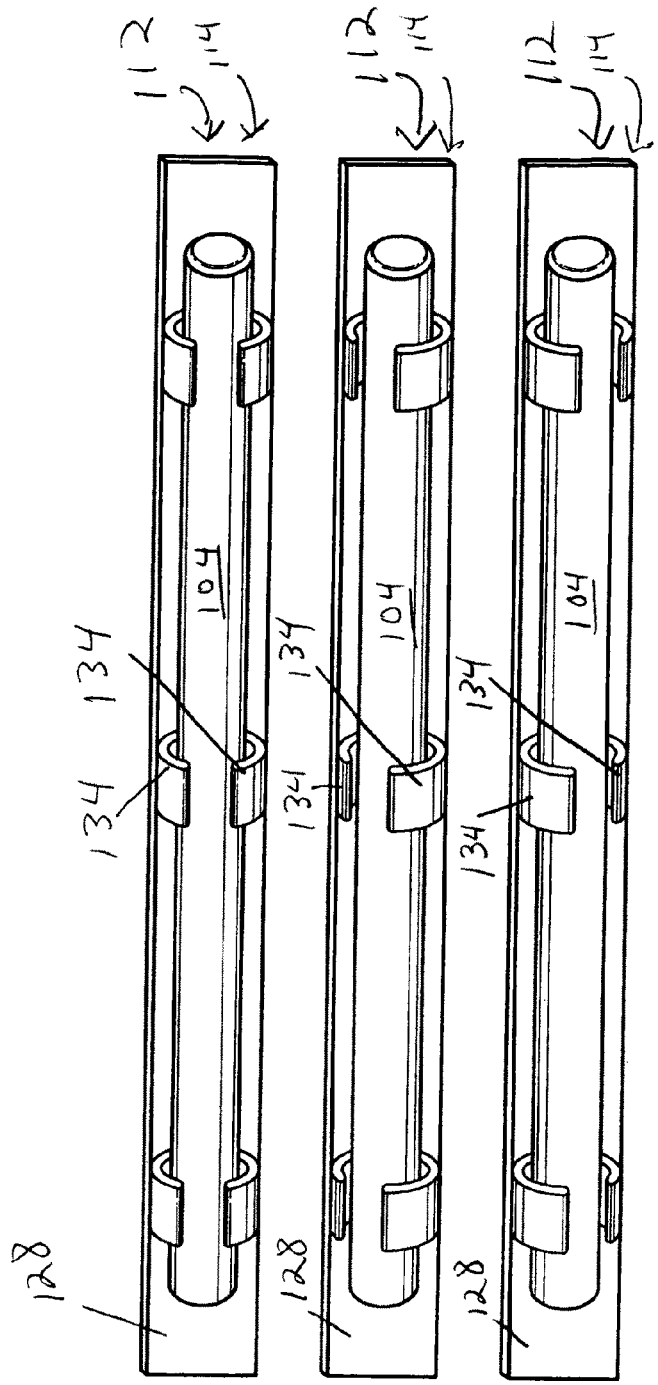
FIG. 42 is a view of a set of prongs with a centered accessible prong gap.
FIG. 43 is a view of a set of prongs with an upward facing accessible prong gap.
FIG. 44 is a view of a set of prongs with a downward facing accessible prong gap.
Figure 45:
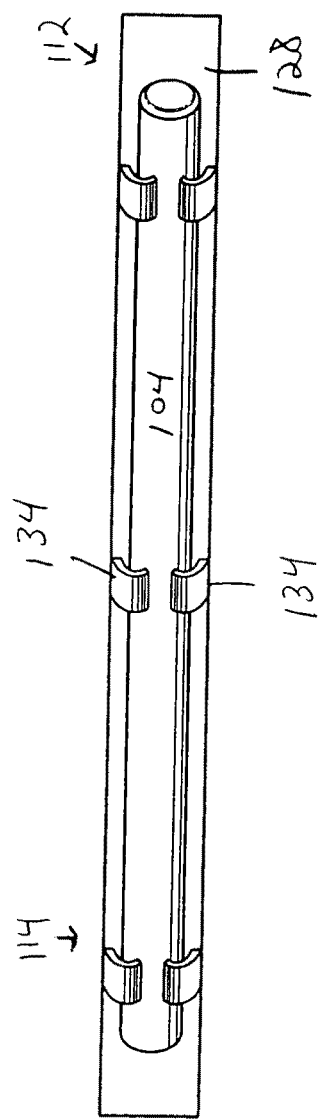
FIG. 45 is a view of a set of prongs with a centered accessible prong gap.

Reference is now made to FIGS. 36-38. It is to be noted that each prong 134 will have a holding device end 136, which is the end of the prong 134 that is closest to the holding device 102 when the prong 134 is attached with the holding device 102, and a gap end 138, which is the free end of the prong 134. Each prong 134 will define a gap "c-c", referred to as the "prong gap 140", which is the area between the gap end 138 of the prong 134 and the inner surface 142 of the prong that is closest to the holding device 102, the holding device 102, or the corresponding attachment piece 112 or attachment piece part 114.

Referring now to FIGS. including but not limited to exemplary FIGS. 23a-e, 24a-d, and 38-40, each prong 134 has an inner surface 142, which is the surface that is facing the fragrance piece 104 when the fragrance piece 104 is attached. The inner surface 142 of the at least one prong 134 can be a variety of lengths, widths and shapes as long as the preferred attachment parameters and/or the more preferred attachment parameters are satisfied, and in some embodiments also as long as the removal and fit attachment parameters and/or the preferred removal and fit parameters are satisfied, when the at least one fragrance piece 104 is attached and the prong 134 is attached with the holding device 102 either integrally, directly or with the assistance of at least one other attachment piece 112 or attachment piece part 114. The use of some materials, which include, but are not limited to, micro fiber and sponge, on the inner surface 142 of a prong 134 can enhance the interaction of the fragrance piece 104 and the inner surface 142 of the prong 134, and thereby in some embodiments enhance the accomplishment of the preferred attachment parameters and/or more preferred attachment parameters.

Referring now to FIGS. including but not limited to exemplary FIGS. 11-13, 24*a-d*, 38, 39 and 41-45, when the at least one prong 134 is viewed from the side, the inner surface or surfaces of the at least one prong 134 define a shape, that will be referred to as the "inner surface shape" 144. The inner surface shape 144 defines a space, referred to as the "fragrance piece space" 146 into which the fragrance piece 104 may be inserted. It is to be noted that when the inner surface shape 144 is defined by at least two prongs 134 with inner surfaces 142 facing each other, the prongs 134 can be either directly across from each other, such as those exemplarily illustrated in FIGS. 41-45, or they can be off-set from each other, such as those exemplarily illustrated in FIGS. 11-13, 38, and 39. If they are off-set from each other the inner surface shape 144 will be made up of all of the prongs 134 with which the at least one fragrance piece 104 interacts when the at least one fragrance piece 104 is attached, as exemplarily illustrated in FIGS. 11-13.

Depending on the size, shape, location and number of prongs 134 and the at least one fragrance piece 104, the at least one fragrance piece 104 may be inserted into the fragrance piece space 146 in a number of ways.

Depending on the shape and size of the fragrance piece 104 and depending on the size, and shape of the prong gap 140, the at least one fragrance piece 104 can be inserted in the at least one prong 134 by inserting the fragrance piece 104 directly into fragrance piece space 146 through the prong gap 140. In order to be able to insert the at least one fragrance piece 104 into the fragrance piece space 146 directly through the prong gap 140, the prong gap 140 must be directly accessible.

Figure 23A:
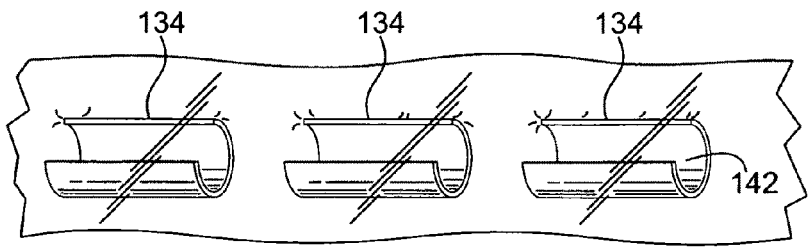
FIGS. 23 A-E are views of prong configurations.
Figure 23B:
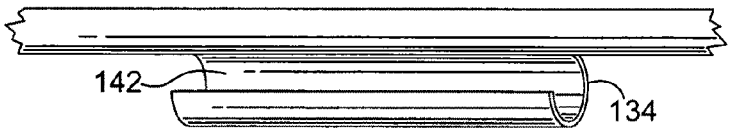
Figure 23C:
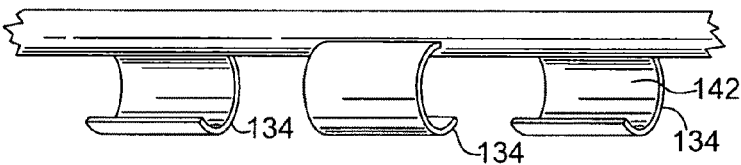
Figure 23D:
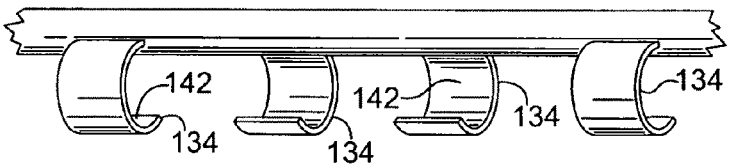
Figure 23E:
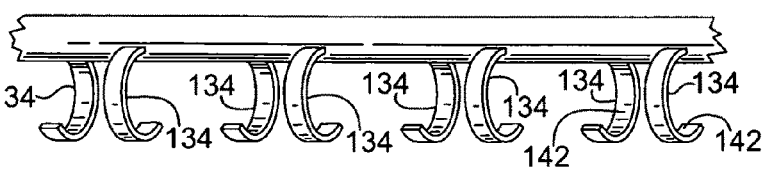
Figure 46:
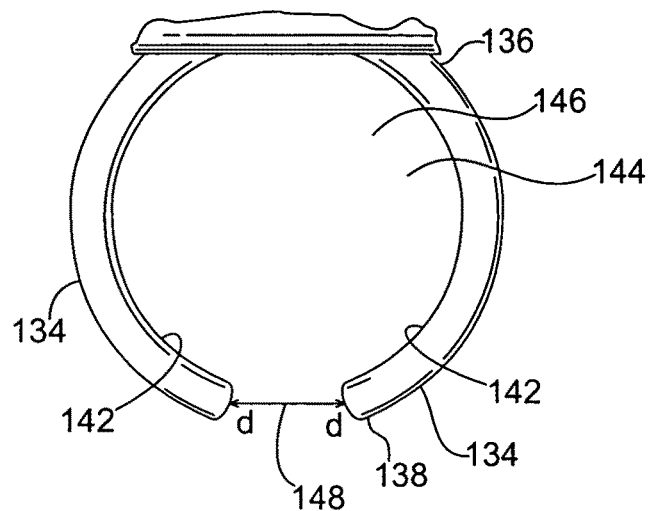
FIG. 46 is a side view of accessible prong gap d-d.
Figure 47:
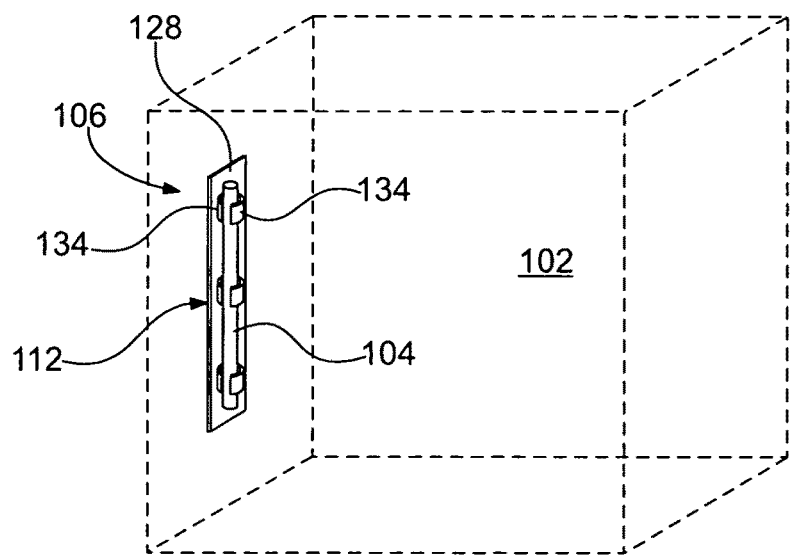
FIGS. 47-51 are views of the same prong attacher facing up, down, forward, backward and diagonally in holding devices.
Figure 48:
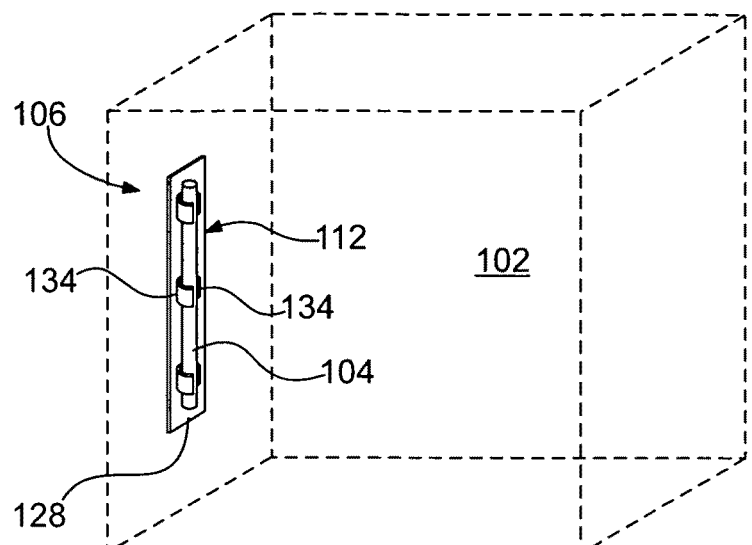
Figure 49:
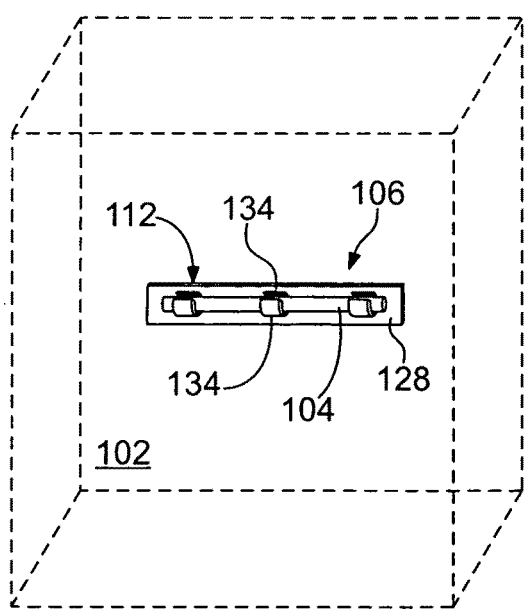
Figure 50:
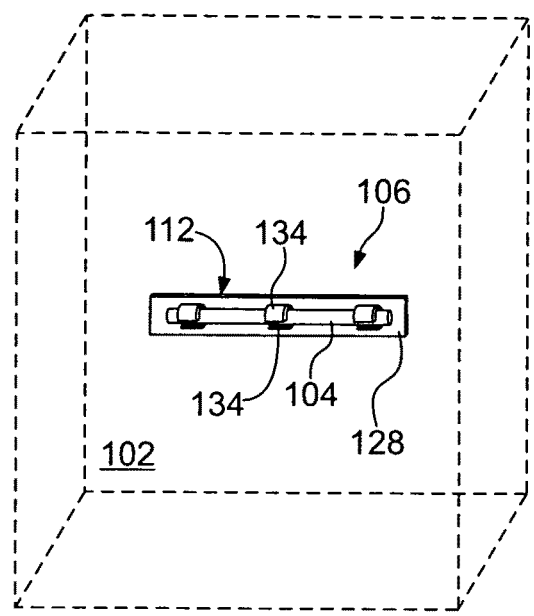
Figure 51:
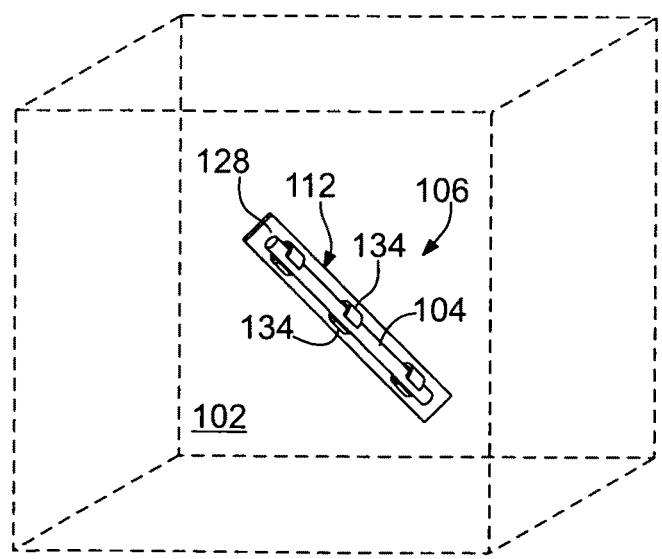

As exemplarily illustrated in FIGS. 37 and 46, when the inner surface shape 144 is created by at least two prongs 134 with inner surfaces 142 facing each other and none of the prong gaps 140 fully overlap each other, a gap "d-d" into the fragrance piece space 146 is provided, which is referred to as an "accessible prong gap 148." As exemplarily illustrated in FIGS. 23*a-b* and 36, when one prong 134 is provided or when all of the prongs 134 are on same side of the fragrance piece 104 when it is attached, the fragrance piece space 146 may be directly accessible through the prong gap 140, and this prong gap "c-c" 140 is also referred to as an accessible prong gap "d-d" 148.

When the inner surface shape is created by at least two prongs 134 with inner surfaces facing each other, all, some or none of the prong gaps 140 may overlap an opposing prong 134. As exemplarily illustrated in FIGS. 24*b-d* if the prong gaps 140 on opposing sides of the fragrance piece space do not overlap, and an accessible prong gap 148 is provided, the fragrance piece 104 may be inserted directly into the fragrance piece space 146 through the accessible prong gap 148 if the accessible prong gap 148 is sufficiently wide for the fragrance piece 104 and/or if the prongs 134 are sufficiently flexible to increase the accessible prong gap 148 to enable the fragrance piece 104 to be inserted. In addition, in some embodiments, even if the prong gaps 140 on opposing sides of the fragrance piece 104 space do overlap, if the prongs 134 are sufficiently flexible to create an accessible prong gap 148 through which the fragrance piece 104 may be inserted, the fragrance piece 104 can be directly inserted into the fragrance piece space 146 through the created accessible prong gap 148.

Referring now to FIG. 40, in some embodiments, the at least one fragrance piece 104 can be attached with the at least one prong 134 by sliding the fragrance piece 104 generally lengthwise into the open fragrance piece space 146 of the at least one prong 134. In addition, in some embodiments, if more than one prong 134 is provided on opposite sides from one another, the at least one fragrance piece 104 also can be inserted in the prongs 134 by moving the fragrance piece 104 in and out (not shown) of the prongs 134.

As exemplarily illustrated in FIGS. 24*a* and 24*d*, in some embodiments the inner surface shape 144 of the at least one prong 134 and the outer surface 110 of the fragrance piece 104 will be made in complimentary shapes. By way of example, and without intending to be exhaustive, the following are examples of complimentary prongs 134 and fragrance pieces 104: circular concave inner surface shape 144 with cylindrical fragrance pieces 104, elongated concave inner surface shape 144 with oval fragrance pieces 104, strait diagonal triangular inner surface shape 144 with triangular fragrance pieces 104, straight right-angled inner surface shape 144 with square or rectangular fragrance pieces 104, star-shaped inner surface shape 144 with star-shaped fragrance pieces 104, and a heart shaped inner surface shape 144 for heart shaped fragrance pieces 104.

However, as illustrated in an exemplary and non-exhaustive manner in FIG. 24*b*, it is to be noted that the inner surface shape 144 of the at least one prong 134 and the outer surface of the fragrance piece 104 are not required to be made in complimentary shapes as long as the preferred attachment parameters and/or the more preferred attachment parameters are satisfied, and in some embodiments also as long as the removal and fit attachment parameters and/or the preferred removal and fit parameters are satisfied, when the fragrance piece 104 is attached when the prong 134 is attached with the holding device 102 either directly or with the assistance of at least one other attachment piece 112 or attachment piece part 114. By way of example, and without intending to be exhaustive, curved fragrance pieces 104 can be used with prongs 134 having straight inner surfaces 142 or inner surface shapes 144 including straight lines connected at 90 degrees from one another, and fragrance pieces 104 with straight sides can be used with prongs 134 having curved inner surfaces 142. In addition, the inner surface shape of the at least one prong 134 and/or the outer surface of the at least one fragrance piece 104 can be irregularly shaped.

Figure 52:
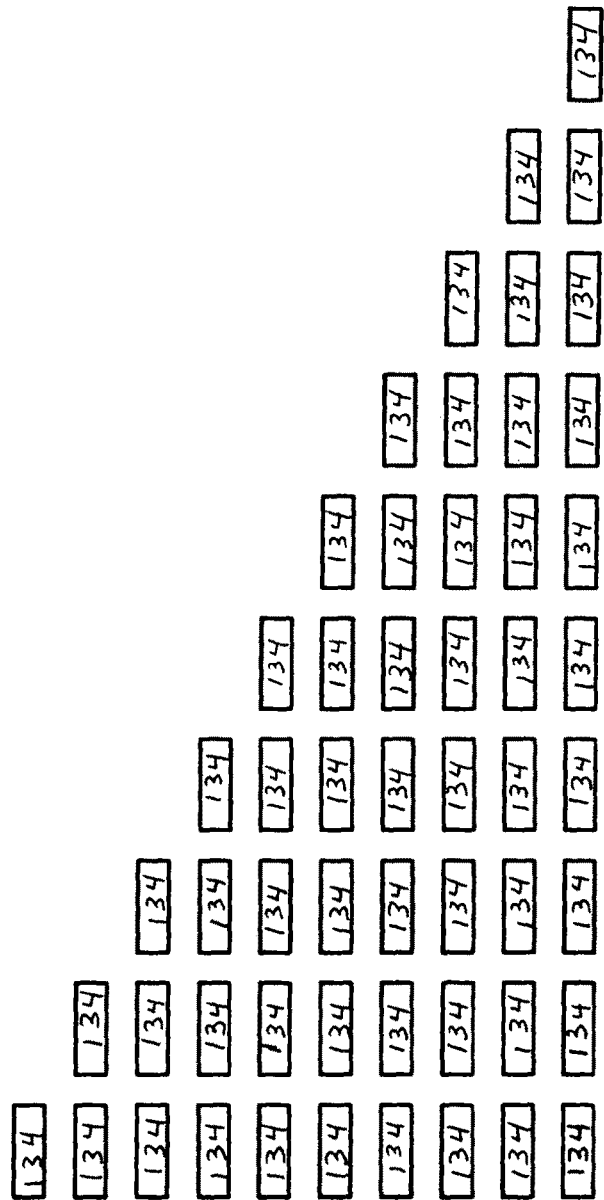
FIG. 52 is a view of a sequential series of some possible configurations for prongs attached next to one another.

The prongs 134 may be of varying sizes, shapes, locations and configurations on the holding device 102 as long as the preferred attachment parameters and/or the more preferred attachment parameters may be obtained, and in some embodiments also as long as the removal and fit attachment parameters and/or the preferred removal and fit parameters may be obtained, with at least one fragrance piece 104. FIGS. 23*a-e* illustrate examples of varying prong 134 sizes, shapes, locations and configurations, however, it is to be understood that these examples are not intended to be exhaustive or limiting. Without intending to be limiting, FIG. 52 illustrates a number of prongs 134 that may be aligned with one another on a holding device 102, attachment piece 112 or attachment piece part 114. While FIG. 52 illustrates between one and ten prongs 134 being aligned, it is to be understood that more than ten prongs 134 can also be aligned for holding devices 102 that are sufficiently large to accommodate them.

Referring now to FIGS. including but not limited to FIGS. 42-51, the accessible prong gap 148 of at least one prong 134 can be located at a variety of places around the at least one prong 134. As a result, when at least one prong 134 is attached with the holding device 102, it may be attached such that the accessible prong gap 148 is located in directions including but not limited to toward the top, bottom, middle, forward, backward, various sides, or diagonally. The placement of the accessible prong gap 148 of the at least one prong 134 in relation to the holding device 102 can enhance the ease of the attachment and removal of the fragrance piece 104 with and from the at least one prong 134 when it is attached with the holding device 102. By way of example, and without intending to be limiting, an upward facing accessible prong gap 148 could be beneficial for a holding device 102 that is often on the floor, such as an under-the-bed storage box, a downward facing accessible prong gap 148 could be beneficial for a use that is overhead, such as an overhead cabinet, a forward facing accessible prong gap 148 could be beneficial to a front-opening holding device 102, such as a kitchen cabinet, and a rear facing prong gap 148 could be beneficial to a rear-opening holding device 102 such as an entertainment cabinet.

It is to be understood that the prongs 134 can be attached with the holding device 102 in a manner whereby the accessible prong gap 148 faces a particular direction, such as but not limited to, forward, backward, up, down, or diagonal. In addition, if the prongs 134 are on an attachment piece 112 or attachment piece part 114 in a manner whereby the accessible prong gap 148 is at an angle, such as exemplarily illustrated in FIGS. 43 and 44, rather than oriented toward the middle, such as exemplarily illustrated in FIG. 42, it would be possible to attach the same attachment piece 112 or attachment piece part 114 in a variety of different ways on at least one holding device 102 such that the direction of the accessible prong gap 148 can be facing in different directions, such as but not limited to forward, exemplarily illustrated in FIG. 47, backward exemplarily illustrated in FIG. 48, up, exemplarily illustrated in FIG. 49, down, exemplarily illustrated in FIG. 50 or diagonal, exemplarily illustrated in FIG. 51.

Referring now to FIGS. including but not limited to exemplary FIGS. 11-13, 23c, 39, and 40, in some embodiments, three prongs 134 can be used to hold a fragrance piece 104. In these embodiments, the three prongs 134 can be arranged with two prongs 134 on one side of the fragrance piece space 146 and one in the middle of the other two, located on the other side of the fragrance piece space 146. In these embodiments, three prongs 134 are preferable to more than three prongs 134 because it in some embodiments it can be easier to slide the fragrance piece 104 in and out of three prongs 134 than more than three prongs 134, while at the same time, the use of three prongs 134 and the arrangement of the prongs 134 on both sides of the fragrance piece space can easily satisfy the preferred attachment parameters and/or more preferred attachment parameters with appropriately shaped and sized fragrance pieces 104.

Referring now to exemplary FIG. 24b, in some embodiments to enable the attachment of the fragrance piece 104 within at least the preferred attachment parameters and/or the more preferred attachment parameters for a fragrance piece 104 having a circular outer shape, at least two generally opposing sides of the outer surface 110 of the fragrance piece 104 will make contact with the inner surface 142 of the at least one prong 134.

Figure 53:
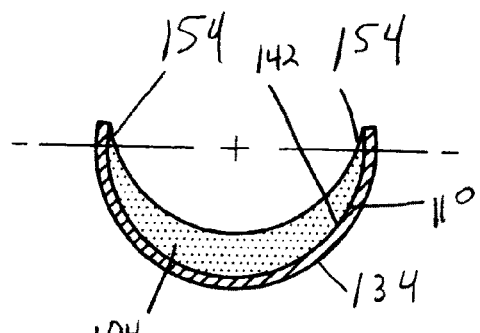
FIGS. 53-58 are side views of various shaped fragrance pieces interacting with partially circular-shaped prongs.

As exemplarily illustrated in FIG. 53, a fragrance piece 104 having a crescent outer shape will have two end points 154. In some embodiments to enable the attachment of the fragrance piece 104 within at least the preferred attachment parameters and/or the more preferred attachment parameters the two end points 154 on the crescent will be able to touch the inner surface 142 of the at least one prong 134 when the fragrance piece 104 is attached with the at least one prong 134.

Figure 54:
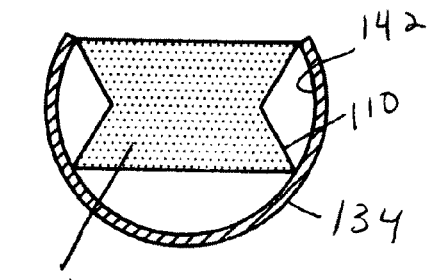

As exemplarily illustrated in FIG. 54 for some embodiments to enable the attachment of the fragrance piece 104 within at least the preferred attachment parameters and/or the more preferred attachment parameters of a fragrance piece 104 having a quadrilateral or rectangular outer shape, all four corners will be able to touch the inner surface of the at least one prong 134 having a circular inner space shape when the fragrance piece 104 is attached with the at least one prong 134.

Figure 31:
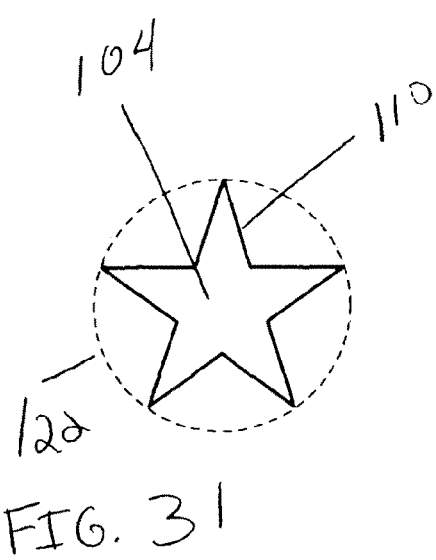
FIG. 31 is a view of an imaginary circle drawn around a star-shaped fragrance piece.
Figure 32A:
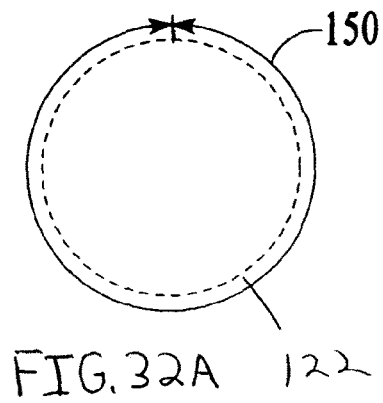
FIGS. 32 A and B are views of the measurement of the circumference of the imaginary circle shown in FIG. 31.
Figure 33:
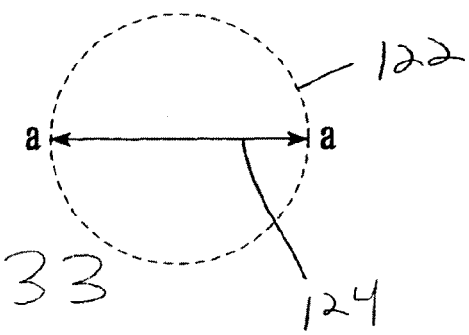
FIG. 33 is a view of the measurement of the diameter of the imaginary circle shown in FIG. 31.
Figure 32B:
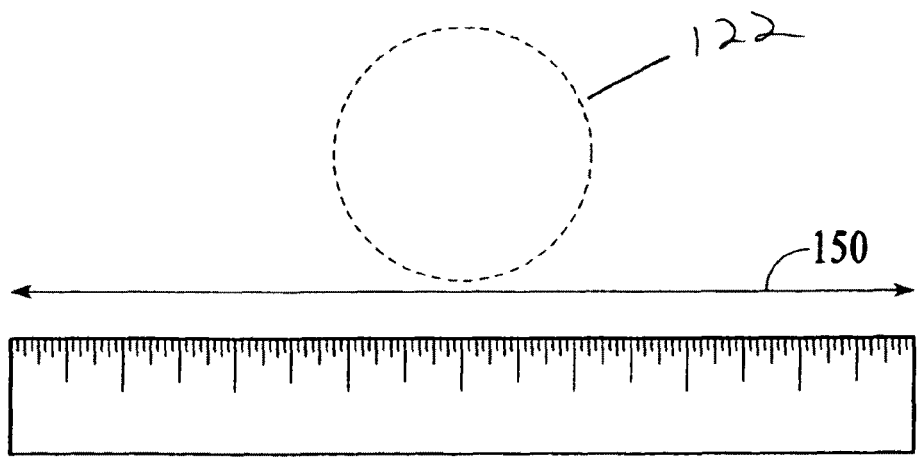
Figure 34:
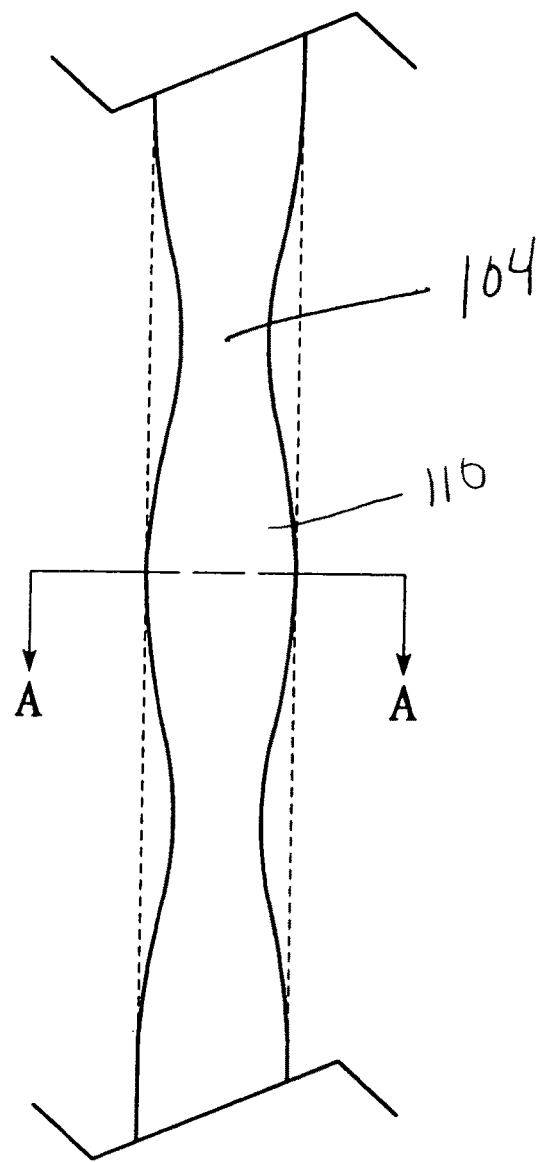
FIG. 34 is a partial side view of a non-uniformly shaped fragrance piece.
Figure 34A:
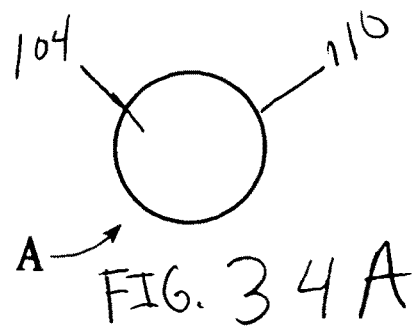

Referring now to exemplary FIGS. 31, 32a-b, 34, 34a, and 55-58 for some embodiments of fragrance pieces 104 having outer shapes in the forms of squares, five-sided stars, pentagons, six-sided stars, and hexagon, the interaction of at least one prong 134 having a generally circular or generally semi-circular inner surface shape and the fragrance piece 104 may be calculated by calculating an imaginary circle 122 drawn around outer surface of the fragrance piece 104, as exemplarily illustrated in FIG. 31. As illustrated in FIGS. 32a and 32b, the circumference of the imaginary circle 122 is then calculated, which is referred to at the "calculated circumference" 150. It is to be noted that in the illustrations illustrating the measurement of the circumference of the imaginary circle 122, the "calculated circumference" 150 is not illustrated as exactly the size of the imaginary circle 122, which is done for clarity of illustration only; it is intended that the calculated circumference 150 is the exact size of the imaginary circle 122. As exemplarily illustrated in FIGS. 34 and 34a, if the outer surface of the fragrance piece 104 is not uniform, the measurement may be taken at the widest point on the fragrance piece 104 that can engage the attacher 106 when the fragrance piece 104 is attached with the holding device 102.

Figure 55:
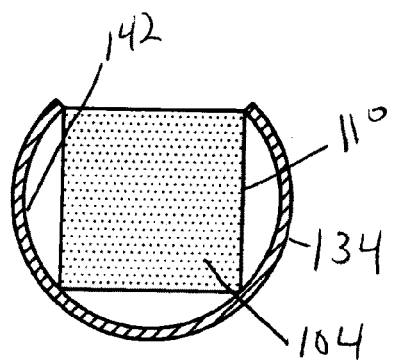

As exemplarily illustrated in FIG. 55 for some embodiments to enable the attachment of the fragrance piece 104 within at least the preferred attachment parameters and/or the more preferred attachment parameters of a fragrance piece 104 having a square outer shape, the length of the accessible prong gap 148 will be less than 25 percent of the length of the calculated circumference 150, and all four corners of the fragrance piece 104 will be able to touch the inner surface of the at least one prong 134 when the fragrance piece 104 is attached with the at least one prong 134.

Figure 56:
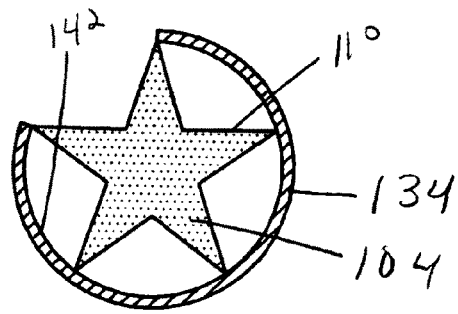

As exemplarily illustrated in FIG. 56 for some embodiments to enable the attachment of the fragrance piece 104 within at least the preferred attachment parameters and/or the more preferred attachment parameters of a fragrance piece 104 having a five-sided star outer shape, the length of the accessible prong gap 148 will be less than 20 percent of the length of the calculated circumference 150 and all five points of the star-shaped fragrance piece 104 will be able to touch the inner surface of the at least one prong 134 when the fragrance piece 104 is attached with the at least one prong 134.

Figure 57:
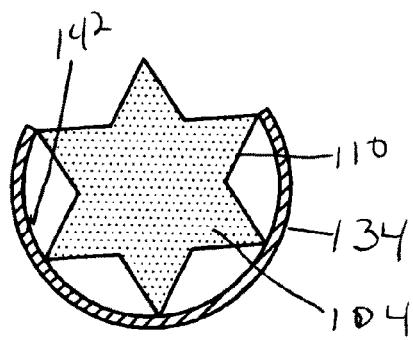

As exemplarily illustrated in FIG. 57 for some embodiments to enable the attachment of the fragrance piece 104 within at least the preferred attachment parameters and/or the more preferred attachment parameters of a fragrance piece 104 having a six-sided star outer shape, the length of the accessible prong gap 148 will be less than one third of the length of the calculated circumference 150 and all six points of the star-shaped fragrance piece 104 will be able to touch the inner surface of the at least one prong 134 when the fragrance piece 104 is attached with the at least one prong 134.

Figure 58:
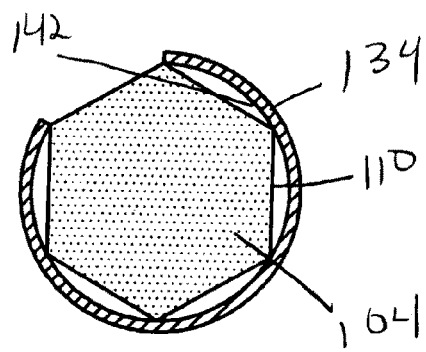
Figure 59:
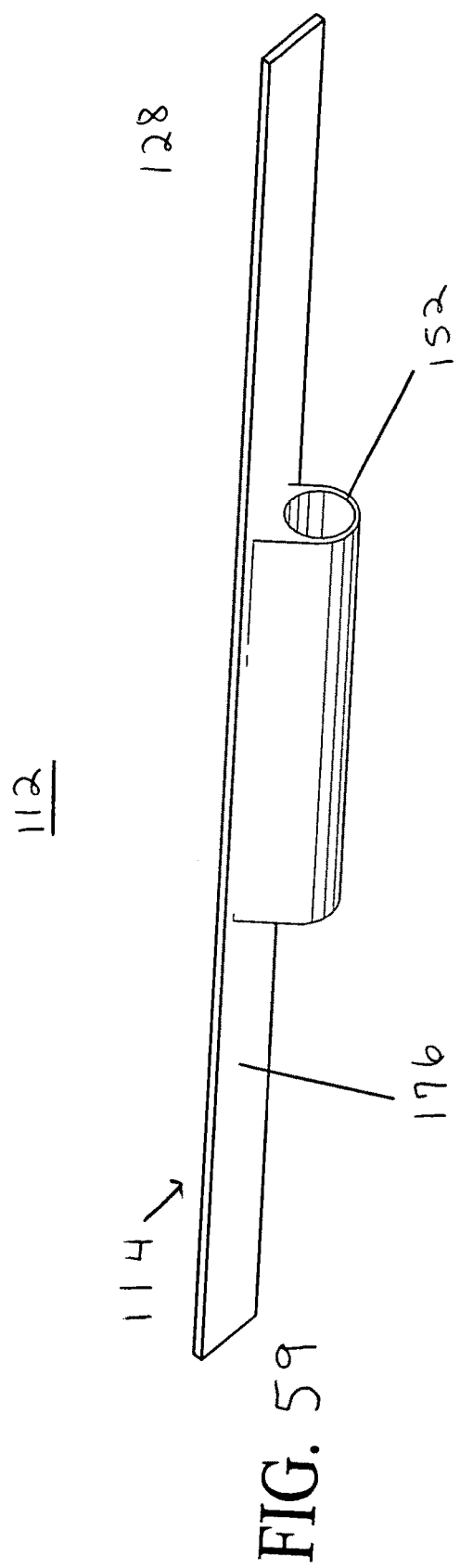
FIG. 59 is a view of a loop integrally molded on a piece of a material.
Figure 60:
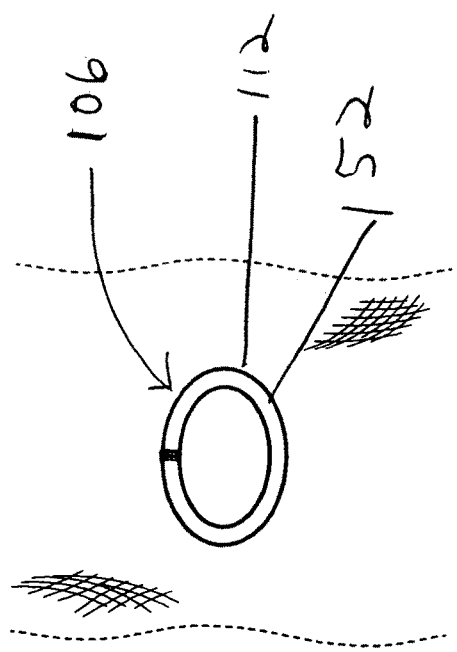
FIG. 60 is a view of a sewn-on loop attacher, attachment piece and/or attachment piece part.
Figures 63, 64, 65:
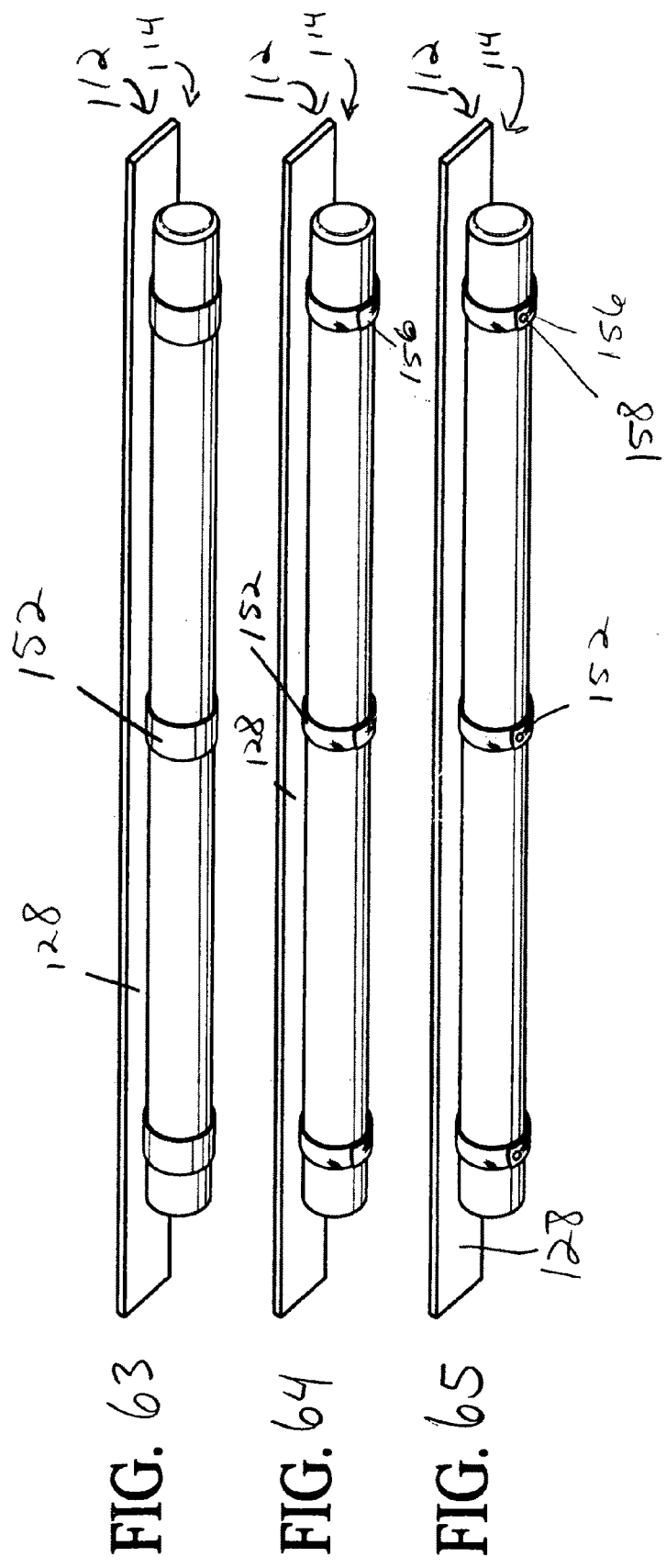
FIG. 63 is a view of three continuous loops and an attached fragrance piece.
FIG. 64 is a view of three loops with hook and loop connectors and an attached fragrance piece.
FIG. 65 is a view of three loops with snap connectors and an attached fragrance piece.
Figure 69:
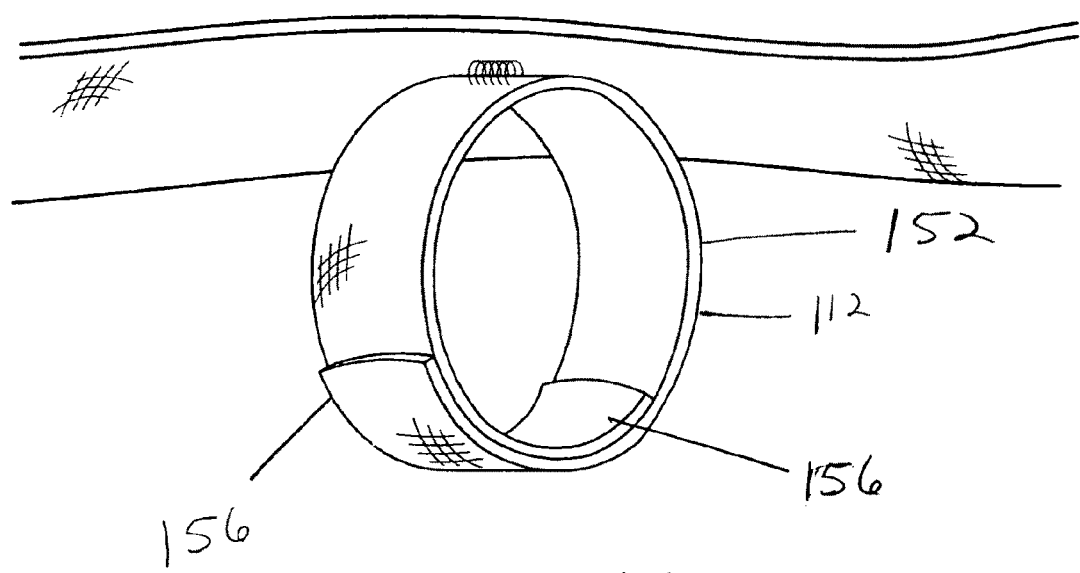
FIG. 69 is a view of a loop sewn onto a piece of material with the loop ends having hook and loop connectors.

As exemplarily illustrated in FIG. 58 for some embodiments to enable the attachment of the fragrance piece 104 within at least the preferred attachment parameters and/or the more preferred attachment parameters of a fragrance piece 104 having a hexagon outer shape, the length of the accessible prong gap 148 will be less than one sixth of the length of the calculated circumference 150 and all six corners of the hexagon shaped fragrance piece 104 will be able to touch the inner surface of the at least one prong 134 when the fragrance piece 104 is attached with the at least one prong 134.

Other embodiments of the scented holding device systems, attacher systems, and devices are exemplarily illustrated in FIGS. including but not limited to, FIGS. 15, 17, 19-21, 26, 59-70, wherein the attachment piece includes at least one loop 152. The at least one loop 152 can be made of many materials, including, but not limited to plastic, metal, wood, fabric, fiberglass, vinyl, polyester, nylon, rubber, natural fibers such as cotton, and/or other fibers. The at least one loop 152 can be made of materials having a memory, referred to as "memory materials", including but not limited to elastic, rubber and memory metal. The at least one loop 152 may vary in size, number, and placement.

The at least one loop 152 may be directly fixedly or removably attached or attachable with the holding device 102 by ways currently known in the art or to be discovered, including but not limited to, tacking, stapling, adhesive, taping, heat sealing, molding, magnetic attraction, bonding, welding, weaving, sewing, hook and loop material, such as but not limited to Velcro®, and/or mechanical interaction, such as but not limited to tongue and groove interaction, or may be directly fixedly or removably attached or attachable with a compatible attachment piece 112 or attachment piece part 114 by ways currently known or to be discovered in the art, including but not limited to tacking, stapling, adhesive, taping, heat sealing, molding, magnetic attraction, bonding, welding, weaving, sewing, hook and loop material, such as but not limited to Velcro®, and/or mechanical interaction, such as but not limited to tongue and groove interaction. As exemplarily illustrated in FIG. 59, the at least one loop 152 can be integrally integrated and/or attached or attachable with the holding device 102 or to an attachment piece part in a manner whereby each loop 152 is an integral part of the holding device 102, attachment piece 112, or attachment piece part 114 by ways currently know in the art, such as, but not limited to by molding, weaving, and ways to be discovered in the art. The attachment piece part 114 can be a piece of a material 128, which is described in more detail in subsequent paragraphs and FIGS. If the at least one loop 152 is integral, attachable or attached with at least one attachment piece 112 or attachment piece part 114, the at least one attachment piece 112 or attachment piece part 114 is integrally integrated and/or fixedly or removably attached or attachable with the holding device 102 either directly or with the assistance of at least one attachment piece part 114. When the at least one loop 152 is attached with the holding device 102 either directly or with the assistance of at least one attachment piece 112 or attachment piece part 114, the fragrance piece 104 will be removably attachable with the at least one loop 152 at least within the required attachment parameters. Preferably, when the at least one loop 152 is attached with the holding device 102, either directly or with the assistance of at least one attachment piece 112 or attachment piece part 114, the fragrance piece 104 will be removably attachable with the at least one loop 152 within the preferred attachment parameters and/or the more preferred attachment parameters. In addition, in some embodiments, when the at least one loop 152 is attached with the holding device 102, either directly or with the assistance of at least one attachment piece 112 or attachment piece part 114, the fragrance piece 104 will be removably attachable with the at least one loop 152 within the removal attachment parameters, the removal and fit attachment parameters and/or the preferred removal and fit attachment parameters.

Each fragrance piece 102 can be attachable with a loop 152 that is in the form of a continuous loop, as exemplarily illustrated in FIGS. 26, and 59-63, or in one or more pieces having at least two loose ends 156 whereby at least two opposing loose ends 156 will be connectable with one another, as exemplarily illustrated in FIGS. 15, and 64-70. Generally, there will be two opposing loose ends 156 that are connectable with each other, however, if one or both of the loose ends 156 are frayed, more than two loose ends 156 can be created. The loose ends 156 can be connectable with each other by connectors 158 including, but not limited to, complimentary pieces of hook and loop material 178, including Velcro®, at least one button and complimentary button hole or loop, snaps, at least one complimentary hook and eye, and at least one hook and complimentary hook catch. Some of the loose end connectors 158 can provide for more than one connection point, and thereby enabling the size of the loop 152 to vary. Thereby, in some embodiments, when the loose end connectors 158 provide for more than one connection point, the connection between the loose ends may be adjusted to enable the at least one fragrance piece 104 to be attachable within the preferred attachment parameters and/or the more preferred attachment parameters, and in some embodiments within the removal attachment parameters, removal and fit attachment parameters and/or preferred removal and fit attachment parameters.

A variable number of loops 152 can be integral with and/or attached or attachable with the holding device 102 either directly or with the assistance of an attachment piece 112 or one or more attachment piece parts 114. In addition, if the at least one loop 152 is removably attachable, such as those exemplarily illustrated in FIGS. 15, 26, and 70, the number and size of the loops 152 can vary, which can be beneficial for a number of reasons, including, but not limited to, varying the number of fragrance pieces 104 to be attached and/or varying the at least one fragrance piece 104 size.

Figure 26:
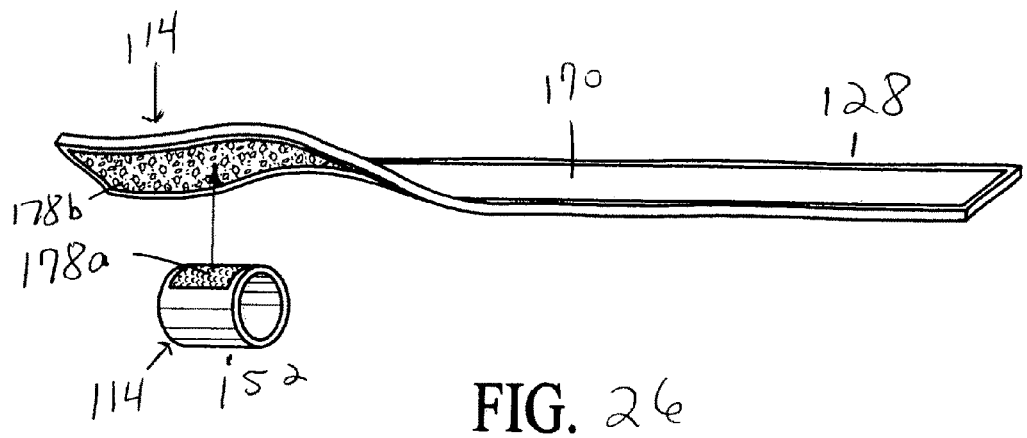
FIG. 26 is a view of a loop attachable with a strip of material with hook and loop material.
Figure 25:
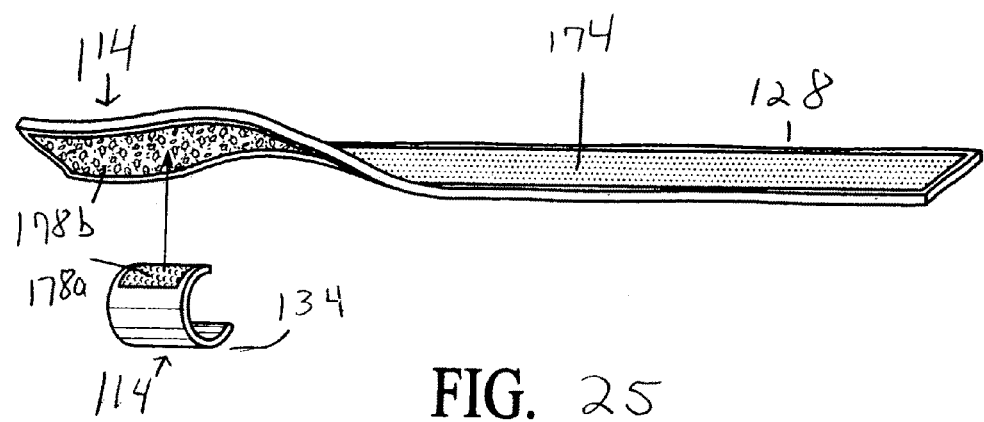
FIG. 25 is a view of a prong attachable with a strip of material with hook and loop material, and the strip of material also having adhesive on the holding device side.
Figure 27:
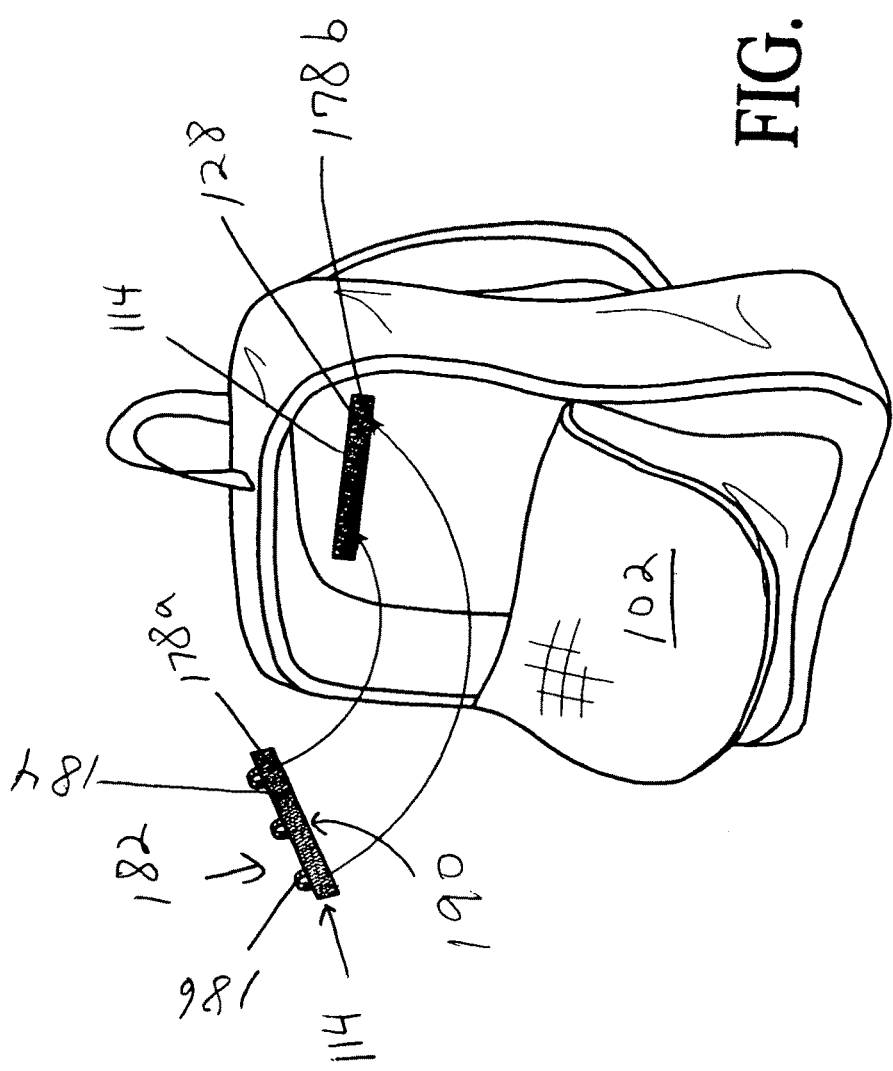
FIG. 27 is a view of a backpack with a hook and loop strip of material, and an attachable supplemental piece.
Figure 70:
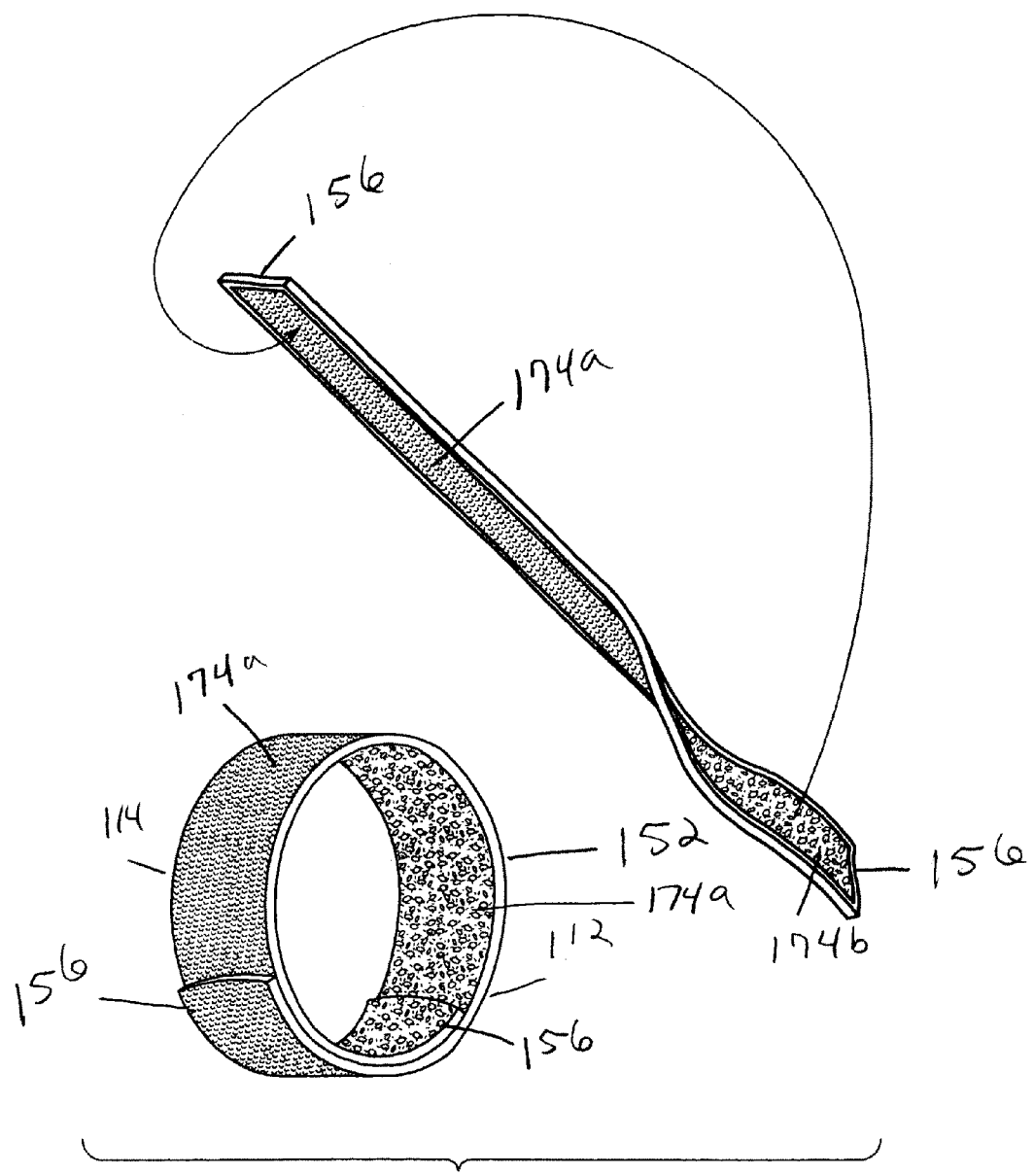
FIG. 70 is a view of a loop formed by two-faced hook and loop material.
Figures 71, 71A:
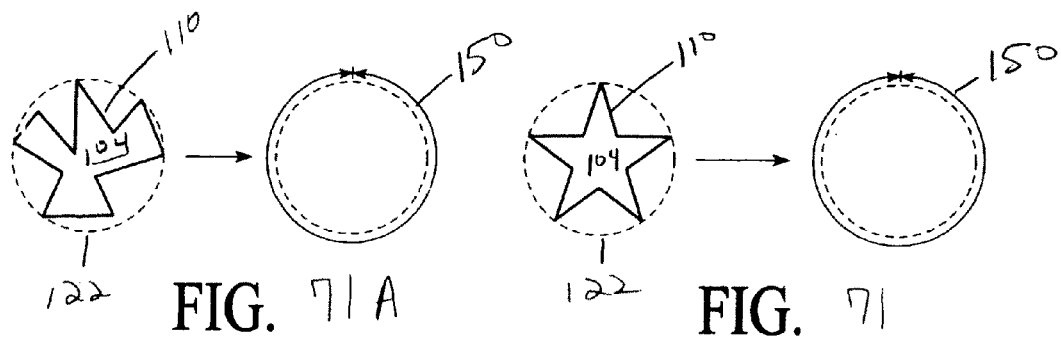
FIGS. 71-75 are views of the calculated circumference of fragrance pieces having various shapes.
Figures 72, 73:
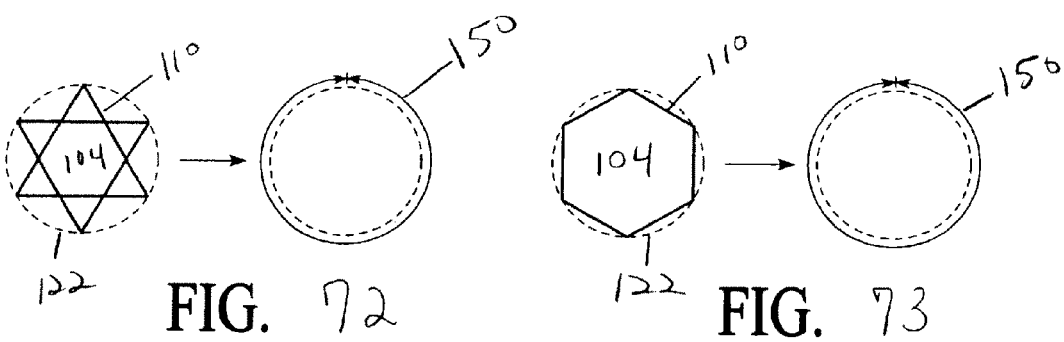
Figures 74, 75:
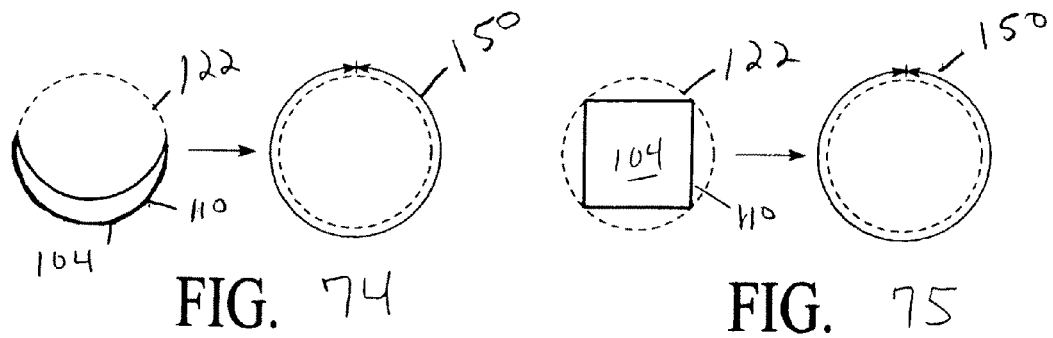

Referring now to FIGS. including but not limited to exemplary FIGS. 26 and 70, in some embodiments, the holding device 102 or attachment piece part 114 can be made of hook or loop material 178. At least part of the outer surface of the at least one loop 152 can be made of the complimentary hook or loop material 178, thereby enabling the loop 152 to be removably attachable anywhere on the complimentary hook or loop material 178 on the holding device 102 or the attachment piece part 114. In addition, the number of loops 152 attached or attachable with the holding device 102 or attachment piece part 114 can vary. As exemplarily illustrated in FIG. 70, a loop 152 can be made from two-sided hook and loop material 178, where one side of the hook and loop material 178 is made of the loop material 178b and the other side is made of the hook material 178a. When two-sided hook and loop material 178 is used to make a loop 152, the loop can be made with either the hook or loop side of the material facing outward, and as a result, the loop may be attachable with a holding device 102 or attachment piece part 114 of which at least a portion is either hook material 178a or loop material 178b.

As exemplarily illustrated in FIGS. including but not limited to exemplary FIGS. 61-65, in some embodiments, if more than one loop 152 is used for a straight fragrance piece 104, each loop 152 can be attached in a generally straight line so that the straight fragrance piece 104 may be easily inserted.

Referring now to FIGS. including but not limited to exemplary FIGS. 17, 60-62 and 69, in other embodiments, at least one loop 152 can be sewn onto the lining, sectional compartment, other interior or exterior portion or structure of a holding device 102, which may include, but is not limited to, a fabric structure, including but not limited to the walls, sides, tops, bottoms or compartment or sectional dividers of a holding device 102, or sewn onto another attachment piece part 114 as exemplarily illustrated. The at least one loop 152 can be placed such that the attached fragrance piece 104 will be oriented in a direction including but not limited to vertical, diagonal or horizontal.

Referring now to FIGS. including but not limited to exemplary FIGS. 31, 32, 34, 34a, 53, and 71-75, in some embodiments, the relationship of the size of the fragrance piece 104 and the size or the at least one loop is calculated by determining the calculated circumference 150 of the outer surface of the fragrance piece 104. As illustrated in FIGS. 32a and 32b, and 71-75 is to be noted that in the illustrations illustrating the measurement of the circumference of the imaginary circle 122, the "calculated circumference" 150 is not illustrated as exactly the size of the imaginary circle 122, which is done for clarity of illustration only; it is intended that the calculated circumference 150 is the exact size of the imaginary circle 122.

When the outer shape of the fragrance piece 104 is circular, the calculated circumference is actually the actual circumference of the fragrance piece 104. Since the calculated circumference is calculated by drawing an imaginary circle around the fragrance piece, in the case of a circular fragrance piece, the imaginary circle and the actual circumference will be the same. Accordingly, the term "calculated circumference" 150 as used herein is intended to include the actual circumference of a circular fragrance piece. In addition, for a circular fragrance piece, the actual circumference, and therefore also the calculated circumference, may be directly measured or it may be measured by ways commonly known in the art, such as, but not limited to, by determining the diameter of the fragrance piece and utilizing the standard Pi calculation of diameter multiplied by about 3.14 equaling the circumference, as exemplarily shown as follows: if the diameter of a circular fragrance piece is 0.2 inches, then the actual circumference, and therefore also the calculated circumference, of the fragrance piece is about 0.63 inches.

In some embodiments, the range of interactions between circumferences of a loop 152 and calculated circumferences 150 of a fragrance piece 104 is in the range of the circumference of the loop being between at least as large as the calculated circumference 150 of a fragrance piece 104 and up to two times the size of the calculated circumference 150 of the fragrance piece 104. The term "circumference" of a loop is intended to mean the interior circumference of the loop and not the exterior circumference of the loop.

In some embodiments, by way of example and without intending to be limiting, when the calculated circumference of the fragrance piece 104 is 0.63 inches, the circumference of the loop 152 would be in the range of no less than 0.63 inches and no more than 0.64 inches. As the calculated circumference of the fragrance piece 104 increases or decreases, the range of circumferences of the loop 152 will increase or decrease proportionately. This embodiment can apply to loops 152 of all materials, including hook and loop materials 178. This range of compatible loop 152 sizes in relation to fragrance piece 104 calculated circumferences may also be used for memory materials, provided that the tension in the stretchiness of the memory material is such that a snug fit may be obtained.

Other embodiments of the scented holding device systems 100, attacher systems, 100a, including attachment piece systems, attachment piece part systems, and/or devices are illustrated in FIGS. including but not limited to exemplary FIGS. 9, 10, 15, 18, and 76-79 wherein the attacher includes at least one clip 162. The at least one clip 162 could be made of many materials, including, but not limited to plastic, metal, wood, fabric, fiberglass, vinyl, polyester, nylon, rubber, natural fibers such as cotton, and/or other fibers.

The at least one clip 162 may be directly fixedly or removably attached or attachable with the holding device 102 by ways currently known in the art or to be discovered, including but not limited to tacking, stapling, bonding, taping, heat sealing, welding, molding, magnetic attraction, weaving, sewing, hook and loop material, such as but not limited to Velcro®, and/or mechanical interaction, such as but not limited to tongue and groove interaction, or may be directly fixedly or removably attached or attachable with a compatible attachment piece 112 or attachment piece part 114 by ways currently known or to be discovered in the art, including but not limited to tacking, stapling, bonding, taping, heat sealing, welding, molding, magnetic attraction, weaving, sewing, hook and loop material, such as but not limited to Velcro®, and/or mechanical interaction, such as but not limited to tongue and groove interaction. The at least one clip 162 can be integrally integrated and/or attached or attachable with the holding device 102, or to an attachment piece 112 or attachment piece part 114 in a manner whereby each clip 162 is an integral part of the holding device 102 or attachment piece 112 or attachment piece part 114 by ways currently know in the art, such as, but not limited to by molding, weaving, and ways to be discovered in the art. The attachment piece part 114 can be a piece of a material 128, which is described in more detail in subsequent paragraphs and FIGS. If the at least one clip 162 is attached with the holding device 102 with at least one attachment piece 112 or attachment piece part 114, the attachment piece 112 or at least one of the attachment piece parts 114 is integrally integrated and/or fixedly or removably attached or attachable with the holding device 102. When the at least one clip 162 is attached with the holding device 102 either directly or with the assistance of at least one attachment piece 112 or attachment piece part 114, the fragrance piece 104 will be removably attachable with the at least one clip 162 within the preferred attachment parameters and/or the more preferred attachment parameters, and in some embodiments also within the removal and fit attachment parameters and/or the preferred removal and fit attachment parameters.

As commonly known in the art, each at least one clip 162 may have two pressure pieces 164 that exert pressure toward each other. As exemplarily illustrated in FIGS. 9, 18, and 77-79, in some embodiments, a fragrance piece 104 can be held in place by the pressure of the clip pressure pieces 164.

Figure 78:
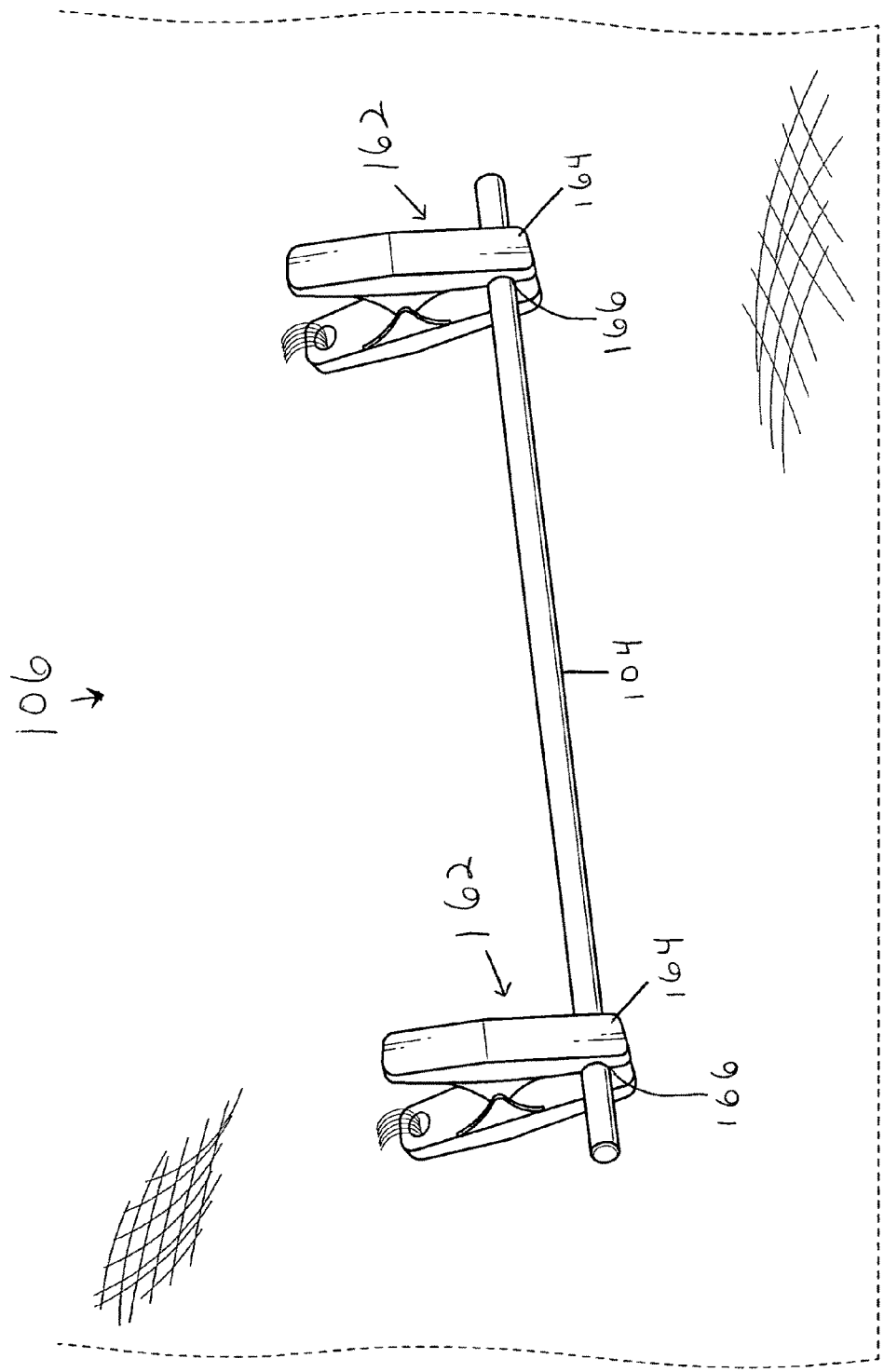
FIG. 78 is a side view of a circular fragrance piece attached with sewn-on clips, where the pressure pieces of the clips have concave shapes.
Figure 79:
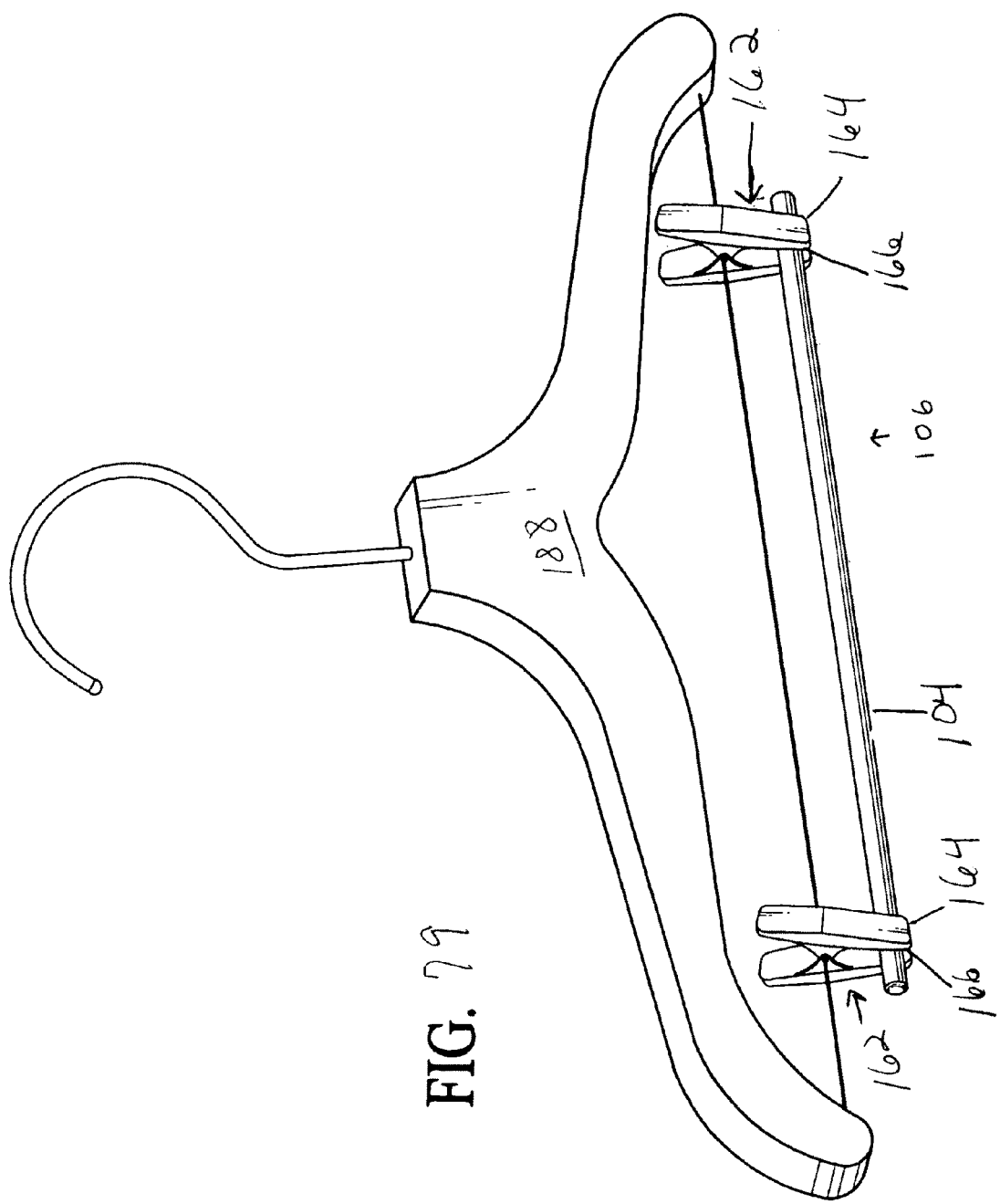
FIG. 79 is a view of a circular fragrance piece attached with two clips on a hanger.
Figure 82:
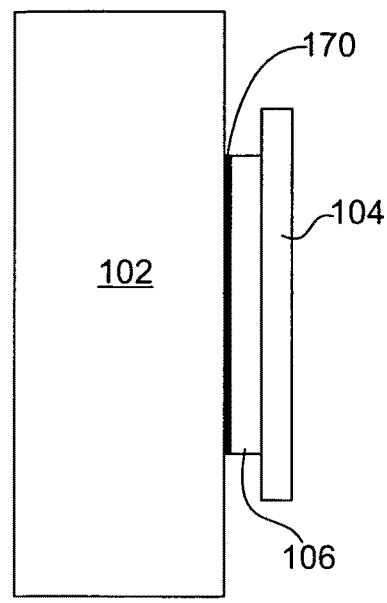
FIGS. 82 and 83 are the same side view of a holding device, a piece of a material, and a fragrance piece, where FIG. 82 highlights the holding device side of the piece of a material and FIG. 83 highlights the fragrance piece side of the piece of a material.
Figure 83:
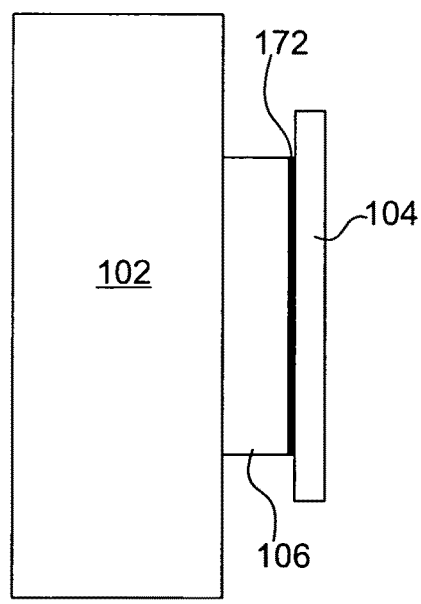
Figure 86:
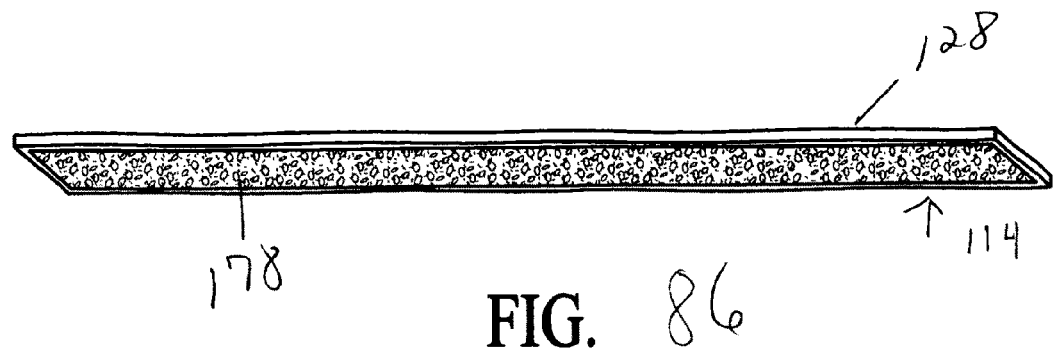
FIG. 86 is a view of a hook and loop material attachment piece part.

In some embodiments, as exemplarily illustrated in FIGS. 18 and 78, the inner surface 166 of the pressure pieces 164 can have a shape that compliments the shape of the fragrance piece 104. For example, and without intending to be limiting, if the fragrance piece 104 has a circular outer surface, the inner surface 166 of the pressure pieces 164 will be concave.

In some embodiments, as exemplarily illustrated in FIG. 9, there can be one fragrance piece 104 for each clip 162. In other embodiments, as exemplarily illustrated in FIGS. 18, 78 and 79, one fragrance piece 104 can be held by more than one clip 162.

In other embodiments, clips 162 that are commonly found on clothes hangers 188 have a space above the clip pressure pieces 164, referred to "pressure piece space" 168. In these embodiments, as exemplarily illustrated in FIGS. 10 and 76, fragrance pieces can be provided that will fit into the pressure piece space 168 within the preferred attachment parameters and/or the more preferred attachment parameters, and in some embodiments also within the removal and fit attachment parameters and/or the preferred removal and fit attachment parameters. In one embodiment, there can be one fragrance piece 104 for each pressure piece space 168. In another embodiment, as exemplarily illustrated in FIG. 10, one fragrance piece 104 can fit into the pressure piece spaces 168 for more than one clip 162.

In another embodiment, the at least one fragrance piece 104 can be attached or attachable with the holding device 102 with adhesive. In this embodiment, adhesive may be applied directly to the holding device 102 or the fragrance piece 104 provided that the fragrance piece 104 may be removably attachable with the holding device 102 within the preferred attachment parameters and/or the more preferred attachment parameters, and in some embodiments also within the removal and fit attachment parameters and/or the preferred removal and fit attachment parameters.

Reference is now made to FIGS. including but not limited to exemplary FIGS. 14-17, 19-22, 23b-23e, 25-27, 30, 35, 40, 42-45, 47-51, 59, 61-67, 69, and 80-86. At least one piece of a material 128 can be an attachment piece. The at least one piece of a material 128 may be directly fixedly or removably attached or attachable with the holding device 102 by ways currently known in the art or to be discovered, including but not limited to tacking, stapling, adhesive, taping, heat sealing, molding, magnetic attraction, bonding, welding, weaving, sewing, hook and loop material, such as but not limited to Velcro®, and/or mechanical interaction, such as but not limited to tongue and groove interaction, or may be directly fixedly or removably attached or attachable with an attachment piece 112 at least one compatible attachment piece part 114 by ways currently known or to be discovered in the art, including but not limited to, tacking, stapling, adhesive, taping, heat sealing, molding, magnetic attraction, bonding, welding, weaving, sewing, hook and loop material, such as but not limited to Velcro®, and/or mechanical interaction, such as but not limited to tongue and groove interaction. The at least one piece of a material 128 can be integrally integrated and/or attached or attachable with the holding device 102 or to an attachment piece 112 or attachment piece part 114 in a manner whereby each piece of a material 128 is an integral part of the holding device 102, attachment piece 112 or attachment piece part 114 by ways currently know in the art, such as, but not limited to by molding, weaving, and ways to be discovered in the art.

If the piece of a material 128 is an attachment piece part 114, it is understood that the attachment piece part 114 will interact with at least one other attachment piece part 114 to enable at least one fragrance piece 104 to be removably attachable with a holding device 102 within at least the required attachment parameters, and in some embodiments also within the removal attachment parameters, the preferred attachment parameters, the more preferred attachment parameters, the removal and fit attachment parameters and/or the preferred removal and fit attachment parameters. It is to be understood that any number of attachment piece parts 114 may be attached or attachable with each other as long as at least one fragrance piece 104 is attachable with the holding device 102 within at least the required attachment parameters, and in some embodiments also within the removal attachment parameters, the preferred attachment parameters, the more preferred attachment parameters, the removal and fit attachment parameters and/or the preferred removal and fit attachment parameters.

In some embodiments, when the at least one piece of a material 128 is attached with the holding device 102 either directly or with the assistance of at least one attachment piece part, the fragrance piece 104 will be removably attachable with the at least one piece of a material 128 or compatible attachment piece part 114 within the removal attachment parameters.

In some embodiments, when the at least one piece of a material 128 is attached with the holding device 102 either directly or with the assistance of at least one attachment piece part, the fragrance piece 104 will be removably attachable with the at least one piece of a material 128 or compatible attachment piece part 114 within the removal and fit attachment parameters.

In some embodiments, when the at least one piece of a material 128 is attached with the holding device 102 either directly or with the assistance of at least one attachment piece part, the fragrance piece 104 will be removably attachable with the at least one piece of a material 128 or compatible attachment piece part 114 within the preferred removal and fit attachment parameters.

In some embodiments, when the at least one piece of a material 128 is attached with the holding device 102 either directly or with the assistance of at least one attachment piece part, the fragrance piece 104 will be removably attachable with the at least one piece of a material 128 or compatible attachment piece part 114 within the preferred attachment parameters.

In some embodiments, when the at least one piece of a material 128 is attached with the holding device 102 either directly or with the assistance of at least one attachment piece part, the fragrance piece 104 will be removably attachable with the at least one piece of a material 128 or compatible attachment piece part 114 within the more preferred attachment parameters.

Specifically referring now to FIGS. including but not limited to exemplary FIGS. 81-84, in some embodiments, the piece of a material 128 will have a side, referred to as the "holding device side" 170 that is attached or attachable with the holding device 102 either directly, or indirectly, by utilizing at least one attachment piece 112 or attachment piece part 114 that is also attached, attachable or integral with the holding device side 170. In addition, the piece of a material 128 will have a side, referred to as the "fragrance piece side" 172 to which the fragrance piece 104 is attachable either directly onto the piece of a material 128 or indirectly by utilizing at least one attachment piece 112 or attachment piece part 114 that is also attachable, attached, or integral with the fragrance piece side 172.

In some embodiments the piece of a material 128 will be in the form of a strip of a material that is longer than it is wide. These strips can be attached with any flat surface or non-flat surface of a holding device 102, provided the strip of a material and the at least one fragrance piece 104 are sufficiently pliable to follow at least a portion of the contour of the non-flat surface such that at least one fragrance piece is attachable with the holding device at least within the required attachment parameters.

The at least one piece of a material 128 can be made from a variety of materials, including but not limited to, plastic, metal, wood, fabric, fiberglass, vinyl, polyester, nylon, rubber, natural fibers such as cotton, and/or other fibers.

In some embodiments, the fragrance piece 104 is attachable with adhesive 174, and/or with at least one slot 116, prong 134, loop 152 and/or clip 162, which is integral with the fragrance piece side 172, is attached or attachable with the fragrance piece side 172, is integral with at least one attachment piece part 114 that is integral with the fragrance piece side 172, is attached or attachable with at least one attachment piece part 114 that is attached or attachable with the fragrance piece side 172, is integral with at least one attachment piece 112 that is integral with the fragrance piece side 172, and/or is attached or attachable with at least one attachment piece 112 that is attached or attachable with the fragrance piece side 172. When the at least one fragrance piece 104 is attached or attachable with at least one attachment piece 112 or attachment piece part 114 that is at least one loop 152 and/or slot 116, the fragrance piece 104 will be removably attachable with the fragrance piece side 172 within at least the required attachment parameters, and preferably, the fragrance piece 104 is removably attachable with the fragrance piece side 172 in a manner whereby the fragrance piece 104 may be removably attachable with the holding device 102 within the preferred attachment parameters and/or the more preferred attachment parameters. In addition, when the at least one fragrance piece 104 is attached or attachable with at least one attachment piece 112 or attachment piece part 114 that is at least one loop 152 and/or slot 116, the fragrance piece 104 will be removably attachable with the fragrance piece side 172 within at least the required attachment parameters, and in some embodiments, the fragrance piece 104 may also be removably attachable with the fragrance piece side 172 in a manner whereby the fragrance piece 104 may be removably attachable with the holding device 102 within the removal attachment parameters, the removal and fit attachment parameters and/or the preferred removal and fit attachment parameters. When the at least one fragrance piece 104 is attached or attachable with at least one attachment piece 112 or attachment piece part 114 that is adhesive, at least one prong 134 and/or clip 162, the fragrance piece 104 is removably attachable with the fragrance piece side 172 in a manner whereby the fragrance piece 104 may be removably attachable with the holding device 102 within the preferred attachment parameters and/or the more preferred attachment parameters, and in some embodiments also within the removal and fit attachment parameters and/or preferred removal and fit attachment parameters.

Without intending to be limiting, following are some additional exemplary embodiments of pieces of materials that can be the attachment piece 112 or attachment piece part 114.

Unless otherwise indicated, the term "adhesive" is intended to include all forms of bonding materials currently known or to be discovered in the art, including, but not limited to, glue, paste, gum, epoxy, tape and cement.

Reference is now made to FIGS. 22 and 84, wherein embodiments of the scented holding device systems 100, attacher systems, 100a, including attachment piece systems, attachment piece part systems, and/or devices are exemplarily illustrated utilizing at least one piece of a material 128 having adhesive 174 on the holding device side 170 and on the fragrance piece side 172. The adhesive 174 on the holding device side 170 of the attachment piece 112 in this embodiment is attachable with a holding device 102, and the fragrance piece 104 is removably attachable with the adhesive 174 on the fragrance piece side 172. In one embodiment the same adhesive could be applied to both the holding device side 170 and the fragrance piece side 172 such that the two sides could be indistinguishable or interchangeable. In another embodiment different types of adhesives 174 could be applied to the holding device side 170 and the fragrance piece side 172, provided that the adhesive 174 on the fragrance piece side 172 will enable the fragrance piece 104 to be removably attachable within the preferred attachment parameters and/or the more preferred attachment parameters, and in some embodiments also within the removal and fit attachment parameters and/or the preferred removal and fit attachment parameters.

In other embodiments, when both sides of a piece of a material 128 include adhesive 174, the fragrance piece side 172 can have, but is not limited to, the following attachment piece parts 114, which have been described in previous paragraphs and drawings, integral with, and/or attachable or attached with the fragrance piece side 172: at least one loop 152, prong 134, slot 116 and/or clip 162.

Figure 85:
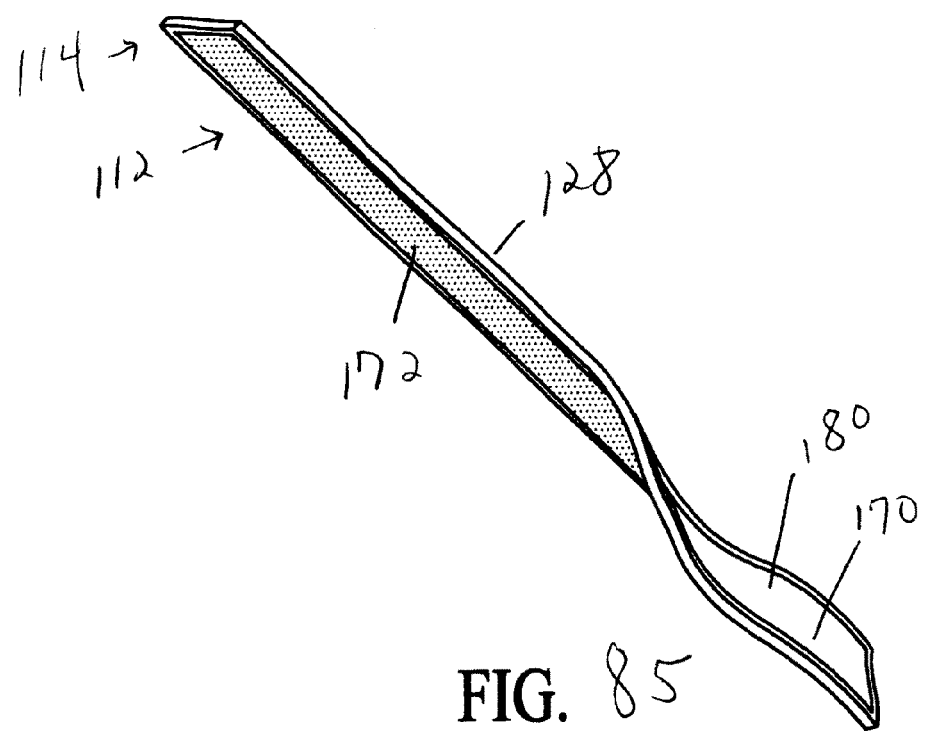
FIG. 85 is a view of piece of a material attachment piece part with adhesive on the fragrance piece side.

Referring now to FIGS. including but not limited to FIG. 85, in which an embodiment of the scented holding device systems 100, attacher systems, 100a, including attachment piece systems, attachment piece part systems, and/or devices and an attachment piece 112 is exemplarily illustrated wherein the attachment piece 112 is a piece of a material 128 having adhesive on the fragrance piece side 172. The non-adhesive side of the attachment piece 112 in this embodiment is the holding device side 170, which is attachable with a holding device 102 by any ways currently known in the art or to discovered, including, but not intending to be limited to, tacking, stapling, heat sealing, molding, magnetic attraction, weaving, sewing, hook and loop material, such as but not limited to Velcro®, and/or mechanical interaction, such as but not limited to tongue and groove interaction. In addition, the piece of a material 128 can be part of a lining, a sectional compartment, or another interior or exterior portion of the holding device 102. The fragrance piece 104 is removably attachable with the holding device 102 with the adhesive 174 on the fragrance piece side 172 provided that the adhesive 174 to which the fragrance piece 104 is attachable will enable the fragrance piece 104 to be removably attachable within the preferred attachment parameters and/or the more preferred attachment parameters, and in some embodiments also within the removal and fit attachment parameters and/or the preferred removal and fit attachment parameters. In other embodiments, the adhesive side of the piece of a material 128, which in these embodiments is the fragrance piece side 172, can have, but is not limited to, the following attachment piece parts 114, which have been described in previous paragraphs, integral, attachable or attached with it: at least one loop 152, prong 134, slot 116, cavity 250 and/or clip 162.

In other embodiments, as exemplarily illustrated in FIGS. including but not limited to FIGS. 16 and 40 the piece of a material 128 can be a piece of material including but not limited to, plastic, metal, wood, fabric, fiberglass, vinyl, polyester, nylon, rubber, natural fibers such as cotton, other fibers, and combinations thereof, which can have adhesive 174 on the holding device side 170. The fragrance piece side 172 can have at least one prong 134, as previously described, made of materials including but not limited to, plastic, metal, wood, fabric, fiberglass, vinyl, polyester, nylon, rubber, natural fibers such as cotton, other fibers, and combinations thereof, that is integrally integrated with by, such as but not limited to, being molded, and/or woven with the piece of a material 128, or attached or attachable with the piece of a material 128 by, but not limited to, tacking, stapling, adhesive, taping, heat sealing, molding, magnetic attraction, bonding, welding, weaving, sewing, hook and loop material, such as but not limited to Velcro®, mechanical interaction, such as but not limited to tongue and groove interaction, and/or attached or attachable in other ways known or to be discovered in the art. As described in previous paragraphs relating to prongs 134, the accessible prong gap 148 of the at least one prong 134 can open in directions including but not limited to toward the top, bottom, side, front, back or diagonal of the holding device 102 when the piece of a material 128 is attached with holding device 102. In addition, as described in previous paragraphs relating to prongs 134, the size, number and location of the at least one prong 134 on the piece of can vary.

In some embodiments, as exemplarily illustrated in FIG. 40, the piece of a material 128 can be a piece of plastic 176 which can have adhesive 174 on the holding device side 170. The fragrance piece side 172 can have at least one plastic prong 134, as previously described, that is integrally integrated with the piece of plastic 176 by being molded with the piece of plastic. In addition, the fragrance piece side 172 can have at least one plastic prong 134, as previously described, that is integrally integrated with the piece of plastic 176 by, such as but not limited to, being woven with the piece of plastic, or attached or attachable with the piece of plastic by, but not limited to, tacking, stapling, adhesive, taping, heat sealing, molding, magnetic attraction, bonding, welding, weaving, sewing, hook and loop material, such as but not limited to Velcro®, mechanical interaction, such as but not limited to tongue and groove interaction, and/or attached or attachable in other ways known or to be discovered in the art. As described in previous paragraphs relating to prongs 134, the accessible prong gap 148 of the at least one prong 134 can open in directions including but not limited to toward the top, bottom, side, front, back or diagonal of the holding device 102 when the piece of a material 128 is attached with holding device 102. In addition, as described in previous paragraphs relating to prongs 134, the size, number and location of the at least one prong 134 on the piece of can vary.

In other embodiments, as exemplarily illustrated in FIGS. including but not limited to FIGS. 17, 19-21, and 66, the piece of a material 128 can be a piece of materials including but not limited to, plastic, metal, wood, fabric, fiberglass, vinyl, polyester, nylon, rubber, natural fibers such as cotton, other fibers, and combinations thereof, which can have adhesive 174 on the holding device side 170. The fragrance piece side 172 can have at least one loop 152, as previously described, made of materials including but not limited to plastic, metal, wood, fabric, fiberglass, vinyl, polyester, nylon, rubber, natural fibers such as cotton, other fibers, and combinations thereof, that is integrally integrated with by, such as but not limited to, being molded, and/or woven with the piece of a material 128, attached or attachable with the piece of a material 128 by, but not limited to, tacking, stapling, adhesive, taping, heat sealing, molding, magnetic attraction, bonding, welding, weaving, sewing, hook and loop material, such as but not limited to Velcro®, mechanical interaction, such as but not limited to tongue and groove interaction, and/or attached or attachable in other ways known or to be discovered in the art. As described in previous paragraphs relating to loops 152, the at least one loop 152 can be a continuous loop or can have at least two loose ends 156 that are connectable with each other. In addition, as described in previous paragraphs relating to loops 152, the size, number and location of the at least one loop 152 on the piece of a material 128 can vary.

In one embodiment, the piece of a material 128 can be a piece of plastic which can have adhesive 174 on the holding device side 170. The fragrance piece side 172 can have at least one plastic loop 152, as previously described, that is integrally integrated with by, such as but not limited to, being molded, and/or woven with the piece of plastic, attached or attachable with the piece of plastic by, but not limited to, tacking, stapling, adhesive, taping, heat sealing, molding, magnetic attraction, bonding, welding, weaving, sewing, hook and loop material, such as but not limited to Velcro®, mechanical interaction, such as but not limited to tongue and groove interaction, and/or attached or attachable in other ways known or to be discovered in the art. As described in previous paragraphs relating to loops 152, the at least one loop 152 can be a continuous loop or can have at least two loose ends 156 that are connectable with each other. In addition, as described in previous paragraphs relating to loops 152, the size, number and location of the at least one loop 152 on the piece of a material 128 can vary.

In other embodiments, as exemplarily illustrated in FIG. 66, the piece of a material 128 can be a piece of fabric which can have adhesive on the holding device side 170. The fragrance piece side 172 can have at least one loop 152 made of various materials, as previously described, that are integrally woven with the fabric piece, attached or attachable with the fabric piece by, but not limited to, tacking, stapling, adhesive, taping, heat sealing, molding, magnetic attraction, bonding, weaving, sewing, hook and loop material, such as but not limited to Velcro®, mechanical interaction, such as but not limited to tongue and groove interaction, and/or attached or attachable in other ways known or to be discovered in the art. As described in previous paragraphs relating to loops 152, the at least one loop 152 can be a continuous loop 152 or can have at least two loose ends 156 that are connectable with each other. In addition, as described in previous paragraphs relating to loops 152, the size, number and location of the at least one loop 152 on the piece of can vary.

In other embodiments, the piece of a material 128 can be a piece of hook or loop material 178 which can have adhesive 174 on the holding device side 170. The fragrance piece side 172 can have at least one loop 152 that is at least partially made of the hook and loop material 178 that compliments the fragrance piece side 172 of the piece of material 128, such that the complimentary pieces of hook and loop material 178 on the piece of a material 128 and the at least one loop 152 are able to interact with each other when the at least one loop 152 is attached with the piece of a material 128. As described in previous paragraphs relating to loops 152, the at least one loop 152 can be a continuous loop or can have at least two loose ends 156 that are connectable with each other. In addition, as described in previous paragraphs relating to loops 152, the size, number and location of the at least one loop 152 on the piece of can vary. The at least one loop 152 can be removable from the piece of a material 128 by separating the hook and loop material 178.

Figure 30:
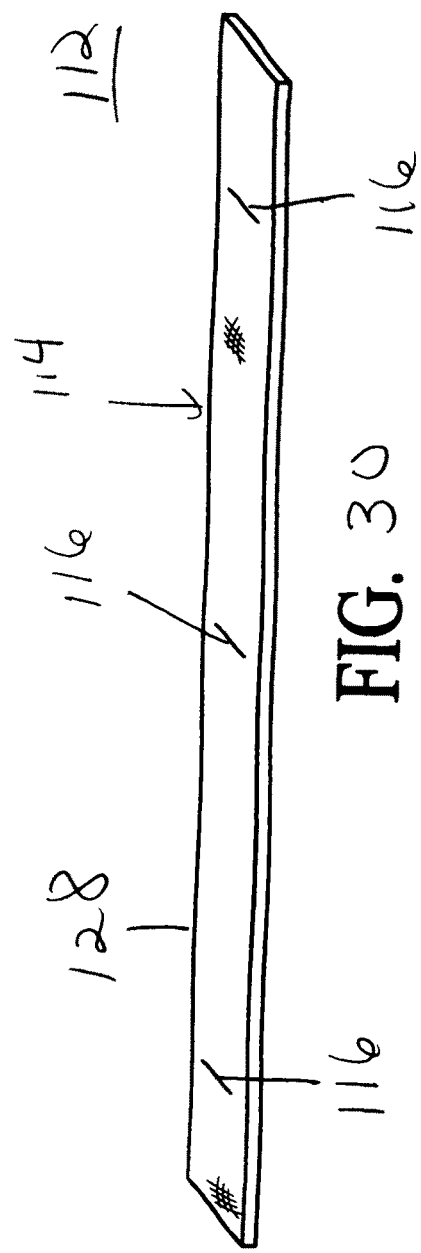
FIG. 30 is a view of a strip of material with a series of slots.

In other embodiments, as exemplarily illustrated in FIGS. including but not limited to FIGS. 30 and 67, of scented holding devices, attachers, attachment pieces, attachment piece parts, scented holding device systems 100, and attacher systems 100a, including attachment piece systems and attachment piece part systems, the attachment piece 112 or attachment piece part 114 is a piece of a material 128 that does not have adhesive on either the holding device side 170 or the fragrance piece side 172. In these embodiments, the piece of a material 128 can be made of materials including but not limited to plastic, metal, wood, fabric, fiberglass, vinyl, polyester, nylon, rubber, natural fibers such as cotton, other fibers, and combinations thereof, and can be attached, attachable, or integral with the holding device 102 by various ways known or to be discovered in the art, including but not limited to, by tacking, stapling, heat sealing, molding, magnetic attraction, bonding, weaving, sewing, hook and loop material, such as but not limited to Velcro®, and/or mechanical interaction, such as but not limited to tongue and groove interaction. In addition, the piece of a material 128 could be part of a lining, sectional compartment, or other interior or exterior portion in the holding device 102. The fragrance piece side 172, can have but is not limited to at least one of the following attachment pieces 112 or attachment piece parts 114, which have been described in previous paragraphs, integral, attachable or attached with it: at least one slot 116, loop 152, prong 134, cavity 250 and/or clip 162. When the at least one fragrance piece 104 is attached or attachable with at least one attachment piece 112 or attachment piece part 114 that is at least one loop 152 and/or slot 116, the fragrance piece 104 can be removably attachable with the fragrance piece side 172 within at least the required attachment parameters, and preferably, the fragrance piece 104 is removably attachable with the fragrance piece side 172 in a manner whereby the fragrance piece 104 may be removably attachable with the holding device 102 within the preferred attachment parameters and/or the more preferred attachment parameters. In addition, when the at least one fragrance piece 104 is attached or attachable with at least one attachment piece 112 or attachment piece part 114 that is at least one loop 152, cavity 250 and/or slot 116, the fragrance piece 104 will be removably attachable with the fragrance piece side 172 within at least the required attachment parameters, and in some embodiments the fragrance piece 104 may also be removably attachable with the fragrance piece side 172 in a manner whereby the fragrance piece 104 may be removably attachable with the holding device 102 within the removal attachment parameters, the removal and fit attachment parameters and/or the preferred removal and fit attachment parameters.

When the at least one fragrance piece 104 is attached or attachable with at least one attachment piece 112 or attachment piece part 114 that is at least one prong 134 and/or clip 162, the fragrance piece 104 is removably attachable with the fragrance piece side 172 in a manner whereby the fragrance piece 104 may be removably attachable with the holding device 102 within the preferred attachment parameters and/or the more preferred attachment parameters, and in some embodiments also within the removal and fit attachment parameters and/or the preferred removal and fit attachment parameters.

Figure 87:
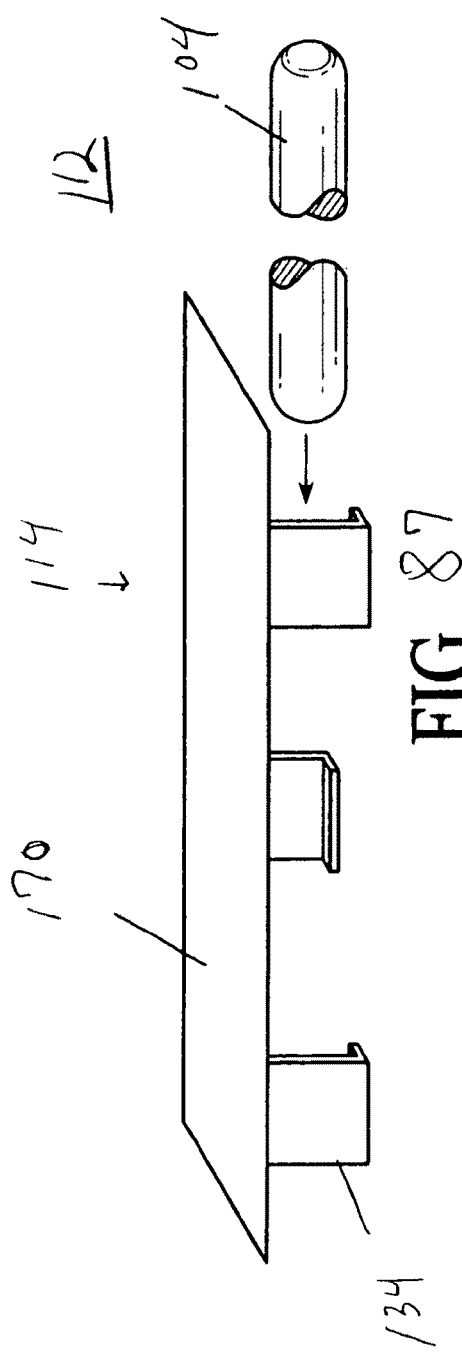
FIG. 87 is a view of three prongs on a piece of a material, and a fragrance piece.

In other embodiments, as exemplarily illustrated in FIGS. including but not limited to FIG. 87, the piece of a material 128 can be a piece of materials including but not limited to, plastic, metal, wood, fabric, fiberglass, vinyl, polyester, nylon, rubber, natural fibers such as cotton, other fibers, and combinations thereof, which does not have adhesive 174 on the holding device side 170. The fragrance piece side 172 can have at least one prong 134, as previously described, made of materials including but not limited to plastic, metal, wood, fabric, fiberglass, vinyl, polyester, nylon, rubber, natural fibers such as cotton, other fibers, and combinations thereof, that is integrally integrated with by, such as but not limited to, being molded, and/or woven with the piece of a material 128, or attached or attachable with the piece of a material 128 by various ways known or to be discovered in the art, including but not limited to, by tacking, stapling, heat sealing, molding, magnetic attraction, taping, adhesive, bonding, weaving, welding, sewing, hook and loop material, such as but not limited to Velcro®, and/or mechanical interaction, such as but not limited to tongue and groove interaction. As described in previous paragraphs relating to prongs 134, the accessible prong gap 148 of the at least one prong 134 can open in directions including but not limited to toward the top, bottom, side, front, back or diagonal of the holding device 102 when the piece of a material 128 is attached with holding device 102. In addition, as described in previous paragraphs relating to prongs 134, the size, number and location of the at least one prong 134 on the piece of can vary.

In other embodiments, the piece of a material 128 can be a piece of plastic which does not have adhesive 174 on the holding device side 170. The fragrance piece side 172 can have at least one plastic prong 134, as previously described, that is integrally integrated with by, such as but not limited to, being molded, and/or woven with the piece of plastic, and/or attached or attachable by various ways known or to be discovered in the art, including but not limited to by tacking, welding, stapling, heat sealing, molding, magnetic attraction, taping, adhesive, bonding, weaving, sewing, hook and loop material, such as but not limited to Velcro®, and/or mechanical interaction, such as but not limited to tongue and groove interaction. As described in previous paragraphs relating to prongs 134, the accessible prong gap 148 of the at least one prong 134 can open in directions including but not limited to toward the top, bottom, side, front, back or diagonal of the holding device 102 when the piece of plastic is attached with holding device 102. In addition, as described in previous paragraphs relating to prongs 134, the size, number and location of the at least one prong 134 on the piece of can vary.

Figure 88:
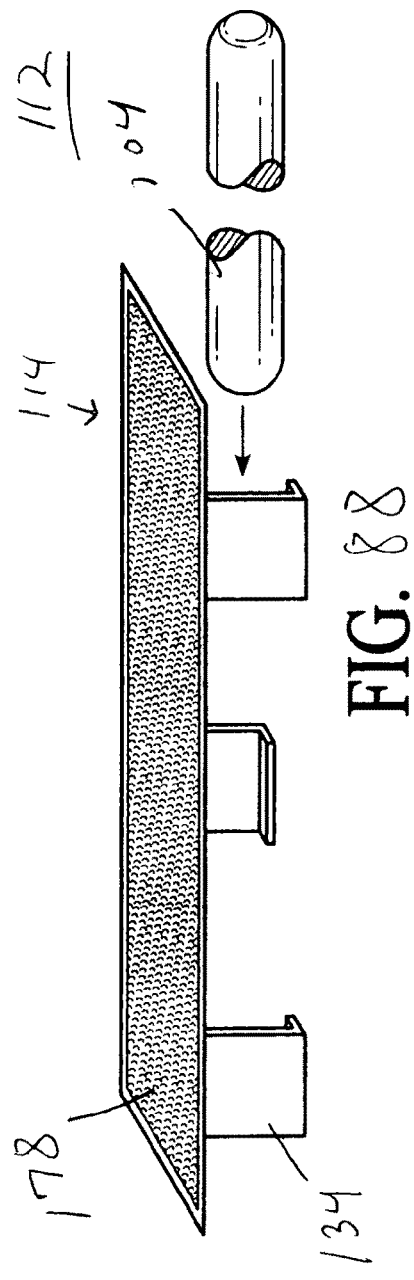
FIG. 88 is a view of three prongs on a piece of a material with hook and loop material on the holding device side, and a fragrance piece.
Figure 89:
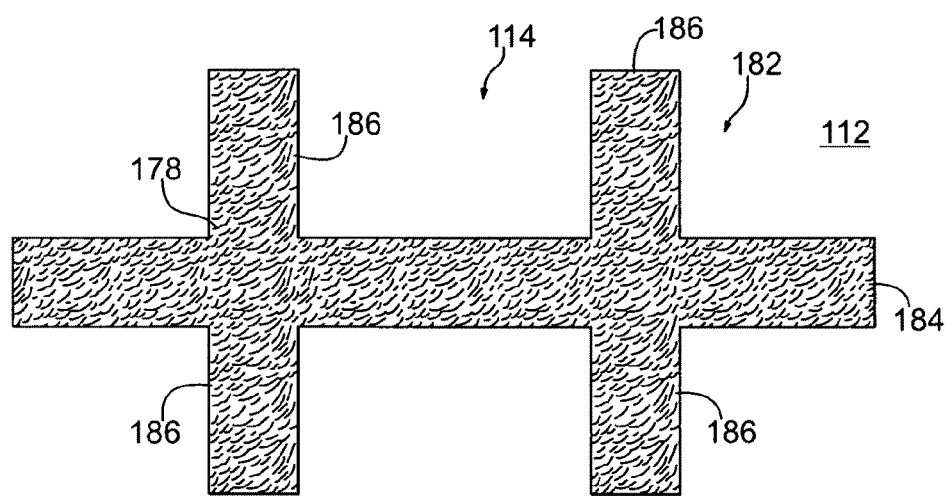
FIG. 89 is a view of a supplemental piece made of two-faced hook and loop material and with two pairs of arms.

In other embodiments, as exemplarily illustrated in FIGS. including but not limited to FIG. 88, the piece of a material 128 can be a piece of hook or loop material 178, and the fragrance piece side 172 can have at least one prong 134, as previously described, made of materials including but not limited to plastic, metal, wood, fabric, fiberglass, vinyl, polyester, nylon, rubber, natural fibers such as cotton, other fibers, and combinations thereof, that is integrally integrated with by, such as but not limited to, being molded, and/or woven with the piece of a material 128, attached or attachable with the piece of a material 128 by, but not limited to, tacking, stapling, adhesive, taping, heat sealing, molding, magnetic attraction, bonding, welding, weaving, sewing, hook and loop material, such as but not limited to Velcro®, mechanical interaction, such as but not limited to tongue and groove interaction, and/or attached or attachable in other ways known or to be discovered in the art. As described in previous paragraphs relating to prongs 134, the accessible prong gap 148 of the at least one prong 134 can open in directions including but not limited to toward the top, bottom, side, front, back or diagonal of the holding device 102 when the piece of a material 128 is attached with holding device 102. In addition, as described in previous paragraphs relating to prongs 134, the size, number and location of the at least one prong 134 on the piece of can vary.

In some embodiments, the fragrance piece side 172 can be made of hook and loop material 178 and the holding device side 170 can be made of fabric. In these embodiments, the fragrance piece side 172 can have at least one prong 134 that is at least partially made of the hook and loop material 178 that compliments the fragrance piece side 172 of the piece of material 128, such that the complimentary pieces of hook and loop material 178 on the piece of a material 128 and the at least one prong 134 are able to interact with each other when the at least one prong 134 is attached with the piece of a material 128. In addition, in a similar embodiment as exemplarily illustrated in FIG. 25, it would be possible to add adhesive to the holding device side 170. In another embodiment, as exemplarily illustrated in FIG. 88, the holding device side 170 can be made of hook and loop material 178 and the fragrance piece side 172 can have at least one prong 134 attached or attachable with it.

In other embodiments, as exemplarily illustrated in FIGS. including but not limited to FIG. 67, the piece of a material 128 can be a piece of materials including but not limited to, plastic, metal, wood, fabric, fiberglass, vinyl, polyester, nylon, rubber, natural fibers such as cotton, other fibers, and combinations thereof, which does not have adhesive 174 on the holding device side 170. The fragrance piece side 172 can have at least one loop 152, as previously described, made of materials including but not limited to plastic, metal, wood, fabric, fiberglass, vinyl, polyester, nylon, rubber, natural fibers such as cotton, other fibers, and combinations thereof, that is integrally integrated with by, such as but not limited to, being molded, and/or woven with the piece of a material 128, and/or attached or attachable by, but not limited to, tacking, stapling, adhesive, taping, heat sealing, molding, magnetic attraction, bonding, welding, weaving, sewing, hook and loop material, such as but not limited to Velcro®, mechanical interaction, such as but not limited to tongue and groove interaction, and/or attached or attachable in other ways known or to be discovered in the art. As described in previous paragraphs relating to loops 152, the at least one loop 152 can be a continuous loop or can have at least two loose ends 156 that are connectable with each other. In addition, as described in previous paragraphs relating to loops 152, the size, number and location of the at least one loop 152 on the piece of a material 128 can vary.

In some embodiments, the piece of a material 128 can be a piece of plastic which does not have adhesive 174 on the holding device side 170. The fragrance piece side 172 can have at least one plastic loop 152, as previously described, that is integrally integrated with by, such as but not limited to, being molded, and/or woven with the piece of plastic, attached or attachable with the piece of plastic by, but not limited to, tacking, stapling, adhesive, taping, heat sealing, molding, magnetic attraction, bonding, welding, weaving, sewing, hook and loop material, such as but not limited to Velcro®, mechanical interaction, such as but not limited to tongue and groove interaction, and/or attached or attachable in other ways known or to be discovered in the art. As described in previous paragraphs relating to loops 152, the at least one loop 152 can be a continuous loop or can have at least two loose ends 156 that are connectable with each other. In addition, as described in previous paragraphs relating to loops 152, the size, number and location of the at least one loop 152 on the piece of a material 128 can vary.

In other embodiments, the piece of a material 128 can be a piece of fabric which does not have adhesive on the holding device side 170. The piece of fabric can be attached or attachable with the holding device 102 by, but not limited to, tacking, stapling, heat sealing, molding, magnetic attraction, magnetic attraction, bonding, welding, weaving, sewing, hook and loop material, such as but not limited to Velcro®, mechanical interaction, such as but not limited to tongue and groove interaction, and/or attached or attachable in other ways known or to be discovered in the art. The fragrance piece side 172 can have at least one loop 152 made of various materials, as previously described, that are integrally woven with the fabric piece, attached or attachable with the fabric piece by, but not limited to, tacking, stapling, adhesive, taping, heat sealing, molding, magnetic attraction, bonding, welding, weaving, sewing, hook and loop material, such as but not limited to Velcro®, mechanical interaction, such as but not limited to tongue and groove interaction, and/or attached or attachable in other ways known or to be discovered in the art. As described in previous paragraphs relating to loops 152, the at least one loop 152 can be a continuous loop 152 or can have at least two loose ends 156 that are connectable with each other. In addition, as described in previous paragraphs relating to loops 152, the size, number and location of the at least one loop 152 on the piece of can vary.

As exemplarily illustrated in FIGS. including but not limited to FIG. 26, the piece of a material 128 can be a piece of hook or loop material 178 which does not have adhesive on the holding device side 170. The piece of hook or loop material 178 can be attached or attachable with the holding device 102 by, but not limited to, tacking, stapling, heat sealing, molding, magnetic attraction, bonding, welding, weaving, sewing, hook and loop material, such as but not limited to Velcro®, mechanical interaction, such as but not limited to tongue and groove interaction, and/or attached or attachable in other ways known or to be discovered in the art. The fragrance piece side 172 can have at least one loop 152 made of the hook and loop material 178 that compliments the fragrance piece side 172 of the piece of hook and loop material. As described in previous paragraphs relating to loops 152, the at least one loop 152 can be a continuous loop 152 or can have at least two loose ends 156 that are connectable with each other. In addition, as described in previous paragraphs relating to loops 152, the size, number and location of the at least one loop 152 on the piece hook and loop material 178 of can vary. The at least one loop 152 can be removable from the piece of hook and loop material 178 by separating the hook and loop material.

In yet other embodiments, as exemplarily illustrated in FIGS. including but not limited to FIG. 30, the piece of a material 128 can have at least one slot 116, as previously described, that is integrally cut into it. In addition, as described in previous paragraphs relating to slots 116, the size, number and location of the at least one slot 116 on the piece of a material 128 of can vary. The holding device side 170 of the piece of a material 128 can be integral with, attached or attachable with the holding device 102, including a part of the holding device, including but not limited to a lining, compartment section piece, or other interior or exterior portion, or to another attachment piece part 114 by, but not limited to, tacking, stapling, adhesive, taping, heat sealing, molding, magnetic attraction, bonding, welding, weaving, sewing, hook and loop material, such as but not limited to Velcro®, mechanical interaction, such as but not limited to tongue and groove interaction, and/or attached or attachable in other ways known or to be discovered in the art.

Figure 14:
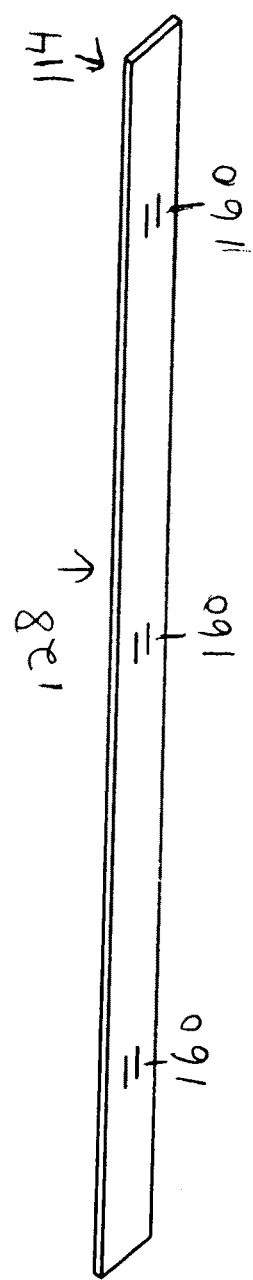
FIG. 14 is view of an attachment piece and/or attachment piece part with three sets of slits.
Figure 15:
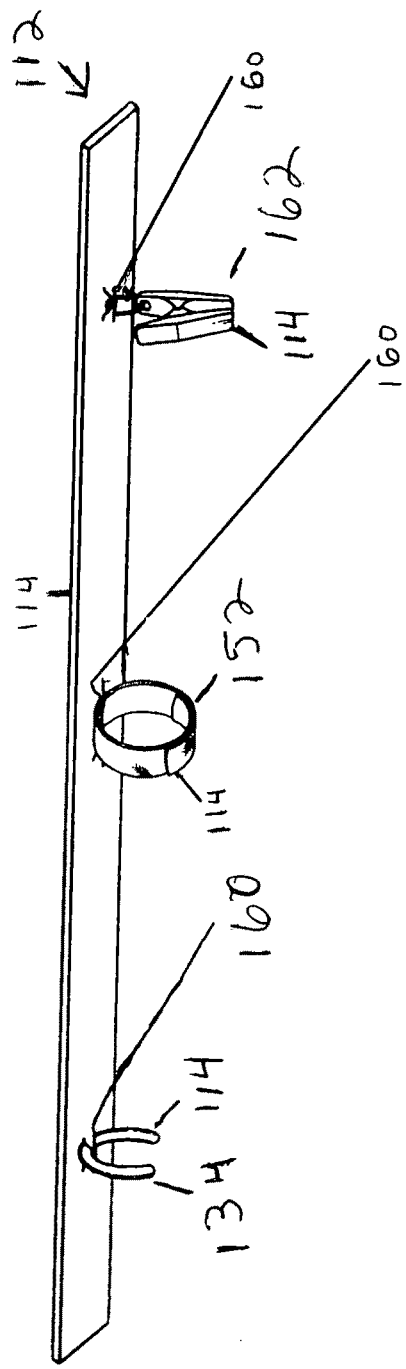
FIG. 15 is a view of the attachment piece and/or attachment piece part of FIG. 14, with a prong, loop and clip attached.

Referring now to FIGS. 14 and 15, without intending to be limiting, the piece of a material 128 can include at least one pair of slits 160 into which at least one prong 134, loop 152 and/or clip 162 may be attached. It is also to be understood, that at least one pair of slits 160 could be directly cut into the holding device, into which at least one prong 134, loop 152 and/or clip 162 may be fixedly or removably attached. The holding device side 170 of the piece of a material 128 can be integral with, attached or attachable with the holding device, including a part of the holding device 102, including but not limited to a lining, compartment section piece, or other interior or exterior portion, or to another attachment piece part 114 by, but not limited to, tacking, stapling, adhesive, taping, heat sealing, molding, magnetic attraction, bonding, welding, weaving, sewing, hook and loop material, such as but not limited to Velcro®, mechanical interaction, such as but not limited to tongue and groove interaction, and/or attached or attachable in other ways known or to be discovered in the art.

Referring now to FIGS. including but not limited to FIGS. 27, 70, 86, 89-91, in other embodiments, the piece of a material 128 can be a piece of hook or loop 152 material, and a supplemental piece 182 can be removably attachable with the hook or loop material on the fragrance piece side 172 of the piece of material. The holding device side 170 of the piece of a material 128 can be integral with, attached or attachable with the holding device 102, including a part of the holding device, including but not limited to a lining, compartment section piece, or other interior or exterior portion, or to another attachment piece part 114 by, but not limited to, tacking, stapling, adhesive, taping, heat sealing, molding, magnetic attraction, bonding, welding, weaving, sewing, hook and loop material, such as but not limited to Velcro®, mechanical interaction, such as but not limited to tongue and groove interaction, and/or attached in other ways known or to be discovered in the art.

In some embodiments, the supplemental piece 182 will be made of two-sided hook and loop material, a piece of which is exemplarily illustrated in FIG. 70. The supplemental piece 182 will have an attachment side 190 that will be attachable with the fragrance piece side 172 of the hook or loop piece of material 178, and that will be made of the hook or loop 152 material that compliments the either hook or loop material 178 that is on the fragrance piece side 172 of the piece of a material 128. The supplemental piece 182 will have a main piece 184 having at least one loop arm 186. In one embodiment, as exemplarily illustrated in FIG. 90, the supplemental piece 182 will have one pair of loop arms 186. As exemplarily illustrated in FIG. 89, the supplemental piece 182 can have two pairs of loop arms 186. It is to be understood that any number of loop arms 186 can be provided as long as the holding device 102 is sufficiently large to hold the piece of hook and loop material 178 of the piece of a material 128 and supplemental piece 182. When the supplemental piece is attached to the hook or loop material 178 of the piece of a material 128, the pair of arms can be folded back and attached, as exemplarily illustrated in FIG. 91 to each other by attaching the hook material 178a of one arm to the loop material 178b of the other arm. Alternatively, if a pair of loop arms are not provided, the at least one loop arm 186 can be curved backward and be attached (not shown) to the main piece 184. In both embodiments, at least one loop 152 is formed that can hold a fragrance piece 104 to the holding device 102. In these manners, each loop 152 can be adjustable for different sizes and shapes of a fragrance piece 104. In addition, as described in previous paragraphs relating to loops 152, the size, number and location of the at least one loop 152 on the piece of a material 128 can vary.

Figure 90:
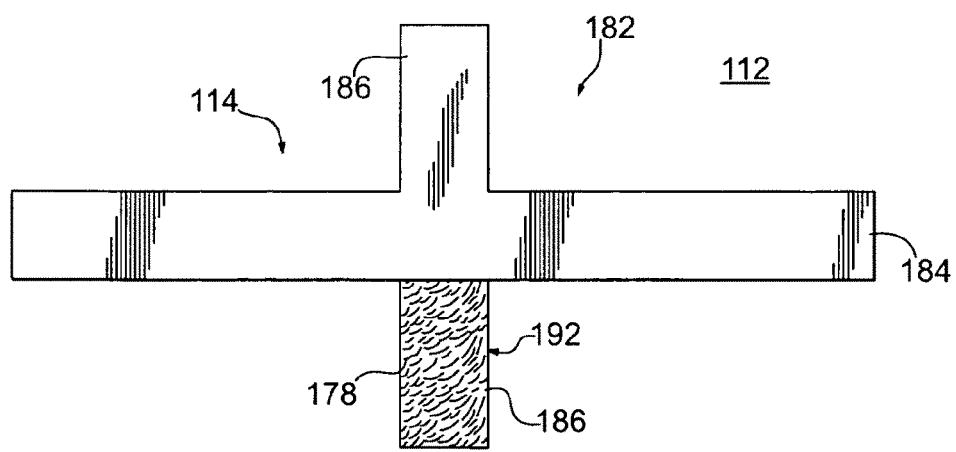
FIG. 90 is a view of a supplemental piece not made of two-faced hook and loop material and with one pairs of arms.
Figure 91:
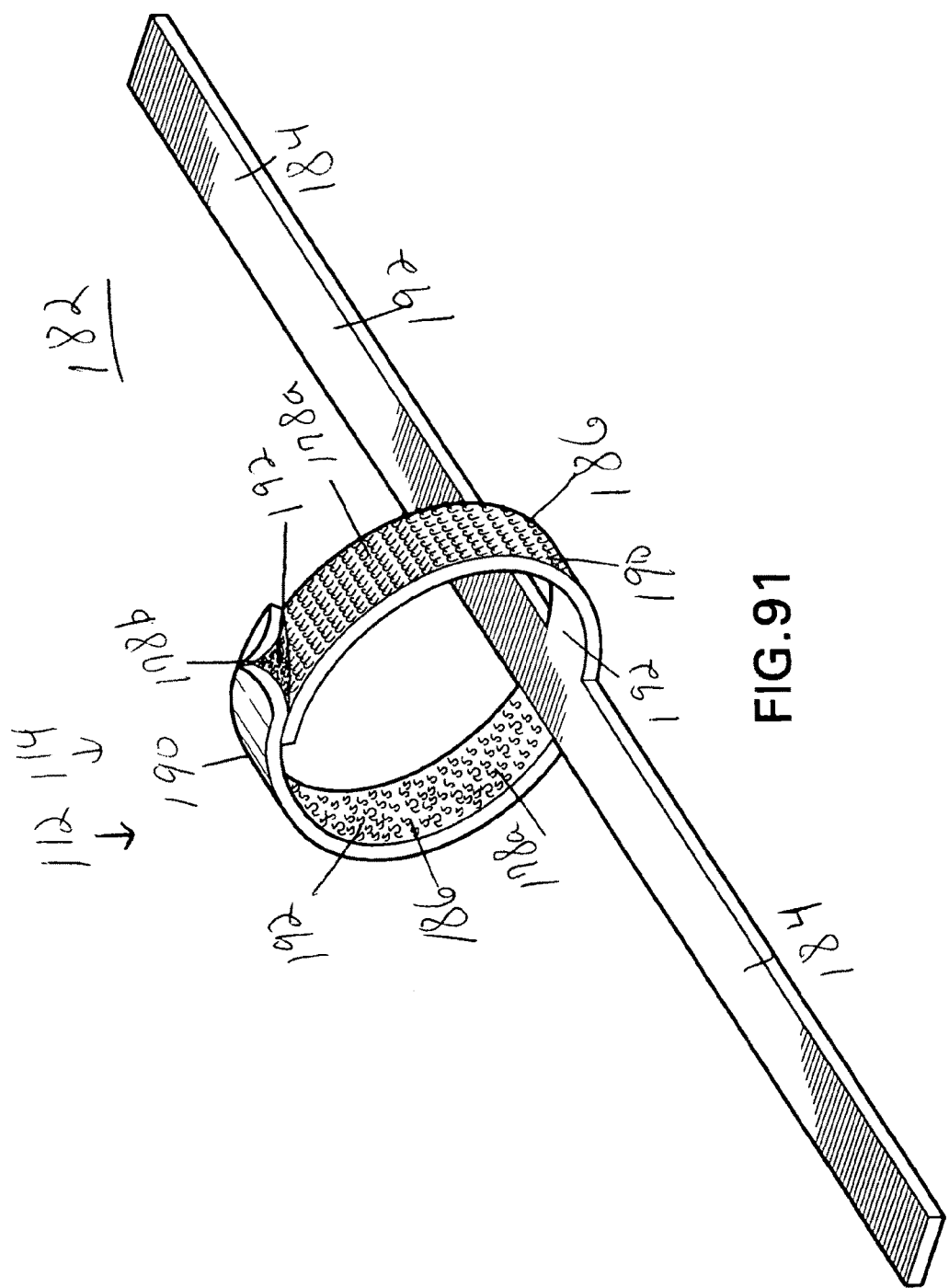
FIG. 91 is a view of a pair of arms connected with one another on a supplemental piece.

When two-sided hook and loop material is not provided for a supplemental piece 182 having at least one pair of arms 186, as exemplarily illustrated in FIG. 90, the attachment side 190 of the main piece 184 and at least one of the arms 186 can be made of the hook or loop material that compliments the piece of a material 128. The non-attachment side 192 of the other at least one complimentary loop arm can be made of the type of hook and loop material that compliments the type of hook and loop material that is on the attachment side 190 of the main piece 184. When the supplemental piece is attached to the hook or loop material 178 of the piece of a material 128, the pair of arms can be folded back and attached, as exemplarily illustrated in FIG. 91 to each other by attaching the hook material 178a of one arm to the loop material 178b of the other arm.

In a manner similar to that previously described in relation to a piece of a material 128 that is made of hook and loop material 178, at least one supplemental piece 182 can be attached or attachable with a holding device 102, or portion thereof, attachment piece 112, and/or attachment piece part 114 that is at least partially made of hook and loop material 178 of a sufficient size such that the supplement piece 182 can be attached to it.

Referring now to FIGS. including, but not limited to, FIGS. 127A, 127B, 128-134, 139-142, 144 and 145, embodiments of the system 100 are exemplarily illustrated wherein the attacher 106 includes at least one cavity 250. The at least one cavity 250 may be located on any accessible portion of the holding device 102. By way of example, and not intending to be exhaustive, the at least one cavity 250 may be located on a portion on the outer structure of the holding device 102, or an interior portion of a holding device 102 such as, but limited to an inner compartment, or other interior portion.

The at least one fragrance piece 104 will be attachable with the at least one cavity 250 within at least the required attachment parameters. Preferably, the interaction of the at least one fragrance piece 104 and the at least one cavity 250 will be within the preferred attachment parameters, and more preferably at least within the more preferred attachment parameters. It is to be understood, however, that the type of materials and/or combination of materials, and/or structure of the fragrance piece 104 and/or cavity 250 that will accomplish the preferred attachment parameters and/or the more preferred attachment parameters between the fragrance piece 104 and the at least one cavity 250 can vary. In addition, in some embodiments, the interaction of the at least one fragrance piece 104 and the at least one cavity 250 will be within the removal attachment parameters, the removal and fit attachment parameters and/or the preferred removal and fit attachment parameters.

Reference is now made to FIGS. including FIGS. 127A, 127B, 128-134, 139-142, 144 and 145, which exemplarily illustrate embodiments of a cavity 250 in a hanger 188 and/or the interaction of at least one fragrance piece 104 and at least one cavity 250 in a hanger 188.

The embodiments exemplarily illustrated in FIGS. 128-134, 139-142, 144 and 145, include a hanger with a cavity 250 in the top end 256 of the hanger 188. In these exemplary illustrated embodiments, the hanger 188 is made of plastic, however other materials currently known in the art or to be discovered for hangers 188 also could be used. FIGS. 139-142 illustrate a portion of a plastic hanger where the exterior surface of the plastic has been coated with micro fiber. As illustrated in FIGS. including but not limited to FIG. 140, in some embodiments a cavity 250 is defined by two opposing side walls 258 and a top wall 260 in the top end 256 of the hanger 188. The cavity 250 can be accessed by an opening 262 in the bottom 264 of the top end of the hanger 188.

In these exemplarily illustrated embodiments, the side walls 258 are generally parallel with each other. Also in these illustrated exemplary embodiments, the bottom ends 266 of the side walls 258, where the opening 262 at the bottom of the hanger is located, project straight downward and do not have any ridges that slant, bend or curve inward or outward. However, it is to be understood that in other embodiments the bottom ends 266 of the side walls 258 could have a variety of ridges that slant, bend or curve inward or outward.

In these exemplarily illustrated embodiments, the side walls 258 are perforated from the outside into the cavity with at least one perforation slot 268. In these exemplarily illustrated embodiments, three perforation slots 268 are include in each side wall. The scent from the fragrance piece 104, while attached to the hanger 188, can access the surrounding area at least through the at least one perforation slot 268 and the bottom opening 262 of the cavity 250.

The cavity in the top end of the hanger can have at least one hanger column 270 that at least partially traverses a portion of the interior of the cavity. When the hanger is hung by the top hook, such as in a closet, the at least one hanger column 270 as exemplarily illustrated in these embodiments is generally vertical.

At least one fragrance piece 104 can be inserted in the bottom opening 262 of the hanger 188. At least one fragrance piece 104 can fill the cavity 250 to varying degrees. In these exemplary illustrated embodiments, the length of the opening is longer than the length of the fragrance piece. However, it is to be understood that in some embodiments if the material of the fragrance piece is sufficiently pliable to enable to fragrance piece to bend inside the cavity, the fragrance piece can be longer than the opening and/or if the tab 244 of the fragrance piece extends below the opening and beyond the length of the rest of the fragrance piece, the length of the fragrance piece can extend beyond the length of the opening at least by the length of the tab. In addition, in some embodiments, more that one fragrance piece can be inserted into the cavity.

In some embodiments, the width of the fragrance piece 104 is almost identical to, equal to or greater than the width of the opening 262 to the cavity 250, such that when the fragrance piece 104 is inserted into the cavity 250, the snugness of the fit of the fragrance piece 104 between the side walls of the cavity, or the friction between the fragrance piece and the interior of the side walls of the cavity, can cause the fragrance piece to remain attached to the hanger, and not to fall out due to gravity, within the desired attachment parameters. In some embodiments, when the width of the fragrance piece is equal to or greater than the width of the opening, the material of the fragrance piece will have some degree of pliability, compression or give to enable to fragrance piece to pass through the opening.

Referring now to FIGS. 125, 137, 139, and 143, in some embodiments, at least one outward facing ridge 272 can be included along at least part of the length of at least one side of a fragrance piece, which can cause further snugness with the side walls 258 of the hanger and additional friction. It is to be understood that in some embodiments, a fragrance piece will not have any ridges, in some embodiments, and in some embodiments a fragrance piece can have at least one ridge on at least one side of the fragrance piece. In some embodiments a fragrance piece can have one ridge on each side of the fragrance piece. In some embodiments a fragrance piece can have one ridge on one side of the fragrance piece. In some embodiments a fragrance piece can have more than one ridge on each side of the fragrance piece or on just one side of the fragrance piece.

Figure 135:
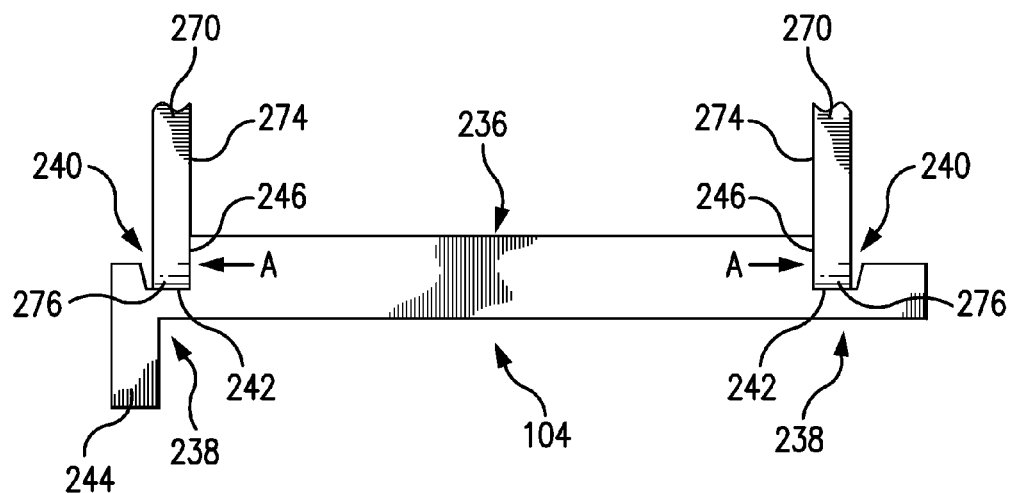
Figure 136:
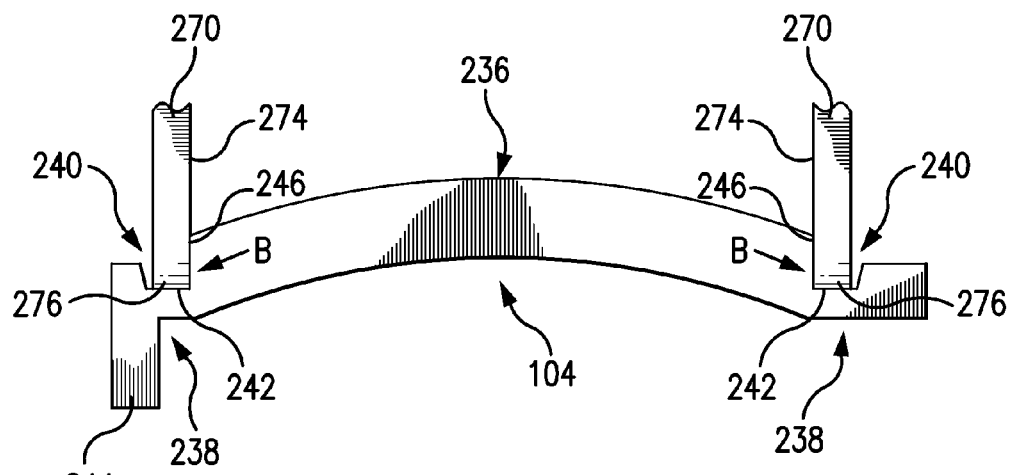
Figure 137:
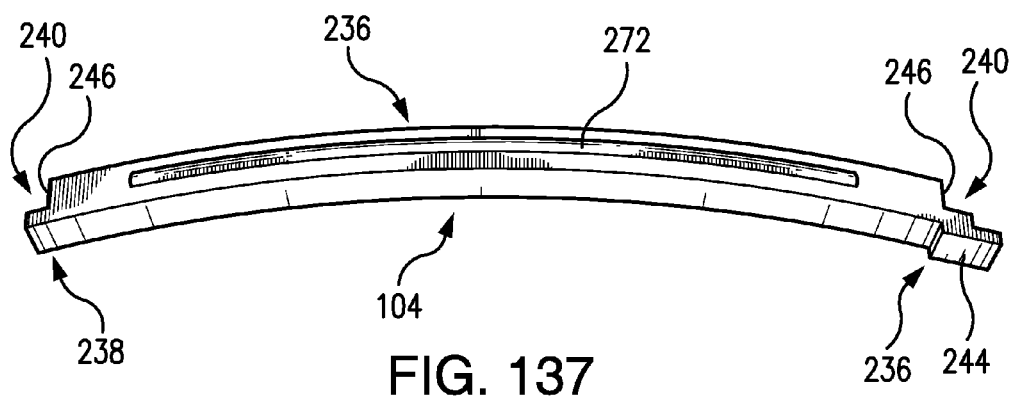
Figure 138:
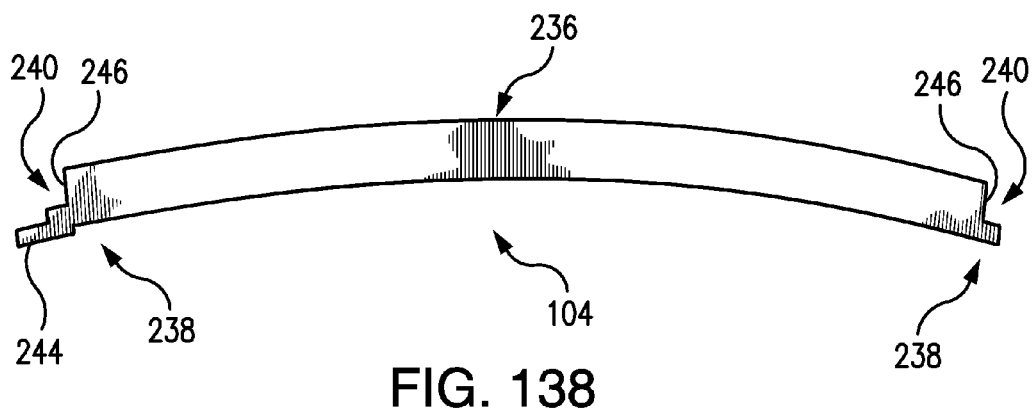
Figure 139:
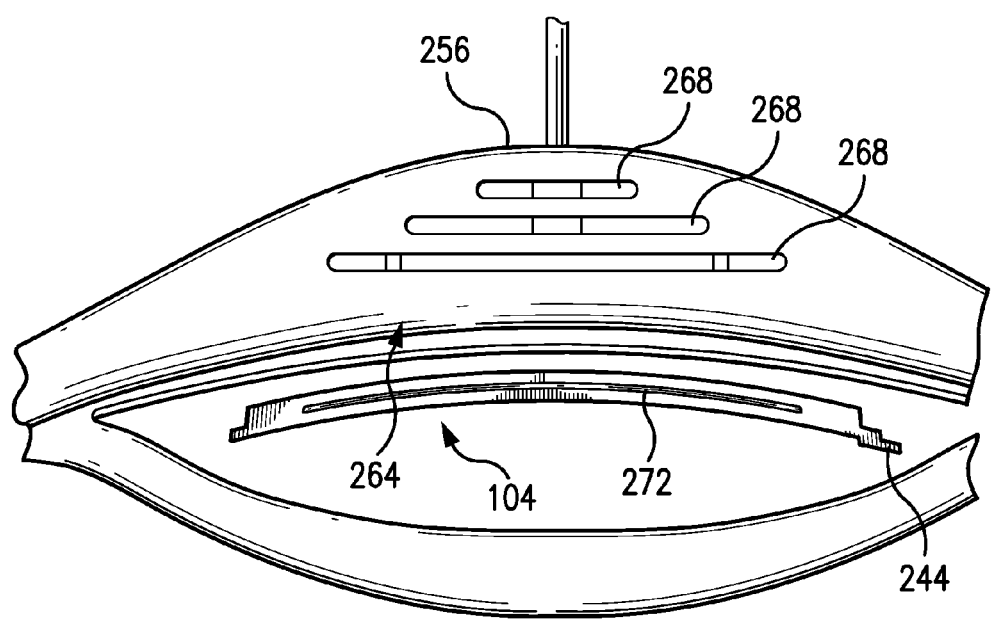
Figure 140:
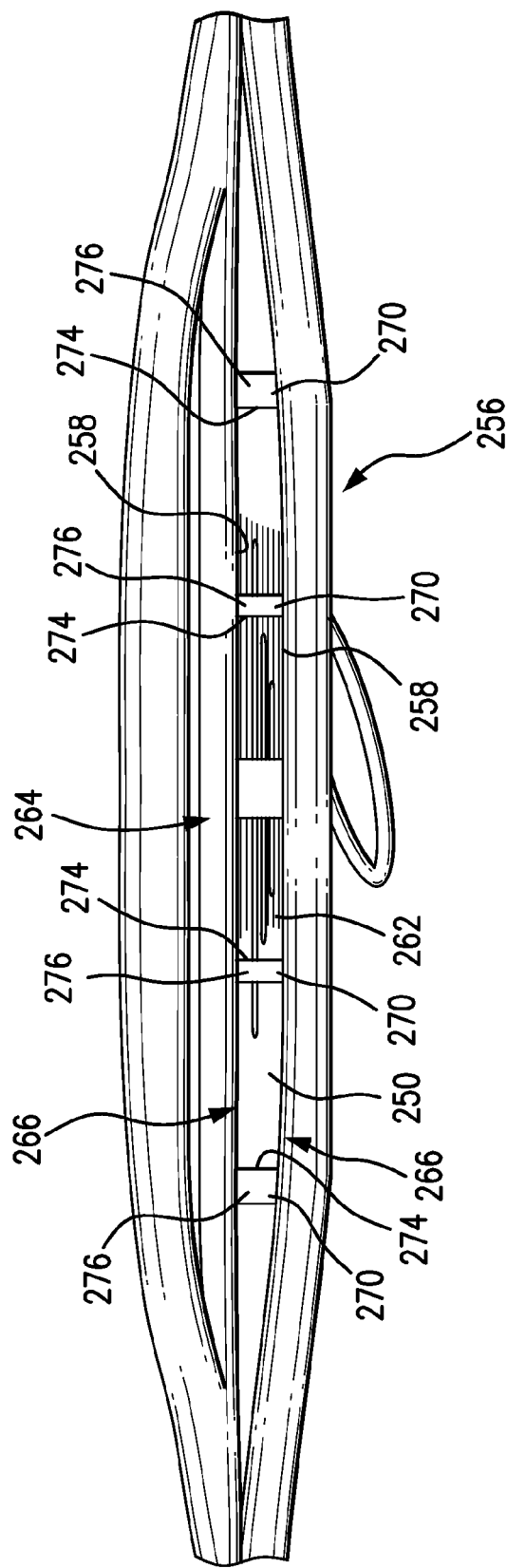
Figure 141:
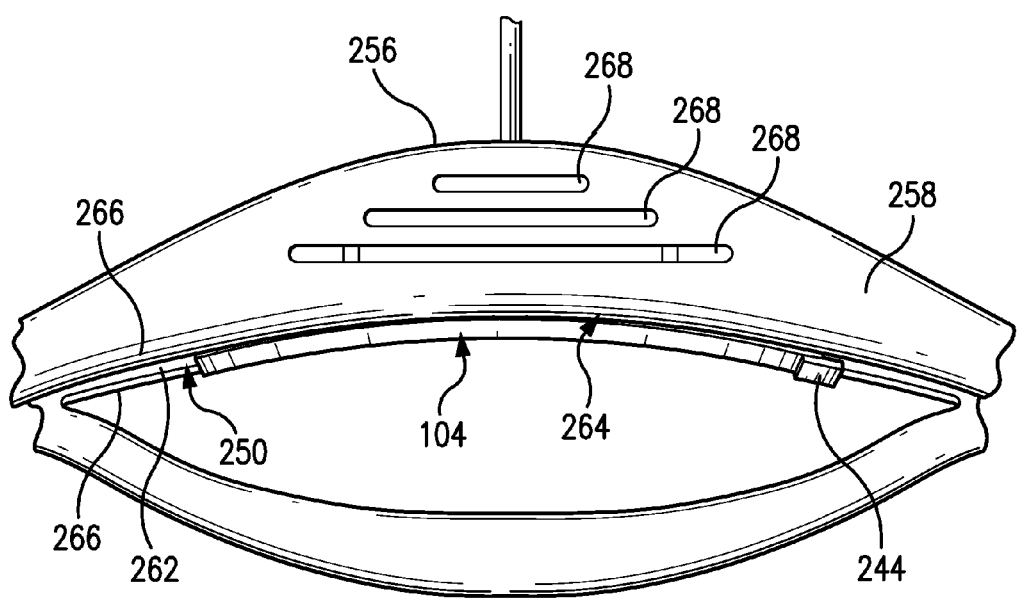
Figure 142:
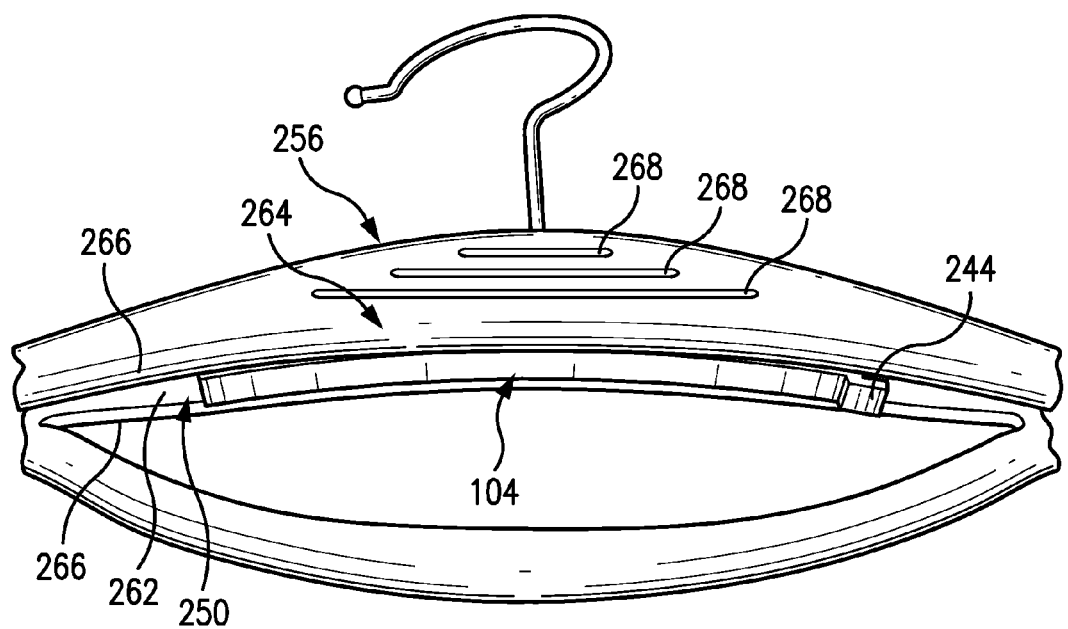

Referring now to FIGS. 135 and 136, in some embodiments, the length of the middle portion 236 of the fragrance piece, from riser 246 to riser 246, is almost identical to, equal to or greater than the length between the center-facing walls 274 of two hanger columns 270. In these embodiments, another attachment mechanism is the horizontal force (indicated by arrows A) of the risers 246 pressing against the center-facing walls 274 of the hanger columns 270, or, if an arch is formed, is the combination of horizontal and vertical force components (indicated by arrows "B") of the risers 246 pressing against the center-facing walls 274 of the hanger columns 270. In some embodiments, when the length of the middle portion of the fragrance piece is equal to or greater than the length between the center-facing walls 274 of two hanger columns 270, the material of the fragrance piece will have some degree of pliability, compression or give to enable to the middle portion of the fragrance piece to fit between the center-facing walls 274 of the hanger columns 270.

Referring now to FIG. 136, in some embodiments when the middle portion of the fragrance piece is pre-shaped in an arch shape or is pliable and is compressed in an arch shape between two center-facing walls 274 of two hanger columns 270, when the risers press against the center-facing walls 274 of two hanger columns 270, a combination of horizontal and vertical force components (indicated by arrows "B") can press against the center-facing walls 274 of two hanger columns 270.

In some embodiments when that fragrance piece has a tab 244, it can accessed by the user to pull the fragrance piece out of the hanger. In addition in some embodiments, to insert the fragrance piece in the cavity, the user can hold the tab, insert the opposing end of the fragrance piece into the opening until the riser impacts a center-facing wall 274 of a hanger column 270, and then push the fragrance piece forward and upward until the other riser can impact and/or be wedged against an opposing center-facing wall 274 of a hanger column 270.

Figure 134:
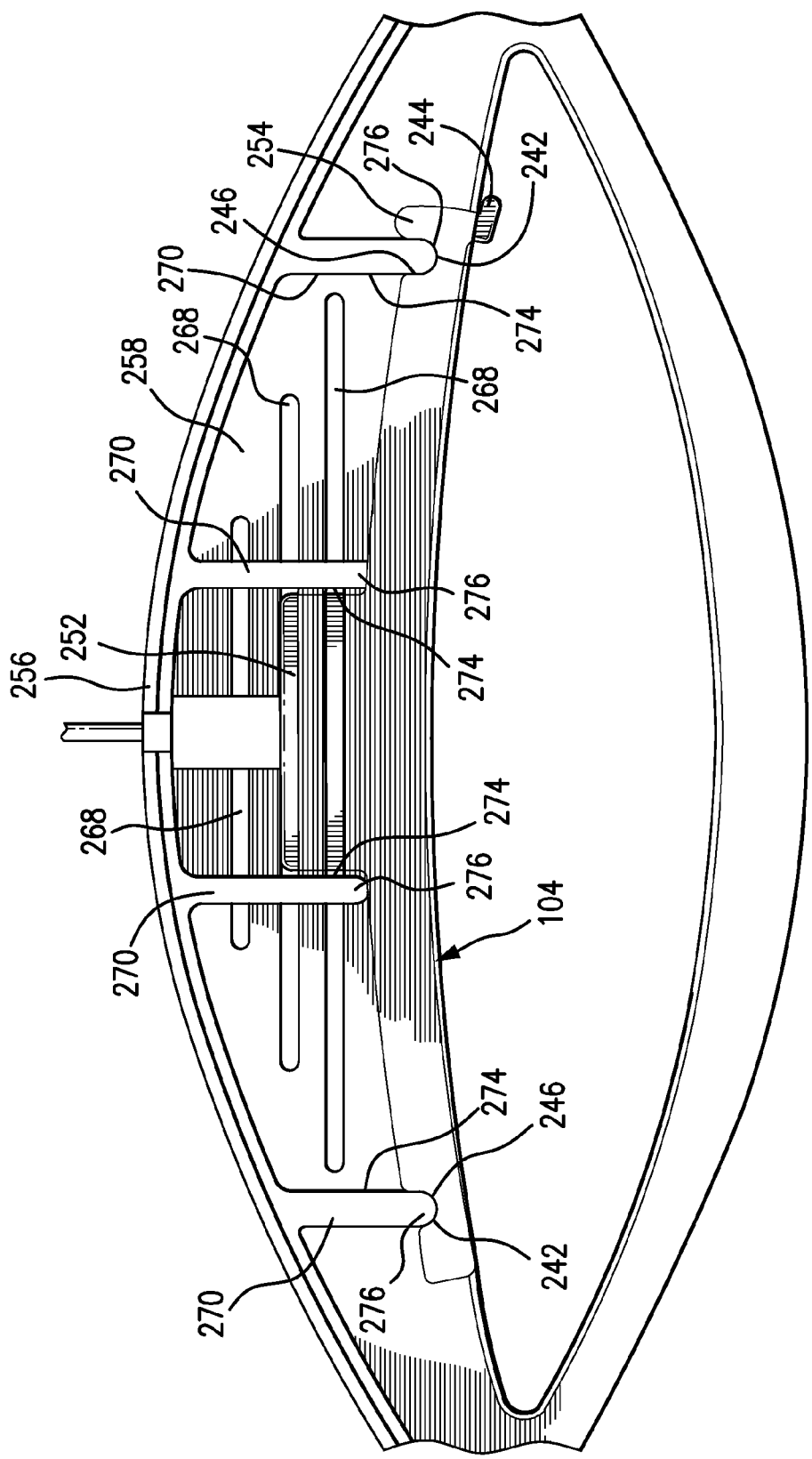

As illustrated in FIG. 134, in some embodiments, the notches 242 in the fragrance piece correspond with the bottom 276 of the hanger columns in the cavity in a mirror image manner.

Referring now to FIGS. 133 and 134, in some embodiments, a portion of the middle portion 236 of the fragrance piece can have a heightened area 252. This additional heighted area can extend further into the cavity than the rest of the fragrance piece. As illustrated in this exemplary embodiment, the hanger can have two hanger columns that do not project as far downward as the other hanger columns and that are more toward the center of the of the hanger than the other hanger columns. In this exemplary embodiment, the additional heightened area of the fragrance piece fits between the center-facing walls of the two hanger columns that do not project as far downward as the other hanger columns.

In some embodiments as exemplarily illustrated in FIG. 144, none for the fragrance piece projects below the opening when the fragrance piece is inserted in the cavity. In some embodiments as exemplarily illustrated in FIGS. 130, 131, 134, 141 and 142, only the tab of the fragrance piece projects below the opening when the fragrance piece is inserted in the cavity. It is to be understood that while the FIGS. 130, 131, 134, 141 and 142 illustrate a tab that projects downward, tabs could also project in other manners, such as but not limited to, downward and to the side. In some embodiments as exemplarily illustrated in FIG. 145, the fragrance piece can project below the opening when the fragrance piece is inserted in the cavity for a portion of all of the length of the fragrance piece.

Reference is now made to exemplary FIGS. including but not limited to, FIGS. 11-13, and 92-100, which illustrate embodiments of a hanger 188 that may be to be used for hanging a variety of garments 200 and/or accessories 202. Preferably, the hanger 188 will be able to be used for hanging a variety of light weight and/or heavy weight garments and/or accessories.

Reference is now made to exemplary FIGS. 11-13, 92-95, 97, and 100, which illustrate at least one prong 134 molded onto the bottom bar 194 of the hanger 188. When the at least one prong is molded onto the bottom bar 194 of the hanger 188, the at least one fragrance piece is removably attachable with the hanger within the removal and fit parameters and/or the preferred removal and fit parameters. Alternatively and/or in addition to being molded on the bottom bar 194, the at least one prong 134 can be attached with the hanger in other ways, as described in previous paragraphs and illustrations relating to prongs. It is to be noted that the location of the prongs 134 at bottom portion 196 of bottom bar 194 of hanger has the benefit of causing the at least one fragrance piece 104 to be close to the bottom of hanger, and thereby minimizing the chance of prongs 134 breaking. In addition, the location and size of the prongs 134 creates a low and streamlined profile that minimizes the touching of the garment to the at least one fragrance piece 104. The size and location of the prongs 134 also enables the user to easily to insert and remove the at least one fragrance piece 104, while at the same time the prongs 134 are able to hold properly sized, as previously described, fragrance pieces 104 within the preferred attachment parameters and/or the more preferred attachment parameters, and in some embodiments also within the removal and fit attachment parameters and/or the preferred removal and fit attachment parameters.

In exemplarily illustrated in these embodiments two sets of three prongs 134 are preferred. In addition, preferably, the two sets of prongs 134 will be located toward the outer edges 198 of the bottom bar of the hanger 188. The location of two sets of prongs 134 near the outer edges 198 of the bottom bar enables the attached at least one fragrance piece 104 to encompass almost the whole width to the garment. As exemplarily illustrated in FIG. 13, one fragrance piece 104 can be attached with each set of prongs 134. However, it would be possible to attach one long fragrance piece 104 that will engage both sets of prongs 134. Additionally, if the prongs 134 and fragrance pieces 104 are sufficiently small, there could be three sets of prongs 134, with a middle set located between the sets located near the outer edges of the bottom of the bottom hanger bar. This configuration would also enable the at least one fragrance piece 104 to encompass almost the whole width of the garment.

However, as previously described, it is also to be understood that in other embodiments the numbers of prongs 134, the numbers of prong 134 sets and the number of prongs 134 in each set can vary from the three prong 134 per set, and the two or three sets per hanger that are exemplarily illustrated in FIGS. 11-13, 92-95, 97, and 100. In addition, as previously described the size and shape of the prongs 134 can also vary. Without intending to be limiting, it would also be possible to have only one set of prongs 134 for one fragrance piece 104 that spans most of the width of the hanger. In addition, without intending to be limiting, it would also be possible to have one long prong 134 that spans most of the width of the hanger for the attachment of at least one fragrance piece 104. The use of two or three fragrance pieces 104 per hanger is preferred, however, as the shorter fragrance pieces 104 can be easier than longer fragrance pieces 104 to attach and remove from the hanger. In addition, the use of more than one fragrance piece 104 per hanger 188, as exemplarily illustrated in FIGS. 11-13 enables the user to vary the number of fragrance pieces 104 attached at one time, and to mix and match fragrances attached at one time.

Reference is now made to FIGS. 92-97b, which exemplarily illustrate a widened shoulder area 204 on at least one top corner area 206 of a hanger 188. The widened shoulder area 204 will have at least one tapering area 132 that gradually tapers. The size and configuration of each widened shoulder area 204 can vary.

Preferably each shoulder widened area 204 will have four tapering areas 132 that gradually taper, as exemplarily illustrated, to provide gradual easement to the widened shoulder area without being destructive to the garment. In this embodiment, each widened shoulder area 204 will have a wide middle area 232 between two narrow end areas 234. The width of the widened shoulder area 204 will gradually taper at the tapering areas 132 located between each narrow end area 234 and wide middle area 232.

In some embodiments, the widened shoulder area 204 can be about 2.5 inches long measured from one narrow end area 234 to the other, and about 1 inch wide measured at the widest point of the wide middle area 232. For an all-purpose hanger, this sized widened shoulder area 206, such as but not limited to the widened shoulder areas exemplarily illustrated in these FIGS., provides a happy medium between giving garments support without stretching the garments by sticking out too far, and without taking up too much room in the closet. However, it is to be understood that other sized widened shoulder areas 204 can be used. By way of example, and without intending to be limiting, a larger widened shoulder area could be used for larger garments, and a smaller size widened shoulder area could also be used for smaller garments.

Figure 93:
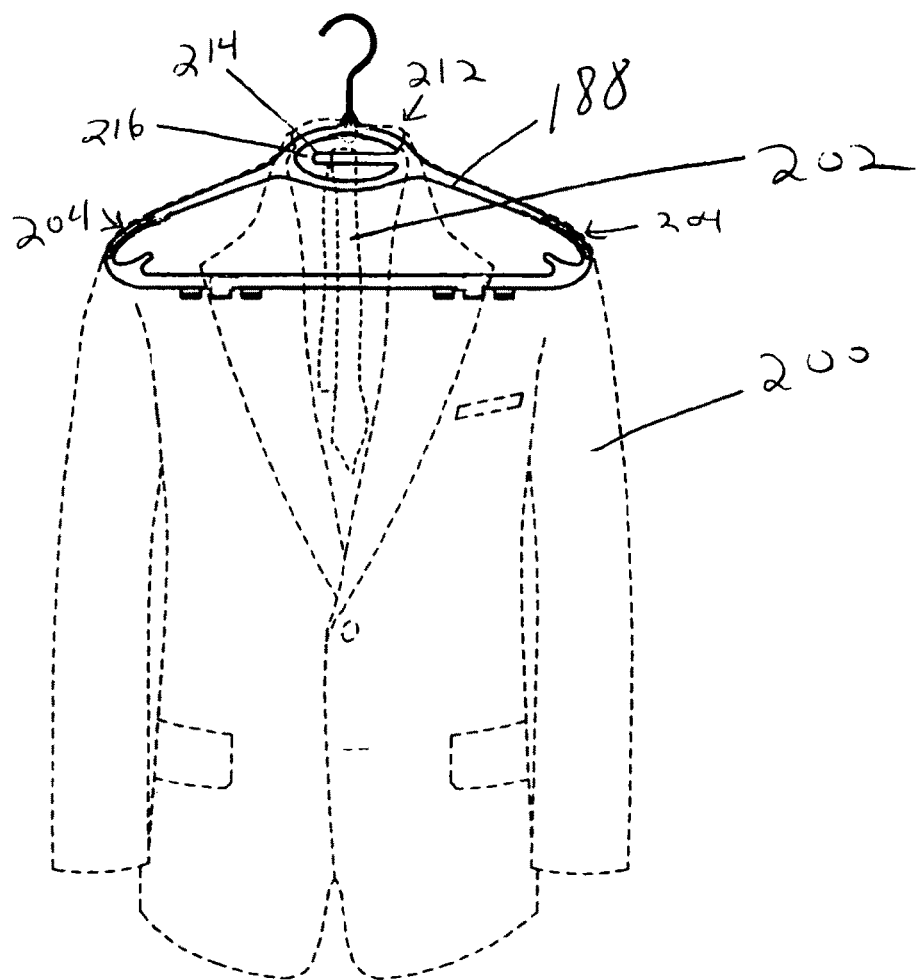
FIGS. 93-95 are views of a hanger in use.
Figure 93A:
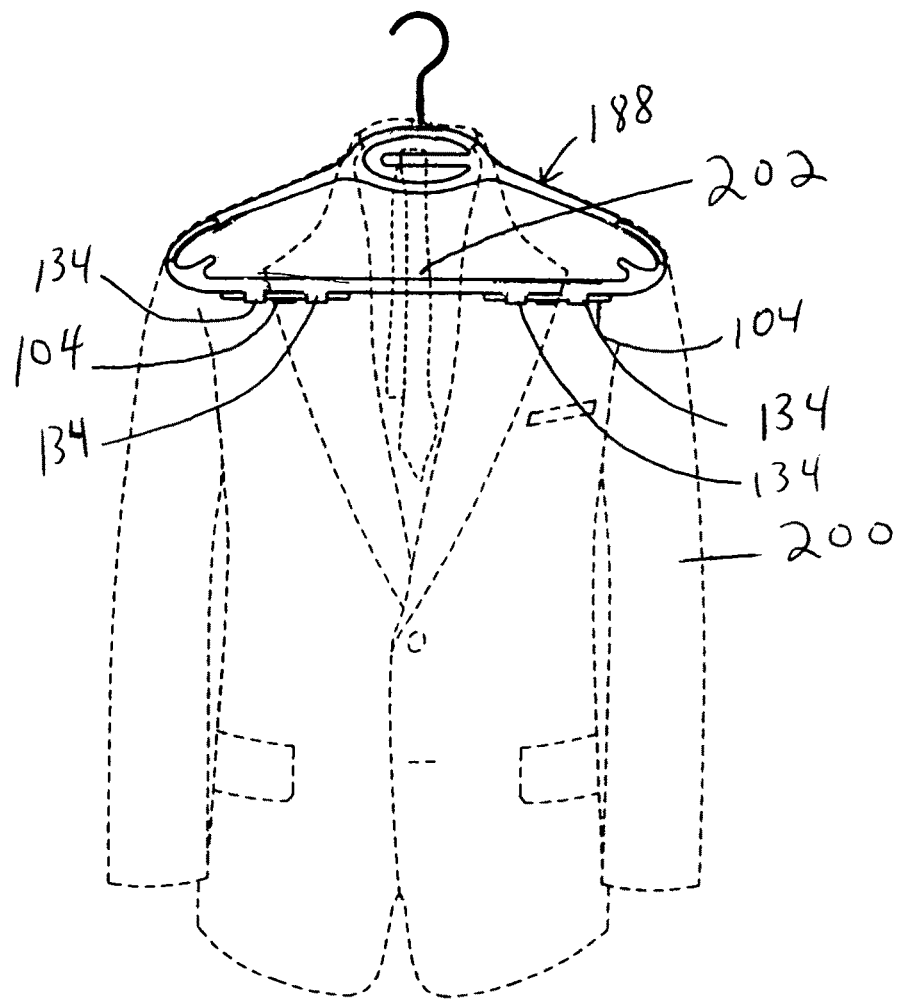
Figure 94:
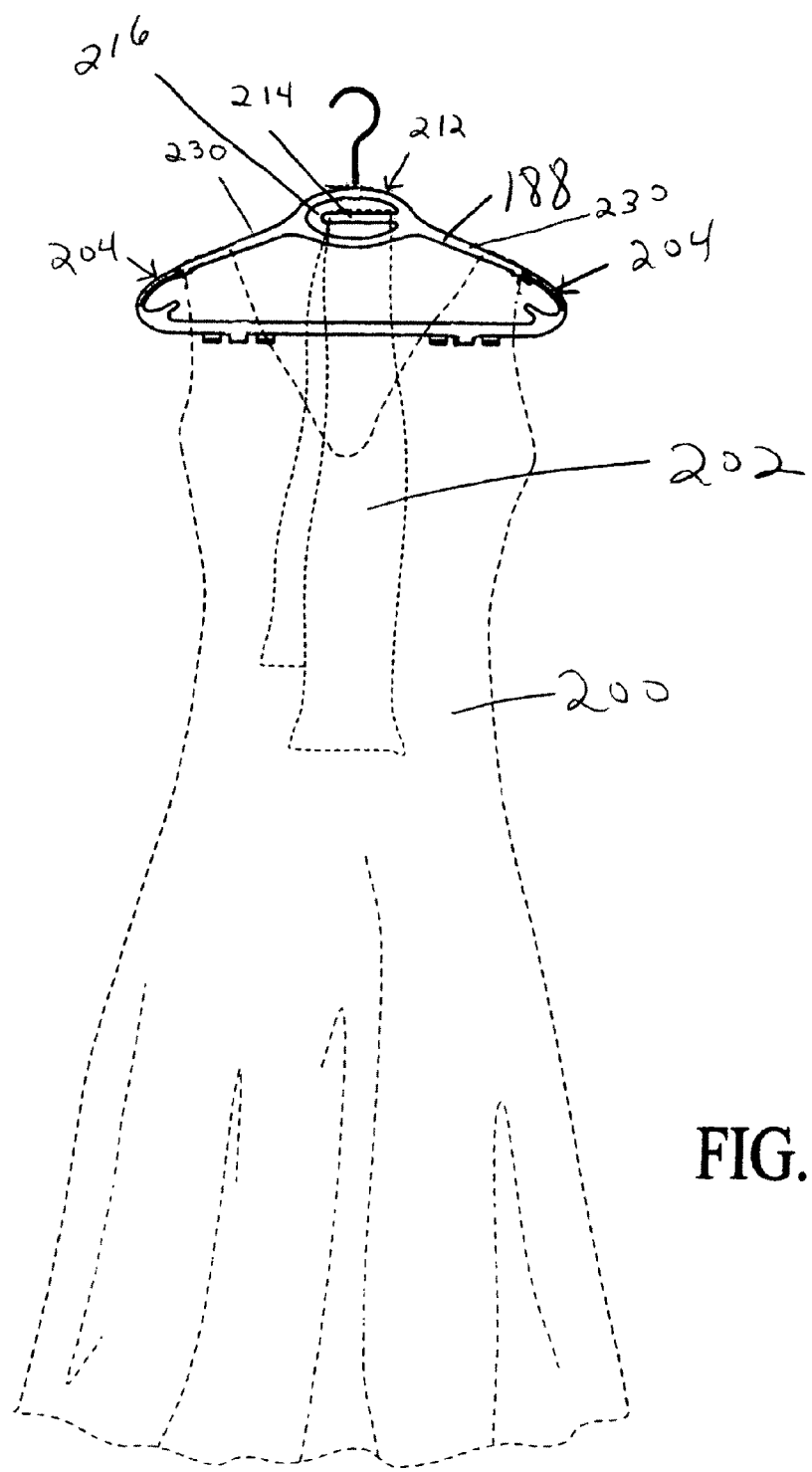
Figure 95:
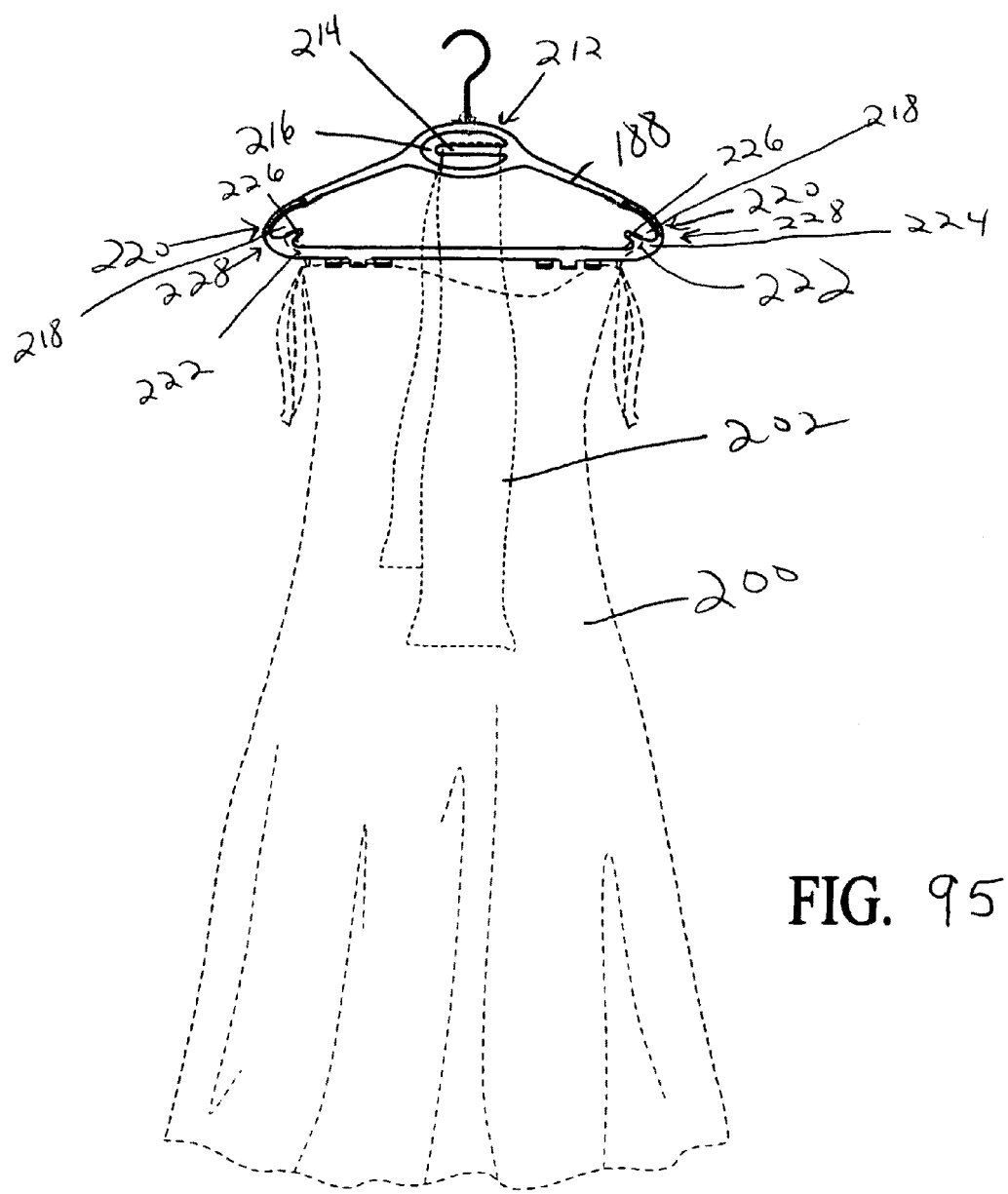

The beneficial uses of the widened shoulder area 204 include, but are not limited to, the following: providing added support to garments 200, especially coats and jackets, as exemplarily illustrated in FIG. 93; holding hanging ribbons 222 on garments including, but not limited to, strapless dresses, skirts, and pants on the hanger by hanging the hanging ribbon 222 between the widened shoulder area and the middle of the upper bar 230 and preventing them from sliding off the top corner area 206 of the hanger; keeping sleeveless garments from sliding off the top corner area 206 of a hanger by hanging the garment on the widened area and/or between the widened area and the middle of the upper bar 230 as exemplarily illustrated in FIG. 94; and keeping garments intact on the hanger, particularly garments with wide necklines that might otherwise slip off the top corner ends 206 of the hanger.

Figure 92:
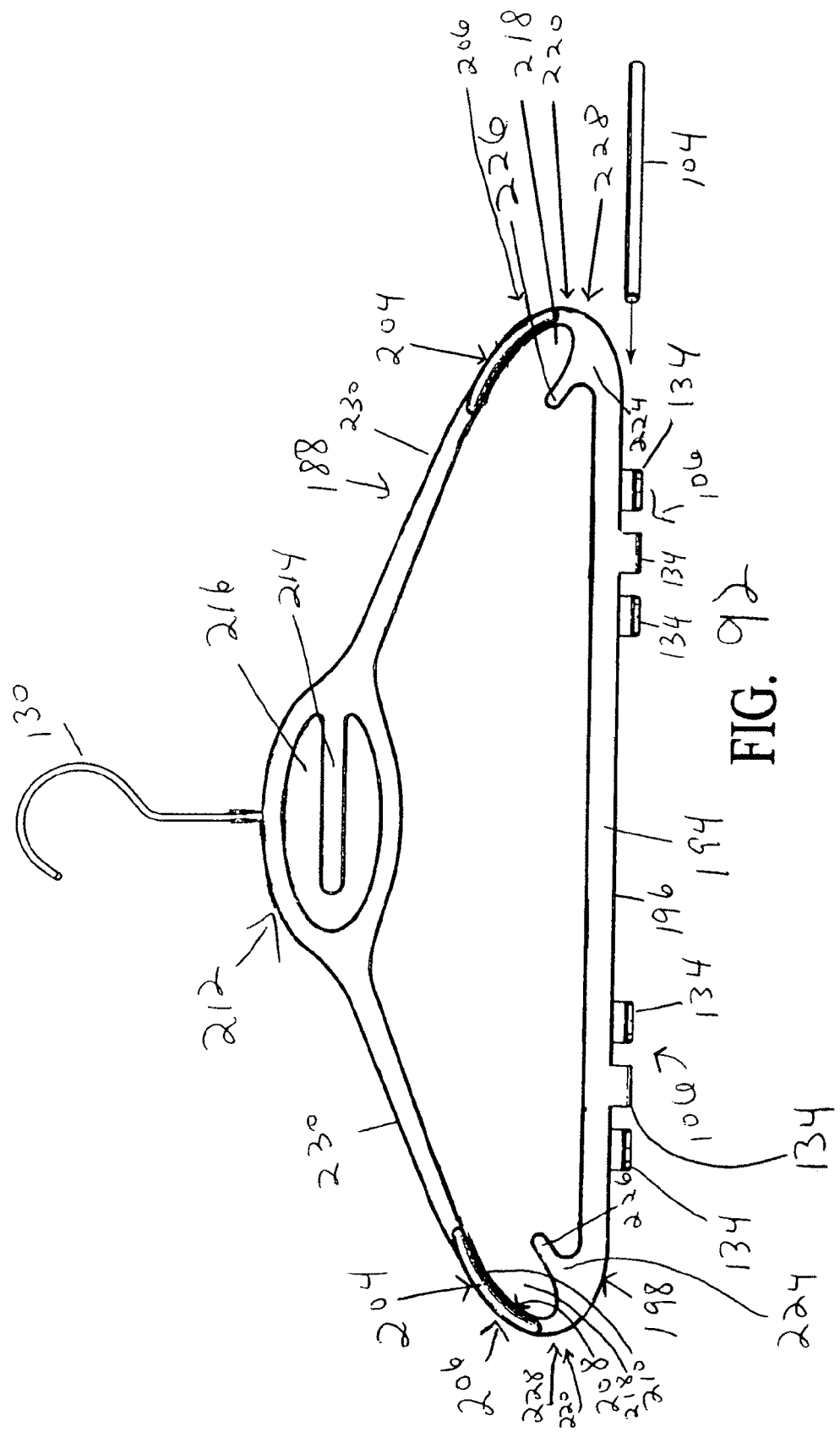
FIG. 92 is a view of a scented hanger and a fragrance piece.
Figure 96:
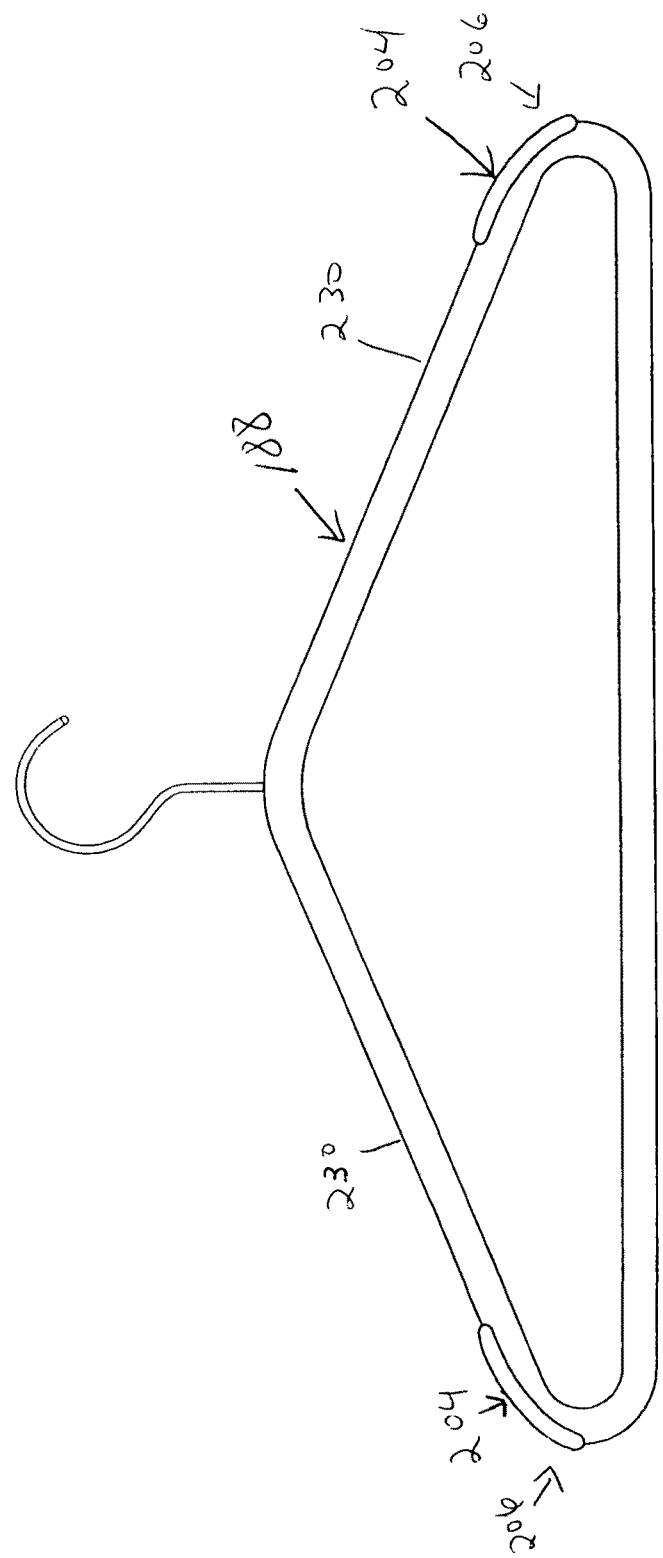
FIG. 96 is a view of widened shoulder areas on a hanger.
Figure 97:
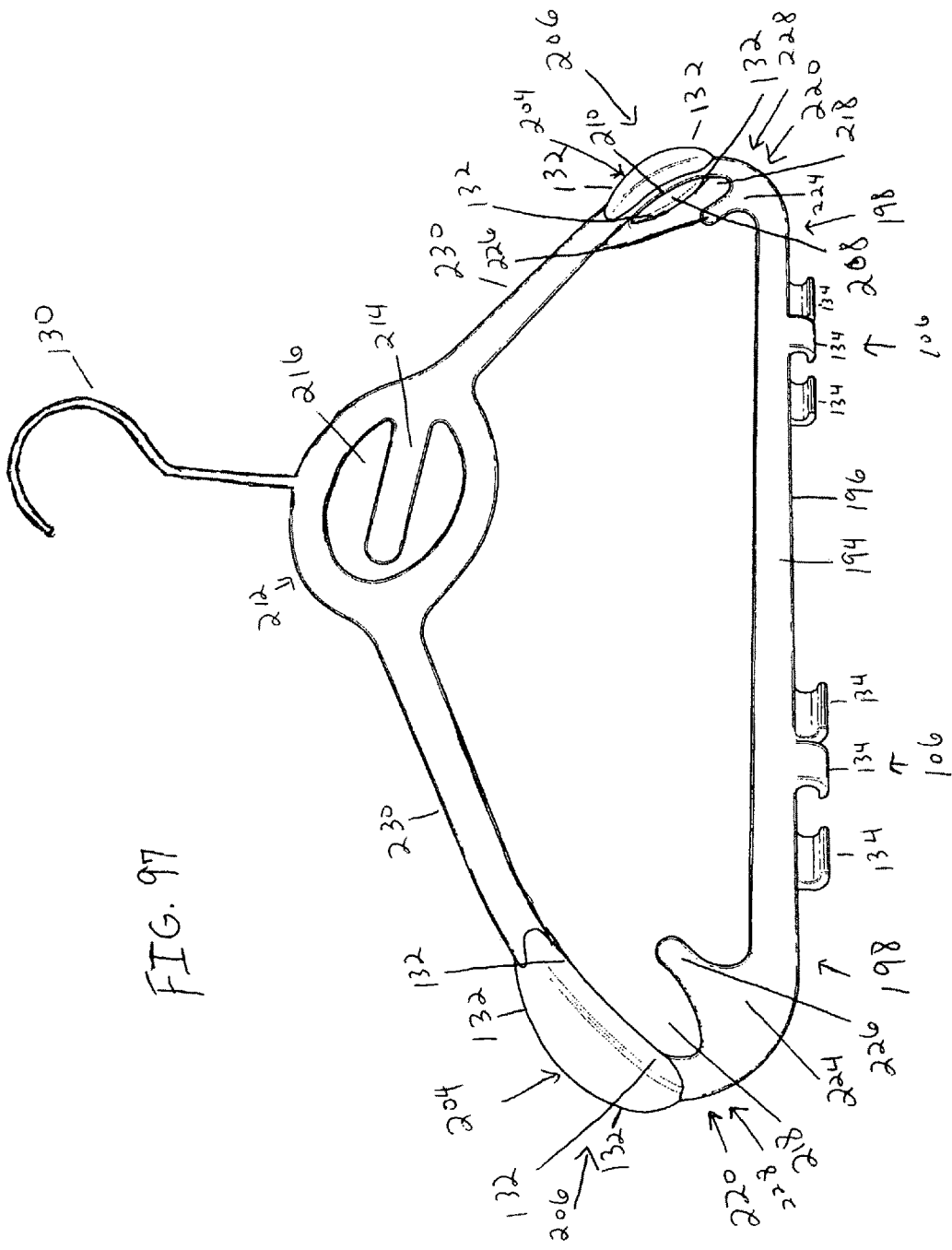
FIG. 97 is a perspective view of a hanger.
Figure 97A:
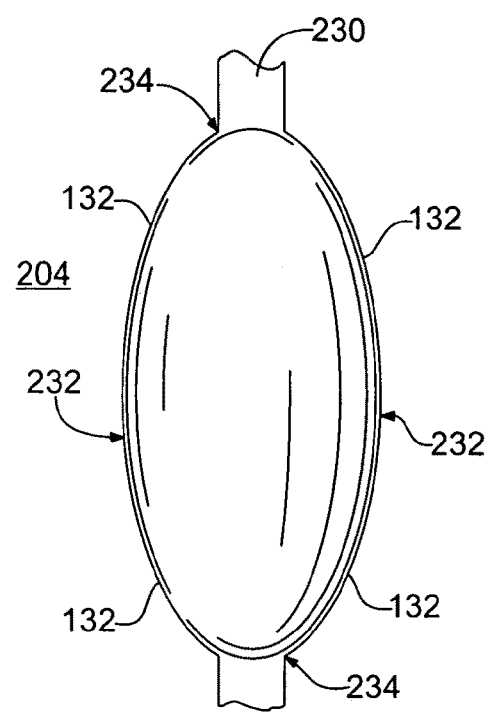
FIG. 97A is a top view of a widened shoulder area.
Figure 97B:
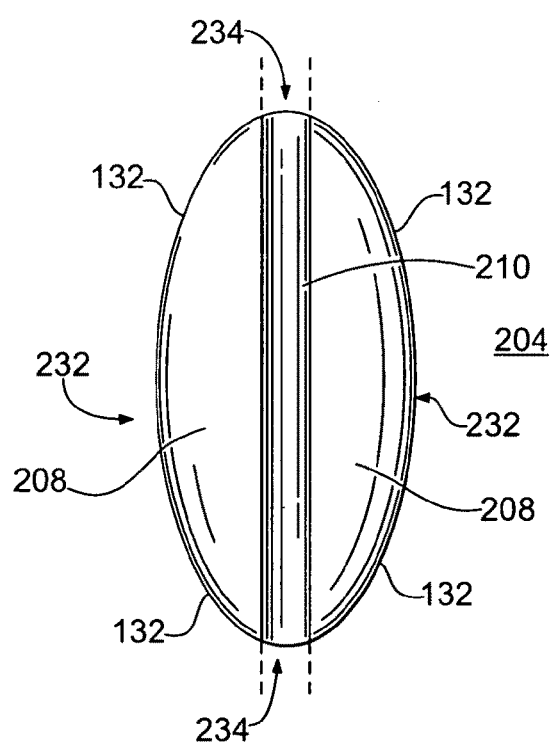
FIG. 97B is a bottom view of a widened shoulder area that includes a ridge.
Figure 98:
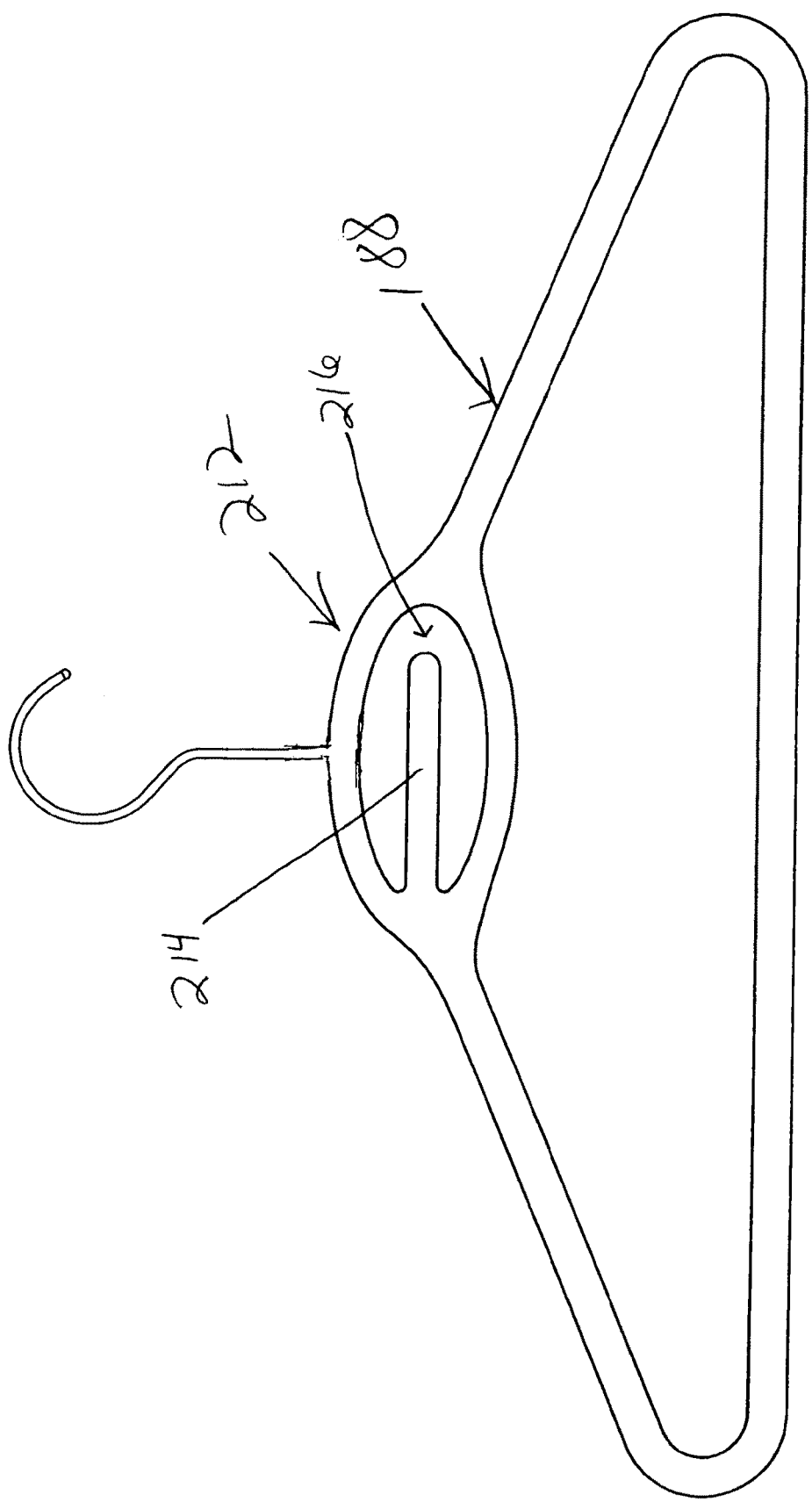
FIG. 98 is a view of a top oval area on a hanger.
Figure 99:
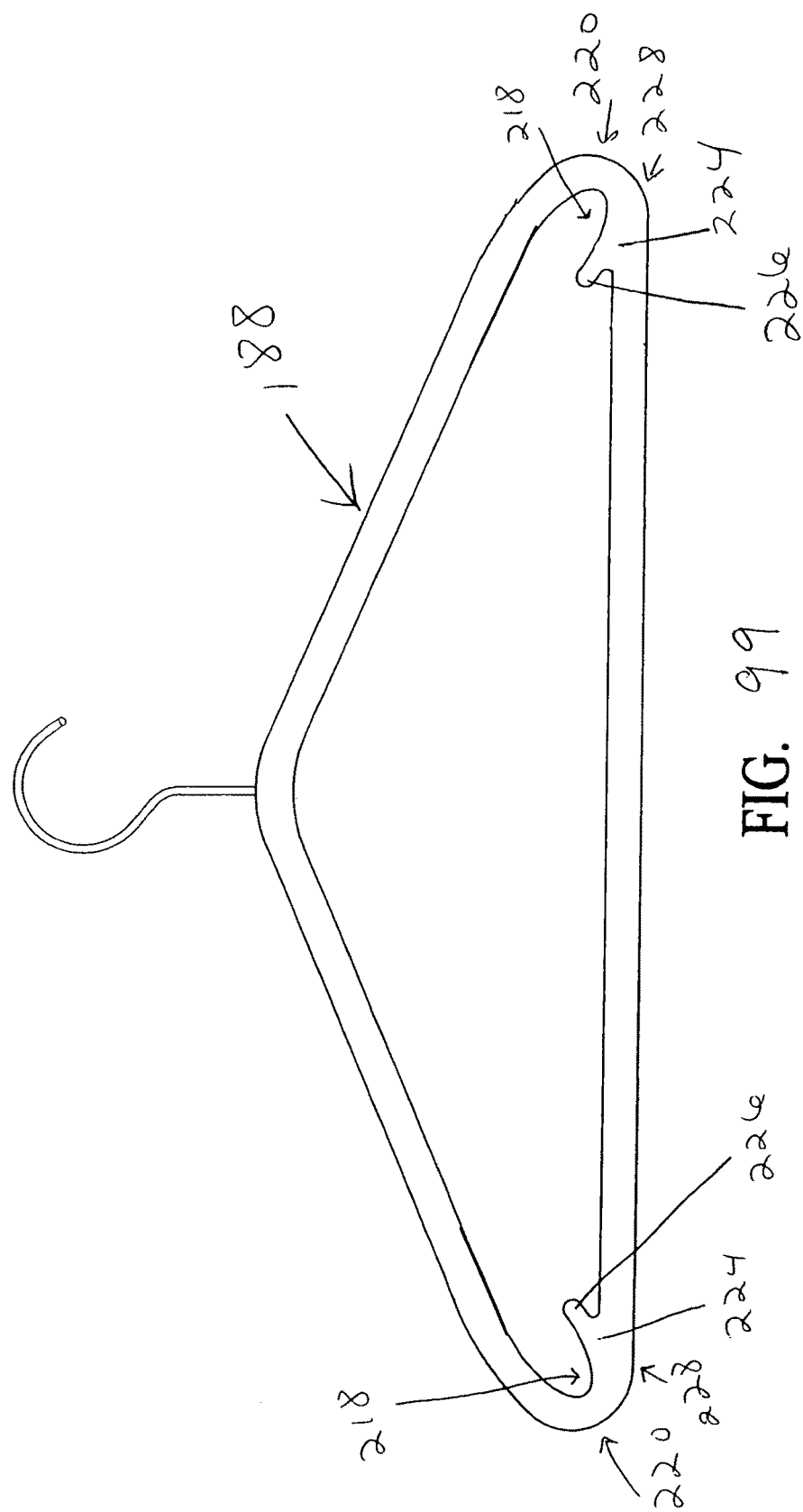
FIG. 99 is a view of side hook areas on a hanger.

As exemplarily illustrated in FIGS. 92, 96-97 the bottom side 208 of the widened area can have at least one ridge 210 that extends the length of the widened shoulder area, which will add strength and support to the hanger.

Referring now to FIGS. 92-95, 97, and 98, a top oval area 212 with a partial center bar 214 is exemplarily illustrated. The large size of the oval opening 216 and the partial center bar 214, as exemplarily illustrated, are beneficial to enable the user to hang clothing accessories 202, including, but not limited to, sashes, belts, jewelry, scarves, ties from the partial center bar 214. The large oval opening 216 enables easy attachment and removal of accessories 202, and enables the attachment of wide or thick accessories. In addition, the wide oval opening 216 enables a long and wide partial center bar 214 to be located therein. The substantial width and length of the partial center bar 214 enhances the ability of a heavy accessory 202, such as but not limited to, a heavy belt or piece of jewelry to be attached with the center bar without causing the bar to break due to the weight of the accessory. In addition, by way of example, and without intending to be limiting, a wide accessory, such as but not limited to a sash could be attached with the partial center bar 214 without having to fold the accessory lengthwise, or otherwise having to reduce the width of the accessory. Further, the large size of the oval opening 216 creates sufficient space for the inclusion of a partial center bar 214 that only partially transects the oval opening 216, thereby enabling the partial center bar 214 to be functional, and as previously described, while at the same time providing for an increased ease of the hanging and removal of accessories than would be possible if the center bar fully transected the oval opening 216.

Reference is now made to FIGS. 92-95, 97, and 99, which exemplarily illustrate a side hook area 228 in at least one corner 220 of a hanger 188. Each side hook area 228 has a side hook space 218 that is partially defined by a hook 226, onto which portions of garments, including but not limited to hanging ribbons 222, and accessories 202 can be attached with the hanger. The large size and location of the side hook space 218 as exemplarily illustrated enable the user to attach garments 200 and accessories 202, including wide or bulky hanging ribbons 222 of garments 200 to the corners 220 of the hanger 188 while at the same time enabling easy hanging and removal of the hanging ribbons 222 and/or other portions of garments 200 and/or accessories 202. The bottom triangle support area 224 below each side hook space 218 adds added support and strength to the hook 226 and the corners 220 of the hanger 188, thereby increasing the weight of the garment 200 and/or accessory 202 that can be hung from the each hook 226 of the hanger without causing the hanger to break.

It is to be understood that the embodiments of the hanger 188 exemplarily illustrated in FIGS. 11-13, and 92-100 and described above, include various embodiments of four main embodiment groups (referred to as a "main groups"). The various embodiments of each main group exemplarily illustrated in FIGS. 11-13, and 92-100 and described above are as follows: group 1) prong 134 embodiments, jointly referred to as "prong embodiments"; group 2) widened shoulder area 204 embodiments, jointly referred to as "widened shoulder area embodiments"; group 3) top oval area 212 embodiments, jointly referred to as "top oval area embodiments"; group 4) side hook area 228 embodiments, jointly referred to as "side hook area embodiments". It is to be understood at least one or all of the embodiments that jointly are referred to as any one of the four main groups could be included in an embodiment of a hanger 188 without the addition the remaining three main groups. For example, and without intending to be limiting, some or all of the embodiments in main group 1, prong embodiments, could be included on a hanger 188, without the inclusion of any of the embodiments in main group 2, widened should area embodiments, main group 3, top oval area embodiments, or main group 4, side hook area embodiments. In addition, some or all of the embodiments that jointly are referred to as embodiments of two of the main groups could be included in an embodiment of the hanger without the addition of the remaining two main groups. For example, and without intending to be limiting, some or all of the embodiments in main group 1, prong embodiments, and some or all of the embodiments in main group 2, widened shoulder area embodiments, could be included on a hanger 188, without the inclusion of any of the embodiments in main group 3, top oval area embodiments, or main group 4, side hook area embodiments. Further, some or all of the embodiments that jointly are referred to as embodiments of three of the main groups could be included in an embodiment of the hanger 188 without the addition of the remaining one main group. For example, and without intending to be limiting, some or all of the embodiments in main group 1, prong embodiments, some or all of the embodiments in main group 2, widened shoulder area embodiments, and some or all of the embodiments in main group 3, top oval area embodiments, could be included on a hanger 188, without the inclusion of any of the embodiments in main group 4, side hook area embodiments. Also, some or all of the embodiments that jointly are referred to as embodiments of all four of the main groups could be included in an embodiment of a hanger 188.

Any of the described embodiments of a hanger 188, can be made of any materials currently known or to be discovered in the art that will be sufficiently strong to support garments and not too heavy to be picked up by a typical user and/or hung in a closet. In addition the actual curved hook portion 130 that is intended to hang over the closet rod can be made of any materials currently known or to be discovered in the art that will be sufficiently strong to support garments and not too heavy to be picked up by a typical user and/or hung in a closet. In some embodiments, the hanger material can be plastic and the actual curved hook portion 130 that is intended to hang over the closet rod will be metal. In some embodiments, the hanger (excluding the curved hook portion 130) can be covered with a variety of materials, including but not limited to micro fiber and/or sponge, which will decrease the slipping of clothes on the hanger, while not damaging the garment. Sponge is very affective, functional, easy to use, adheres to the hanger, and can enhance the interaction between a fragrance piece and a prong within the preferred attachment parameters and/or the more preferred attachment parameters, and in some embodiments also within the removal and fit attachment parameters and/or the preferred removal and fit attachment parameters. Micro fiber is very affective, functional, easy to use, resists ripping, adheres to the hanger, is fairly durable, and can enhance the interaction between a fragrance piece and a prong within the preferred attachment parameters and/or the more preferred attachment parameters, and in some embodiments also within the removal and fit attachment parameters and/or the preferred removal and fit attachment parameters. It is to be understood that in some embodiments, the curved hook portion 130 can also be covered with a variety of materials including but not limited to micro fiber and/or sponge.

Reference is now made to FIGS. 101-107.

Figure 101:
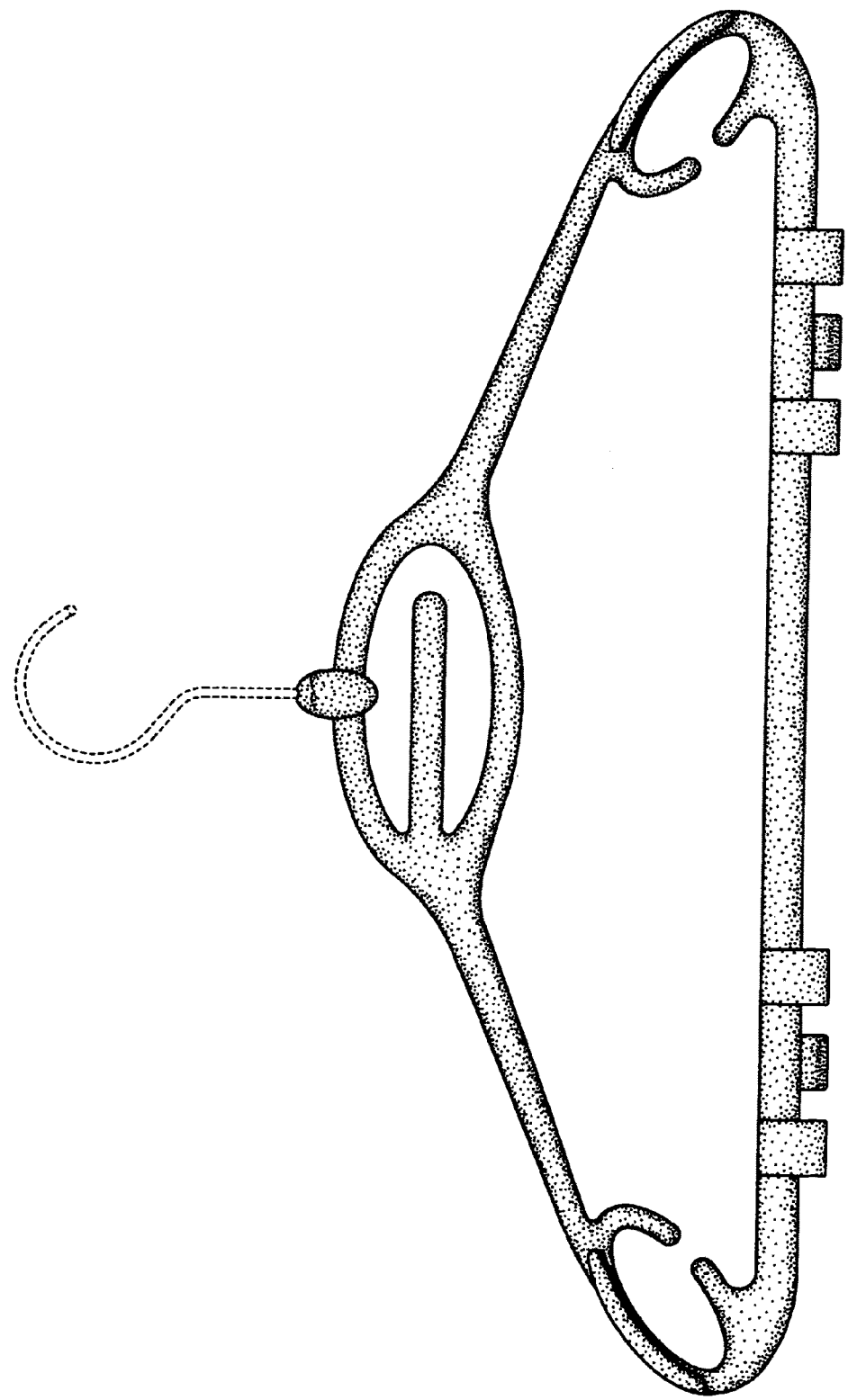
FIG. 101 is an isometric front view of a hanger showing a new design.
Figure 102:
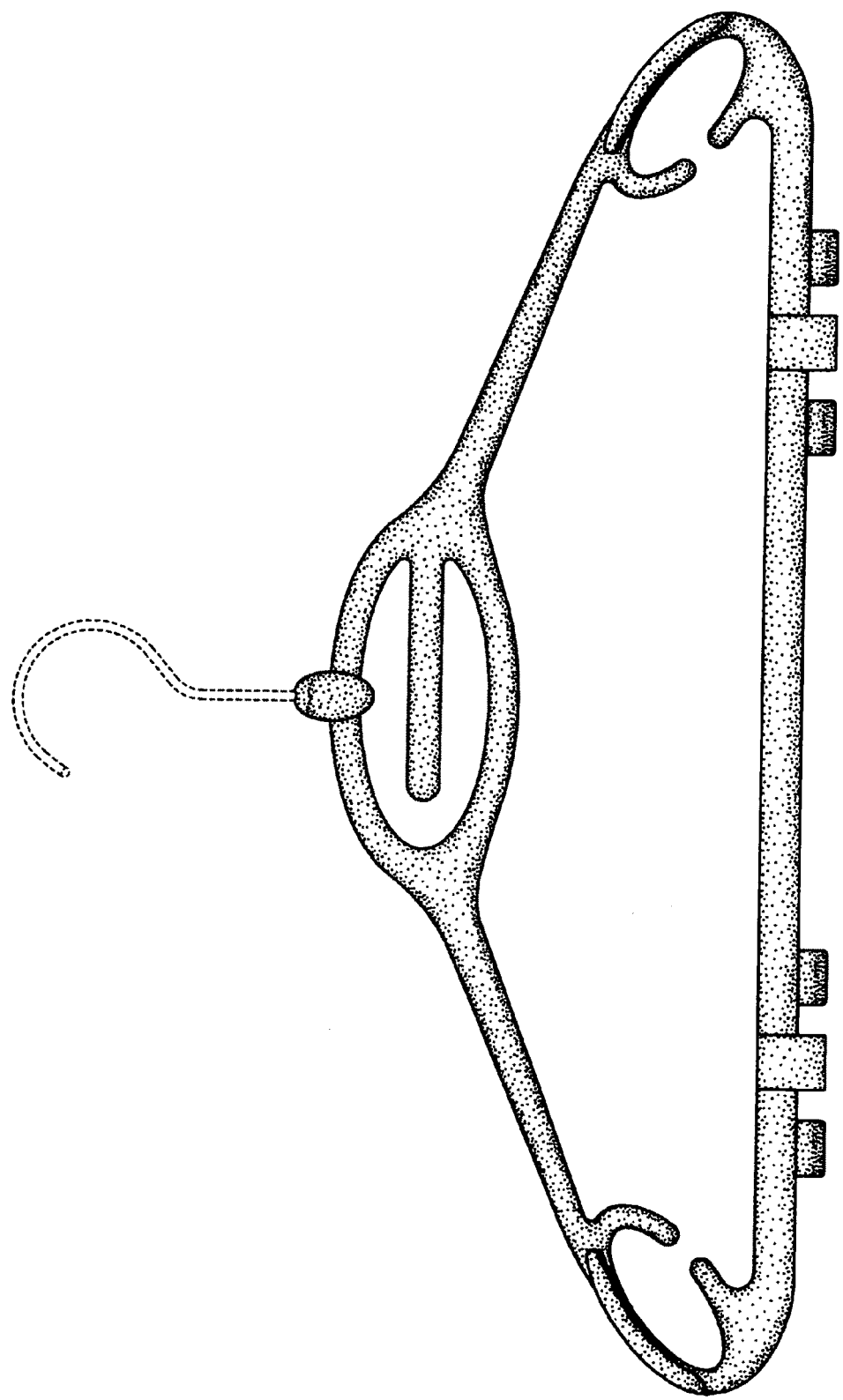
FIG. 102 is an isometric rear view thereof.
Figure 103:
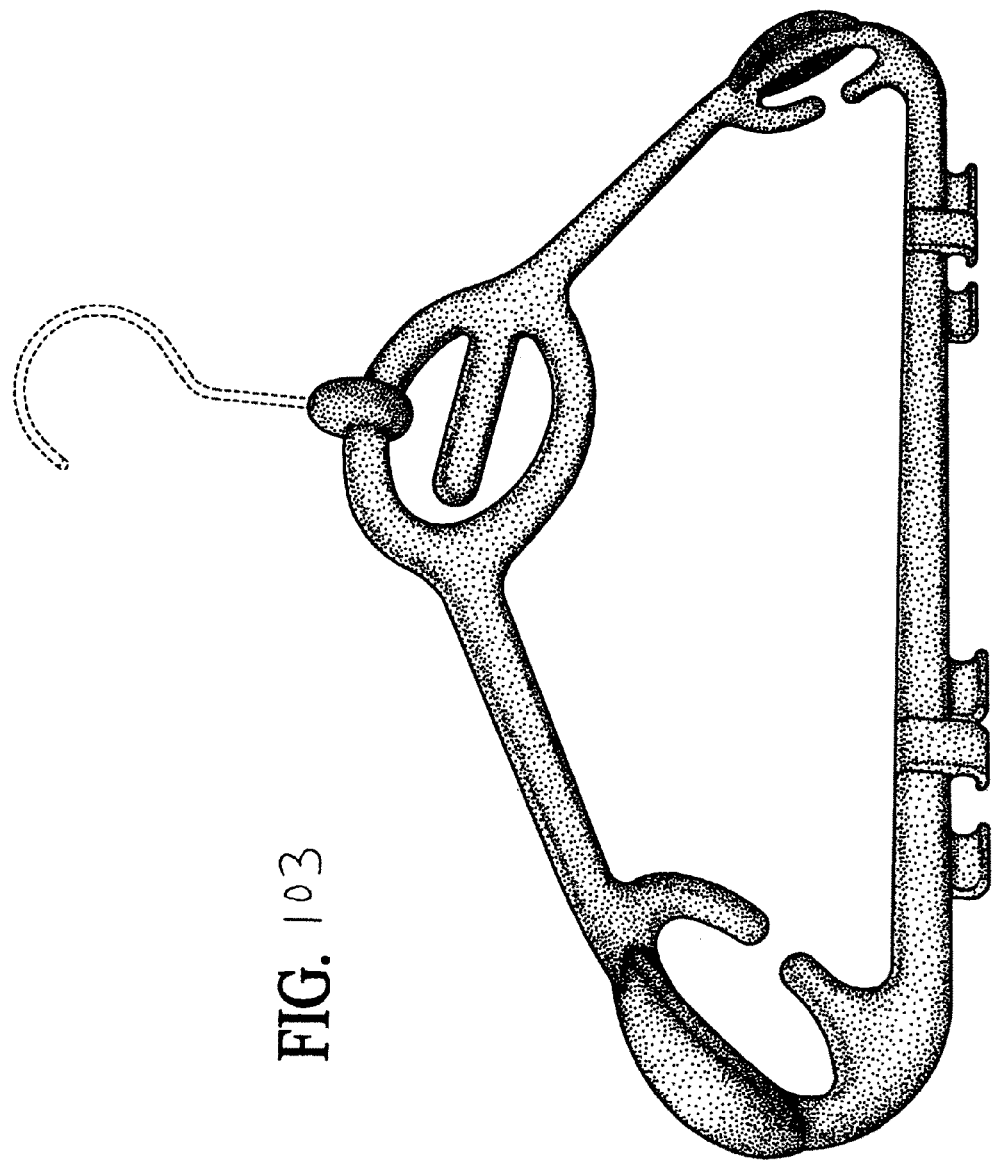
FIG. 103 is a perspective rear view thereof.
Figure 107:
FIG. 107 is an isometric right side view thereof.
Figure 106:
FIG. 106 is an isometric left side view thereof.

I, Carol Boyd, have invented a new design for a hanger as set forth in the following specification:

FIG. 101 is an isometric front view of a hanger showing my new design;

FIG. 102 is an isometric rear view thereof;

FIG. 103 is a perspective rear view thereof;

FIG. 104 is an isometric bottom view thereof;

FIG. 105 is an isometric top view thereof;

FIG. 106 is an isometric left side view thereof;

FIG. 107 is an isometric right side view thereof.

Reference is now made to FIGS. 108-124.

Figure 108:
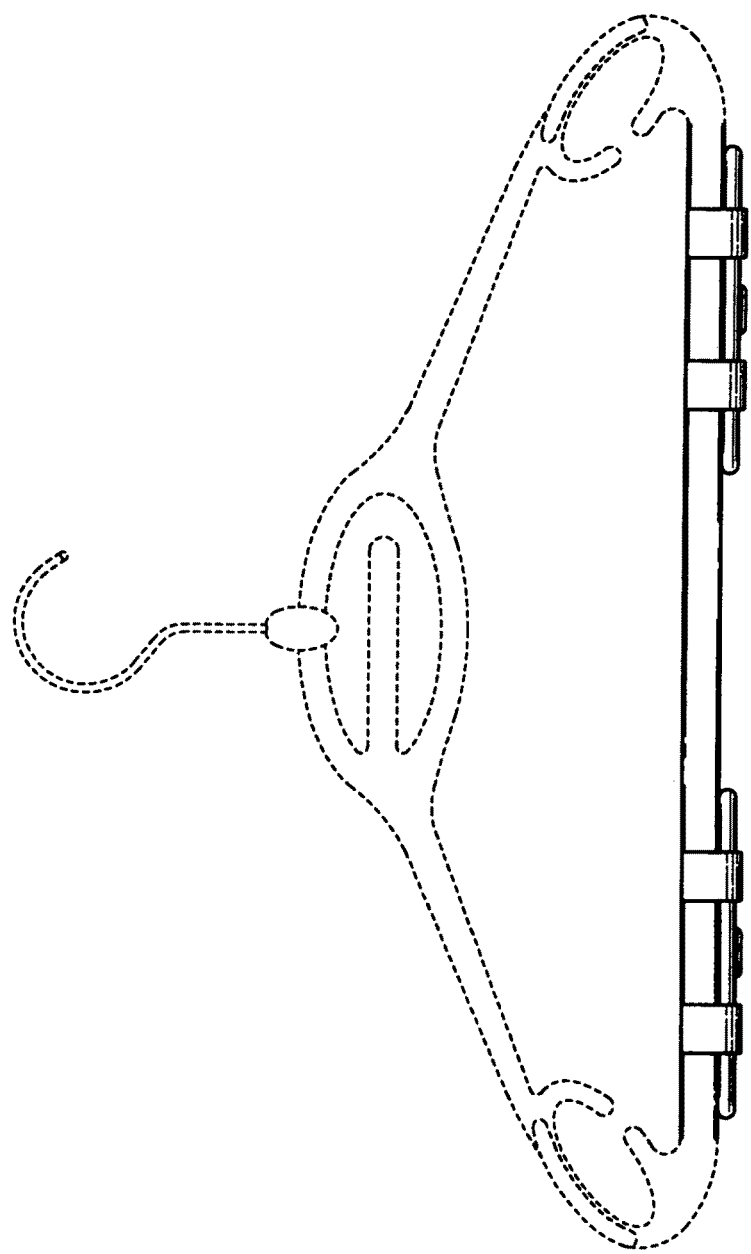
FIG. 108 is an isometric front view of a scented bottom bar of hanger showing a new design.
Figure 109:
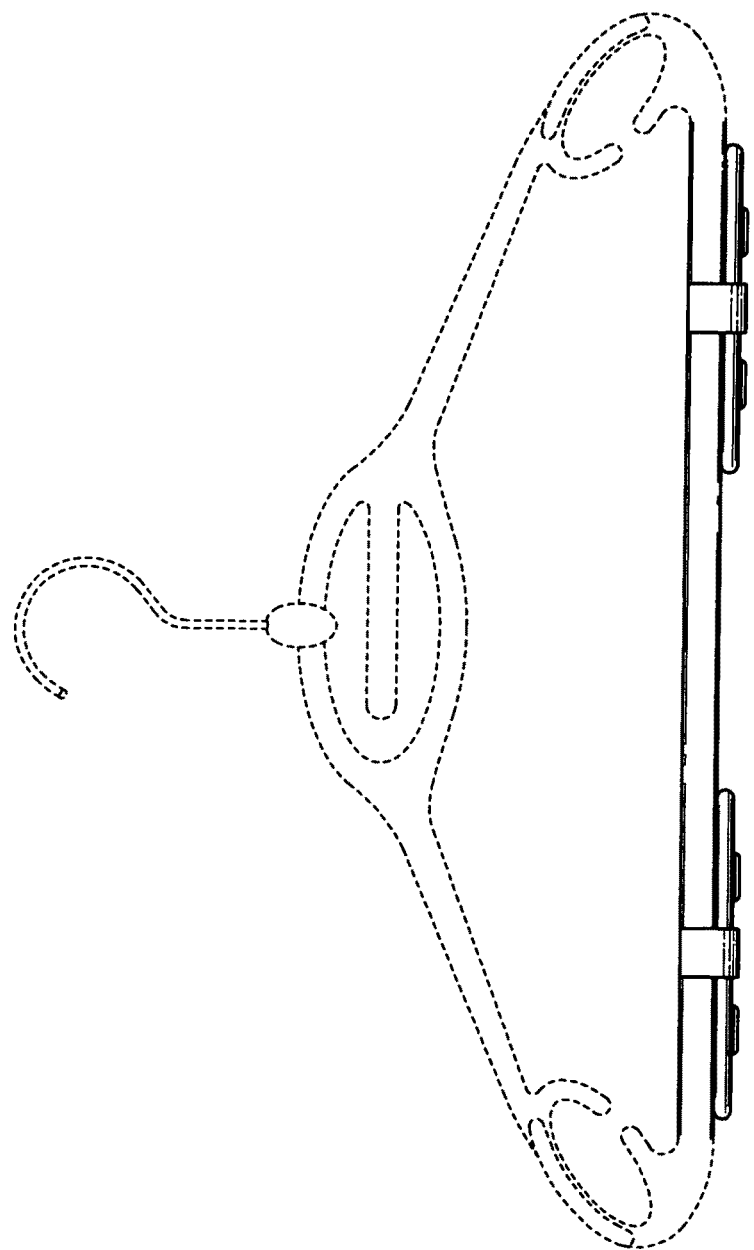
FIG. 109 is an isometric rear view thereof.
Figure 110:
FIG. 110 is an isometric bottom view thereof.
Figure 111:
FIG. 111 is an isometric top view thereof.
Figure 113:
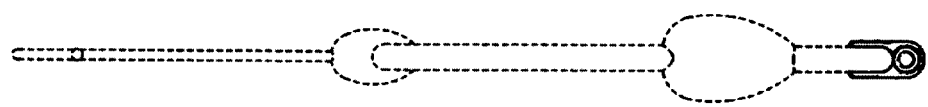
FIG. 113 is an isometric right side view thereof.
Figure 112:
FIG. 112 is an isometric left side view thereof.
Figure 114:
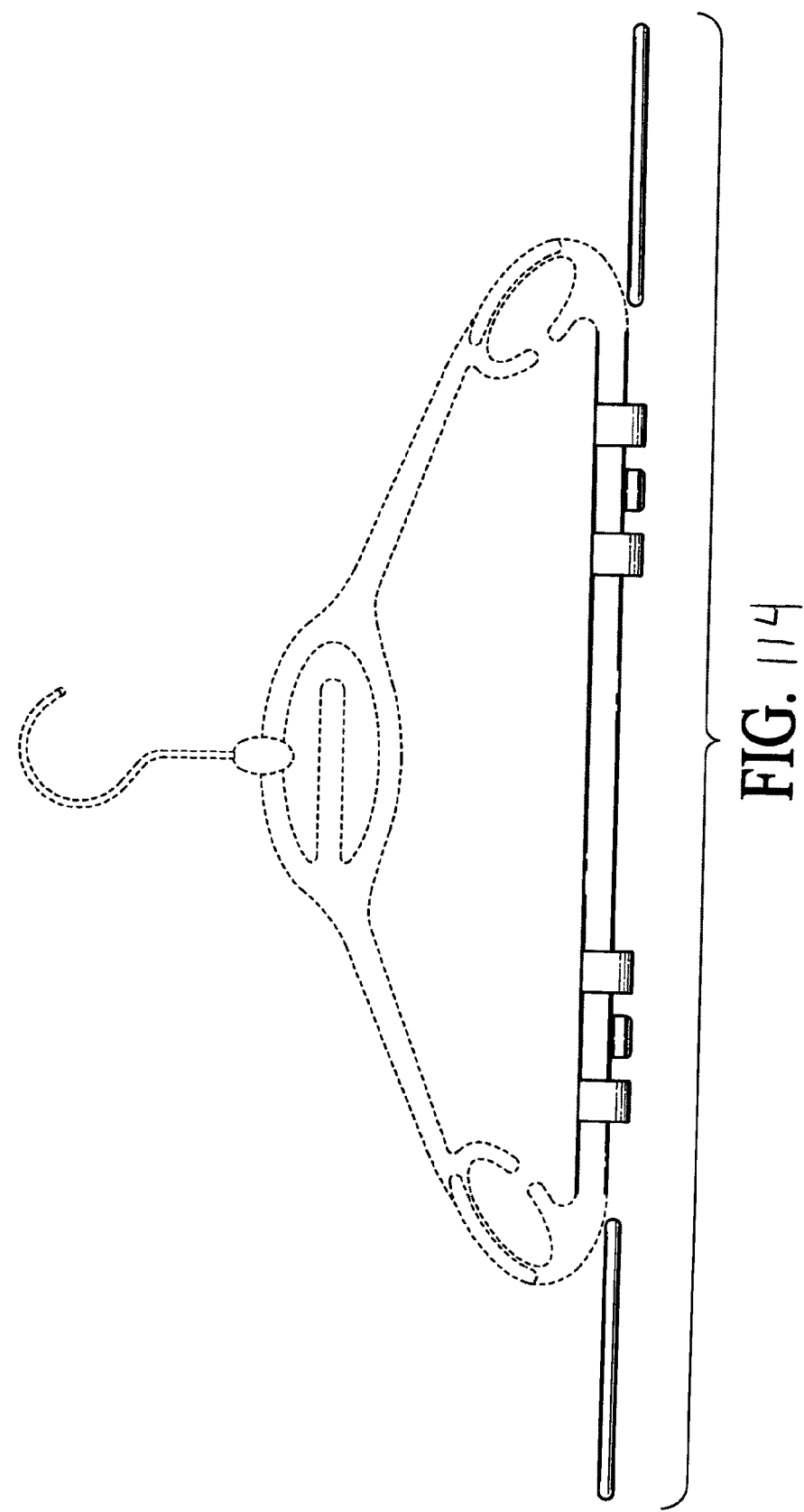
FIG. 114 is an exploded view of the isometric front view of a scented bottom bar of hanger.
Figure 115:
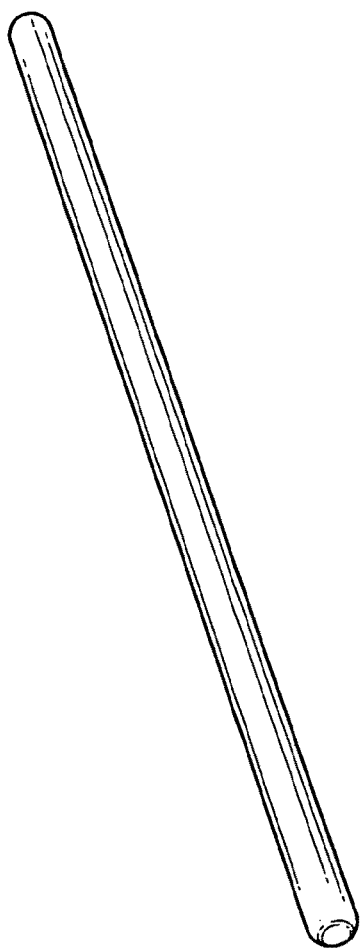
FIG. 115 is a perspective front view of a fragrance piece shown removed from the scented bottom bar of a hanger for clarity of disclosure.
Figure 117:
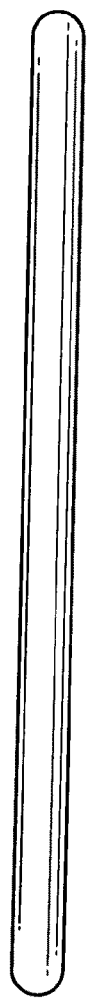
FIG. 117 is an isometric rear view a fragrance piece shown removed from the scented bottom bar of a hanger for clarity of disclosure.
Figure 118:
FIG. 118 is an isometric right side view a fragrance piece shown removed from the scented bottom bar of a hanger for clarity of disclosure.
Figure 116:
FIG. 116 is an isometric left side view a fragrance piece shown removed from the scented bottom bar of a hanger for clarity of disclosure.
Figure 119:
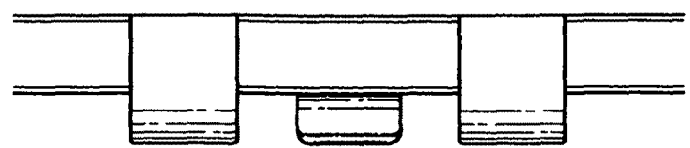
FIG. 119 is an isometric front view of one set of prongs with the fragrance piece removed, shown removed from the scented bottom bar of a hanger for clarity of disclosure.
Figure 120:
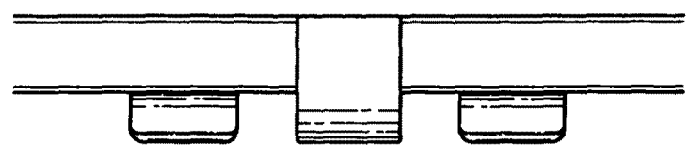
FIG. 120 is an isometric rear view of one set of prongs with the fragrance piece removed, shown removed from the scented bottom bar of a hanger for clarity of disclosure.
Figure 121:
FIG. 121 is an isometric bottom view a of one set of prongs with the fragrance piece removed, shown removed from the scented bottom bar of a hanger for clarity of disclosure.
Figure 122:
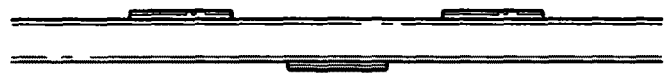
FIG. 122 is an isometric top view a of one set of prongs with the fragrance piece removed, shown removed from the scented bottom bar of a hanger for clarity of disclosure.
Figure 123:
FIG. 123 is an isometric left side view of one set of prongs with the fragrance piece removed, shown removed from the scented bottom bar of a hanger for clarity of disclosure.
Figure 124:
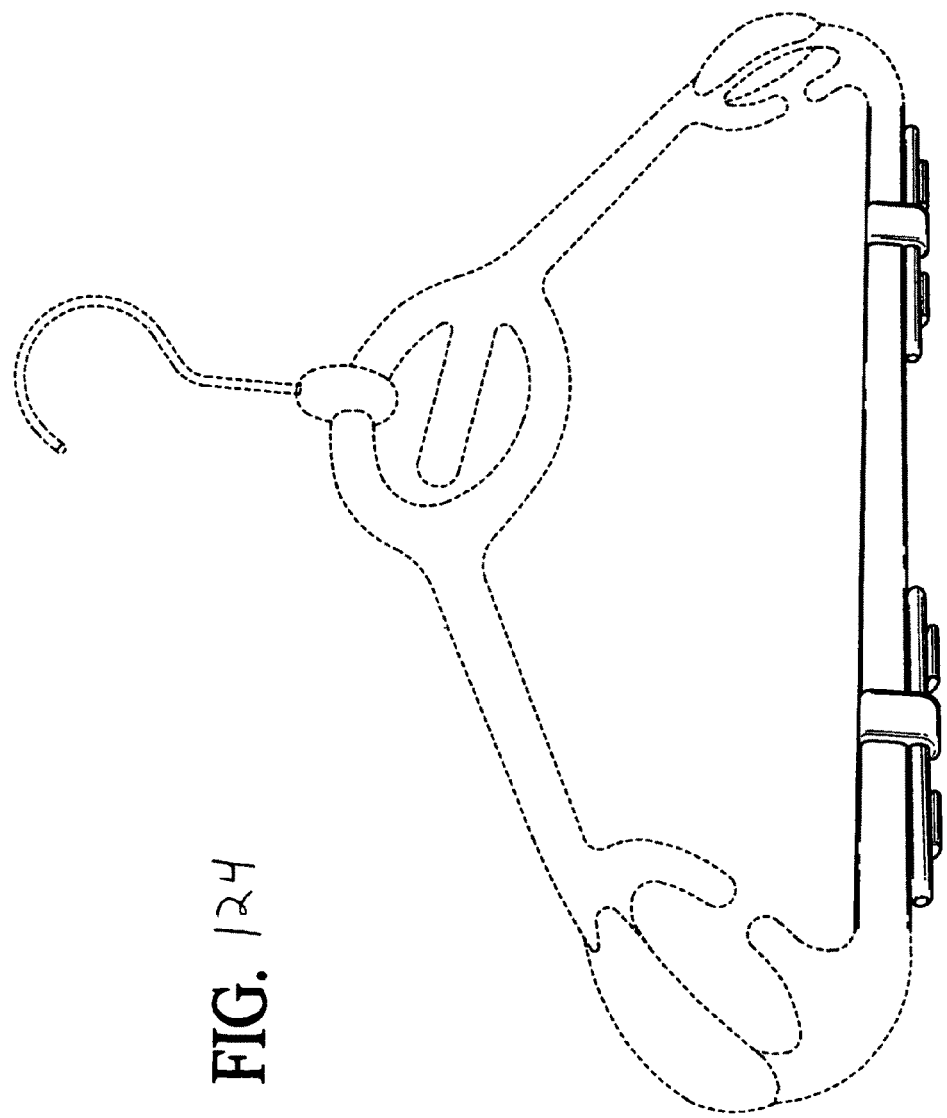
FIG. 124 is a perspective rear view of a scented bottom bar of hanger showing a new design.

I, Carol Boyd, have invented a new design for a scented bottom bar of a hanger as set forth in the following specification. The bottom bar includes two sets of prongs to attach fragrance pieces to the bottom bar of the hanger and two fragrance pieces used to emit at least one scent:

FIG. 108 is an isometric front view of a scented bottom bar of hanger showing my new design;

FIG. 109 is an isometric rear view thereof;

FIG. 110 is an isometric bottom view thereof;

FIG. 111 is an isometric top view thereof;

FIG. 112 is an isometric left side view thereof;

FIG. 113 is an isometric right side view thereof;

FIG. 114 is an exploded view of the isometric front view of a scented bottom bar of hanger;

FIG. 115 is a perspective front view of a fragrance piece shown removed from the scented bottom bar of a hanger for clarity of disclosure;

FIG. 116 is an isometric left side view a fragrance piece shown removed from the scented bottom bar of a hanger for clarity of disclosure;

FIG. 117 is an isometric rear view a fragrance piece shown removed from the scented bottom bar of a hanger for clarity of disclosure;

FIG. 118 is an isometric right side view a fragrance piece shown removed from the scented bottom bar of a hanger for clarity of disclosure;

FIG. 119 is an isometric front view of one set of prongs with the fragrance piece removed, shown removed from the scented bottom bar of a hanger for clarity of disclosure;

FIG. 120 is an isometric rear view of one set of prongs with the fragrance piece removed, shown removed from the scented bottom bar of a hanger for clarity of disclosure;

FIG. 121 is an isometric bottom view of one set of prongs with the fragrance piece removed, shown removed from the scented bottom bar of a hanger for clarity of disclosure;

FIG. 122 is an isometric top view of one set of prongs with the fragrance piece removed, shown removed from the scented bottom bar of a hanger for clarity of disclosure;

FIG. 123 is an isometric left side view of one set of prongs with the fragrance piece removed, shown removed from the scented bottom bar of a hanger clarity of disclosure;

FIG. 124 is a perspective rear view of a scented bottom bar of hanger showing my new design.

I claim:

1. A scented garment hanger system, said system comprising:
    at least one fragrance piece;
    said system further comprising at least one garment hanger, said at least one garment hanger comprising at least one attacher, said at least one attacher comprising at least one cavity;
    said at least one garment hanger comprising a top end, said top end comprising said at least one cavity, wherein said at least one cavity is an interior cavity, said at least one cavity comprising at least one opening to the exterior, at least one of said at least one openings to the exterior comprising a bottom opening;
    said top end further comprising two opposing side walls;
    said top end further comprising two hanger columns, each of said two hanger columns further comprising a center-facing wall, and wherein said at least one fragrance piece further comprises a riser at each end area and a middle portion therebetween, wherein said middle portion is longer than the length of the distance between each of said center-facing walls;
    said at least one fragrance piece being removably attachable with said at least one garment hanger by said at least one cavity, and wherein said at least one fragrance piece is removably attachable with said at least one cavity without requiring said at least one cavity to be removed from said from said at least one garment hanger.

2. The system of claim 1, wherein said at least one fragrance piece is removably attachable to said hanger by being removably insertable into said bottom opening, whereby when said at least one fragrance piece is inserted in said hanger, said middle portion is leveraged between each of said center-facing walls.

3. The system of claim 2 wherein when said at least one fragrance piece is removably inserted in said cavity, said middle portion bends in an arc shape.

* * * * *